(12) United States Patent
Smith

(10) Patent No.: US 10,846,371 B2
(45) Date of Patent: Nov. 24, 2020

(54) METHODS AND KITS FOR DETERMINING A PERSONALIZED TREATMENT REGIMEN FOR A SUBJECT SUFFERING FROM A PATHOLOGIC DISORDER

(71) Applicant: YISSUM RESEARCH DEVELOPMENT COMPANY OF THE HEBREW UNIVERSITY OF JERUSALEM LTD., Jerusalem (IL)

(72) Inventor: Yoav Smith, Jerusalem (IL)

(73) Assignee: YISSUM RESEARCH DEVELOPMENT COMPANY OF THE HEBREW UNIVERSITY OF JERUSALM LTD., Jerusalem (IL)

(*) Notice: Subject to any disclaimer, the term of this patent is extended or adjusted under 35 U.S.C. 154(b) by 1022 days.

(21) Appl. No.: 15/303,427

(22) PCT Filed: Apr. 2, 2015

(86) PCT No.: PCT/IL2015/050363
§ 371 (c)(1),
(2) Date: Oct. 11, 2016

(87) PCT Pub. No.: WO2015/155766
PCT Pub. Date: Oct. 15, 2015

(65) Prior Publication Data
US 2017/0039343 A1 Feb. 9, 2017

Related U.S. Application Data

(60) Provisional application No. 61/977,966, filed on Apr. 10, 2014.

(51) Int. Cl.
G06F 19/00 (2018.01)
G16B 20/00 (2019.01)
C12Q 1/6883 (2018.01)

(52) U.S. Cl.
CPC ....... *G06F 19/3456* (2013.01); *C12Q 1/6883* (2013.01); *G16B 20/00* (2019.02);
(Continued)

(58) Field of Classification Search
CPC ........ C12Q 2600/156; C12Q 2600/106; C12Q 2600/158; C12Q 2600/118; C12Q 1/70;
(Continued)

(56) References Cited

U.S. PATENT DOCUMENTS 8,583,380 B2 * 11/2013 Stephan ............... C12Q 1/6886
435/6.11
2009/0157324 A1    6/2009 Smith
(Continued)

FOREIGN PATENT DOCUMENTS

WO       2010/076788        7/2010
WO    WO2015/155766      * 10/2015

OTHER PUBLICATIONS

Dong (2017) Identification of candidate genes for Rituximab response in Rheumatoid Arthritis with weighted gene co-expression network analysis. Chinese Automation Congress (CAC), Jinan, pp. 5786-5791.*

(Continued)

*Primary Examiner* — Mary K Zeman
(74) *Attorney, Agent, or Firm* — The Roy Gross Law Firm, LLC; Roy Gross

(57) ABSTRACT

The invention relates to methods and kits for determining and optimizing a personalized treatment regimen for a subject suffering from a pathologic disorder based on calculating the value of M, that indicates the ability of said subject to eliminate said disorder. The invention specifically relates to optimization of interferon treatment of viral disorders.

5 Claims, 42 Drawing Sheets

Specification includes a Sequence Listing.

(52) U.S. Cl.
CPC . *C12Q 2600/106* (2013.01); *C12Q 2600/158* (2013.01); *G01N 2800/52* (2013.01); *Y02A 90/24* (2018.01); *Y02A 90/26* (2018.01)

(58) Field of Classification Search
CPC .. C12Q 2600/112; C12Q 1/6876; C12Q 1/68; C12Q 1/6883; G01N 2800/52; G01N 33/6893; G01N 33/57484; G01N 2800/50; G01N 33/5023; G01N 33/68; G01N 2800/102; G01N 2333/186; G01N 2570/00; G01N 2800/26; G01N 33/5005; G01N 33/5091; G01N 33/53; G01N 33/6863; G01N 2800/7095; G01N 33/564; G01N 33/563; G16H 50/30; G16H 40/63; G16H 50/20; G16H 10/40; G16H 15/00; G16H 20/30; G16H 20/70; G16H 30/40; G16H 40/20; G16H 40/67; G16H 50/50; G16H 50/70; G16H 70/40; G16H 20/10; G16H 10/20; G16H 20/00; G16H 20/40; G16H 70/20; G16H 70/00; G16B 20/00; G16B 25/00; G16B 40/00; G16B 5/00; G16B 25/10; G16B 45/00; G16B 50/00; G16B 5/20; G16B 20/20; G16B 30/00; G16B 40/10; Y02A 90/26; Y02A 90/24; G06K 9/00228; A61K 47/6803; A61K 47/6849; A61K 38/1774; A61K 38/1793; A61P 37/00; A61P 37/02; A61P 19/02; A61P 37/06; G06F 16/285; G06F 17/18; G06F 19/326; G06F 19/3456; C40B 40/06; C40B 40/08; C40B 40/10

See application file for complete search history.

(56) References Cited

U.S. PATENT DOCUMENTS

| | | | | |
|---|---|---|---|---|
| 2013/0041683 A1* | 2/2013 | Boissel | ............... | G16B 5/00 705/2 |
| 2014/0135225 A1* | 5/2014 | Crow | ............... | C12Q 1/6883 506/9 |
| 2014/0141983 A1* | 5/2014 | Singh | ............... | C12Q 1/6883 506/7 |
| 2015/0167085 A1* | 6/2015 | Salomon | ............ | G01N 33/6893 506/3 |

OTHER PUBLICATIONS

Paran et al. (2018) Expression levels of selected genes can predict individual rheumatoid arthritis patient response to tumor necrosis factor alpha blocker treatment. Current Medical Research and Opinion, 34: 10 1777-1783.*
Mould et al: Basic Concepts in Population Modeling, Simulation, and Model-Based Drug Development—Part 2: Introduction to Pharmacokinetic Modeling Methods, 2(4):e38, CPT:Pharmacometrics & Systems Pharmacology (2013).
GenBank Accession No. NP_066401 for interferon alpha-7 precursor [*Homo sapiens*] downloaded from the NCBI database on Jun. 26, 2017, pp. 1-2.
GenBank Accession No. NM_002170 for *Homo sapiens* interferon alpha 8 (IFNA8), mRNA downloaded from the NCBI database on Jun. 26, 2017, pp. 1-3.
GenBank Accession No. NP_002161 for interferon alpha-8 precursor [*Homo sapiens*] downloaded from the NCBI database on Jun. 26, 2017, pp. 1-2.
GenBank Accession No. NM_002171 for *Homo sapiens* interferon alpha 10 (IFNA10), mRNA downloaded from the NCBI database on Jun. 26, 2017, pp. 1-3.
GenBank Accession No. NP_002162 for interferon alpha-10 precursor [*Homo sapiens*] downloaded from the NCBI database on Jun. 26, 2017, pp. 1-3.
GenBank Accession No. NM_006900 for *Homo sapiens* interferon alpha13 (IFNA13), mRNA downloaded from the NCBI database on Jun. 26, 2017, pp. 1-3.
GenBank Accession No. NP_008831 for interferon alpha-1/13 precursor [*Homo sapiens*] downloaded from the NCBI database on Jun. 26, 2017, pp. 1-2.
GenBank Accession No. NM_002172 for *Homo sapiens* interferon alpha 14 (IFNA14), mRNA downloaded from the NCBI database on Jun. 26, 2017, pp. 1-3.
GenBank Accession No. NP_002163 for interferon alpha-14 precursor [*Homo sapiens*] downloaded from the NCBI database on Jun. 26, 2017, pp. 1-3.
GenBank Accession No. NM_002173 for *Homo sapiens* interferon alpha 16 (IFNA16), mRNA downloaded from the NCBI database on Jun. 26, 2017, pp. 1-2.
GenBank Accession No. NP_002164 for interferon alpha-16 precursor [*Homo sapiens*] downloaded from the NCBI database on Jun. 26, 2017, pp. 1-2.
GenBank Accession No. NM_021268 for *Homo sapiens* interferon alpha 17 (IFNA17), mRNA downloaded from the NCBI database on Jun. 26, 2017, pp. 1-3.
GenBank Accession No. NP_067091 for interferon alpha-17 precursor [*Homo sapines*] downloaded from the NCBI database on Jun. 26, 2017, pp. 1-3.
GenBank Accession No. NM_002175 for *Homo sapiens* interferon alpha 21 (IFNA21), mRNA downloaded from the NCBI database on Jun. 26, 2017, pp. 1-3.
GenBank Accession No. NP_002166 for interferon alpha-21 precursor [*Homo sapiens*] downloaded from the NCBI database on Jun. 26, 2017, pp. 1-3.
GenBank Accession No. NM_002176 for *Homo sapiens* interferon beta 1 (IFNB1), mRNA downloaded from the NCBI database on Jun. 26, 2017, pp. 1-3.
GenBank Accession No. NP_002167 for interferon beta precursor [*Homo sapiens*] downloaded from the NCBI database on Jun. 26, 2017, pp. 1-3.
GenBank Accession No. NM_002177 for *Homo sapiens* interferon omega 1 (IFNW1), mRNA downloaded from the NCBI database on Jun. 26, 2017, pp. 1-3.
GenBank Accession No. NP_002168 for interferon omega-1 precursor [*Homo sapiens*] downloaded from the NCBI database on Jun. 26, 2017, pp. 1-2.
GenBank Accession No. NM_000619 for *Homo sapiens* interferon gamma (IFNG), mRNA downloaded from the NCBI database on Jun. 26, 2017, pp. 1-4.
Gene Expression Omnibus Accession No. GSE30719 for Microarray Analysis of West Nile Virus infected Human Retinal Pigment Epithelium downloaded from the NCBI database on Jun. 26, 2017, pp. 1-2.
Gene Expression Omnibus Accession No. GSE18816 for Expression data of influenza A infected human macrophages downloaded from the NCBI database on Jun. 26, 2017, pp. 1-2.
Gene Expression Omnibus Accession No. GSE13052 for Dengue VN Microarray MD and DF study downloaded from the NCBI database on Jun. 26, 2017, pp. 1-2.
Gene Expression Omnibus Accession No. GSE17183 for Hepatic gene expression before and during interferon and ribavirin combination therapy downloaded from the NCBI database on Jun. 26, 2017, pp. 1-2.
Gene Expression Omnibus Accession No. GSE16214 for Expression data from relapsing-remitting MS samples downloaded from the NCBI database on Jun. 26, 2017, pp. 1-2.
Gene Expression Omnibus Accession No. GSE 5549 for Modulation of gene expression in a human cell line caused by poliovirus, vacciniavirus and interferon downloaded from the NCBI database on Jun. 26, 2017, pp. 1-2.
Gene Expression Omnibus Accession No. GSE15245 for Prediction of acute multiple sclerosis relapses by transcription levels of peripheral blood cells downloaded from the NCBI database on Jun. 26, 2017, pp. 1-2.

(56) References Cited

OTHER PUBLICATIONS

Gene Expression Omnibus Accession No. GSE 37107 for Genome-wide transcription analysis of whole blood prior to rituximab treatment in relation to clinical response downloaded from the NCBI database on Jun. 26, 2017, pp. 1-2.

Gene Expression Omnibus Accession No. GSE 42296 for Distinct, non-overlapping gene panels of peripheral blood gene expression predict response to infliximab therapy in rheumatoid arthritis and Crohn's disease downloaded from the NCBI database on Jun. 26, 2017, pp. 1-2.

Gene Expression Omnibus Accession No. GSE18464 for IFN-a-induced monocyte phenotype in chronic unsuppressed HIV infection downloaded from the NCBI database on Jun. 26, 2017, pp. 1-2.

Gene Expression Omnibus Accession No. GSE27248 for Molecular Characterization of In Vivo Adjuvant Activity in Ferrets Vaccinated against Influenza Virus downloaded from the NCBI database on Jun. 26, 2017, pp. 1-2.

Gene Expression Omnibus Accession No. GSE31518 for Host cell gene expression in Influenza A virus (A/Singaporte/478/2009 (pH1N1)) infected A549 cells at 2, 4, 6, 8 and 10 hours post infection downloaded from the NCBI database on Jun. 26, 2017, pp. 1-2.

Gene Expression Omnibus Accession No. GSE31471 for Host cell gene expression in Influenza A/Duck/Malaysia/01(H9N2) infected A549 cells at 2, 4, 6, 8 and 10 hours post infection downloaded from the NCBI database on Jun. 26, 2017, pp. 1-2.

Gene Expression Omnibus Accession No. GSE31472 for Host Cell gene expression in Influenza A/duck/Malaysia/F118/08/2004 (H5N2) infected A549 cells at 2, 4, 6, 8, and 10 hours post infection downloaded from the NCBI database on Jun. 26, 2017, pp. 1-2.

Gene Expression Omnibus Accession No. GSE52428 for Host gene expression signatures of influenza A H1N1 and H3N2 virus infection in adults downloaded from the NCBI database on Jun. 26, 2017, pp. 1-2.

Gene Expression Omnibus Accession No. GSE838 for Individual-specific variation of gene expression in peripheral blood leukocytes downloaded from the NCBI database on Jun. 26, 2017, pp. 1-2.

Gene Expression Omnibus Accession No. GSE3649 for Individuality and variation in gene expression patterns in human blood downloaded from the NCBI database on Jun. 26, 2017, pp. 1-2.

Gene Expression Omnibus Accession No. GSE32862 for Synthetic double stranded RNA reliably induces innate immunity similar to a live viral vaccine in humans downloaded from the NCBI database on Jun. 26, 2017, pp. 1-2.

Gene Expression Omnibus Accession No. GSE13699 for Immune response to the yellow fever vaccine 17D downloaded from the NCBI database on Jun. 26, 2017, pp. 1-2.

GenBank Accession No. NP_000610 for interferon gamma precursor [*Homo sapiens*] downloaded from the NCBI database on Jun. 26, 2017, pp. 1-3.

Alisi, et al., Oral Communications HCV and Ethanol Induce Mitosis Dys-regulation via Different Intracellular Pathways, Digestive and Liver Disease, 2008, pp. A1-A40, vol. 40.

Chen, et al., Hepatic Gene Expression Discriminates Responders and Nonresponders in Treatment of Chronic Hepatitis C Viral Infection, Gastroenterology, 2005, pp. 1437-1444, vol. 128.

Grinde, et al., Modulation of gene expression in a human cell line caused by poliovirus, vaccinia virus and interferon, Virology Journal, 2007, pp. 1-9, vol. 4:24.

Sadler, et al., Interferon-inducible antiviral effectors, Nat Rev Immunol., Jul. 2008, pp. 559-568, vol. 8(7).

Stiffler, et al., Focal Distribution of Hepatitis C Virus RNA in Infected Livers, PLoS ONE, Aug. 2009, pp. 1-7.

Sturzebecher, et al., Expression profiling identifies responder and non-responder phenotypes to interferon-β in multiple sclerosis, Brain, 2003, pp. 1419-1429, vol. 126.

Taylor, et al., Changes in Gene Expression during Pegylated Interferon and Ribavirin Therapy of Chronic Hepatitis C Virus Distinguish Responders from Nonresponders to Antiviral Therapy, Journal of Virology, Apr. 2007, pp. 3391-3401, vol. 81, No. 7.

Van Baarsen, et al., Pharmacogenomics of Interferon-β Therapy in Multiple Sclerosis: Baseline IFN Signature Determines Pharmacological Differences between Patients, PLos ONE, Apr. 2008, pp. 1-9, vol. 3, issue 4.

Zeremski, et al., Interferon γ-Inducible Protein 10, A Predictive Marker of Successful Treatment Response in Hepatitis C Virus/HIV-Coinfected Patients, J. Acquir Immune Defic Syndr, Jul. 2007, pp. 262-268, vol. 45, No. 3.

GenBank Accession No. NM_005101 for *Homo sapiens* ISG15 ubiquitin-like modifier (ISG15), mRNA downloaded from the NCBI database on Jun. 26, 2017, pp. 1-4.

GenBank Accession No. NP_005092.1 for Ubiquitin-like protein ISG15 [*Homo sapiens*] downloaded from the NCBI database on Jun. 26, 2017, pp. 1-3.

GenBank Accession No. NM_001548 for *Homo sapiens* interferon induced protein with tetratricopeptide repeats 1 (IFIT1), transcript variant 1, mRNA downloaded from the NCBI database on Jun. 26, 2017, pp. 1-6.

GenBank Accession No. NP_001539 for interferon-induced protein with tetratricopeptide repeats 1 isofrom 1 [*Homo sapiens*] downloaded from the NCBI database on Jun. 26, 2017, pp. 1-4.

GenBank Accession No. NM_001547 for *Homo sapiens* interferon induced protein with tetraticopeptide repeats 2 (IFIT2), mRNA downloaded from the NCBI database on Jun. 26, 2017, pp. 1-5.

GenBank Accession No. NP_001538 for interferon-induced protein with tetratricopeptide repeats 2 [*Homo sapiens*] downloaded from the NCBI database on Jun. 26, 2017, pp. 1-3.

GenBank Accession No. NM_001031683 for *Homo sapiens* interferon induced protein with tetratricopeptide repeats 3 (IFIT3), transcript variant 2, mRNA, downloaded from the NCBI database on Jun. 26, 2017, pp. 1-5.

GenBank Accession No. NM_001549 for *Homo sapiens* interferon induced protein with tetratricopepetide repeats 3 (IFIT3), transcript variant 1, mRNA downloaded from the NCBI database on Jun. 26, 2017, pp. 1-5.

GenBank Accession No. NP_001026853 for interferon-induced protein with tetratricopeptide repeats 3 isoform a ] *Homo sapiens*] downloaded from the NCBI database on Jun. 26, 2017, pp. 1-4.

GenBank Accession No. NP_001540 for interferon-induced protein with tetratricopeptide repeats 3 isoform a [*Homo sapiens*] downloaded from the NCBI database on Jun. 26, 2017, pp. 1-4.

GenBank Accession No. NM_012420 for *Homo sapiens* interferon induced protein with tetratricopeptide repeats 5 (IFIT5), mRNA downloaded from the NCBI database on Jun. 26, 2017, pp. 1-5.

GenBank Accession No. NP_036552 for interferon-induced protein with tetratricopeptide repeats 5 [*Homo sapiens*] downloaded from the NCBI database on Jun. 26, 2017, pp. 1-4.

GenBank Accession No. NM_016816 for *Homo sapiens* 2'-5'-oligoadenylate synthetase 1 (OAS1), transcript variant 1, mRNA downloaded from the NCBI database on Jun. 26, 2017, pp. 1-4.

GenBank Accession No. NM_002534 for *Homo sapiens* 2'-5'-oligoadenylate synthetase 1 (OAS1), transcript variant 2, mRNA downloaded from the NCBI database on Jun. 26, 2017, pp. 1-4.

GenBank Accession No. NM_001032409 for *Homo sapiens* 2'-5'-oligoadenylate synthetase 1 (OAS1), transcript variant 3, mRNA downloaded from the NCBI database on Jun. 26, 2017, pp. 1-4.

GenBank Accession No. NP_058132 for 2'-5'-oligoadenylate synthase 1 isoform 1 [*Homo sapiens*] downloaded from the NCBI database on Jun. 26, 2017, pp. 1-3.

GenBank Accession No. NP_002525 for 2'-5'-oligoadenylate synthase 1 isoform 2 [*Homo sapiens*] downloaded from the NCBI database on Jun. 26, 2017, pp. 1-3.

GenBank Accession No. NP_001027581 for 2'-5'-oligoadenylate synthase 1 isoform 3 [*Homo sapiens*] downloaded from the NCBI database on Jun. 26, 2017, pp. 1-3.

GenBank Accession No. NM_016817 for *Homo sapiens* 2'-5'-oligoadenylate synthetase 2 (OAS2), transcript variant 1, mRNA downloaded from the NCBI database on Jun. 26, 2017, pp. 1-4.

GenBank Accession No. NM_002535 for *Homo sapiens* 2'-5'-oligoadenylate synthetase 2 (OAS2), transcript variant 2, mRNA downloaded from the NCBI database on Jun. 26, 2017, pp. 1-4.

(56) References Cited

OTHER PUBLICATIONS

GenBank Accession No. NM_001032731 for *Homo sapiens* 2'-5'-oligoadenylate synthetase 2 (OAS2), transcript variant 3, mRNA downloaded from the NCBI database on Jun. 26, 2017, pp. 1-3.
GenBank Accession No. NP_058197 for 2'-5'-oligoadenylate synthase 2 isoform 2 [*Homo sapiens*] downloaded from the NCBI database on Jun. 26, 2017, pp. 1-3.
GenBank Accession No. NP_002526 for 2'-5'-oligoadenylate synthase 2 isoform 2 [*Homo sapiens*] downloaded from the NCBI database on Jun. 26, 2017, pp. 1-3.
GenBank Accession No. NP_001027903 for 2'-5'-oligoadenylate synthase 2 isoform 3 [*Homo sapiens*] downloaded from the NCBI database on Jun. 26, 2017, pp. 1-3.
GenBank Accession No. NM_006187 for *Homo sapiens* 2'-5'-oligoadenylate synthetase 3 (OAS3), mRNA downloaded from the NCBI database on Jun. 26, 2017, pp. 1-6.
GenBank Accession No. NP_061782 for 2'-5'-oligoadenylate synthase 3 [*Homo sapiens*] downloaded from the NCBI database on Jun. 26, 2017, pp. 1-4.
GenBank Accession No. NM_003733 for *Homo sapiens* 2'-5'-oligoadenylate synthetase like (OASL), transcript variant 1, mRNA downloaded from the NCBI database on Jun. 26, 2017, pp. 1-4.
GenBank Accession No. NM_198213 for *Homo sapiens* 2'-5'-oligoadenylate synthetase like (OASL), transcript variant 2, mRNA downloaded from the NCBI database on Jun. 26, 2017, pp. 1-3.
GenBank Accession No. NP_003724 for 2'-5'-oligoadenylate synthase-like protein isoform a [*Homo sapiens*] downloaded from the NCBI database on Jun. 26, 2017, pp. 1-3.
GenBank Accession No. NP_937856 for 2'-5'-oligoadenylate synthase-like protein isoform b [*Homo sapiens*] downloaded from the NCBI database on Jun. 26, 2017, pp. 1-3.
GenBank Accession No. NM_016323 for *Homo sapiens* HECT and RLD domain containing E3 ubiquitin protein ligase 5 (HERC5), mRNA downloaded from the NCBI database on Jun. 26, 2017, pp. 1-5.
GenBank Accession No. NP_057407 for E3 ISG15—protein ligase HERC5 [*Homo sapiens*] downloaded from the NCBI database on Jun. 26, 2017, pp. 1-3.
GenBank Accession No. NM_017414 for *Homo sapiens* ubiquitin specific peptidase 18 (USP18), mRNA downloaded from the NCBI database on Jun. 26, 2017, pp. 1-4.
GenBank Accession No. NP_059110 for ubl carboxyl-terminal hydrolase 18 [*Homo sapiens*] downloaded from the NCBI database on Jun. 26, 2017, pp. 1-3.
GenBank Accession No. NM_080657 for *Homo sapiens* radical S-adenosyl methionine domain containing 2 (RSAD2), mRNA downloaded from the NCBI database on Jun. 26, 2017, pp. 1-3.
GenBank Accession No. NP_542388 for radical S-adenosyl methionine domain-containing protein 2 [*Homo sapiens*] downloaded from the NCBI database on Jun. 26, 2017, pp. 1-3.
GenBank Accession No. NM_002462 for *Homo sapiens* MX dynamin like GTPase 1 (MX1), transcript variant 2, mRNA downloaded from the NCBI database on Jun. 26, 2017, pp. 1-5.
GenBank Accession No. NM_001178046 for *Homo sapiens* MX dynamin like GTPase 1 (MX1), transcript variant 3, mRNA downloaded from the NCBI database on Jun. 26, 2017, pp. 1-5.
GenBank Accession No. NM_001144925 for *Homo sapiens* MX dynamin like GTPase 1 (MX1), transcript variant 1, mRNA downloaded from the NCBI database on Jun. 26, 2017, pp. 1-5.
GenBank Accession No. NP_002453 for interferon-induced GTP-binding protein Mx1 isoform a [*Homo sapiens*] downloaded from the NCBI database on Jun. 26, 2017, pp. 1-4.
GenBank Accession No. NP_001171517 for interferon-induced GTP-binding protein Mx1 isoform a [*Homo sapiens*] downloaded from the NCBI database on Jun. 26, 2017, pp. 1-4.
GenBank Accession No. np_001138397 for interferon-induced GTP-binding protein Mx1 isoform a [*Homo sapiens*] downloaded from the NCBI database on Jun. 26, 2017, pp. 1-4.
GenBank Accession No. NM_006820 for *Homo sapiens* interferon induced protein 44 like (IFI44L0, mRNA downloaded from the NCBI database on Jun. 26, 2017, pp. 1-4.
GenBank Accession No. NP_006811 for interferon-induced protein 44-like [*Homo sapiens*] downloaded from the NCBI database on Jun. 26, 2017, pp. 1-2.
GenBank Accession No. NM_014314 for *Homo sapiens* DExD/H-box helicase 58 (DDX58), mRNA downloaded from the NCBI database on Jun. 26, 2017, pp. 1-5.
GenBank Accession No. NP_055129 for probable ATP-dependent RNA helicase DDX58 [*Homo sapiens*] downloaded from the NCBI database on Jun. 26, 2017, pp. 1-4.
GenBank Accession No. AF294032 for *Homo sapiens* UBE1L protein (UBE1L) gene, complete cds downloaded from the NCBI database on Jun. 26, 2017, pp. 1-5.
GenBank Accession No. AAG49557 for UBE1L protein [*Homo sapiens*} downloaded from the NCBI database on Jun. 26, 2017, pp. 1-2.
GenBank Accession No. NM_198183 for *Homo sapiens* ubiquitin conjugating enzyme E2 L6 (UBE2L6), transcript variant 2, mRNA downloaded from the NCBI database on Jun. 26, 2017, pp. 1-3.
GenBank Accession No. NM_004223 for *Homo sapiens* ubiquitin conjugating enzyme E2 L6 (UBE2L6), transcript variant 1, mRNA downloaded from the NCBI database on Jun. 26, 2017, pp. 1-3.
GenBank Accession No. NP_937826 for ubiquitin/ISG15-conjugating enzyme E2 L6 isoform 2 [*Homo sapiens*] downloaded from the NCBI database on Jun. 26, 2017, pp. 1-3.
GenBank Accession No. NP_004214 for ubiquitin/ISG15-conjugating enzyme E2 L6 isoform 1 [*Homo sapiens*] downloaded from the NCBI database on Jun. 26, 2017, pp. 1-3.
GenBank Accession No. NM_001130080 for *Homo sapiens* interferon alpha inducible protein 27 (IFI27), transcript variant 1, mRNA downloaded from the NCBI database on Jun. 26, 2017, pp. 1-3.
GenBank Accession No. NM_005532 for *Homo sapiens* interferon alpha inducible protein 27 (IFI27), transcript variant 2, mRNA downloaded from the NCBI database on Jun. 26, 2017, pp. 1-3.
GenBank Accession No. NP_001123552 for interferon alpha-inducible protein27, mitochondrial isoform 1 [*Homo sapiens*] downloaded from the NCBI database on Jun. 26, 2017, pp. 1-2.
GenBank Accession No. NP_005523 for interferon alpha-inducible protein 27, mitochondrial isoform 2 [*Homo sapiens*] downloaded from the NCBI database on Jun. 26, 2017, pp. 1-3.
GenBank Accession No. NM_022168 for *Homo sapiens* interferon induced with helicase C domain 1 (IFIH1), mRNA downloaded from the NCBI database on Jun. 26, 2017, pp. 1-5.
GenBank Accession No. NP_071451 for interferon-induced helicase C domain-containing protein 1 [*Homo sapiens*] downloaded from the NCBI database on Jun. 26, 2017, pp. 1-4.
GenBank Accession No. NM_016562 for *Homo sapiens* toll like receptor 7 (TLR7), mRNA downloaded from the NCBI database on Jun. 26, 2017, pp. 1-7.
GenBank Accession No. NP_057646 for toll-like receptor 7 precursor [*Homo sapiens*] downloaded from the NCBI database on Jun. 26, 2017, pp. 1-6.
GenBank Accession No. NM_001572 for *Homo sapiens* interferon regulatory factor 7 (IRF7), transcript variant a, mRNA downloaded from the NCBI database on Jun. 26, 2017, pp. 1-4.
GenBank Accession No. NM_004029 for *Homo sapiens* interferon regulatory factor 7 (IRF7), transcript variant b, mRNA downloaded from the NCBI database on Jun. 26, 2017, pp. 1-3.
GenBank Accession No. NP_001563 for interferon regulatory factor 7 isoform a [*Homo sapiens*] downloaded from the NCBI database on Jun. 26, 2017, pp. 1-3.
GenBank Accession No. NP_004020 for interferon regulatory factor 7 isoform b [*Homo sapiens*] downloaded from the NCBI database on Jun. 26, 2017, pp. 1-3.
GenBank Accession No. NM_022873 for *Homo sapiens* interferon alpha inducible protein 6 (IFI6), transcript variant 3, mRNA downloaded from the NCBI database on Jun. 26, 2017, pp. 1-3.
GenBank Accession No. NM_022872 for *Homo sapiens* interferon alpha inducible protein 6 (IFI6), transcript variant 2, mRNA downloaded from the NCBI database on Jun. 26, 2017, pp. 1-3.

(56) References Cited

OTHER PUBLICATIONS

GenBank Accession NM_002038 for *Homo sapiens* interferon alpha inducible protein 6 (IFI6), transcript variant 1, mRNA downloaded from the NCBI database on Jun. 26, 2017, pp. 1-3.
GenBank Accession No. NP_075011 for interferon alpha-inducible protein 6 isoform c precursor [*Homo sapiens*] downloaded from the NCBI database on Jun. 26, 2017, pp. 1-2.
GenBank Accession No. NP_075010 for interferon alpha-inducible protein 6 isoform b precursor [*Homo sapiens*] downloaded from the NCBI database on Jun. 26, 2017, pp. 1-2.
GenBank Accession No. NP_002029 for interferon alpha-inducible protein 6 isoform a precursor [*Homo sapiens*] downloaded from the NCBI database on Jun. 26, 2017, pp. 1-3.
GenBank Accession No. NM_007315 for *Homo sapiens* signal transducer and activator of transcription 1 (STAT1), transcript variant alpha, mRNA downloaded from the NCBI database on Jun. 26, 2017, pp. 1-6.
GenBank Accession No. NM_139266 for *Homo sapiens* signal transducer and activator of transcription 1 (STAT1), transcript variant beta, mRNA downloaded from the NCBI database on Jun. 26, 2017, pp. 1-5.
GenBank Accession No. NP_009330 for signal transducer and activator of transcription 1-alpha/beta isoform alpha [*Homo sapiens*] downloaded from the NCBI database on Jun. 26, 2017, pp. 1-3.
GenBank Accession No. NP_644671 for signal transducer and activator of transcription 1-alpha/beta isoform beta [*Homo sapiens*] downloaded from the NCBI database on Jun. 26, 2017, pp. 1-3.
GenBank Accession No. NM_006417 for *Homo sapiens* interferon induced protein 44 (IFI44), transcript variant 1, mRNA downloaded from the NCBI database on Jun. 26, 2017, pp. 1-3.
GenBank Accession No. NP_006408 for interferon-induced protein 44 [*Homo sapiens*] downloaded from the NCBI database on Jun. 26, 2017, pp. 1-2.
GenBank Accession No. NM_002759 for *Homo sapiens* eukaryotic translation initiation factor 2-alpha kinase 2 (E1F2A1(2), mRNA downloaded from the NCBI database on Jun. 26, 2017, pp. 1-3.
GenBank Accession No. NC_000002 for *Homo sapiens* chromosome 2, GRCh37.p13 Primary Assembly downloaded from the NCBI database on Jun. 26, 2017, pp. 1-2.
GenBank Accession No. NM_024119 for *Homo sapiens* DExH-box helicase 58 (DHX58), mRNA downloaded from the NCBI database on Jun. 26, 2017, pp. 1-4.
GenBank Accession No. NC_000017 for *Homo sapiens* chromosome 17, GRCh37.p13 Primary Assembly downloaded from the NCBI database on Jun. 26, 2017, pp. 1-2.
GenBank Accession No. NM_024013 for *Homo sapiens* interferon alpha1 (IFNA1), mRNA downloaded from the NCBI database on Jun. 26, 2017, pp. 1-3.
GenBank Accession No. NP_076918 for interferon alpha-1/13 precursor [*Homo sapiens*] downloaded from the NCBI database on Jun. 26, 2017, pp. 1-2.
GenBank Accession No. NM_000605 for *Homo sapiens* interferon alpha 2 (IFNA2), mRNA downloaded from the NCBI database on Jun. 26, 2017, pp. 1-3.
GenBank Accession No. NP_000596 for interferon alpha-2 precursor [*Homo sapiens*] downloaded from the NCBI database on Jun. 26, 2017, pp. 1-3.
GenBank Accession No. NM_021068 for *Homo sapiens* interferon alpha 4 (IFNA4), mRNA downloaded from the NCBI database on Jun. 26, 2017, pp. 1-3.
GenBank Accession No. NP_066546 for interferon alpha-4 precursor [*Homo sapiens*] downloaded from the NCBI database on Jun. 26, 2017, pp. 1-3.
GenBank Accession No. NM_002169 for *Homo sapiens* interferon alpha 5 (IFNA5), mRNA downloaded from the NCBI database on Jun. 26, 2017, pp. 1-2.
GenBank Accession No. NP_002160 for interferon alpha-5 precursor [*Homo sapiens*] downloaded from the NCBI database on Jun. 26, 2017, pp. 1-2.
GenBank Accession No. NM_021002 for *Homo sapiens* interferon alpha 6 (IFNA6), mRNA downloaded from the NCBI database on Jun. 26, 2017, pp. 1-3.
GenBank Accession No. NP_066282 for interferon alpha-6 precursor [*Homo sapiens*] downloaded from the NCBI database on Jun. 26, 2017, pp. 1-2.
GenBank Accession No. NM_021057 for *Homo sapiens* interferon alpha 7 (IFNA7), mRNA downloaded from the NCBI database on Jun. 26, 2017, pp. 1-3.

\* cited by examiner

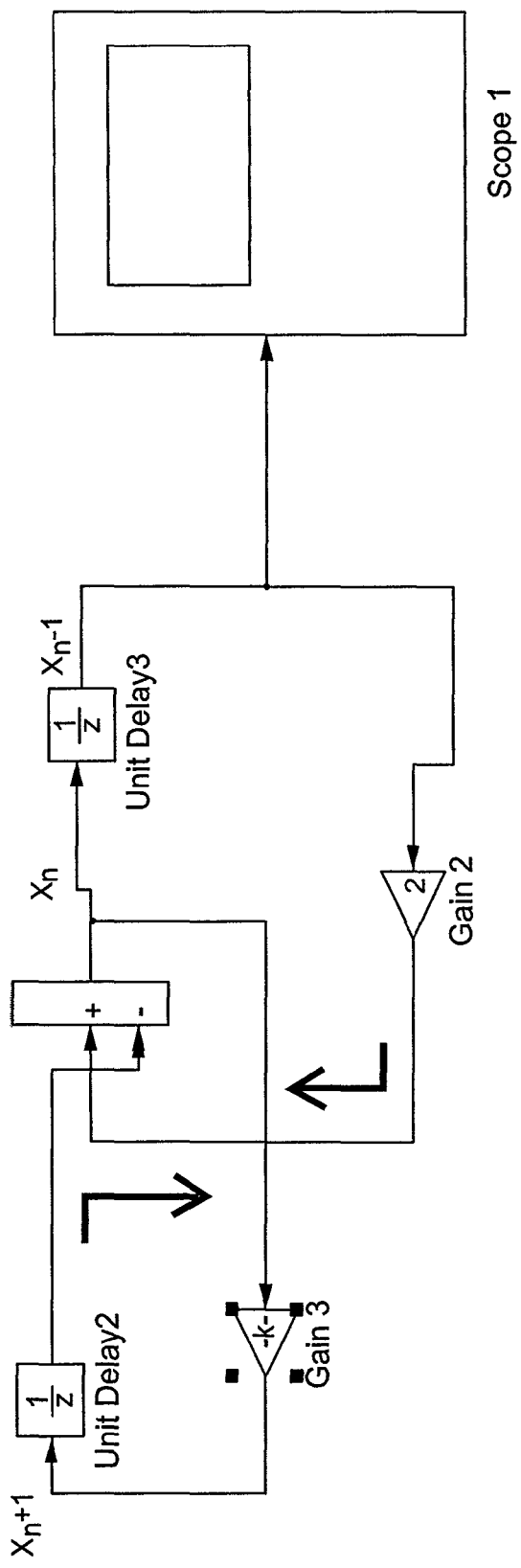
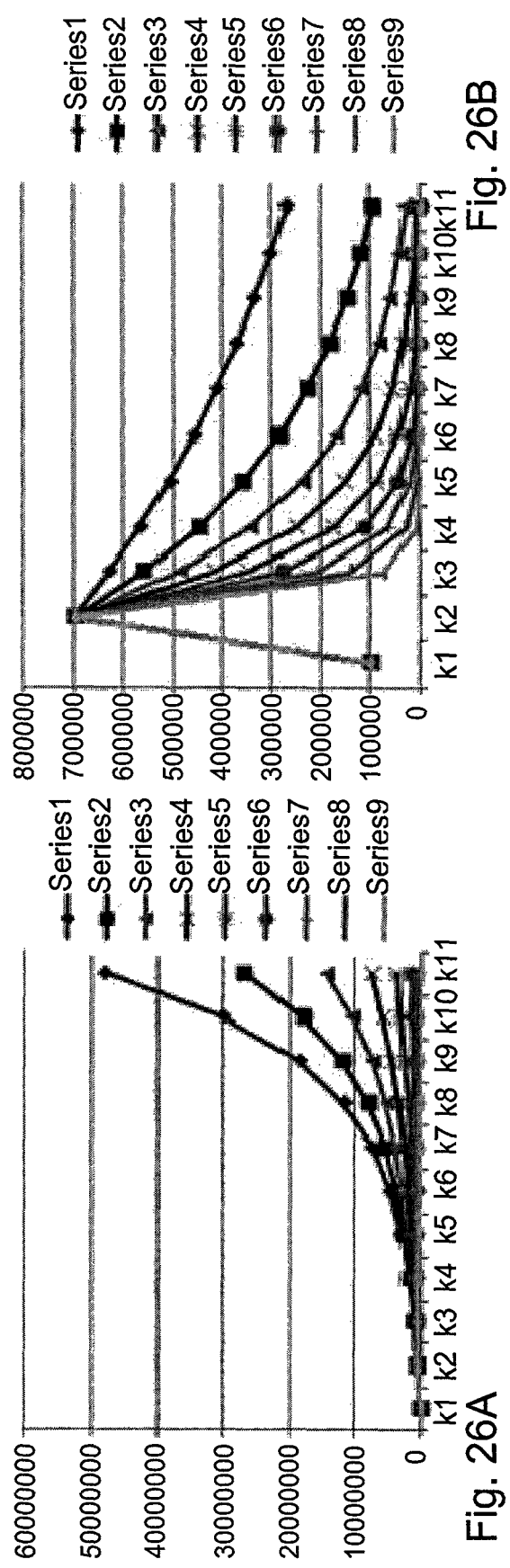
Fig. 26A
Fig. 26B

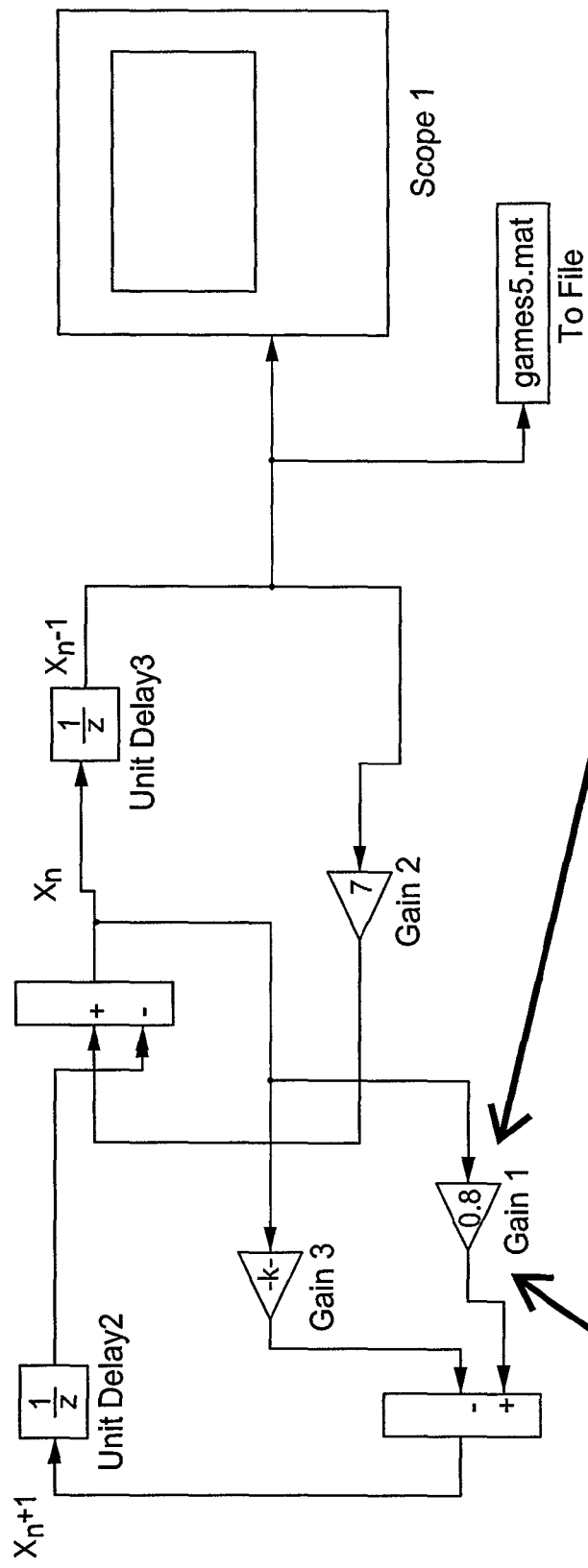
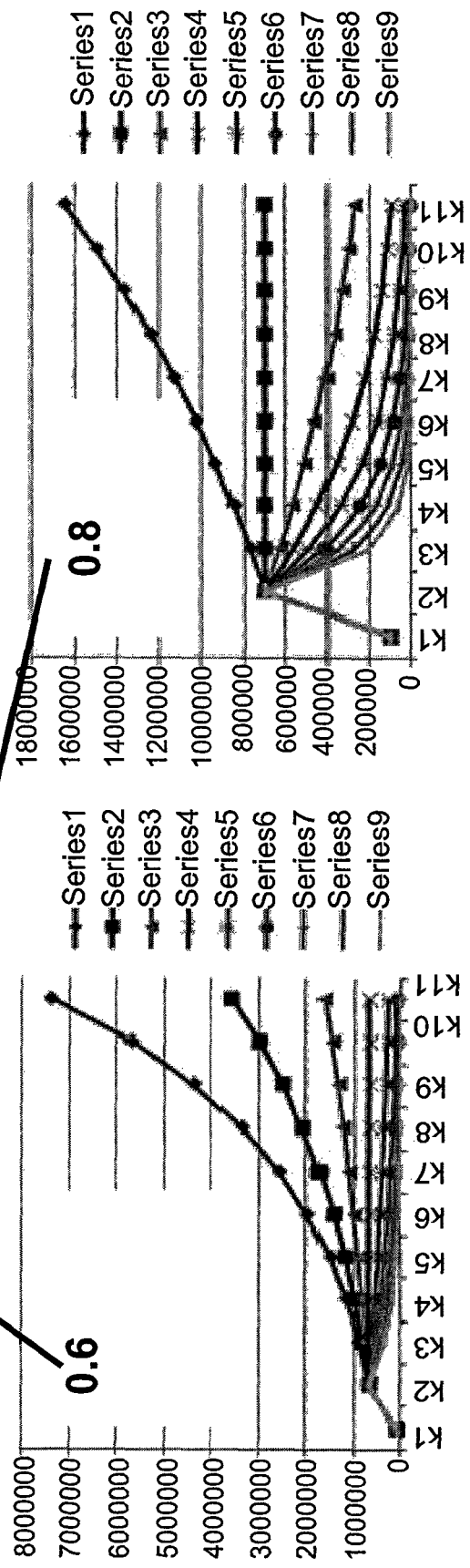
Fig. 27A
Fig. 27B

METHODS AND KITS FOR DETERMINING A PERSONALIZED TREATMENT REGIMEN FOR A SUBJECT SUFFERING FROM A PATHOLOGIC DISORDER

FIELD OF THE INVENTION

The invention relates to personalized medicine. More specifically, the invention provides methods and kits for determining and optimizing a treatment regimen of a medicament, for a subject suffering from a pathologic disorder.

BACKGROUND REFERENCES

References considered to be relevant as background to the presently disclosed subject matter are listed below:
Chen Limin, et al., Gastroenterology 128:1437-1444 (2005).
Taylor, M W, et al., Journal of Virology 81:3391-3401 (2007).
van Baarsen L G, et al., PLoS ONE 3:e1927 (2008).
Zeremski M, et al., J. Acquir. Immune. Defic. Syndr. 45:262-268 (2007).
Tarantino G, et al., Digestive and Liver Disease 40:A1-A40 (2008).
US2009/157324
WO10/076788
Sadlet A J et al, Nature Reviews Immunology 8: 559 (2008)
Grinde B, et al, Virol J. 4: 24 (2007)
David Stiffler1 J. et al., PLoS ONE 4(8) e6661 (2009)

Acknowledgement of the above references herein is not to be inferred as meaning that these are in any way relevant to the patentability of the presently disclosed subject matter.

BACKGROUND OF THE INVENTION

Determining treatment protocols that may be suitable for each individual or a subset of individuals is highly desirable. Clinical diagnosis and management has been long focused on clinical sign and symptoms of a patient in order to treat specific diseases. Recently along with the advances in genetic profiling, it became possible to understand the impact of genetic variability as measured in individuals or subsets of individuals on the disease progression.

Personalized medicine is therefore aimed at enabling decisions and practices to the individual patient by use for example of genetic information.

It has been recently shown that evaluating the differences in the genetic profile of the two or more groups of patients can provide valuable insight into resistant to treatment.

For example, interferon therapy is widely used in the treatment of a variety of diseases including for example, multiple sclerosis (MS), hepatitis B, hepatitis C, inflammatory diseases and many cancers types. However, not all subjects treated with interferon equally respond to this therapy and moreover, responsive subjects experience relapse of the disease after remission periods. In fact, in both MS and type 1 hepatitis C Virus (HCV) the success of treatment is only about 50%, namely about half of the patients administered with interferon will not benefit but rather experience only related side effects.

Chen et al. 2005, compared the gene expression levels in liver specimens taken before treatment from 15 non-responders and 16 responders to Pegylated interferon (IFN-alpha), identified 18 genes that have a significantly different expression between all responders and all non-responders and concluded that up-regulation of a specific set of interferon-responsive genes predict non response to exogenous treatment.

Taylor M., et al. 2007, found that the induced levels of known interferon-stimulated genes such as the OAS1, OAS2, MX1, IRF-7 and TLR-7 genes is lower in poor-response patients than in marked- or intermediate-response patients.

Van Baarsen et al., 2008 show that the expression level of interferon response genes in the peripheral blood of multiple sclerosis patients prior to treatment can serve a role as a biomarker for the differential clinical response to interferon beta.

Zeremaki M., et al., 2007 showed that PEG-interferon induced elevations in IP-10 are greater in responders than in non-responders after the first PEG-interferon dose.

Tarantino et al., 2008 described that serum levels of B-Lymphocyes stimulator (BLyS) have a potential role as a predictor of outcome in patients with acute hepatitis C.

The Inventor previous US Patent Application, US2009157324 describes a computational method for selecting a group of genes from a predetermined group of genes whose expression level is significantly different among a first group of individuals (being for example responders to a treatment) and comparing their expression in a second group of individuals (for example not responders). The statistical significance of each group of genes is determined in both up regulated genes or down regulated genes, namely their expression in the first group is higher or lower than in the second group, respectively. The genes in both groups (up regulated and down regulated) are ranked according to number of times each gene was ranked in the highest statistical significant score. A subset of genes having the highest score, either up regulated or down regulated are then selected as biomarkers.

In another application by the Inventor, International Patent Publication WO10076788, computational and experimental methods are provided for predicting the responsiveness of a subject to interferon therapy by measuring the expression level of various genes such as OAS3, IFI6, ISG15, OAS2, IFIT1, KIR3DL3, KIR3DL2, KIR3DL1, KIR2DL1, KIR2DL2, KIR2DL3, KLRG1, KIR3DS1, CD160, HLA-A, HLA-B, HLA-C, HLA-F, HLA-G and IFI27. Specifically, the inventor has found that OAS3, IFI6, ISG15, OAS2 and IFIT1 are up-regulated in patients that do not respond to interferon treatment as compared to patients that respond to interferon therapy or compared to healthy controls.

Thus, the correlations between genetic profiling and personalized medicine, namely treatment regimens, needs to be considered for predicting response to therapy, predicting treatment success and monitoring disease prognosis and pathogenesis, specifically chances for disease relapse.

SUMMARY OF THE INVENTION

A first aspect of the invention relates to a method for determining and optimizing a personalized treatment regimen for a subject suffering from a pathologic disorder. In certain embodiments, the method of the invention comprises the step of:

First step (a) involves calculating and determining the value of M. The value M indicates the ability, capability of a specific subject, in this case, the examined subject, to eliminate the specific disorder. More specifically, the value of the individual's M reflects the efficiency of the specific tested subject in cellular elements that are required for challenging and eliminating a specific disorder. In certain embodiments the M value indicates the strength of the individual's innate immunity, and may be used for predicting it's ability to eliminate a specific disorder.

The next step (b), involves determining the value of M1 that indicates the minimal ability required for eliminating said disorder.

In the nest step (c), providing the dose A1 and number B1 of administrations of such dose to obtain an amount C1 of a specific medicament required for eliminating a specific disorder in subjects having a value of M that is equal or above the optimal M1 value, wherein A1*B1=C1.

The next step (d) involves calculating the dose A and number B of administrations of such specific dose A to obtain an amount C1 required for the examined subject having the specific M value determined and calculated in step (a). More specifically, the specific optimal dose required for a successful treatment for the tested subject would be A=A1/(M1/M). The specific number of administrations of such dose may be calculated using the formula B=B1*(M1/M); thereby determining and optimizing the treatment regimen for the specific tested subject.

A further aspect of the invention relates to a kit for determining and optimizing a personalized treatment regimen for a subject suffering from a pathologic disorder.

In certain embodiments, such kit may comprise elements required for performing any of the methods described above. More specifically, such kit may comprise:

(a) detecting molecules specific for determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1 L, UBE2L6, IFI27, IFIH1, TLR7, IRF7 and IFI6 genes in a biological sample. In certain embodiments the kits of the invention may further comprise detecting molecules for the STAT1, IFI44, EIF2AK2 and DHX58 genes and any combinations thereof with any of the marker genes of the invention.

The kit of the invention further comprises (b), means for calculating the M value of a tested subject. As noted above, the M value indicates the ability of said subject to eliminate said disorder. The kit of the invention further comprises (c) means for calculating the value of M1 or a standard M1 value calculated for a responder population. As indicated above, the M1 value indicates the minimal ability, or in other words, the optimal M1 value required for a successful elimination of the disorder. Finally, the kit of the invention comprises (d) means for calculating the dose A and number B of administrations of said dose A to obtain an amount C of said medicament required for said subject.

In yet a further aspect, the invention provides a computer software product for determining and optimizing a personalized treatment regimen for a subject suffering from a pathologic disorder. Such product comprising a computer readable medium in which program instructions are stored, which instructions, when read by a computer, cause the computer to: (a) calculate and determine the value of M that indicates the ability of said subject to eliminate said disorder; (b) determine the value of M1, that indicates the minimal ability required for eliminating said disorder. (c) calculate the dose A and number B of administrations of said dose A to obtain an amount C required for said subject having said M determined/calculated in step (a), from predetermined dose A1 and number B1 of administrations of said dose, using the formula of A=A1/(M1/M) and B=B1*(M1/M).

BRIEF DESCRIPTION OF THE DRAWINGS

In order to understand the disclosure and to see how it may be carried out in practice, embodiments will now be described, by way of non-limiting example only, with reference to the accompanying drawings, in which:

FIGS. 26A-26B is a graph showing simulation of replication vs. immune defense, per different M. As can be seen for the same individual with an M value suitable for K=3, that is calculated as follows $M=1-\frac{1}{3}=0.66$ being infected by a variety of viruses with varying K (multiplication rate). FIG. 26A shows that at K rate higher than 3, the virus progresses. FIG. 26B shows situation where K smaller than M, attenuation of the virus is achieved. The X-axis represents time from initial infection different k values and the Y-axis represents the virus load per the different k values.

FIGS. 27A-27B is a graph showing simulation instructing how much PI is needed per each individuals M and virus K. The PI effectively increases the individuals M, FIG. 27A shows an individual with M=0.6, FIG. 27B shows an individual with M=0.8 both are affected by the same range of PI injections. The better M the quicker an individual to become a responder with the same PI.

FIG. 37C shows MATLAB simulation of the model with k=1.92 and p=0 as described herein.

DETAILED DESCRIPTION OF THE INVENTION

Figure 1:
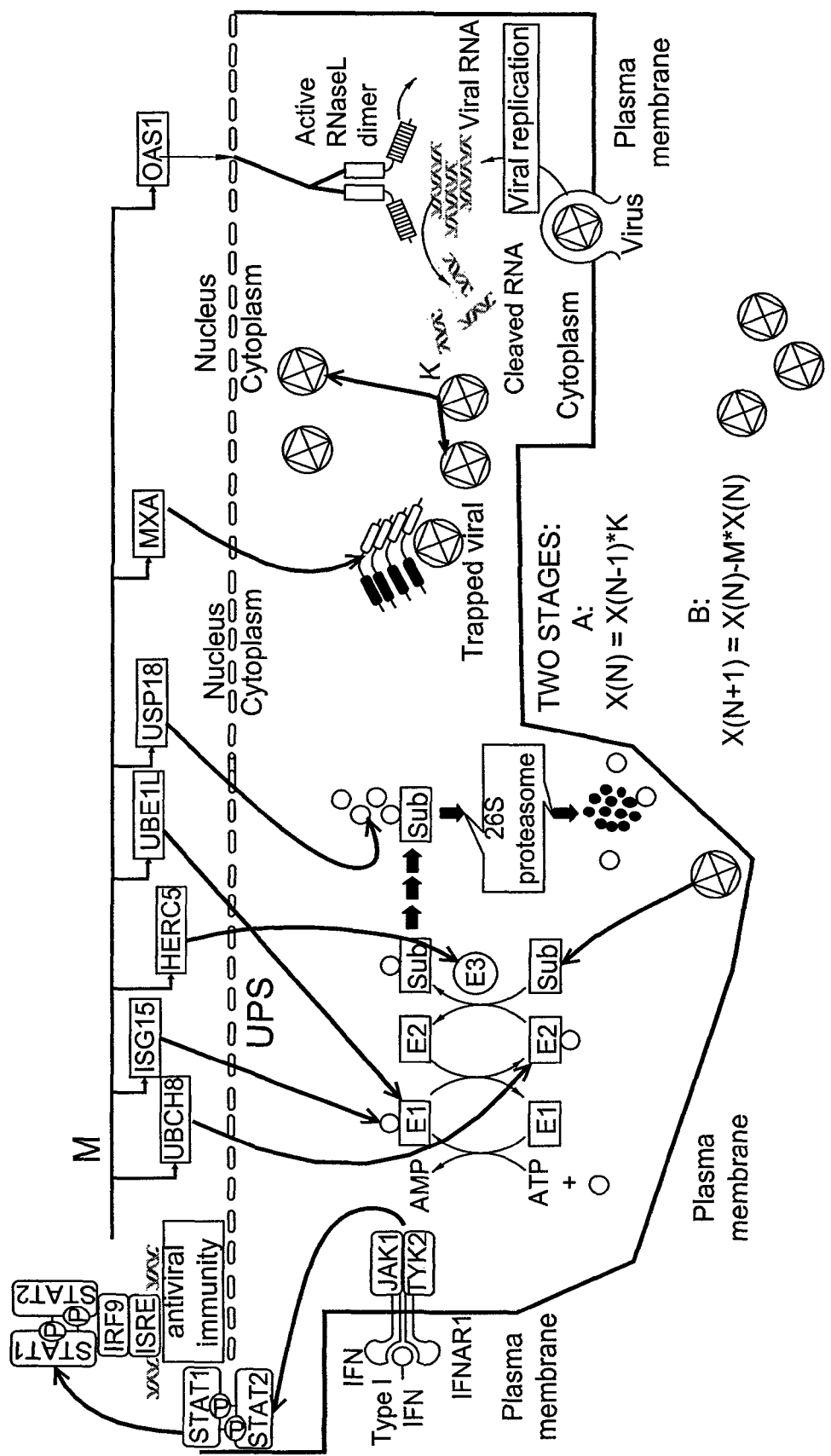
FIG. 1 shows a schematic representation at the cellular level of a cell infected with a virus that is multiplied by a rate K followed by the regulation of specific genes caused either by the immune system or by an external treatment that may lead to viral elimination by rate M. The virus or other viruses may penetrate other cells by a certain rate. As schematically illustrated here, the virus may be destroyed by the activity of a set of proteins encoded by a set of genes for example, ISG15, USP18, HERC5 and OAS, in the UPS (Ubiquitin Proteasome System).

The importance of adjusting suitable treatment protocols is highly valuable and clinically desired in view of the fact that a large number of treatment protocols are often associated with some extent of undesired side effects, and moreover, may be unsuccessful. Thus, optimizing a treatment protocol before and/or at early stages after initiation of treatment and/or throughout or after a treatment period may avoid inadequate treatments, reduce unnecessary side effects and improve chance of success.

Interferon is widely clinically used for treatment of a variety of diseases including for example inflammatory diseases such as hepatitis C infections, autoimmune diseases such as multiple sclerosis and different types of proliferative disorders. Significant therapeutic advances were made in the treatment of interferon associated diseases however, it is still difficult to determine at the time of disease diagnosis and treatment adjustments, which patients will respond to treatment and which would eventually relapse. Surprisingly, although interferon is considered as a state of art therapy in treatment of these diseases, many of the treated patients do not respond to the therapy and even if they do, many of the patients experience a relapse of the disease.

Thus, there is a critical need for reliable tailor-made optimization methods that will provide gaudiness and identification of treatment success and failure, breakthrough point and predict inadequate treatments, providing efficient dosing regimens of interferon.

Thus, a first aspect of the invention relates to a method for determining and optimizing a personalized treatment regimen for a subject suffering from a pathologic disorder. In certain embodiments, the method of the invention comprises the step of:

First step (a) involves calculating and determining the value of M. It should be further noted that the value M indicates the ability of a specific subject, in this case, the examined subject, to eliminate the specific disorder. More specifically, the value of the individual's M reflects the efficiency of the specific tested subject in requiting cellular elements that are required for challenging and eliminating a specific disorder. In certain embodiments the M value indicates the strength of the individual's innate immunity, and may be used for predicting the individual's ability to eliminate a specific disorder.

The next step (b), involves determining the value of M1 that indicates the minimal ability required for eliminating the specific disorder. Moreover, the value M1 reflects the optimal threshold of the ability and efficiency of requiting elements required for eliminating a specific disorder. It should be noted that this value is calculated for populations of subjects that perform successful recovery in response to a certain treatment. In some embodiments, this group of subjects may be considered a "responders".

In the next step (c), providing the dose A1 and number B1 of administrations of such dose to obtain an amount C1 of a specific medicament required for eliminating a specific disorder in subjects having a value of M that is equal or above the optimal M1 value, wherein $A1*B1=C1$.

The next step (d) involves calculating the dose A and number B of administrations of such specific dose A to obtain an amount C1 required for the examined subject having the specific M value determined and calculated in step (a). More specifically, the specific optimal dose required for a successful treatment for the tested subject would be $A=A1/(M1/M)$. The specific number of administrations of such dose may be calculated using the formula $B=B1*(M1/M)$; thereby determining and optimizing the treatment regimen for the specific tested subject.

According to more specific embodiments of the method of the invention, calculating the value of M of the tested individual may be performed using different approaches. It should be noted that such determination may be performed using any of the approaches of the invention or any combination thereof.

More specifically, determination of the specific M value of the tested individual may be performed by (I) using a static analysis. More specifically, "static" analysis means that the M value may be calculated for a specific individual even before starting a treatment with the particular medicament, and would not reflect any change occurring in response to such treatment.

In some embodiments, such approach may comprise the steps of:

First (Ia), determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes in a biological sample of the tested subject, to obtain an expression value $Ex_{samp}$ in the tested sample. In certain embodiments of the method of the invention the level of expression of at least one of STAT1, IFI44, EIF2AK2 and DHX58 genes may be also determined.

In the next step (Ib), providing a standard curve, specifically, predetermined standard curve of expression values of subjects suffering from the same pathologic disorder.

In the next step (Ic) Obtaining a maximal expression value $Ex_{max}$ and a minimal expression value $Ex_{min}$ from the standard curve of (Ib), indicating the variance in the gene expression of a certain marker gene in a predetermined population; and finally, step (Id) Calculating the M value of the tested sample. Such calculation is based on using the following formula wherein $M=1-[(Ex_{samp}-Ex_{min})/(Ex_{max}-Ex_{min})]$.

In yet another embodiment, as an approach for determining the individual's M value, an induced dynamic analysis (II) may be used. It should be appreciated that such approach is based on pre measurements of the M value for an individual, specifically, before such individual was affected by a certain pathologic disorder. More specifically, using such approach, the specific M value of a specific individual may be predetermined, providing information that may be used in the future in case such subject may be affected by any pathologic disorder. More specifically, such predetermined individual value may serve as valuable information that may be used for optimizing treatment regimen for such individual. Moreover, the method of the invention provides the use of such M value for specifically optimized treatment regimen suitable for a certain pathologic disorder.

In more specific embodiment, the induced dynamic analysis (II) comprises the steps of:

First (IIa), determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes in a biological sample of said subject, to obtain an expression value in the tested sample.

In the second step (IIb) exposing the tested subject to an immuno-stimulant. Alternatively, this step may be performed in vitro, more specifically, a sample of the examined subject may be contacted with an immuno-stimulant.

The next step (IIc) involves determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes in a sample of said individual that has been exposed to said immuno-stimulant. In case of the alternative in vitro analysis, determining the level of at least one of these marker genes in at least one other biological sample of the tested subject that has been contacted in vitro with the immuno-stimulant, as indicated in step (IIb).

In the next step (IId) calculating the rate of change between the expression value obtained in step (IIa), and the expression value obtained in step (IIc), thereby obtaining the rate of change in the sample $RC_{samp}$, more specifically, the rate of change in the expression of at least one of the marker genes of the invention, in response to such immuno-stimulant. Such change of expression reflects the intrinsic ability of the tested subject in requiting elements that may be involved in eliminating of any disorder, and therefore reflects the specific ability a certain subject to challenge disorders.

In the next step (IIe), providing a standard curve, specifically, predetermined standard curve of the rate of change in the expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes or any combinations thereof in subjects treated with said immuno-stimulant. It should be noted that such predetermined standard curve is based on a population of healthy subjects (or non-diseased subjects) treated with the same immuno-stimulant.

In step (IIf) obtaining a maximal rate of change value $RC_{max}$ and a minimal rate of change $RC_{min}$ value from said standard curve of (IIe); and In final step (IIg), calculating the M value of the tested sample using the formula: wherein $M=[(RC_{samp}-RC_{min})/(RC_{max}-RC_{min})]$, thereby obtaining an M value of said subject.

In yet another alternative approach, were predetermined M values of an individual are not available, the invention provides a method for optimizing treatment regimen for a subject that has been already started a certain treatment, using a dynamic analysis (III) comprising:

In the first step (IIIa), determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes in a biological sample of the tested subject, to obtain an expression value in the tested sample. It should be noted that such sample should be obtained prior the initiation of the specific treatment with said medicament.

In the next step (IIIb) determining the level of expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes in at least one other biological sample of the tested subject. Such at least one other sample should be obtained after the initiation of the specific treatment.

In step (IIIc) calculating the rate of change between the expression value obtained in step (IIIa), and the expression value obtained in step (IIIb), thereby obtaining the rate of change in the sample $RC_{samp}$, in response to such treatment.

In the next step (IId) providing a standard curve, specifically, predetermined standard curve of the rate of change in the expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes, and optionally of STAT1, IFI44, EIF2AK2 and DHX58 genes in subjects suffering from the same disorder that were treated with the same medicament.

In step (IIe) obtaining a maximal rate of change value $RC_{max}$ and a minimal rate of change value $RC_{min}$ from the standard curve, specifically, predetermined standard curve of (IId); and Finally in (IIf), calculating the M value of the tested sample using the following formula: wherein $M=[(RC_{samp}-RC_{min})/(RC_{max}-RC_{min})]$, thereby obtaining an M value of said subject.

As indicated above, an essential step in the method of the invention is the determination of the expression level of several specific marker genes provided herein. In certain embodiments, these marker genes include at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 or any combinations thereof.

In certain embodiments the methods of the invention may further use the STAT1, IFI44, EIF2AK2 and DHX58 genes and any combinations thereof with any of the marker genes of the invention.

It should be therefore appreciated that the method of the invention may use at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five or at least twenty six of said marker genes, specifically of any one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7, IFI6, STAT1, IFI44, EIF2AK2 and DHX58 genes and any combinations thereof. In yet some other embodiments the methods of the invention may use 1, 2, 3, 4, 5, 6, 7, 8, 9, 10, 11, 12, 13, 14, 15, 16, 17, 18, 19, 20, 21, 22, 23, 24, 25 and 26 or more or any combination of the marker genes of the invention. In yet further embodiments, the methods and kits of the invention may use any of the marker genes of the invention with any combination thereof with additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 and more, specifically, 110, 120, 130, 140, 150, 160, 170, 180, 190, 200 and more, specifically, 300, 350 or 400 further marker genes or control reference genes or any combinations thereof. In certain embodiments, such control reference gene (having an equal expression in samples of responsive and non-responsive subjects) may be a house keeping gene, for example, GAPDH or actin.

As mentioned above, the method and kits of the invention may use the marker genes provided herein, ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7, IFI6, STAT1, IFI44, EIF2AK2 and DHX58 genes and any combination thereof.

More specifically, ISG15 ubiquitin-like modifier (ISG15) gene (GenBank Accession No. NM_005101; SEQ ID NO: 1) encodes the ISG15 protein (GenBank Accession No. NP_005092.1; SEQ ID NO: 2). ISG15 is reported to be an ubiquitin-like protein that is conjugated to intracellular target proteins after IFN-alpha or IFN-beta stimulation. Its enzymatic pathway is partially distinct from that of ubiquitin, differing in substrate specificity and interaction with ligating enzymes. ISG15 conjugation pathway uses a dedicated E1 enzyme, but seems to converge with the ubiquitin conjugation pathway at the level of a specific E2 enzyme. Targets include STAT1, SERPINA3G/SPI2A, JAK1, MAPK3/ERK1, PLCG1, EIF2AK2/PKR, MX1/MxA, and RIG-1. It undergoes deconjugation by USP18/UBP43. It shows specific chemotactic activity towards neutrophils and activates them to induce release of eosinophil chemotactic factors. It was suggested to serve as a trans-acting binding factor directing the association of ligated target proteins to intermediate filaments.

Interferon-induced protein with tetratricopeptide repeats 1 (IFIT1) gene (GenBank Accession No. NM_001548; SEQ ID NO: 3) encodes the IRF1 protein (GenBank Accession No. NP_001539; SEQ ID NO: 4).

Interferon-induced protein with tetratricopeptide repeats 2 (IFIT2) gene (GenBank Accession No. NM_001547; SEQ ID NO: 5) encodes the IFIT2 protein (GenBank Accession No. NP_001538; SEQ ID NO: 6).

Interferon-induced protein with tetratricopeptide repeats 3 (IFIT3) gene (GenBank Accession Nos. NM_001031683; SEQ ID NO: 7, NM_001549; SEQ ID NO: 9) encodes the IFIT3 protein (GenBank Accession Nos. NP_001026853; SEQ ID NO: 8, NP_001540; SEQ ID NO: 10).

Interferon-induced protein with tetratricopeptide repeats 5 (IFIT5) gene (GenBank Accession No. NM_012420; SEQ ID NO: 11) encodes the IFIT5 protein (GenBank Accession No. NP_036552; SEQ ID NO: 12).

2'-5'-oligoadenylate synthetase 1 (OAS1) gene (GenBank Accession No. NM_016816 SEQ ID NO:13, NM_002534

SEQ ID NO:15, NM_001032409 SEQ ID NO:17) encodes the OAS1 protein (GenBank Accession No. NP_058132 SEQ ID NO:14, NP_002525 SEQ ID NO:16, NP_001027581 SEQ ID NO:18). OAS1 encodes a member of the 2-5A synthetase family, essential proteins involved in the innate immune response to viral infection. The encoded protein is induced by interferons and uses adenosine triphosphate in 2'-specific nucleotidyl transfer reactions to synthesize 2',5'-oligoadenylates (2-5As). These molecules activate latent RNase L, which results in viral RNA degradation and the inhibition of viral replication. The three known members of this gene family are located in a cluster on chromosome 12. Mutations in this gene have been associated with host susceptibility to viral infection. Alternatively spliced transcript variants encoding different isoforms have been described.

2'-5'-oligoadenylate synthetase 2 (OAS2) gene (GenBank Accession No. NM_016817 SEQ ID NO:19, NM_002535 SEQ ID NO:21, NM_001032731 SEQ ID NO:23) encodes the OAS2 protein (GenBank Accession No. NP_058197 SEQ ID NO:20, NP_002526 SEQ ID NO:22, NP_001027903 SEQ ID NO:24).

2'-5'-oligoadenylate synthetase 3 (OAS3) gene (GenBank Accession No. NM_006187 SEQ ID NO:25) encodes the OAS3 protein (GenBank Accession No. NP_006178.2 SEQ ID NO:26). OAS3 may play a role in mediating resistance to virus infection, control of cell growth, differentiation, and apoptosis. OAS3 synthesizes preferentially dimeric 2',5'-oligoadenylate molecules. GTP can be an alternative substrate.

2'-5'-oligoadenylate synthetase-like (OASL) gene (GenBank Accession Nos. NM_003733; SEQ ID NO: 27, NM_198213; SEQ ID NO: 29) encodes the OASL protein (GenBank Accession Nos. NP_003724; SEQ ID NO: 28, NP_937856; SEQ ID NO: 30).

HECT and RLD domain containing E3 ubiquitin protein ligase 5 (HERC5) gene (GenBank Accession No. NM_016323; SEQ ID NO: 31) encodes the HERC5 protein (GenBank Accession No. NP_057407 SEQ ID NO: 32). HERC5 gene is a member of the HERC family of ubiquitin ligases and encodes a protein with a HECT domain and five RCC1 repeats. Pro-inflammatory cytokines up regulate expression of this gene in endothelial cells. The HERC5 protein localizes to the cytoplasm and perinuclear region and functions as an interferon-induced E3 protein ligase that mediates ISGylation of protein targets. It is a major E3 ligase for ISG15 conjugation. HERC5 Acts as a positive regulator of innate antiviral response in cells induced by interferon. Makes part of the ISGylation machinery that recognizes target proteins in a broad and relatively non-specific manner.

Ubiquitin specific peptidase 18 (USP18) gene (GenBank Accession No. NM_017414; SEQ ID NO: 33) encodes the USP18 protein (GenBank Accession No. NP_059110 SEQ ID NO: 34). The protein encoded by this gene belongs to the ubiquitin-specific proteases (UBP) family of enzymes that cleave ubiquitin from ubiquitinated protein substrates. It is highly expressed in liver and thymus, and is localized to the nucleus. USP18 protein efficiently cleaves only ISG15 (a ubiquitin-like protein) fusions, and deletion of this gene in mice results in a massive increase of ISG15 conjugates in tissues, indicating that this protein is a major ISG15-specific protease. Mice lacking this gene are also hypersensitive to interferon, suggesting a function of this protein in down-regulating interferon responses, independent of its isopeptidase activity towards ISG15. USP18 can efficiently cleave only ISG15 fusions including native ISG15 conjugates linked via isopeptide bonds. Necessary to maintain a critical cellular balance of ISG15-conjugated proteins in both healthy and stressed organisms Radical S-adenosyl methionine domain containing 2 (RSAD2) gene (GenBank Accession No. NM_080657; SEQ ID NO: 35) encodes the RSAD2 protein (GenBank Accession No. NP_542388; SEQ ID NO: 36). RSAD2 is reported to be involved in antiviral defense. It was suggested to impair virus budding by disrupting lipid rafts at the plasma membrane, a feature which is essential for the budding process of many viruses. In addition, it was reported to act through binding with and inactivating FPPS, an enzyme involved in synthesis of cholesterol, farnesylated and geranylated proteins, ubiquinones dolichol and heme. Moreover, it is considered to play a major role in the cell antiviral state induced by type I and type II interferon. Finally, it was reported to display antiviral effect against HIV-1 virus, hepatitis C virus, human cytomegalovirus, and aphaviruses, but not vesiculovirus.

Myxovirus (influenza virus) resistance 1 (MX1) gene (GenBank Accession No. NM_002462 SEQ ID NO:37, NM_001178046 SEQ ID NO:39, NM_001144925 SEQ ID NO:41) encodes the MX1 protein (GenBank Accession No. NP_002453 SEQ ID NO:38, NP_001171517 SEQ ID NO:40, NP_001138397 SEQ ID NO:42). In mouse, the interferon-inducible Mx protein is responsible for a specific antiviral state against influenza virus infection. The protein encoded by this gene is similar to the mouse protein as determined by its antigenic relatedness, induction conditions, physicochemical properties, and amino acid analysis. This cytoplasmic protein is a member of both the dynamin family and the family of large GTPases. Two transcript variants encoding the same protein have been found for this gene. MX1 may regulate the calcium channel activity of TRPCs. Ring-like assemblies may induce membrane tabulation.

Interferon-induced protein 44-like (IFI44L) gene (GenBank Accession No. NM_006820.3; SEQ ID NO: 43) encodes the IFI44L protein (GenBank Accession No. NP_006811; SEQ ID NO: 44) that belongs to the IFI44 family of proteins is located in the cytoplasm and exhibits a low antiviral activity against hepatitis C. The expression of the protein is induced by type I interferon.

DEAD (Asp-Glu-Ala-Asp) box polypeptide 58 (DDX58) gene (GenBank Accession No. NM_014314; SEQ ID NO: 45) encodes the DDX58 protein (GenBank Accession No. NP_055129; SEQ ID NO: 46). DEAD box proteins, characterized by the conserved motif Asp-Glu-Ala-Asp (DEAD), are putative RNA helicases which are implicated in a number of cellular processes involving RNA binding and alteration of RNA secondary structure. This gene encodes a protein containing RNA helicase-DEAD box protein motifs and a caspase recruitment domain (CARD). It is involved in viral double-stranded (ds) RNA recognition and the regulation of immune response. It is an innate immune receptor which acts as a cytoplasmic sensor of viral nucleic acids and plays a major role in sensing viral infection and in the activation of a cascade of antiviral responses including the induction of type I interferons and pro-inflammatory cytokines. Upon ligand binding it associates with mitochondria antiviral signaling protein (MAVS/IPS1) which activates the IKK-related kinases: TBK1 and IKBKE which phosphorylate interferon regulatory factors: IRF3 and IRF7 which in turn activate transcription of antiviral immunological genes, including interferons (IFNs); IFN-alpha and IFN-beta. Detects both positive and negative strand RNA viruses including members of the families Paramyxoviridae: Human respiratory synctial virus and measles virus (MeV), Rhabdoviridae: vesicular stomatitis virus (VSV), Orthomyxoviridae: influenza A and B virus, Flaviviridae: Japanese encephalitis virus (JEV), hepatitis C virus (HCV), dengue virus (DENY) and west Nile virus (WNV).

E1-like ubiquitin-activating enzyme (UBE1L) gene (GenBank Accession No. AF294032; SEQ ID NO: 79) encodes the UBE1L protein (GenBank Accession No. AAG49557; SEQ ID NO: 80). UBE1L is the E1-like ubiquitin-activating enzyme for the IFN-stimulated gene, 15-kDa protein (ISG15).

Ubiquitin-conjugating enzyme E2L6 (UBE2L6) gene (GenBank Accession No. NM_198183 SEQ ID NO: 81; GenBank Accession No. NM_004223 SEQ ID NO: 83) encodes the UBE2L6 protein (GenBank Accession No. NP_937826 SEQ ID NO: 82; GenBank Accession No. NP_004214 SEQ ID NO: 84). The UBE2L6 gene encodes a member of the E2 ubiquitin-conjugating enzyme family. This enzyme is highly similar in primary structure to the enzyme encoded by the UBE2L3 gene. UBE2L6 catalyzes the covalent attachment of ubiquitin or ISG15 to other proteins. UBE2L6 functions in the E6/E6-AP-induced ubiquitination of p53/TP53. It also promotes ubiquitination and subsequent proteasomal degradation of FLT3.

Interferon alpha-inducible protein 27 (IFI27) gene (GenBank Accession Nos. NM_001130080 and NM_005532; SEQ ID NOs: 85, 87, respectively) encodes the IFI27 protein (GenBank Accession Nos. NP_001123552 and NP_005523; SEQ ID NOs: 86, 88, respectively). The IFI27 protein was reported to promote cell death and mediate IFN-induced apoptosis characterized by a rapid and robust release of cytochrome C from the mitochondria and activation of BAX and caspases 2, 3, 6, 8 and 9.

Interferon induced with helicase C domain 1 (IFIH1) gene (GenBank Accession No. NM_022168 SEQ ID NO: 89) encodes the IFIH1 protein (GenBank Accession No. NP_071451 SEQ ID NO: 90). IFIH1 is an innate immune receptor which acts as a cytoplasmic sensor of viral nucleic acids and plays a major role in sensing viral infection and in the activation of a cascade of antiviral responses including the induction of type I interferons and proinflammatory cytokines. Its ligands include mRNA lacking 2'-O-methylation at their 5' cap and long-dsRNA (>1 kb in length). Upon ligand binding it associates with mitochondria antiviral signaling protein (MAVS/IPS1) which activates the IKK-related kinases.

Toll-like receptor 7 (TLR-7) gene (GenBank Accession No. NM_016562 SEQ ID NO: 91) encodes the TLR-7 protein (GenBank Accession No. NP_057646 SEQ ID NO: 92). The protein encoded by this gene is a member of the Toll-like receptor (TLR) family which plays a fundamental role in pathogen recognition and activation of innate immunity. TLRs are highly conserved from Drosophila to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This gene is predominantly expressed in lung, placenta, and spleen, and lies in close proximity to another family member, TLR8, on chromosome X.

Interferon regulatory factor 7 (IRF7) gene (GenBank Accession Nos. NM_001572 SEQ ID NO: 93; NM_004029 SEQ ID NO: 95) encodes the IRF7 protein (GenBank Accession Nos. NP_001563 SEQ ID NO: 94; NP_004020 SEQ ID NO: 96). IFR7 is reported to be a transcriptional activator. It binds to the interferon-stimulated response element (ISRE) in IFN promoters and in the Q promoter (Qp) of EBV nuclear antigen 1 (EBNA1). It is also reported to function as a molecular switch for antiviral activity. It is reported to be activated by phosphorylation in response to infection. The activation leads to nuclear retention, DNA binding, and depression of transactivation ability.

Interferon, alpha-inducible protein 6 (IFI6) gene (GenBank Accession Nos. NM_022873, SEQ ID NO:97; NM_022872, SEQ ID NO:99; NM_002038, SEQ ID NO:101) encodes the IFI6 protein (GenBank Accession Nos. NP_075011, SEQ ID NO:98; NP_075010, SEQ ID NO:100; NP_002029, SEQ ID NO:102). IFI6 gene was first identified as one of the many genes induced by interferon. The encoded IFI6 protein may play a critical role in the regulation of apoptosis.

In yet another embodiment, the methods, kits and compositions of the invention may further include detecting molecules for the STAT1 gene. Signal transducer and activator of transcription 1 (STAT1) gene (GenBank Accession No. NM_007315 SEQ ID NO:103, NM_139266 SEQ ID NO:104) encodes the STAT1 protein (GenBank Accession No. NP_009330 SEQ ID NO:105, NP_644671 SEQ ID NO: 106). Signal transducer and transcription activator that mediates cellular responses to interferons (IFNs), cytokine KITLG/SCF and other cytokines and growth factors.

Interferon-induced protein 44 (IFI44) gene (GenBank Accession No. NM_006417; SEQ ID NO: 107) encodes the IFI44 protein (GenBank Accession No. NP_006408; SEQ ID NO: 108), that was reported to aggregate to form microtubular structures.

EIF2AK2 eukaryotic translation initiation factor 2-alpha kinase 2 (EIF2AK2) gene (GenBank Accession No. NM_002759.1; SEQ ID NO: 109) encodes the EIF2AK2 protein (GenBank Accession No. NC_000002.11; SEQ ID NO: 110). The protein encoded by this gene is a serine/threonine protein kinase that is activated by autophosphorylation after binding to dsRNA. The activated form of the encoded protein can phosphorylate translation initiation factor EIF2S1, which in turn inhibits protein synthesis. This protein is also activated by manganese ions and heparin. Three transcript variants encoding two different isoforms have been found for this gene.

DHX58 DHX58 (DEXH (Asp-Glu-X-His) box polypeptide 58), gene (GenBank Accession No. NM_024119; SEQ ID NO: 111) encodes the DHX58 protein (GenBank Accession No. NC_000017.10; SEQ ID NO: 112). DHX58 acts as a regulator of DDX58/RIG-I and IFIH1/MDA5 mediated antiviral signaling. Cannot initiateantiviral signaling as it lacks the CARD domain required for activating MAVS/IPS1-dependent signaling The terms "level of expression" or "expression level" are used interchangeably and generally refer to a numerical representation of the amount (quantity) of a polynucleotide which encodes an amino acid product or protein in a biological sample.

"Expression" generally refers to the process by which gene-encoded information is converted into the structures present and operating in the cell. For example, biomarker gene expression values measured in Real-Time Polymerase Chain Reaction, sometimes also referred to as RT-PCR or quantitative PCR (qPCR), represent luminosity measured in a tested sample, where an intercalating fluorescent dye is integrated into double-stranded DNA products of the qPCR reaction performed on reverse-transcribed sample RNA, i.e., test sample RNA converted into DNA for the purpose of the assay. The luminosity is captured by a detector that converts the signal intensity into a numerical representation which is said expression value, in terms of miRNA. Therefore, according to the invention "expression" of a gene, specifically, a gene encoding the biomarker genes of the invention may refer to transcription into a polynucleotide. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. Methods for determining the level of expression of the biomarkers of the invention will be described in more detail herein after.

In certain and specific embodiments, the step of determining the level of expression to obtain an expression value by the method of the invention further comprises an additional and optional step of normalization. According to this embodiment, in addition to determination of the level of expression of the biomarkers of the invention, the level of expression of at least one suitable control reference gene (e.g., housekeeping genes) is being determined in the same sample. According to such embodiment, the expression level of the biomarkers of the invention obtained in step (a) is normalized according to the expression level of said at least one reference control gene obtained in the additional optional step in said test sample, thereby obtaining a normalized expression value. Optionally, similar normalization is performed also in at least one control sample or a representing standard when applicable.

The term "expression value" thus refers to the result of a calculation, that uses as an input the "level of expression" or "expression level" obtained experimentally and by normalizing the "level of expression" or "expression level" by at least one normalization step as detailed herein, the calculated value termed herein "expression value" is obtained.

More specifically, as used herein, "normalized values" are the quotient of raw expression values of marker genes, divided by the expression value of a control reference gene from the same sample, such as a stably-expressed housekeeping control gene. Any assayed sample may contain more or less biological material than is intended, due to human error and equipment failures Importantly, the same error or deviation applies to both the marker genes of the invention and to the control reference gene, whose expression is essentially constant. Thus, division of the marker gene raw expression value by the control reference gene raw expression value yields a quotient which is essentially free from any technical failures or inaccuracies (except for major errors which destroy the sample for testing purposes) and constitutes a normalized expression value of said marker gene. This normalized expression value may then be compared with normalized cutoff values, i.e., cutoff values calculated from normalized expression values. In certain embodiments, the control reference gene may be a gene that maintains stable in all samples analyzed in the microarray analysis.

It should be noted that normalized biomarker genes expression level values that are higher (positive) or lower (negative) in comparison with a corresponding predetermined standard expression value or a cut-off value in a control sample predict to which population of patients the tested sample belongs.

It should be appreciated that in some embodiments an important step in determining the expression level is to examine whether the normalized expression value of any one of the biomarker genes of the tested sample is within the range of the expression value of a standard population or a cutoff value for such population.

More specifically, the specific expression values of the tested samples are compared to a predetermined cutoff value. As used herein the term "comparing" denotes any examination of the expression level and/or expression values obtained in the samples of the invention as detailed throughout in order to discover similarities or differences between at least two different samples. It should be noted that comparing according to the present invention encompasses the possibility to use a computer based approach.

As described hereinabove, the method of the invention refers to a predetermined cutoff value. It should be noted that a "cutoff value", sometimes referred to simply as "cutoff" herein, is a value that meets the requirements for both high diagnostic sensitivity (true positive rate) and high diagnostic specificity (true negative rate).

It should be noted that the terms "sensitivity" and "specificity" are used herein with respect to the ability of one or more markers, to correctly classify a sample as belonging to a pre-established population associated with responsiveness to treatment with a certain medicament.

In certain alternative embodiments, a control sample may be used (instead of, or in addition to, pre-determined cutoff values). Accordingly, the normalized expression values of the biomarker genes used by the invention in the test sample are compared to the expression values in the control sample. In certain embodiments, such control sample may be obtained from at least one of a healthy subject, a subject suffering from the same pathologic disorder, a subject that responds to treatment with said medicament and a non-responder subject.

The term "response" or "responsiveness" to a certain treatment refers to an improvement in at least one relevant clinical parameter as compared to an untreated subject diagnosed with the same pathology (e.g., the same type, stage, degree and/or classification of the pathology), or as compared to the clinical parameters of the same subject prior to interferon treatment with said medicament.

The term "non responder" to treatment with a specific medicament, refers to a patient not experiencing an improvement in at least one of the clinical parameter and is diagnosed with the same condition as an untreated subject diagnosed with the same pathology (e.g., the same type, stage, degree and/or classification of the pathology), or experiencing the clinical parameters of the same subject prior to treatment with the specific medicament.

In case the method of the invention uses the dynamic approaches for determining the M value of the tested individual, at least two samples may be obtained from the subjects. These samples should be obtained from different time points, before and after the treatment, and therefore may be considered as "temporally separated samples". As indicated above, in accordance with some embodiments of the invention, in order to asses response and determine the rate of change in the expression of the marker genes of the invention upon treatment with a specific medicament, at least two "temporally-separated" test samples must be collected from the treated patient and compared thereafter in order to obtain the rate of expression change in the biomarker genes. In practice, to detect a change in the biomarker genes expression, at least two "temporally-separated" test samples and preferably more must be collected from the patient.

The expression of at least one of the markers is then determined using the method of the invention, applied for each sample. As detailed above, the rate of change in marker expression is calculated by determining the ratio between the two expression values, obtained from the same patient in different time-points or time intervals.

This period of time, also referred to as "time interval", or the difference between time points (wherein each time point is the time when a specific sample was collected) may be any period deemed appropriate by medical staff and modified as needed according to the specific requirements of the patient and the clinical state he or she may be in. For example, this interval may be at least one day, at least three days, at least three days, at least one week, at least two weeks, at least three weeks, at least one month, at least two months, at least three months, at least four months, at least five months, at least one year, or even more.

More specifically, one sample should be obtained prior to treatment with the specific medicament. Prior as used herein is meant the first time point is at any time before initiation of treatment, ideally several minutes before initiation of treatment. However, it should be noted that any time point before initiation of the treatment, including hours, days, weeks, months or years, may be useful for this method and is therefore encompassed by the invention. The second time point is collected from the same patient after hours, days, weeks, months or even years after initiation of treatment. More specifically, at least 3 hours, at least 4 hours, at least 6 hours, at least 10 hours, at least 12 hours, at least 24 hours, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 32 days, at least 33 days, at least 40 days, at least 50 days, at least 60 days, at least 70 days, at least 78 days, at least 80, at least 90 days, at least 100 days, at least 110, at least 120 days, at least 130 days, at least 140 days or at least 150 days after initiation of treatment.

In some embodiments, the second time point is obtained between 1 hour to 24 month after initiation of the treatment. In some other embodiments, the second time point is between 1 hour to 6 hours after initiation of the treatment. In yet some other embodiments, the second time point is between 1 month to 3 month after initiation of the treatment.

In practice, for assessing response to a specific treatment, at least two test samples (before and after treatment) must be collected from the treated patient, and preferably more. The expression level of the genes is then determined using the method of the invention, applied for each sample. As detailed above, the expression value is obtained from the experimental expression level. The rate of change of each biomarker expression, namely at least one of the genes indicated by the invention, is then calculated and determined by dividing the two expression values obtained from the same patient in different time-points or time intervals one by the other.

It should be appreciated that in some embodiments, the term "before treatment" may also encompass samples that are obtained from a treated subject, between two treatments. More specifically, in cases wherein the interval between treatments is once a day, a week, a month, a year or every several days, months or years, "before treatment" may be obtained right before the next treatment. The second "after treatment" sample may be taken after several hours or days of the treatment as indicated above.

It should be noted that it is possible to divide the prior-treatment expression value by the after treatment expression value and vise versa. For the sake of clarity, as used herein, the rate of change is referred as the ratio obtained when dividing the expression value obtained at the later time point of the time interval by the expression value obtained at the earlier time point (for example before initiation of treatment).

For example, this interval may be at least one day, at least three days, at least three days, at least one week, at least two weeks, at least three weeks, at least one month, at least two months, at least three months, at least four months, at least five months, at least one year, or even more. Permeably the second point is obtained at the earlier time point that can provide valuable information regarding assessing response of the patient to interferon treatment or to treatment with any other drug, medicament or any other combination of drugs or medicaments.

The rate of change in the expression value of the different marker genes of the invention may reflect either reduction or elevation of expression. More specifically, "reduction" or "down-regulation" of the marker genes as a result of interferon treatment includes any "decrease", "inhibition", "moderation", "elimination" or "attenuation" in the expression of said genes and relate to the retardation, restraining or reduction of the biomarker genes expression or levels by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

Alternatively, "up-regulation" of any one of the bio-marker genes as a result of interferon or any other drug treatment includes any "increase", "elevation", "enhancement" or "elevation" in the expression of said genes and relate to the enhancement and increase of at least one of the biomarker genes expression or levels by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

As appreciated, a predetermined rate of change calculated for a pre-established population as detailed above for example encompasses a range for the rate of change having a low value and a high value, as obtained from a population of individuals including healthy controls, responders and non-responders to said medicament. Thus a subgroup of responsive patients can be obtained from the entire tested population. In this pre-established responsive population, the low value may be characterized by a low response whereas the high value may be associated with a high response as indicated by regular clinical evaluation. Therefore, in addition to assessing responsiveness to treatment, the rate of change may provide insight into the degree of responsiveness. For example, a calculated rate of change that is closer in its value to the low value may be indicative of a low response and thus although the patient is considered responsive, increasing dosing or frequency of administration may be considered. Alternatively, a calculated rate of change that is closer in its value to the high value may be indicative of a high response, even at times leading to remission and thus lowering the administration dosage may be considered.

For clarity, when referring to a pre-established population associated with responsiveness, or the ability to eradicate pathogens, it is meant that a statistically-meaningful group of patients treated with a specific medicament was analyzed as disclosed herein, and the correlations between the biomarker gene/s expression values (and optionally other patient clinical parameters) and responsiveness to such treatment was calculated. The population may optionally be further divided into sub-populations according to other patient parameters, for example gender and age.

Another embodiment of the method of the invention defines the step of calculating the value of M1, the optimal threshold required for successful elimination of the pathologic disorder. In such embodiment, this optimal M1 value may be determined using two alternative approaches:

In one embodiment, determination of the M1 value may be performed by the steps of:

First (Ia) Providing a K value for the specific disorder. It should be noted that the K value reflects the severity of the disorder. For example, disorders caused by a viral infection, the K value may be the multiplicity rate of such virus, in other words, the pathogen growth rate. Methods for obtaining the multiplicity rate of a virus (the K value of the present application) are described for example in Ruy M. Ribeiro et al., PLOS Pathogens 8 (8):e1002881 (2012); Deborah Cromer et al., Journal of Virology 87: 3376-3381 (2013); Ying Fang et al., J. Virol. Methods. 173(2): 251-258 (2011) and Stiffler J D, et al. PLoS ONE 4(8): e6661. doi:10.1371/journal.pone.0006661 (2009).

In the next step (Ib) involves calculating the M1 using the formula, wherein $M1 \geq 1-(1/k)$, thereby determining the M1 value.

Another alternative approach for determining the M1 value, may involve the use of standard curve, specifically, predetermined standard curve of a responder population thereby calculating for such curve, the optimal M1 value.

According to some embodiments, the method of the invention may be specifically practiced using 4 or 5 marker genes. More specifically, in some embodiments, the method of the invention may use the expression value of OAS2, HERC5, UPS18, UBE216 and optionally of ISG15 genes. In some embodiments, the method of the invention may use OAS2, HERC5, UPS18 and UBE216 as markers for calculating M. In yet further embodiments, the method of the invention may use OAS2, HERC5, UPS18, UBE216 and ISG15 genes.

According to certain embodiments, the method of the invention may be specifically suitable for determining and optimizing a personalized interferon treatment regimen for a subject suffering from a pathologic disorder.

More specifically, the methods of the invention described herein, relate to interferon treatment, specifically, to optimize interferon treatment regimen to a specific individual, as a personalized medicine approach. As used herein the term "interferon" or "IFN" which is interchangeably used herein, refers to a synthetic, recombinant or purified interferon, and encompasses interferon type I that binds to the cell surface receptor complex IFN-a receptor (IFNAR) consisting of IFNAR1 and IFNAR2 chains; interferon type II that binds to the IFNGR receptor; and interferon type III, that binds to a receptor complex consisting of IL10R2 (also called CRF2-4) and IFNLR1 (also called CRF2-12).

Interferon type I in human includes interferon alpha 1 (GenBank Accession No. NM_024013 and NP_076918; SEQ ID NOs: 47 and 48 respectively), interferon alpha 2 (GenBank Accession No. NM_000605 and NP_000596; SEQ ID NO: 49 and 50, respectively), Interferon alpha-4 (GenBank Accession No. NM_021068 and NP_066546; SEQ ID NO: 51 and 52, respectively), Interferon alpha-5 (GenBank Accession No. NM_002169 and NP_002160; SEQ ID NO: 53 and 54, respectively), Interferon alpha-6 (GenBank Accession No. NM_021002 and NP_066282; SEQ ID NO: 55 and 56, respectively), Interferon alpha-7 (GenBank Accession No. NM_021057 and NP_066401; SEQ ID NO: 57 and 58, respectively), Interferon alpha-8 (GenBank Accession No. NM_002170 and NP_002161; SEQ ID NO: 59 and 60, respectively), Interferon alpha-10 (GenBank Accession No. NM_002171 and NP_002162; SEQ ID NO: 61 and 62, respectively), Interferon alpha-1/13 (GenBank Accession No. NM_006900 and NP_008831; SEQ ID NO: 63 and 64, respectively), Interferon alpha-14 (GenBank Accession No. NM_002172 and NP_002163; SEQ ID NO: 65 and 66, respectively), Interferon alpha-16 (GenBank Accession No. NM_002173 and NP_002164; SEQ ID NO: 67 and 68, respectively), Interferon alpha-17 (GenBank Accession No. NM_021268 and NP_067091; SEQ ID NO: 69 and 70, respectively) and Interferon alpha-21 (GenBank Accession No. NM_002175 and NP_002166; SEQ ID NO: 71 and 72, respectively), Interferon, beta 1 (GenBank Accession No. NM_002176 and NP_002167; SEQ ID NO: 73 and 74, respectively), and Interferon omega-1 (GenBank Accession No. NM_002177 and NP_002168; SEQ ID NOs: 75 and 76 respectively)].

Interferon type II in humans is Interferon-gamma (GenBank Accession No. NM_000619 and NP_000610; SEQ ID NOs: 77 and 78 respectively).

As used herein the phrase "interferon treatment" refers to administration of interferon into a subject in need thereof. It should be noted that administration of interferon may comprise a single or multiple dosages, as well as a continuous administration, depending on the pathology to be treated and a clinical assessment of the subject receiving the treatment.

Various modes of interferon administration are known in the art. These include, but are not limited to, injection (e.g., using a subcutaneous, intramuscular, intravenous, or intradermal injection), intranasal administration and oral administration.

According to some embodiments of the invention, interferon treatment is provided to the subject in doses matching his weight, at a frequency of once a week, for a period of up to 48 weeks.

Non-limiting examples of interferon treatment and representative diseases includes the following interferon beta-1a (multiple sclerosis), interferon beta-Ib (multiple sclerosis), recombinant IFN-a2b (various cancers).

As appreciated in the art, interferon alfa-2a treatment is known as Roferon. Interferon alpha 2b treatment is by Intron A or Reliferon or Uniferon. Interferon beta-1a is sold under the trade names Avonex and Rebif. CinnaGen is a biosimilar compound. Interferon beta-1b is sold under trade names Betaferon, Betaseron, Extavia and ZIFERON.

Interferon treatment may comprise PEGylated interferon i.e., conjugated to a polyethylene glycol (PEG) polymer. For example, PEGylated interferon alpha 2a is sold under the trade name Pegasys. PEGylated interferon alpha 2a in Egypt is sold under the trade name Reiferon Retard. PEGylated interferon alpha 2b is sold under the trade name PegIntron.

The interferon treatment can also comprise a combination of interferon and ribavirin. For example, PEGylated interferon alpha 2b plus ribavirin is sold under the trade name Pegetron.

In yet another specific embodiment, determining the level of expression of at least one of said ISG15, IFIT1-5, OAS1-3L, HERC5, USP18, IFIT2, RSAD2, ISIT1, MX1, IFIT3, IFI44L, OASL, OAS1, OAS2, OAS3, DIX5B, UBE1L, UBE2L6, IFI27, IFIH1, TLR7, IRF7 and IFI6 genes, and optionally of STAT1, IFI44, EIF2AK2 and DHX58 genes in a biological sample of the tested subject in order to calculate the specific M value of the individual as described herein above, may be performed by the step of contacting detecting molecules specific for said genes with a biological sample of said subject, or with any nucleic acid or protein product obtained therefrom.

The term "contacting" means to bring, put, incubate or mix together. As such, a first item is contacted with a second item when the two items are brought or put together, e.g., by touching them to each other or combining them. In the context of the present invention, the term "contacting" includes all measures or steps which allow interaction between the at least one of the detection molecules for the biomarker genes and optionally one suitable control reference gene and the nucleic acid or amino acid molecules of the tested sample. The contacting is performed in a manner so that the at least one of detecting molecule of the genes and at least one suitable control reference gene can interact with or bind to the nucleic acid molecules or alternatively, a protein product of the at least one biomarker gene, in the tested sample. The binding will preferably be non-covalent, reversible binding, e.g., binding via salt bridges, hydrogen bonds, hydrophobic interactions or a combination thereof.

In certain embodiments, the detection step further involves detecting a signal from the detecting molecules that correlates with the expression level of said genes or any product thereof in the sample from the subject, by a suitable means. According to some embodiments, the signal detected from the sample by any one of the experimental methods detailed herein below reflects the expression level of said genes or product thereof. Such signal-to-expression level data may be calculated and derived from a calibration curve. Thus, in certain embodiments, the method of the invention may optionally further involve the use of a calibration curve created by detecting a signal for each one of increasing pre-determined concentrations of said genes or product. Obtaining such a calibration curve may be indicative to evaluate the range at which the expression levels correlate linearly with the concentrations of said genes or product. It should be noted in this connection that at times when no change in expression level of genes or product is observed, the calibration curve should be evaluated in order to rule out the possibility that the measured expression level is not exhibiting a saturation type curve, namely a range at which increasing concentrations exhibit the same signal.

It must be appreciated that in certain embodiments such calibration curve as described above may by also part or component in any of the kits provided by the invention herein after.

In more specific embodiments, the detecting molecules used by the method of the invention for determining the expression level of the marker genes, may be selected from isolated detecting nucleic acid molecules and isolated detecting amino acid molecules.

According to certain embodiments, the method of the invention may use nucleic acid detecting molecules that may comprise isolated oligonucleotide/s, each oligonucleotide specifically hybridizes to a nucleic acid sequence of said at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes (optionally further of STAT1, IFI44, EIF2AK2 and DHX58 genes) and optionally, to a control reference gene. More specifically, such detecting molecule may be at least one of, a pair of primers, at least one primer and/or nucleotide probe/s or any combination thereof. It should be noted that in some embodiments, each of said oligonucleotides is specifically directed against a specific marker gene or against a specific control gene (e.g., house keeping genes).

As used herein, "nucleic acid molecules" or "nucleic acid sequence" are interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations.

As used herein, the term "oligonucleotide" is defined as a molecule comprised of two or more deoxyribonucleotides and/or ribonucleotides, and preferably more than three. Its exact size will depend upon many factors which in turn, depend upon the ultimate function and use of the oligonucleotide. The oligonucleotides may be from about 3 to about 1,000 nucleotides long. Although oligonucleotides of 5 to 100 nucleotides are useful in the invention, preferred oligonucleotides range from about 5 to about 15 bases in length, from about 5 to about 20 bases in length, from about 5 to about 25 bases in length, from about 5 to about 30 bases in length, from about 5 to about 40 bases in length or from about 5 to about 50 bases in length. More specifically, the detecting oligonucleotides molecule used by the composition of the invention may comprise any one of 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 bases in length. It should be further noted that the term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly.

As indicated throughout, in certain embodiments when the detecting molecules used are nucleic acid based molecules, specifically, oligonucleotides. It should be noted that the oligonucleotides used in here specifically hybridize to nucleic acid sequences of the biomarker genes of the invention. Optionally, where also the expression of at least one of the biomarker genes is being examined, the method of the invention may use as detecting molecules oligonucleotides that specifically hybridize to a nucleic acid sequence of said at least one of the genes. As used herein, the term "hybridize" refers to a process where two complementary nucleic acid strands anneal to each other under appropriately stringent conditions. Hybridizations are typically and preferably conducted with probe-length nucleic acid molecules, for example, 5-100 nucleotides in length, 5-50, 5-40, 5-30 or 5-20.

As used herein "selective or specific hybridization" in the context of this invention refers to a hybridization which occurs between a polynucleotide encompassed by the invention as detecting molecules, and the specific biomarker gene and/or any control reference gene, wherein the hybridization is such that the polynucleotide binds to the gene or any control reference gene preferentially to any other RNA in the tested sample. In a specific embodiment a polynucleotide which "selectively hybridizes" is one which hybridizes with a selectivity of greater than 60 percent, greater than 70 percent, greater than 80 percent, greater than 90 percent and most preferably on 100 percent (i.e. cross hybridization with other RNA species preferably occurs at less than 40 percent, less than 30 percent, less than 20 percent, less than 10 percent). As would be understood to a person skilled in the art, a detecting polynucleotide which "selectively hybridizes" to the biomarker genes or any control reference gene can be designed taking into account the length and composition.

The measuring of the expression of any one of the biomarker genes and any control reference gene or any combination thereof can be done by using those polynucleotides as detecting molecules, which are specific and/or selective for the biomarker genes of the invention to quantitate the expression of said biomarker genes or any control reference gene. In a specific embodiment of the invention, the polynucleotides which are specific and/or selective for said genes may be probes or a pair of primers. It should be further appreciated that the methods, as well as the compositions and kits of the invention may comprise, as an oligonucleotide-based detection molecule, both primers and probes.

The term, "primer", as used herein refers to an oligonucleotide, whether occurring naturally as in a purified restriction digest, or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 10-30 or more nucleotides, although it may contain fewer nucleotides. More specifically, the primer used by the methods, as well as the compositions and kits of the invention may comprise 10, 11, 12, 13, 14, 15, 16, 17, 18, 19, 20, 21, 22, 23, 24, 25, 26, 27, 28, 29 or 30 nucleotides or more. In certain embodiments, such primers may comprise 30, 40, 50, 60, 70, 80, 90, 100 nucleotides or more. In specific embodiments, the primers used by the method of the invention may have a stem and loop structure. The factors involved in determining the appropriate length of primer are known to one of ordinary skill in the art and information regarding them is readily available.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 5 or preferably, 8 nucleotides in length. A probe may be 5, 6, 7, 8, 9, 10, 11, 12, 13, 14, 15, 16, 17, 18, 19, 20, 21, 22, 23, 24, 25, 26, 27, 28, 29 and up to 30 nucleotides in length as long as it is less than the full length of the target marker gene. Probes can include oligonucleotides modified so as to have a tag which is detectable by fluorescence, chemiluminescence and the like. The probe can also be modified so as to have both a detectable tag and a quencher molecule, for example TaqMan® and Molecular Beacon® probes, that will be described in detail below.

The oligonucleotides and analogs thereof may be RNA or DNA, or analogs of RNA or DNA, commonly referred to as antisense oligomers or antisense oligonucleotides. Such RNA or DNA analogs comprise, but are not limited to, 2-'0-alkyl sugar modifications, methylphosphonate, phosphorothiate, phosphorodithioate, formacetal, 3-thioformacetal, sulfone, sulfamate, and nitroxide backbone modifications, and analogs, for example, LNA analogs, wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs. Probes may also be mixtures of any of the oligonucleotide analog types together or in combination with native DNA or RNA. At the same time, the oligonucleotides and analogs thereof may be used alone or in combination with one or more additional oligonucleotides or analogs thereof.

Thus, according to one embodiment, such oligonucleotides are any one of a pair of primers or nucleotide probes, and wherein the level of expression of at least one of the biomarker genes is determined using a nucleic acid amplification assay selected from the group consisting of: a Real-Time PCR, micro array, PCR, in situ hybridization and comparative genomic hybridization.

The term "amplification assay", with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. More specifically, as used herein, the term "amplified", when applied to a nucleic acid sequence, refers to a process whereby one or more copies of a particular nucleic acid sequence is generated from a template nucleic acid, preferably by the method of polymerase chain reaction.

"Polymerase chain reaction" or "PCR" refers to an in vitro method for amplifying a specific nucleic acid template sequence. The PCR reaction involves a repetitive series of temperature cycles and is typically performed in a volume of 50-100 microliter. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i)

annealing of primers required for amplification to a target nucleic acid sequence contained within the template sequence, (ii) extending the primers wherein the nucleic acid polymerase synthesizes a primer extension product. "A set of polynucleotide primers", "a set of PCR primers" or "pair of primers" can comprise two, three, four or more primers.

Real time nucleic acid amplification and detection methods are efficient for sequence identification and quantification of a target since no pre-hybridization amplification is required Amplification and hybridization are combined in a single step and can be performed in a fully automated, large-scale, closed-tube format.

Methods that use hybridization-triggered fluorescent probes for real time PCR are based either on a quench-release fluorescence of a probe digested by DNA Polymerase (e.g., methods using TaqMan®, MGB-TaqMan®), or on a hybridization-triggered fluorescence of intact probes (e.g., molecular beacons, and linear probes). In general, the probes are designed to hybridize to an internal region of a PCR product during annealing stage (also referred to as amplicon). For those methods utilizing TaqMan® and MGB-TaqMan® the 5'-exonuclease activity of the approaching DNA Polymerase cleaves a probe between a fluorophore and a quencher, releasing fluorescence.

Thus, a "real time PCR" or "RT-PCT" assay provides dynamic fluorescence detection of amplified genes or any control reference gene produced in a PCR amplification reaction. During PCR, the amplified products created using suitable primers hybridize to probe nucleic acids (TaqMan® probe, for example), which may be labeled according to some embodiments with both a reporter dye and a quencher dye. When these two dyes are in close proximity, i.e. both are present in an intact probe oligonucleotide, the fluorescence of the reporter dye is suppressed. However, a polymerase, such as AmpliTaq Gold™, having 5'-3 nuclease activity can be provided in the PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequencing apparatus, the fluorescent signal produced by the reporter dye is detected and/or quantified. The increase in fluorescence is a direct consequence of amplification of target nucleic acids during PCR. The method and hybridization assays using self-quenching fluorescence probes with and/or without internal controls for detection of nucleic acid application products are known in the art, for example, U.S. Pat. Nos. 6,258,569; 6,030,787; 5,952,202; 5,876,930; 5,866,336; 5,736,333; 5,723,591; 5,691,146; and 5,538,848.

More particularly, QRT-PCR or "qPCR" (Quantitative RT-PCR), which is quantitative in nature, can also be performed to provide a quantitative measure of gene expression levels. In QRT-PCR reverse transcription and PCR can be performed in two steps, or reverse transcription combined with PCR can be performed. One of these techniques, for which there are commercially available kits such as TaqMan® (Perkin Elmer, Foster City, Calif.), is performed with a transcript-specific antisense probe. This probe is specific for the PCR product (e.g. a nucleic acid fragment derived from a gene, or in this case, from a pre-miRNA) and is prepared with a quencher and fluorescent reporter probe attached to the 5 end of the oligonucleotide. Different fluorescent markers are attached to different reporters, allowing for measurement of at least two products in one reaction.

When Taq DNA polymerase is activated, it cleaves off the fluorescent reporters of the probe bound to the template by virtue of its 5-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in any solid support, for example, slides, microplates, 96 well plates, 384 well plates and the like so that samples derived from many individuals are processed and measured simultaneously. The TaqMan® system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces fluorescence proportional to the amount of PCR product.

Both TaqMan® and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other known systems to quantitatively measure mRNA expression products include Molecular Beacons® which uses a probe having a fluorescent molecule and a quencher molecule, the probe capable of forming a hairpin structure such that when in the hairpin form, the fluorescence molecule is quenched, and when hybridized, the fluorescence increases giving a quantitative measurement of gene expression.

According to this embodiment, the detecting molecule may be in the form of probe corresponding and thereby hybridizing to any region or part of the biomarker genes or any control reference gene. More particularly, it is important to choose regions which will permit hybridization to the target nucleic acids. Factors such as the Tm of the oligonucleotide, the percent GC content, the degree of secondary structure and the length of nucleic acid are important factors.

It should be further noted that a standard Northern blot assay can also be used to ascertain an RNA transcript size and the relative amounts of the biomarker genes or any control gene product, in accordance with conventional Northern hybridization techniques known to those persons of ordinary skill in the art.

The invention further contemplates the use of amino acid based molecules such as proteins or polypeptides as detecting molecules disclosed herein and would be known by a person skilled in the art to measure the protein products of the marker genes of the invention. Techniques known to persons skilled in the art (for example, techniques such as Western Blotting, Immunoprecipitation, ELISAs, protein microarray analysis, Flow cytometry and the like) can then be used to measure the level of protein products corresponding to the biomarker of the invention. As would be understood to a person skilled in the art, the measure of the level of expression of the protein products of the biomarker of the invention requires a protein, which specifically and/or selectively binds to the biomarker genes of the invention.

As indicated above, the detecting molecules of the invention may be amino acid based molecules that may be referred to as protein/s or polypeptide/s. As used herein, the terms "protein" and "polypeptide" are used interchangeably to refer to a chain of amino acids linked together by peptide bonds. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds. It should be noted that peptide bond as described herein is a covalent amid bond formed between two amino acid residues.

In specific embodiments, the detecting amino acid molecules are isolated antibodies, with specific binding selectively to the proteins encoded by the biomarker genes as detailed above. Using these antibodies, the level of expression of proteins encoded by the genes may be determined using an immunoassay which is selected from the group consisting of FACS, a Western blot, an ELISA, a RIA, a slot blot, a dot blot, immunohistochemical assay and a radio-imaging assay.

In yet other specific embodiments, the method of the invention may use any sample. In more specific embodiment, such sample may be any one of peripheral blood mononuclear cells and biopsies of organs or tissues.

It should be noted that any of the detecting molecules used by the methods, compositions and kits of the invention are isolated and purified. Still further, it must be understood that any of the detecting molecules (for example, primers and/or probes) or reagents used by the compositions, kits, arrays and in any step of the methods of the invention are non-naturally occurring products or compounds, As such, none of the detecting molecules of the invention are directed to naturally occurring compounds or products.

According to certain embodiments, the sample examined by the method of the invention may be any one of peripheral blood mononuclear cells and biopsies of organs or tissues.

Still further, according to certain embodiments, the method of the invention uses any appropriate biological sample. The term "biological sample" in the present specification and claims is meant to include samples obtained from a mammal subject.

It should be recognized that in certain embodiments a biological sample may be for example, bone marrow, lymph fluid, blood cells, blood, serum, plasma, urine, sputum, saliva, faeces, semen, spinal fluid or CSF, the external secretions of the skin, respiratory, intestinal, and genitourinary tracts, tears, milk, any human organ or tissue, any sample obtained by lavage, optionally of the breast ducal system, plural effusion, sample of in vitro or ex vivo cell culture and cell culture constituents. More specific embodiments, the sample may be any one of peripheral blood mononuclear cells and biopsies of organs or tissues.

According to an embodiment of the invention, the sample is a cell sample. More specifically, the cell is a blood cell (e.g., white blood cells, macrophages, B- and T-lymphocytes, monocytes, neutrophiles, eosinophiles, and basophiles) which can be obtained using a syringe needle from a vein of the subject. It should be noted that the cell may be isolated from the subject (e.g., for in vitro detection) or may optionally comprise a cell that has not been physically removed from the subject (e.g., in vivo detection).

According to a specific embodiment, the sample used by the method of the invention is a sample of peripheral blood mononuclear cells (PBMCs).

The phrase, "peripheral blood mononuclear cells (PBMCs)" as used herein, refers to a mixture of monocytes and lymphocytes. Several methods for isolating white blood cells are known in the art. For example, PBMCs can be isolated from whole blood samples using density gradient centrifugation procedures. Typically, anticoagulated whole blood is layered over the separating medium. At the end of the centrifugation step, the following layers are visually observed from top to bottom: plasma/platelets, PBMCs, separating medium and erythrocytes/granulocytes. The PBMC layer is then removed and washed to remove contaminants (e.g., red blood cells) prior to determining the expression level of the polynucleotide (s) bio-markers of the invention.

In yet another embodiment, the sample may be a biopsy of human organs or tissue, specifically, liver biopsy.

According to some embodiments, the sample may be biopsies of organs or tissues. The biopsies may be obtained by a surgical operation from an organ or tissue of interest, for example liver biopsy, cerebrospinal fluid (CSF), brain biopsy, skin biopsy.

The term biopsy used herein refers to a medical test commonly performed by a surgeon or an interventional radiologist involving sampling of cells or tissues for examination. It is the medical removal of tissue from a living subject to determine the presence or extent of a disease. The tissue is generally examined under a microscope by a pathologist, and can also be analyzed chemically. When an entire lump or suspicious area is removed, the procedure is called an excisional biopsy. When only a sample of tissue is removed with preservation of the histological architecture of the tissue's cells, the procedure is called an incisional biopsy or core biopsy. When a sample of tissue or fluid is removed with a needle in such a way that cells are removed without preserving the histological architecture of the tissue cells, the procedure is called a needle aspiration biopsy.

According to some embodiments of the invention, the cell is a liver cell.

It should be noted that liver cells (hepatic cell) can be obtained by a liver biopsy (e.g., using a surgical tool or a needle). It should be noted that certain embodiments of the invention contemplate the use of different biological samples.

According to certain embodiments, the method of the invention may be specifically suitable for optimizing personalized treatment regimen for a subject suffering from an immune-related disorder.

It should be noted that an "Immune-related disorder" is a condition that is associated with the immune system of a subject, either through activation or inhibition of the immune system, or that can be treated, prevented or diagnosed by targeting a certain component of the immune response in a subject, such as the adaptive or innate immune response.

In more specific embodiments, the immune-related disorder may be any one of an infectious condition, autoimmune disease and a proliferative disorder.

It should be appreciated that the method of the invention may be applicable for determining the appropriate treatment regimen for a specific individual affected with any disorder, for example, any disorder caused by any pathogenic agent. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocyto* genes.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum.*

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania.*

The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishmania,* and *Toxoplasma* species.

The term "viruses" is used in its broadest sense to include viruses of the families adenoviruses, papovaviruses, herpesviruses: simplex, varicella-zoster, Epstein-Ban, CMV, pox viruses: smallpox, vaccinia, hepatitis B, rhinoviruses, hepatitis A, poliovirus, rubella virus, hepatitis C, arboviruses, rabies virus, influenza viruses A and B, flaviviruses, measles virus, mumps virus, HIV, HTLV I and II.

As shown by the following Examples, the method of the invention may be particularly useful for optimizing treatment for HCV infected subjects. Therefore, the method of the invention may be used for optimizing treatment in subjects suffering from viral infections, for example, Hepatitis C virus infection (type 1, 2, 3 or 4), or HCV or influenza infections.

According to a particular embodiment, the subject is suffering from an infectious condition caused by hepatitis C virus (HCV).

As used herein the term "HCV" refers to hepatitis C virus having genotype I (also known as HCV Type 1), genotype 2 (also known as HCV Type 2), genotype 3 (also known as HCV Type 3), genotype 4 (also known as HCV Type 4), genotype 5 (also known as HCV Type 5) or genotype 6 (also known as HCV Type 6).

The phrase "HCV infection" encompasses acute (refers to the first 6 months after infection) and chronic (refers to infection with hepatitis C virus which persists more than 6 month) infection with the hepatitis C virus. Thus, according to some embodiments of the invention, the subject is diagnosed with chronic HCV infection.

According to some embodiments of the invention, the subject is infected with HCV type I. According to some embodiments of the invention, the subject is infected with HCV type 2, 3 or 4. More specifically, Hepatitis C virus (HCV or sometimes HVC) is a small (55-65 nm in size), enveloped, positive-sense single-stranded RNA virus of the family Flaviviridae and as indicated herein, is the cause of hepatitis C in humans. The hepatitis C virus particle consists of a core of RNA, surrounded by an icosahedral protective shell of protein, and further encased in a lipid (fatty) envelope of cellular origin. The Hepatitis C virus has a positive sense single-stranded RNA genome consisting of a single open reading frame that is 9600 nucleotide bases long.

Hepatitis C is an infectious disease affecting primarily the liver, is caused by the hepatitis C virus (HCV). The infection is often asymptomatic, but chronic infection can lead to scarring of the liver and ultimately to cirrhosis, which is generally apparent after many years. In some cases, those with cirrhosis will go on to develop liver failure, liver cancer, or life-threatening esophageal and gastric varices. The invention in some embodiments thereof provides methods, kits and compositions for predicting responsiveness of HCV patients to treatment, specifically, interferon.

Still further, in certain embodiments the method of the invention may be particularly suitable for optimizing treatment regimen for subjects suffering from an infectious condition caused by any one of HCV, dengue virus, influenza, poliovirus, HIV (human immuno deficiency virus), West Nile virus (WNV) infection and Middle East respiratory syndrome coronavirus (MERS-CoV).

According to some particular embodiments, the subject may be a subject suffering from an infectious condition caused by a CMV (cytomegalovirus). In more specific embodiments, the virus may be Human cytomegalovirus (HCMV). CMV belongs to the Herpesviridae family that may be also referred to herein as herpesviruses. HCMV may be also referred to as Human herpesvirus 5 (HHV-5). HCMV infections are frequently associated with the salivary glands. HCMV infection is typically unnoticed in healthy people, but can be life-threatening for the immunocompromised, such as HIV-infected persons, organ transplant recipients, or new born infants. It should be therefore appreciated that the method if the invention may be applicable for determining treatment regimen also for subjects infected by CMV.

A subset of immune-mediated diseases is known as autoimmune diseases. As used herein autoimmune diseases arise from an inappropriate immune response of the body against substances and tissues normally present in the body. In other words, the immune system mistakes some part of the body as a pathogen and attacks its own cells. This may be restricted to certain organs (e.g. in autoimmune thyroiditis) or involve a particular tissue in different places (e.g. Goodpasture's disease which may affect the basement membrane in both the lung and the kidney). Autoimmune disease are categorized by Witebsky's postulates (first formulated by Ernst Witebsky and colleagues in 1957) and include (i) direct evidence from transfer of pathogenic antibody or pathogenic T cells, (ii) indirect evidence based on reproduction of the autoimmune disease in experimental animals and (iii) circumstantial evidence from clinical clues. The treatment of autoimmune diseases is typically done by compounds that decrease the immune response.

Non-limiting examples for autoimmune disorders include Multiple Sclerosis (MS), inflammatory arthritis, rheumatoid arthritis (RA), Eaton-Lambert syndrome, Goodpasture's syndrome, Greaves disease, Guillain-Barr syndrome, autoimmune hemolytic anemia (AIHA), hepatitis, insulin-dependent diabetes mellitus (IDDM) and NIDDM, systemic lupus erythematosus (SLE), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, arthritis, alopecia areata, polymyalgia rheumatica, Wegener's granulomatosis, Reiter's syndrome, Behget's syndrome, ankylosing spondylitis, pemphigus, bullous pemphigoid, dermatitis herpetiformis, inflammatory bowel disease, ulcerative colitis and Crohn's disease and fatty liver disease.

In yet another embodiment, the subject is suffering from Multiple sclerosis (MS).

Thus, in more specific embodiment, the method of the invention may be particularly useful for optimizing treatment, specifically, interferon treatment for a subject suffering from an autoimmune disorder, specifically, Multiple sclerosis (MS).

As used herein the phrase "multiple sclerosis" (abbreviated MS, formerly known as disseminated sclerosis or encephalomyelitis disseminata) is a chronic, inflammatory, demyelinating disease that affects the central nervous system (CNS). Disease onset usually occurs in young adults, is more common in women, and has a prevalence that ranges between 2 and 150 per 100,000 depending on the country or specific population.

MS is characterized by presence of at least two neurological attacks affecting the central nervous system (CNS) and accompanied by demyelinating lesions on brain magnetic resonance imaging (MRI). MS takes several forms, with new symptoms occurring either in discrete episodes (relapsing forms) or slowly accumulating over time (progressive forms). Most people are first diagnosed with relapsing-remitting MS (RRMS) but develop secondary-progressive MS (SPMS) after a number of years. Between episodes or attacks, symptoms may go away completely, but permanent neurological problems often persist, especially as the disease advances.

Relapsing-remitting multiple sclerosis (RRMS) occurring in 85 percent of the patients and a progressive multiple sclerosis occurring in 15 percent of the patients.

According to some embodiments of the invention, the method of the invention may be particularly applicable for subjects diagnosed with RRMS, where early diagnosis of relapse may improve the treatment.

In certain embodiments, the methods of the invention may be also useful for determining and optimizing treatment regimen for subjects suffering from Rehumatoid arthritis (RA). It should be appreciated that there are different forms of arthritis that may be generally grouped into two main categories, inflammatory arthritis, and degenerative arthritis, each with different causes. Therefore, according to one specific embodiments the method of the invention may be specifically applicable for inflammatory arthritis. It should be noted that inflammatory arthritis is characterized by synovitis, bone erosions, osteopenia, soft-tissue swelling, and uniform joint space narrowing. More specifically, the hallmarks of joint inflammation are synovitis and erosion of bone. The latter will initially appear as a focal discontinuity of the thin, white, subchondral bone plate. Normally, this subchondral bone plate can be seen even in cases of severe osteopenia, whereas its discontinuity indicates erosion.

Still further, the method of the invention may be applicable for determining the most effective personally tailored treatment regimen for a subject suffering from a malignant disorder.

As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods of the present invention may be applicable for non-solid and solid tumors.

Malignancy, as contemplated in the present invention may be selected from the group consisting of carcinomas, melanomas, lymphomas and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be hepaotcellular carcinoma, colon cancer, melanoma, myeloma, acute or chronic leukemia.

In certain embodiments, the methods of the invention may be also useful for determining and optimizing treatment regimen for subjects suffering from a proliferative disorder, specifically a cancer, even in cases the medicament is used only as an adjuvant treatment for cell therapy. More specifically, the methods and kits of the invention may be used for optimizing interferon treatment regimen in cases that interferon is being used as an adjuvant for cell therapy, for example in melanoma patients.

It should be noted that in certain embodiments, were the method of the invention uses an induced dynamic approach for determining the M value of the tested individual, an immuno-stimulant suitable for such method may be any one of a synthetic double stranded RNA (poly ICLC), yellow fever (YF) vaccine 17D (YF17D), TLR stimulants such as double-strand RNA or GC.

In some specific embodiments, Poly ICLC as used herein is an immunostimulant comprising a synthetic complex of carboxymethylcellulose, polyinosinic-polycytidylic acid, and poly-L-lysine double-stranded RNA. Poly ICLC may stimulate the release of cytotoxic cytokines and induce interferon-gamma production.

A further aspect of the invention relates to a kit for determining and optimizing a personalized treatment regimen for a subject suffering from a pathologic disorder.

In certain embodiments, such kit may comprise elements required for performing any of the methods described above. More specifically, such kit may comprise:

(a) detecting molecules specific for determining the level of expression of at least one of ISG15, IFIT1-5, OAS1-3L, HERC5, USP18, IFIT2, RSAD2, ISIT1, MX1, IFIT3, IFI44L, OASL, OAS1, OAS2, OAS3, DIX5B, UBE1L, UBE2L6, IFI27, IFIH1, TLR7, IRF7 and IFI6 genes in a biological sample.

The kit of the invention further comprises (b), means for calculating the M value of a tested subject. As noted above, the M value indicates the ability of said subject to eliminate said disorder.

The Kit of the invention further comprises (c) means for calculating the value of M1 or a standard M1 value calculated for a responder population. As indicated above, the M1 value indicates the minimal ability, or specifically, the optimal M1 value required for a successful elimination of the disorder.

Finally, the kit of the invention comprises (d) means for calculating the dose A and number B of administrations of said dose A to obtain an amount C of said medicament required for said subject.

According to some specific embodiments, means for calculating the value of M comprised within the kit of the invention should enable determination of the M value by any of the different approaches mentioned by the invention. More specifically, the kit of the invention may comprise at least one of:

(I) means for performing static analysis for measuring the individual's M value, comprising:

(Ia) detecting molecules specific for determining the level of expression of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes in a biological sample for determining an expression value $Ex_{samp}$ in said sample;

(Ib) a standard curve, specifically, a predetermined standard curve of expression values of subjects suffering from the same pathologic disorder. Alternatively, the kit of the invention may comprise predetermined values, specifically, maximal expression value $Ex_{max}$ and a minimal expression value $Ex_{min}$ calculated from such standard curve. In yet another embodiment, the kit of the invention may comprise control samples of at least one individual having a $Ex_{max}$ expression value and at least one individual having an $Ex_{min}$ expression value; and (Ic) a formula for calculating M value, more specifically, such formula is $M=[(EX_{samp}-EX_{min})/(EX_{max}-Ex_{min})]$. It should be further noted that the kit of the invention may further comprise instructions for determining the expression of any one of the marker genes used by the invention. Moreover, the kit of the invention may further comprise instructions for calculating the required values from the standard curve as well as instructions for calculating the M value using the formula provided.

In yet another alternative or additional embodiment, the kit of the invention may comprise means for performing an induced dynamic analysis (II). It should be noted that such analysis should be performed on healthy individuals. In more specific embodiments, such means comprise:

(IIa) detecting molecules specific for determining the level of expression of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes in a biological sample for determining an expression value $Ex_{samp}$ in the tested sample before and after stimulation of the subject (or in case of in vitro stimulation of a sample of said subject) with an immuno-stimulant. The kit of the invention further comprises means for calculating the rate of change $RC_{samp}$ in the expression value $Ex_{samp}$ of the sample before and after stimulation;

(IIb) an immuno-stimulant;

(IIc) a standard curve, specifically, predetermined standard curve of the rate of change in the expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes (and optionally of STAT1, IFI44, EIF2AK2 and DHX58 genes) in subjects (specifically, healthy subjects) treated with said immuno-stimulant. Alternatively, the kit of the invention may comprise predetermined maximal rate of change value $RC_{max}$ and a minimal rate of change $RC_{min}$ value calculated from such standard curve; and (IId) the kit further comprises a formula for calculating said M value. Such formula is $M=[(RC_{samp}-RC_{min})/(RC_{max}-RC_{min})]$. The kit of the invention further comprises instructions for determining the expression of any one of the marker genes used by the invention. Moreover, the kit of the invention may further comprise instructions for calculating the required values from the standard curve as well as instructions for calculating the M value using the formula provided.

In yet another embodiment, the kit of the invention may comprise means for a dynamic analysis (III) comprising:

(IIIa) detecting molecules specific for determining the level of expression of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes (and optionally of STAT1, IFI44, EIF2AK2 and DHX58 genes) in a biological sample for determining an expression value $Ex_{samp}$ in the examined sample before and after treatment of the tested subject with said specific medicament, and for calculating the rate of change $RC_{samp}$ in the expression value $Ex_{samp}$ of the tested sample.

The kit of the invention further comprises (IIb) a standard curve, specifically, predetermined standard curve of the rate of change in the expression of at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 (and optionally of STAT1, IFI44, EIF2AK2 and DHX58 genes) genes in subjects suffering from the same disorder and treated with the same medicament. Alternatively, the kit of the invention may comprise predetermined maximal rate of change value $RC_{max}$ and minimal rate of change value $RC_{min}$ calculated from such standard curve; and The kit of the invention further comprises (IIc) a formula for calculating the M value/More specifically, such formula is $M=[(RC_{samp}-RC_{min})/(RC_{max}-RC_{min})]$.

It should be further noted that the kit of the invention may further comprise instructions for determining the expression of any one of the marker genes used by the invention. Moreover, the kit of the invention may further comprise instructions for calculating the required values from the standard curve as well as instructions for calculating the M value using the formula provided.

According to certain embodiments, means for calculating the value of M1 comprised within the kit of the invention may comprise:

(a) a standard curve, specifically, predetermined K value of the specific disorder;

(b) a formula for calculating said M1 value. More specifically, such formula is $M1 \geq 1-(1/k)$.

In yet another embodiment, the kit of the invention comprises means for calculating the dose A and number B of administrations of said dose A to obtain an amount C of said medicament required for said subject. It should be note that these means include for example, a predetermined dose A1 and predetermined number B1 of administrations of said dose to obtain a predetermined amount C1 of said medicament required for eliminating said disorder in subjects having a value of M that is equal or above said M1 value. These means further comprise the formulas $A=A1/(M1/M)$ and $B=B1*(M1/M)$; that are required for calculating the dose required for the tested subject.

According to some embodiments, the kit of the invention may be specifically practiced using 4 or 5 marker genes.

More specifically, in some embodiments, the kit of the invention may comprise detecting molecule specific for determining the expression value of OAS2, HERC5, UPS18, UBE216 and optionally of ISG15 genes. In some embodiments, the kit of the invention may comprise detecting molecules specific for OAS2, HERC5, UPS18 and UBE216. In yet further embodiments, the kit of the invention may comprise detecting molecules specific for OAS2, HERC5, UPS18, UBE216 and ISG15 genes.

According to one specific embodiment, the kit of the invention comprises detecting molecules that are isolated oligonucleotides, each oligonucleotide specifically hybridize to a nucleic acid sequence of at least one of genes and optionally, to a control reference gene. More specifically, such detecting molecules may be at least one of pair of primer/s at least one primer, and/or nucleotide probes.

According to specific embodiments, the kit of the invention may further comprise at least one reagent for conducting a nucleic acid amplification based assay selected from the group consisting of a Real-Time PCR, micro arrays, PCR, in situ Hybridization and Comparative Genomic Hybridization.

According to some specific embodiments, the kit of the invention may be specifically suitable for determining and optimizing a personalized interferon treatment regimen for a subject suffering from a pathologic disorder.

In more specific embodiments, the detecting molecules comprised within the kit of the invention are selected from isolated detecting nucleic acid molecules and isolated detecting amino acid molecules.

In more specific embodiments, such nucleic acid detecting molecule comprises isolated oligonucleotides, each oligonucleotide specifically hybridizes to a nucleic acid sequence of said at least one of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes (and optionally of STAT1, IFI44, EIF2AK2 and DHX58 genes) and optionally, to a control reference gene.

Still further, such detecting molecule may be at least one of a pair of primers or nucleotide probes.

In one embodiment, the polynucleotide-based detection molecules of the invention may be in the form of nucleic acid probes which can be spotted onto an array to measure RNA from the sample of a subject to be diagnosed.

As defined herein, a "nucleic acid array" refers to a plurality of nucleic acids (or "nucleic acid members"), optionally attached to a support where each of the nucleic acid members is attached to a support in a unique pre-selected and defined region. These nucleic acid sequences are used herein as detecting nucleic acid molecules. In one embodiment, the nucleic acid member attached to the surface of the support is DNA. In a preferred embodiment, the nucleic acid member attached to the surface of the support is either cDNA or oligonucleotides. In another embodiment, the nucleic acid member attached to the surface of the support is cDNA synthesized by polymerase chain reaction (PCR). In another embodiment, a "nucleic acid array" refers to a plurality of unique nucleic acid detecting molecules attached to nitrocellulose or other membranes used in Southern and/or Northern blotting techniques. For oligonucleotide-based arrays, the selection of oligonucleotides corresponding to the gene of interest which are useful as probes is well understood in the art.

As indicated above, assay based on micro array or RT-PCR may involve attaching or spotting of the probes in a solid support. As used herein, the terms "attaching and "spotting" refer to a process of depositing a nucleic acid onto a substrate to form a nucleic acid array such that the nucleic acid is stably bound to the substrate via covalent bonds, hydrogen bonds or ionic interactions.

As used herein, "stably associated" or "stably bound" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" or "solid support", when referring to an array, refers to a material having a rigid or semi-rigid surface. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly) vinylidendifmoride, polystyrene, polycarbonate, a charged membrane, such as nylon or nitrocellulose, or combinations thereof. Preferably, at least one surface of the substrate will be substantially flat. The support may optionally contain reactive groups, including, but not limited to, carboxyl, amino, hydroxyl, thiol, and the like. In one embodiment, the support may be optically transparent. As noted above, the solid support may include polymers, such as polystyrene, agarose, sepharose, cellulose, glass, glass beads and magnetizable particles of cellulose or other polymers. The solid-support can be in the form of large or small beads, chips or particles, tubes, plates, or other forms.

The method of the invention may be used for personalized medicine, namely adjusting and customizing healthcare with decisions and practices being suitable to the individual patient by use of genetic information and any additional information collected at different stages of the disease.

According to specific embodiments, the biological sample may be a blood sample. Specifically, the biological sample is a sample of peripheral blood mononuclear cells (PBMCs). The kit of the invention may therefore optionally comprise suitable mans for obtaining said sample. More specifically, for using the kit of the invention, one must first obtain samples from the tested subjects. To do so, means for obtaining such samples may be required. Such means for obtaining a sample from the mammalian subject can be by any means for obtaining a sample from the subject known in the art. Examples for obtaining e.g. blood or bone marrow samples are known in the art and could be any kind of finger or skin prick or lancet based device, which basically pierces the skin and results in a drop of blood being released from the skin. In addition, aspirating or biopsy needles may be also used for obtaining spleen lymph nodes tissue samples. Samples may of course be taken from any other living tissue, or body secretions comprising viable cells, such as biopsies, saliva or even urine.

The inventors consider the kit of the invention in compartmental form. It should be therefore noted that the detecting molecules used for detecting the expression levels of the biomarker genes may be provided in a kit attached to an array. As defined herein, a "detecting molecule array" refers to a plurality of detection molecules that may be nucleic acids based or protein based detecting molecules (specifically, probes, primers and antibodies), optionally attached to a support where each of the detecting molecules is attached to a support in a unique pre-selected and defined region.

For example, an array may contain different detecting molecules, such as specific antibodies or primers. As indicated herein before, in case a combined detection of the biomarker genes expression level, the different detecting molecules for each target may be spatially arranged in a predetermined and separated location in an array. For example, an array may be a plurality of vessels (test tubes), plates, micro-wells in a micro-plate, each containing different detecting molecules, specifically, probes, primers and antibodies, against polypeptides encoded by the marker genes used by the invention. An array may also be any solid support holding in distinct regions (dots, lines, columns) different and known, predetermined detecting molecules.

As used herein, "solid support" is defined as any surface to which molecules may be attached through either covalent or non-covalent bonds. Thus, useful solid supports include solid and semi-solid matrixes, such as aero gels and hydro gels, resins, beads, biochips (including thin film coated biochips), micro fluidic chip, a silicon chip, multi-well plates (also referred to as microtiter plates or microplates), membranes, filters, conducting and no conducting metals, glass (including microscope slides) and magnetic supports. More specific examples of useful solid supports include silica gels, polymeric membranes, particles, derivative plastic films, glass beads, cotton, plastic beads, alumina gels, polysaccharides such as Sepharose, nylon, latex bead, magnetic bead, paramagnetic bead, super paramagnetic bead, starch and the like. This also includes, but is not limited to, microsphere particles such as Lumavidin™. Or LS-beads, magnetic beads, charged paper, Langmuir-Blodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

It should be further appreciated that any of the reagents, substances or ingredients included in any of the methods and kits of the invention may be provided as reagents embedded, linked, connected, attached, placed or fused to any of the solid support materials described above.

According to other embodiments, the kit of the invention may be suitable for examining samples such as peripheral blood mononuclear cells and biopsies of organs or tissues.

According to some embodiments, the kit of the invention is specifically suitable for optimizing a treatment regimen for subjects suffering from an immune-related disorder.

In more specific embodiments, such immune-related disorder may be any one of an infectious condition, an auto-immune disease, and a proliferative disorder.

In certain embodiments, the kit of the invention is suitable for optimizing treatment regimen to a subject suffering from an infectious condition caused by any one of HCV, dengue virus, influenza, poliovirus, HIV (human immune-deficiency virus) and West Nile virus (WNV) infection.

In yet other embodiments, the kit of the invention may be suitable for optimizing treatment regimen for a subject suffering from Multiple sclerosis (MS).

In yet other embodiments, the kit of the invention may be suitable for optimizing treatment regimen for a subject suffering from Rheumatoid Arthritis (RA).

In more specific embodiments, were the kit of the invention comprises means for determining the M value using the induced dynamic approach, the kit of the invention may comprises at least one immuno-stimulant that may be any one of a synthetic double stranded RNA (poly ICLC), yellow fever (YF) vaccine 17D (YF17D).

In yet a further aspect, the invention provides a computer software product for determining and optimizing a personalized treatment regimen for a subject suffering from a pathologic disorder. Such product comprising a computer readable medium in which program instructions are stored, which instructions, when read by a computer, cause the computer to:

(a) calculate and determine the value of M that indicates the ability of said subject to eliminate said disorder;

(b) determine the value of M1, that indicates the minimal ability required for eliminating said disorder.

(c) calculate the dose A and number B of administrations of said dose A to obtain an amount C required for said subject having said M determined/calculated in step (a), from predetermined dose A1 and number B1 of administrations of said dose, using the formula of $A=A1/(M1/M)$ and $B=B1*(M1/M)$.

Still further, it must be understood that in certain embodiments, the invention further provides a prognostic composition comprising (a) detecting molecules specific for determining the level of expression of ISG15, IFIT1, IFIT2, IFIT3, IFIT5, OAS1, OAS2, OAS3, OASL, HERC5, USP18, RSAD2, MX1, IFI44L, DDX58, UBE1L, UBE2L6, IFI27, IFIH1, TLR7, IRF7 and IFI6 genes (and optionally of STAT1, IFI44, EIF2AK2 and DHX58 genes) and (b) a biological sample. In certain embodiments, the biological sample may be obtained from the subject that is to be prognosed. In some embodiments, the sample may be a control sample, as discussed herein before. In an optional embodiment, the detecting molecules may be attached to a solid support. As such, the composition of the invention may be specifically suitable for performing any of the prognostic methods disclosed by the invention.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient", "individual" or "subject in need" it is meant any organism who may be affected by the above-mentioned conditions, and to whom the treatment and diagnosis methods herein described is desired, including humans. More specifically, the composition of the invention is intended for mammals. By "mammalian subject" is meant any mammal for which the proposed therapy is desired, including human, equine, canine, and feline subjects, most specifically humans.

It should be noted that specifically in cases of non-human subjects, the method of the invention may be performed using administration via injection, drinking water, feed, spraying, oral gavages and directly into the digestive tract of subjects in need thereof.

The term "treatment or prevention" refers to the complete range of therapeutically positive effects of administrating to a subject including inhibition, reduction of, alleviation of, and relief from, a condition known to be treated with interferon, for example an immune-related disorder as detailed herein. More specifically, treatment or prevention of relapse or recurrence of the disease includes the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to ±10% The terms "comprises", "comprising", "includes", "including", "having" and their conjugates mean "including but not limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

As used herein the term "about" refers to ±10%. The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "about" as used herein indicates values that may deviate up to 1 percent, more specifically 5 percent, more specifically 10 percent, more specifically 15 percent, and in some cases up to 20 percent higher or lower than the value referred to, the deviation range including integer values, and, if applicable, non-integer values as well, constituting a continuous range.

It must be noted that, as used in this specification and the appended claims, the singular forms "a", "an" and "the" include plural referents unless the content clearly dictates otherwise.

EXAMPLES

Experimental Procedures

The expression levels of the genes of interest were obtained from publicly available data bases [http://www.ncbi.nlm.nih.gov/geo/] using the following Gene Expression Omnibus Accession Nos:

Gene Expression Omnibus Accession No. GSE30719 (described in Example 2A) describes genetic data from retinal pigment epithelial (RPE) infected with immunopathogenic West Nile virus (WNV). RNA was extracted after 24 hours and analyzed using Affymetrix arrays.

Gene Expression Omnibus Accession No. GSE18816 (described in Example 2B) describes peripheral-blood leucocytes that were separated from buffy coats of three healthy blood donors and were differentiated for 14 days before use. Differentiated macrophages infected with H1N1 and H5N1 viruses at a multiplicity of infection (MOI) of two were analyzed. Total RNA was extracted from cells after 1, 3, and 6 h post-infection, and the gene expression profiling was performed using an Affymetrix Human Gene 1.0 ST microarray platform.

Gene Expression Omnibus Accession No. GSE13052 (described in Example 2C) describes studies from whole blood transcriptional profiles of children infected 4 days with dengue virus with different clinical outcomes. The tested subjects included 9 acute dengue shock samples, 9 acute uncomplicated dengue samples, 6 autologous follow up dengue samples and 6 autologous follow up uncomplicated dengue patients. Microarray data was normalized using Gene spring GX7 software, statistical analysis was performed in Multiexperiment viewer software. Pathway analysis was performed using Ingenuity Pathway analysis online software.

Gene Expression Omnibus Accession No. GSE17183 (described in Example 3A) provides data from liver biopsy from 30 patients before and one week after starting combination therapy with IFN+Rib. Hepatocytes and liver-infiltrating lymphocytes (LILs) were obtained from 12 patients using laser capture micro dissection (LCM).

Gene Expression Omnibus Accession No. GSE16214 (described in Example 3B) provides data from PBMC samples that were collected from relapsing-remitting MS subjects and CIS subjects. The first time point was chosen for each subject with multiple measurements based on an at least three months of treatment criteria. We thereafter analyzed the data for each treatment category.

Gene Expression Omnibus Accession No. GSE 5549 (described in Example 3C) provides gene expression microarrays data obtained from embryonic fibroblast cell line was synchronously infected with poliovirus in the absence or presence of interferon-α, or with vacciniavirus, a virus that is not inhibited by interferon. The cells were incubated for 1 h with either poliovirus or vacciniavirus, washed and incubated for another 4 to 16 h. Total RNA from three parallel cell cultures were used for each time point and compared with mock infected cells.

Gene Expression Omnibus Accession No. Gene Expression Omnibus Accession No. GSE15245 (described in Example 4)

Gene Expression Omnibus Accession No. GSE 37107 and GEO 42296, disclosed gene profiling of RA patients treated with RTX or infliximab, respectively (described in Example 5).

Gene Expression Omnibus Accession No. GSE18464 provides gene expression data of CD 14+ monocytes isolated from 55 subjects, 22 with HIV HVL, 22 with HIV LVL and 11 HIV seronegative controls (described in Example 6).

Gene Expression Omnibus Accession No. GSE27248 provides gene expression of Ferrets (3 ferrets in each group) immunized with different adjuvant human seasonal vaccines of CFA plus vaccine, CpG plus vaccine, pegylated IFN-alpha plus vaccine and vaccine alone (PBS plus vaccine) (described in Example 7).

Gene Expression Omnibus Accession No. GSE31518, GSE31471 and GSE31472 (described in Example 10) provide gene expression data obtained at 2, 4, 6, 8 and 10 hours post infection of three different host cell lines (A549, MDCK and CEF) with three different Influenza A virus strains, pH1N1 (A/Singapore/478/2009), H9N2 and H5N2.

Gene Expression Omnibus Accession No. GSE52428 (described in Example 10) provide gene expression data obtained from microarrays assay of peripheral blood at baseline and every 8 hours for 7 days following intranasal influenza A H1N1 or H3N2 inoculation in healthy volunteers.

Gene Expression Omnibus Accession No. GSE838 (described in Example 8A) provides gene expression data in peripheral blood leukocytes (PBL) from normal individuals sampled multiple times over periods ranging from several weeks up to 6 months.

Gene Expression Omnibus Accession No. GSE3649 (described in Example 8B) provides data of variation in gene expression patterns in the blood of healthy individuals, by using cDNA microarrays.

Gene Expression Omnibus Accession No. GSE32862 (described in Example 9) provides data from synthetic double stranded RNA that induces innate immunity similar to a live viral vaccine in humans. The innate immune response in humans to synthetic double stranded RNA (poly ICLC), a ligand for TLR3 and MDA-5 cytosolic RNA helicase was studied. Transcriptional analysis of blood samples from eight volunteers, after subcutaneous administration of poly ICLC were obtained and analyzed.

Gene Expression Omnibus Accession No. GSE13699 (described in Example 9) provides data of the immune response to the yellow fever vaccine 17D.

The data was downloaded from the each one of these selected Gene Expression Omnibus Accession and was analyzed using custom programs written in MATLAB.

Specifically, after verifying normalization of data (such as RMA quantile on Affymetrix arrays) and averaging multiple probes per gene, MATLAB mattest is carried out with permutations to calculate pvals. In brief, mattest perform two-sample t-test to evaluate differential expression of genes from two experimental conditions or phenotypes.

Example 1

A Mathematical Model for Determining a Treatment Regimen

The model developed in here is based on a biological situation in which an animal cell is being infected with a virus having a multiplicity rate K. The cell may be subjected to additional viruses penetrating the cytoplasm by a rate P. The viral infection is reduced or terminated at a rate of M (A person's M is considered to be from 0 to 1. For example, a value of M=0.5 means half of existing viruses will be destroyed).

The viral infection may be terminated by the immune system of a subject that upon infection is induced and thus capable of destroying the virus by itself with no external therapy. Alternately, the viral infection may be terminated by injection of an appropriate treatment for example with IFN that leads to distraction of the virus. After the IFN effect is diminished, infection may occur again.

The following set of equations was designed generally to describe the above situation:

The period at which the cell is being infected with a virus starts at time X(N−1) and ends at time X(N), the virus load at both time points should be therefore described as follows:

$$X(N)=X(N-1)*K+P*X(N-1);$$

The period at which the virus is destroyed either by the immune system, by administration of treatment for example interferon or combination of both starts at time (N) and ends at time (N+1). The virus load (X) at the start point X(N) and the end time point X(N+1) is described as follows:

$$X(N+1)=X(N)-M*X(N);$$

As shown above, the virus load at a certain time point depends on the ability of said individual to eliminate and reduce said virus, as reflected by the M value. The following equations were used in MATLAB for simulation purposes.

FIG. 1 [based on schematics from Sadler A J. et al. *Nature Reviews Immunology* 8:559-568 (July 2008)], shows a schematic representation of such a model at a cellular level and emphasizes the ongoing balance between invading virus that is multiplying in the cytoplasm at a rate K and the effect of defending genes that are participating and assisting to diminish the virus. As detailed above, these genes are regulated either by the immune response, external treatment or combination of the two.

Figure 2:
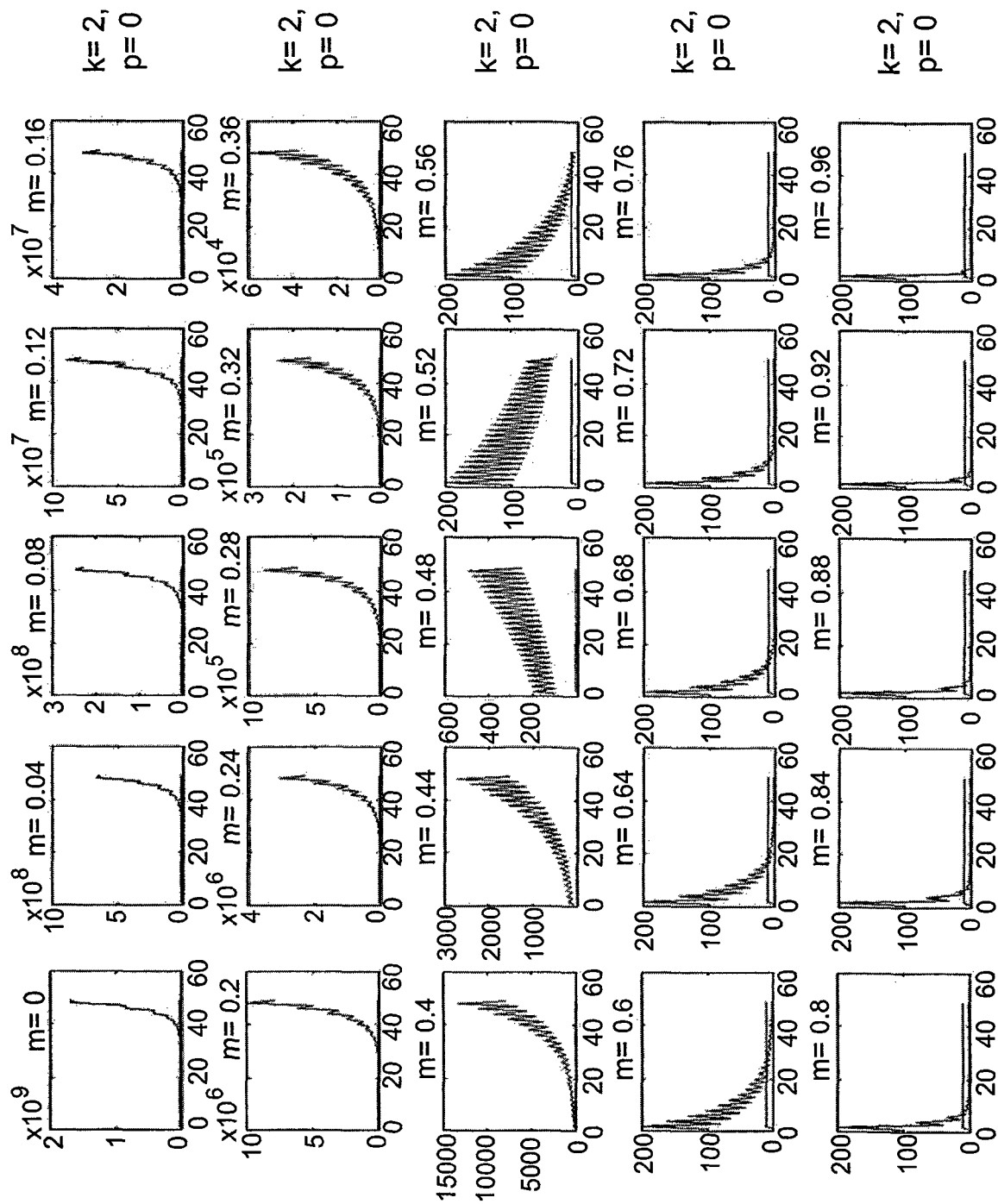
FIG. 2 shows MATLAB simulation of the model with k=2 and p=0 as constant parameters and M being varied from 0 to 1. The lower line represents 0.1 of initial load and provides information whether the down regulation was more than one tenth of the initial virus load.

FIG. 2 shows simulations of the above model equations by assuming the following: P=0 (namely, no additional virus from neighboring cells is penetrating to the cell) and K=2 (namely, the virus population doubles itself. The value of M was varied throughout the simulation from 0 to 1. The results in FIG. 2 show the virus amount (virus load) as a function of the rate of M during time. As can be seen at lower M values of 0.04 to 0.48, the virus is capable of multiplying and hence the disease is progressing, as the immune system is not succeeding in elimination thereof. The effect of M is observed as follows: upon increasing the value of M for example from 0.04 to 0.36, the amount of virus is reduced, indicating that that the viral load is reduced to some extend as a function of M. Increasing M to a value higher than 0.6 shows that the viral load is reduced, namely the disease is eliminated. This may indicate that the immune system is succeeding in stopping the virus.

The simulation shown in FIG. 2, shows that a person having at least an M value of 0.6 will reach this limit using 12 shots (3 month), or he can reach this limit with 4 shots if he has M greater than 0.8. On the x axis the peaks represent IFN cycles assuming they are given once a week.

The model clearly shows that X(0) the initial load, has no impact on response rate as setting the initial load of the virus to different values does not change the curves, namely there is a dependency only on the relations between M and K, specifically, the ability of the individual and the virulence of the pathogen.

Figure 3:
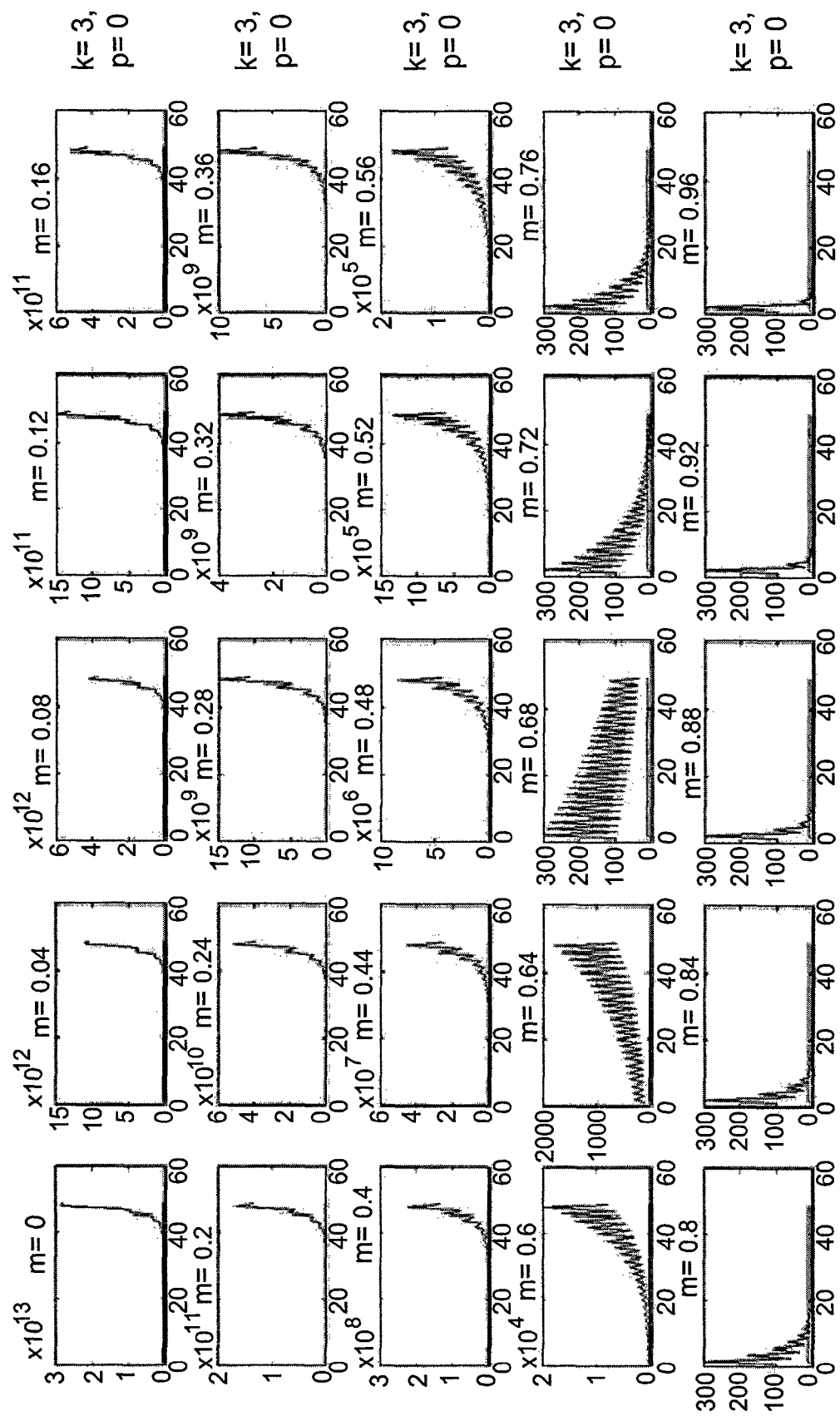
FIG. 3 shows MATLAB simulation of the model with k=3 and p=0 as constant parameters and M being varied from 0 to 1. The lower line represents 0.1 of initial load and provides information whether the down regulation was more than one tenth of the initial virus load.
Figure 4:
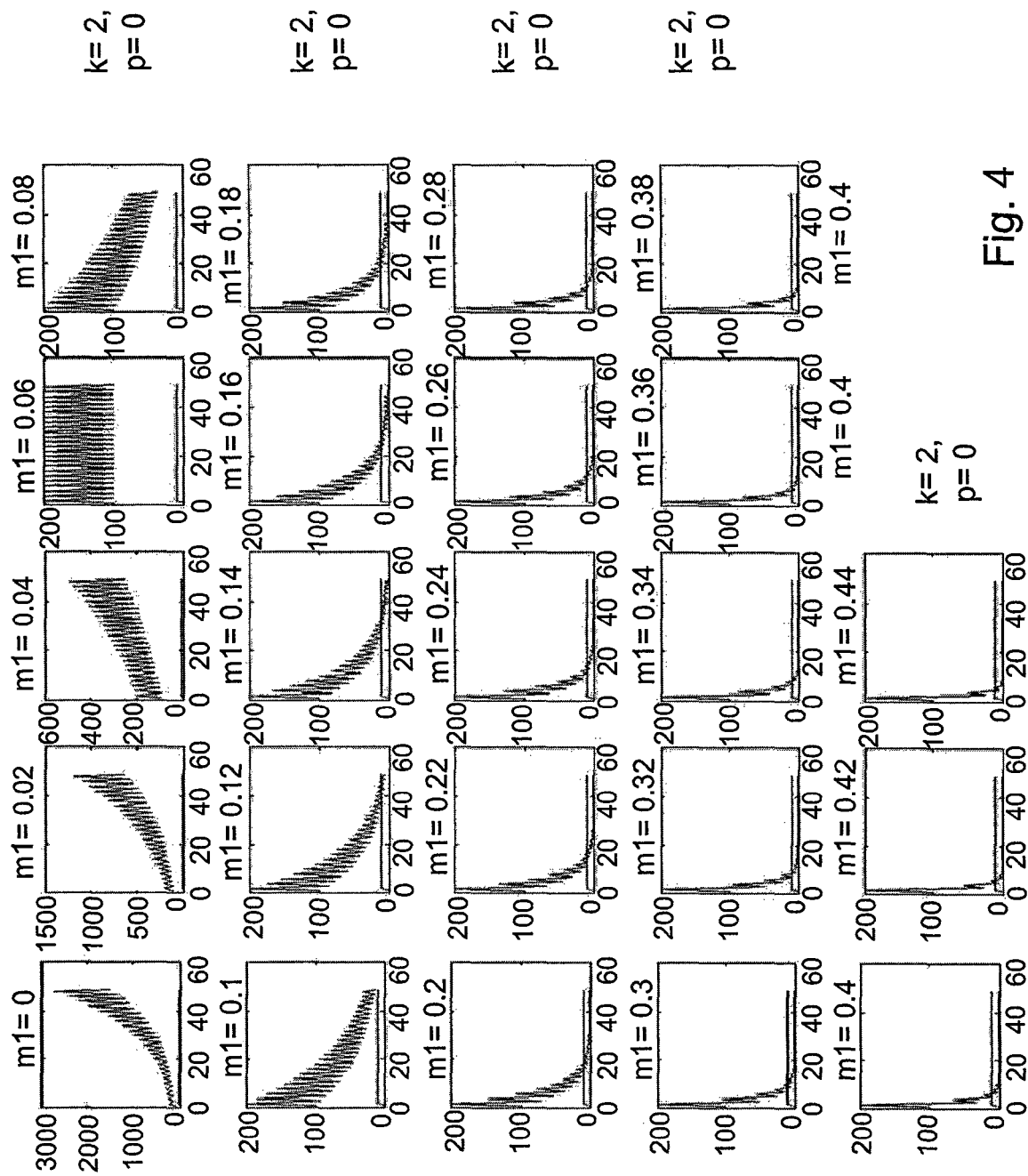
FIG. 4 shows MATLAB simulation of the model including PI administration with k=2, p=0 and M=0.44 as constant parameters and M1 being varied from 0 to 0.44. As shown by the figure, the optimal M1 should be over 0.3 using the PI treatment.

FIG. 3 shown similar simulations, however, in this simulation the virus is simulated to multiply faster and k is set to 3. The results show that the response curves for the different M's in this new situation are different (FIG. 3). For example, the virus amount is reduced at a large M value of about 0.68. In other words, for eliminating more virulent viruses, a larger M is required.

The assumption for P=0 is based on virological consideration for example once the virus penetrates the cell penetrations of other viruses from the exterior are blocked.

These two simulation results can be interpreted as follows:

First—assuming that an individual is infected with a virus, initially the immune system responds to this infection in an attempt to destroy the virus. The virus is multiplied by a rate K and the immune system of the tested subject may be viewed as a component having the rate M. The "decision" or determination if a person will be able to fight the viral infection on its own depends on the interplay between M and K as shown in FIGS. 2 and 3. The simulation using different M values may be viewed as a heterogeneous population having varying immune system capabilities.

Second—assuming that an individual is infected with a virus and is being treated with an anti viral treatment directed to distraction of the virus. The virus is multiplied by a rate K and the antiviral treatment may be viewed as a component having the rate M. The interplay between M and K as shown in FIGS. 2 and 3 may be used for determining if a person will cure from the viral infection using the treatment. The simulation with different M values may be viewed as different treatments regimens (dosing and timing), or a heterogeneous population having varying response to treatment (possibly because of immune response) or combinations of the two. In such a situation, the time unit (X-axis) may be considered as the number of treatment administrations (for example injections) to be used.

The clinical implications of this model suggest that if an intrinsic M of an individual can be measured, it may be possible to precisely predict if an individual will be able to use its own immune system to fight, eradicate and/or eliminate a viral infection (assuming K is known). This model may be further used to predict if an individual is a responder or non responder to treatment with a specific therapeutic agent, for example, IFN treatment. This can be used to predict the outcome of the response, namely what will be the viral amount (viral load) at the end of the treatment and as such, may help in determining the required dosage regimen accordingly. Moreover, this model may be used for calculating and determining the rate of the elevation in the M value required for eliminating of a specific virus having a specific K rate in a specific viral load. Such elevation of M may be achieved by designing an appropriate treatment regimen.

For example, a person that is characterized by having a M value of 0.6 is being administered with IFN in order to treat a viral infection of a virus that has a K value of 2 (namely, doubles itself every week), will need 12 injections to reach one tenth of his initial load. The results may also serve for prediction of the interval time between treatments, namely, if the time between the injections is shortened from a week to 3 days, an individual may reach the targeted virus load in half the time.

As known in the art, occasionally infectious disease/s are also treated with a new generation of compounds known as Protease Inhibitors (PI), or with a combination of interferon with any "new generation" drug. Thus, the model incorporates a further possibility that after a subject is being infected with a virus, interferon is administered together with a Protease Inhibitor.

In such a case the virus is in fact affected by interferon and the protease inhibitors, reflected by M1. Accordingly, the equation $$X(N+1)=X(N)-M*X(N);$$

is now represented as:

$$X(N+1)=X(N)-M*X(N)-M1*X(N);$$

FIG. 4 shows a simulation of a situation with K of 2, P of 0 and M is 0.44. In such case, the tuning should be M1 greater than 0.3 to shift an original non-responder person having a basic rate of M=0.44 to a responder. In fact, having a value of M1 of 0.14 seems to be sufficient to be considered as a responder.

Turning to FIG. 2, a person with M=0.44 being infected with a virus of k=2 and assume D p=0, seems not to recover from the infection. However, the use of the correct M1 value that may be achieved in this case using combined treatment with Protease Inhibitors might help as seen in FIG. 4.

M may be considered as a result of the amount of IFN genes that are released upon infection and/or upon treatment (such as for example ISG15, HERC5, USP18, OAS2, OAS 3, OASL, IFI44L). Thus, in case treatment includes PI, the M1 value is added to the value of M that may be now considered as a total amount required for eliminating existing viruses. Similarly, the methods of the invention provide any specific regimen of treatment, being personally adapted to achieve the required M1 value in a person having a particular M value that is required to achieve the desired result of virus elimination, or elimination of any of the disease symptoms.

The following examples provide results obtained from statistical analysis of data base information and are aimed at showing the importance of combining genetic data from different groups of individuals, and uses thereof in determining a suitable Taylor-made treatment for each individual. Specifically, the inventor have used data from healthy individuals, healthy individuals after stimulation of the immune system, individuals infected with different types of viruses (having different lethality potential) and patients treated with appropriate treatments. The complete data presented in the Examples below provide a comprehensive analysis and a unique understanding on a representative arsenal of genes and the degree to which each gene can be up regulated.

Moreover, the data presented herein clearly indicate that the value of M is an individual value for each subject and determination thereof (prior to the occurrence of any pathologic disorder), may reflect the ability of a given subject to overcome pathologic disorders, specifically, viral infections. Furthermore, predetermination of such characterizing M value for each individual enables determination, optimization and fine tuning of treatment regimen specifically suitable and effective for such individual.

Example 2

Gene Profiling after Viral Infections

The purpose of this example was to find a minimal representative set of genes that are regulated after infection and that measuring their expression will enable determination of the capability of an individual to overcome a viral infection. More specifically, a set of genes enabling the determination of the specific M value of a given individual.

Example 2A

Genes Expression in West Nile Virus (WNV) Infected RPE

Figure 5:
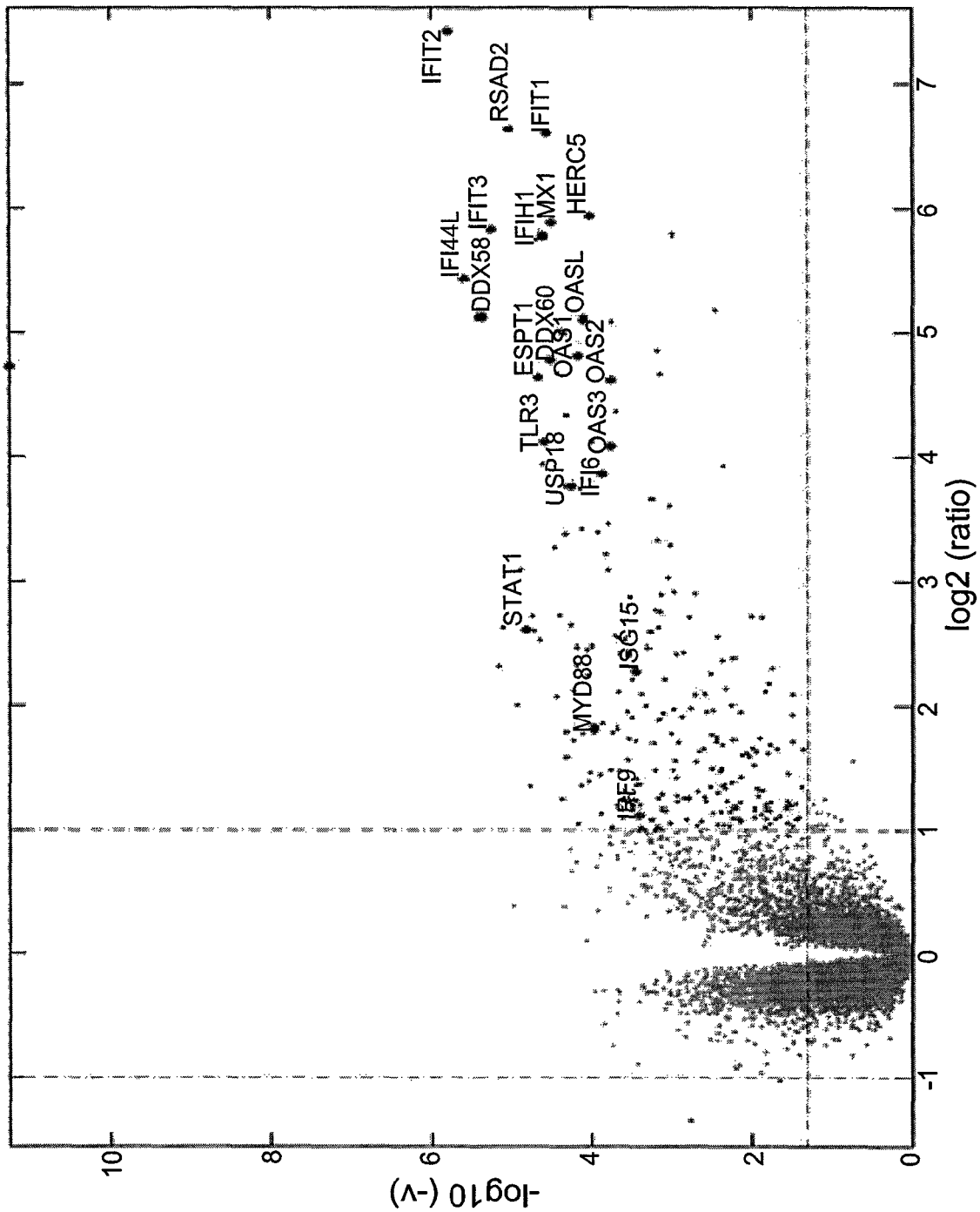
FIG. 5 is a volcano plot showing the significant changes in the expression level of different genes in West Nile virus (WNV) infected retinal pigment epithelial (RPE). Expression data was obtained Gene Expression Omnibus Accession No. GSE30719. The "X"-axis represents log 2 of ratio between gene expression measured after 24 hours after infection and a baseline level of the same gene measured before infection, the points present to the right of the right vertical line (shown at a value of 1 on the x-axis), represent genes that were up regulated by more than 2 folds. The "Y" axis shows the p value assigned to each point. The horizontal line corresponds to p-value of 0.05, with points above this line correspond to a p values lower than 0.05 (namely, more significant).

FIG. 5 shows a representation of genes, each depicted by a different point, such that each point represents the ratio of the specific gene between its expression 24 hours after infection and its base line value. Each point corresponds to an average value of the ratio of the specific gene calculated for all the tested individuals. Each gene (point) is assigned with a value along the X axis that corresponds to the regulation fold (either up regulation or down regulation) and with a value along the Y axis corresponding to the significant of the regulation. Thus, this analysis provides a quantitative indication for the dominating genes that are regulated in infected individuals with respect to a baseline level determined before infection.

The analysis was obtained by averaging all probes per gene analyzed using volcano analysis on their RMA affymetrix normalized data, at 24 h post infection.

The results indicate that in individuals who were infected with the virus, a high number of genes were up regulated. Specifically, IFIT1-5, OAS1-3L, ISG15, HERC5, USP18 and triggering genes like TLR3, IFIH1, DDX58(RIG-I)

Example 2B

Gene Expression in Macrophages Infected with H1N1 and H5N1 Viruses

As appreciated, human disease caused by highly pathogenic avian influenza (HPAI) H5N1 can lead to a rapidly progressive viral pneumonia leading to acute respiratory distress syndrome.

Figure 6:
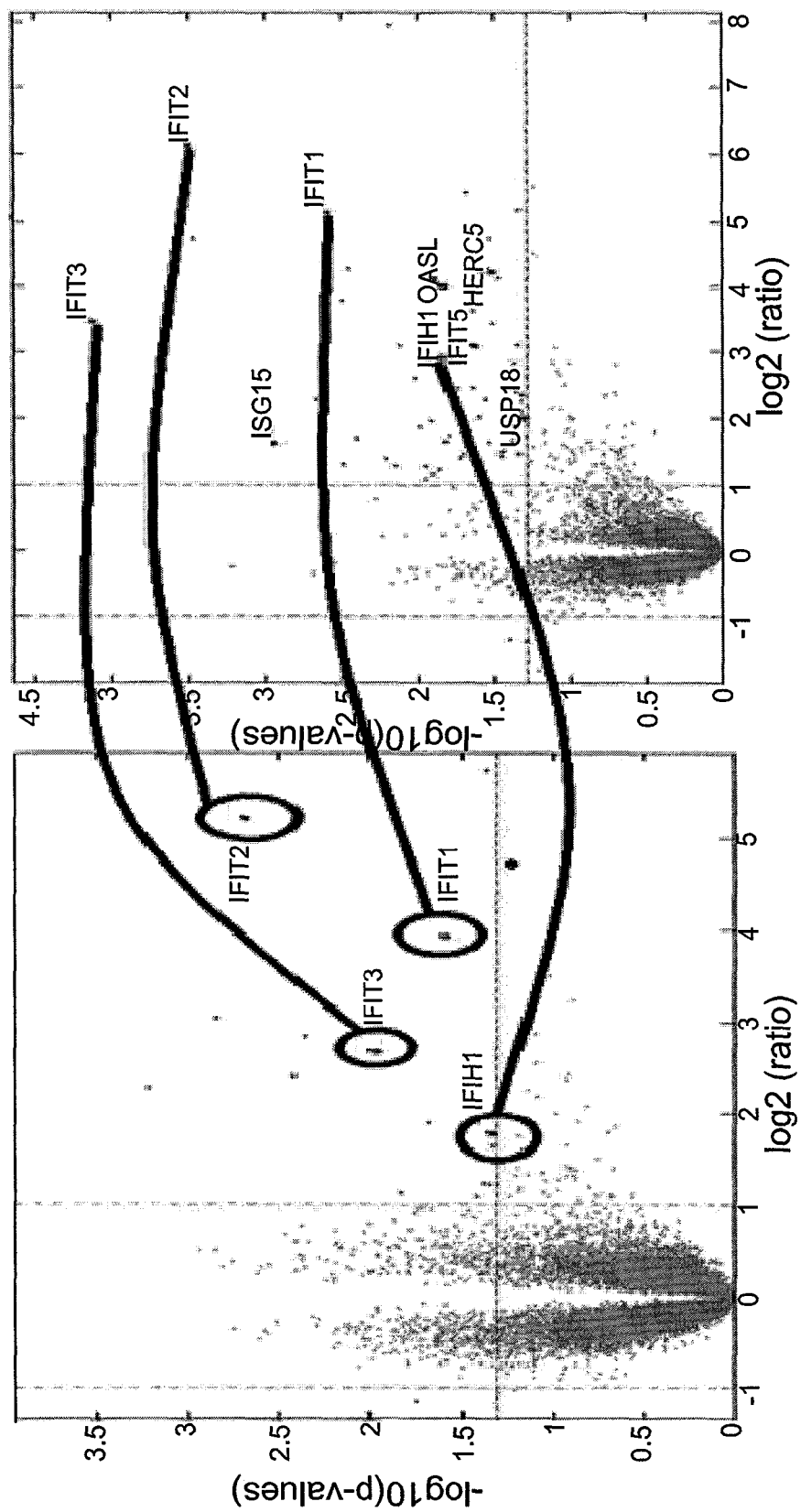
FIG. 6 is a volcano plot showing the significant changes in the expression level of different genes in H1N1 (left) compare to H5N1 (right). Expression data was obtained from Gene Expression Omnibus Accession No. GSE18816. The "X"-axis represents log 2 of ratio between gene expression measured after 6 hours after infection and a baseline level of the same gene measured before infection, the points present to the right of the right vertical line (shown at a value of 1 on the x-axis), represent genes that were up regulated by more than 2 folds. The "Y" axis shows the p value assigned to each point. The horizontal line corresponds to p-value of 0.05, with points above this line correspond to a p values lower than 0.05 (namely, more significant).

Table 1 shows a list of genes that were found to be up regulated 6 hours post infection in the more challenging H5N1 compare to H1N1. FIG. 6 is a volcano plot showing the genes that are up regulated six hours post infection with both viruses.

As shown in Table 1 and FIG. 6, the group of genes including the ISG15, HERC5, USP18, OAS, IFIT and IFI44 show an enhanced up regulation pattern after infection with H5N1.

As can be seen, the degree of up regulation for each gene is increased after infection with H5N1 compared to H1N1.

These results suggest that an increased immune response is provided by the host upon infection with H5N1 that is considered more lethal. This enhanced host response may be mediated for example by IFIH1 (MDA5) and DDX58 (RIG-I) gene products.

TABLE 1

| IFN Genes up regulated in the more challenging H5N1 compare to H1N1 at 6 hours post infection. | |
|---|---|
| Gene Name | Fold Change |
| LAMP3 | 2.019927 |
| OASL | 1.740487 |
| HERC5 | 1.66951 |
| IFNA13///IFNA1 | 1.605767 |
| RSAD2 | 1.257327 |
| ISG15 | 1.22565 |
| DDX58 | 1.22122 |
| IFIT1 | 1.173913 |
| IFIH1 | 1.141153 |
| IFNA8 | 1.098233 |
| IFIT2 | 0.884427 |
| DHX58 | 0.843863 |

TABLE 1-continued

| IFN Genes up regulated in the more challenging H5N1 compare to H1N1 at 6 hours post infection. | |
|---|---|
| Gene Name | Fold Change |
| IFIT3 | 0.7848 |
| IFI44 | 0.77259 |
| OAS2 | 0.745073 |
| USP41///USP18 | 0.739487 |
| IFIT5 | 0.722987 |
| MX1 | 0.65857 |

Example 2C

Gene Expression in Whole Blood Transcriptional Profiles of Children Infected 4 Days with Dengue Virus Genetic expression from blood obtained from children infected with dengue virus (dengue fever) that developed to dengue shock syndrome (DSS) was compared to well-matched patients with uncomplicated dengue.

Figure 7:
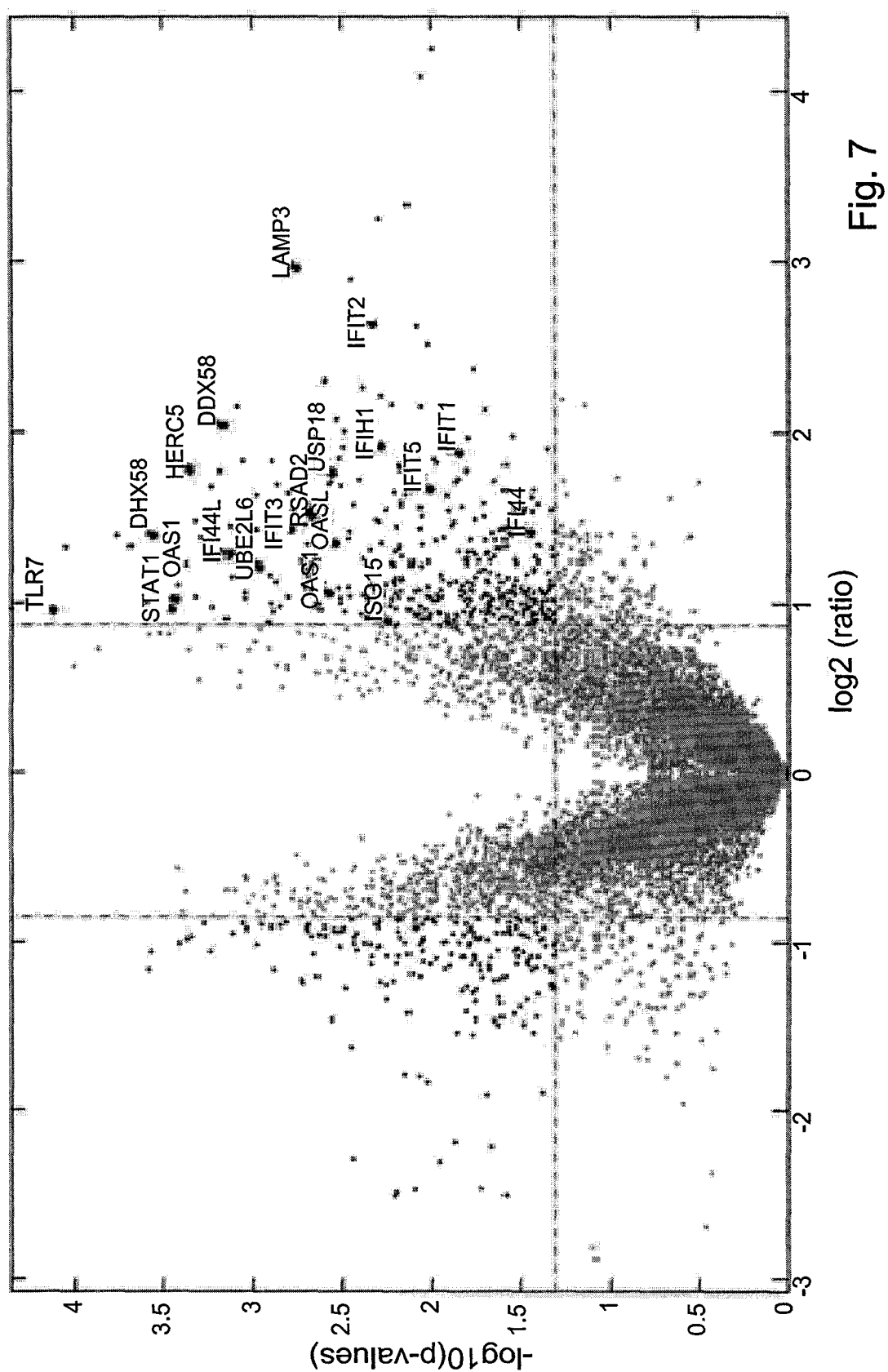
FIG. 7 is a volcano plot showing the significant changes in the expression level of different genes in blood of children infected with dengue virus. Expression data was obtained from Gene Expression Omnibus Accession No. GSE13052. The "X"-axis represents log 2 of ratio between gene expression measured 4 days after infection in 9 acute dengue shock patients and a baseline level of the same gene measured in 9 acute uncomplicated dengue patients, the points present to the right of the right vertical line (shown at a value of 1 on the x-axis), represent genes that were up regulated by more than 2 folds. The "Y" axis shows the p value assigned to each point. The horizontal line corresponds to p-value of 0.05, with points above this line correspond to a p values lower than 0.05 (namely, more significant).

FIG. 7 is a volcano plot showing the group of genes that are regulated for children presenting with dengue shock syndrome (DSS) and well-matched patients with uncomplicated dengue. The plot shows uncomplicated vs. DSS.

The genes include ISG15, HERC5, UBE2L6, USP18, OAS, IFIT, and IFI44. These results show that this set of genes is regulated to protect the host from the infection. Without being bound by any theory, the inventors suggest that this is mediated by IFIH1 (MDA5), DDX58 (RIG-I) and TLR7.

Taken together the results shown in all the individuals infected with different viruses having different lethality potential, that a representative set of genes that is being unregulated. The set of genes include for example IFIT2, RSAD2, ISIT1, HERC5, MX1, IFIT3, IFI44L, OASL, OAS1, OAS2, OAS3, DDX58, DHX58, ISG15, USP18, and UBE2L.

These genes that are involved in innate immunity may be used as an indicator for the ability of a specific individual to eliminate that pathologic disorder.

Example 3

Gene Profiling after Interferon Treatment

Example 3A

Gene Analysis in HCV Patients Treated with Interferon

Figure 8:
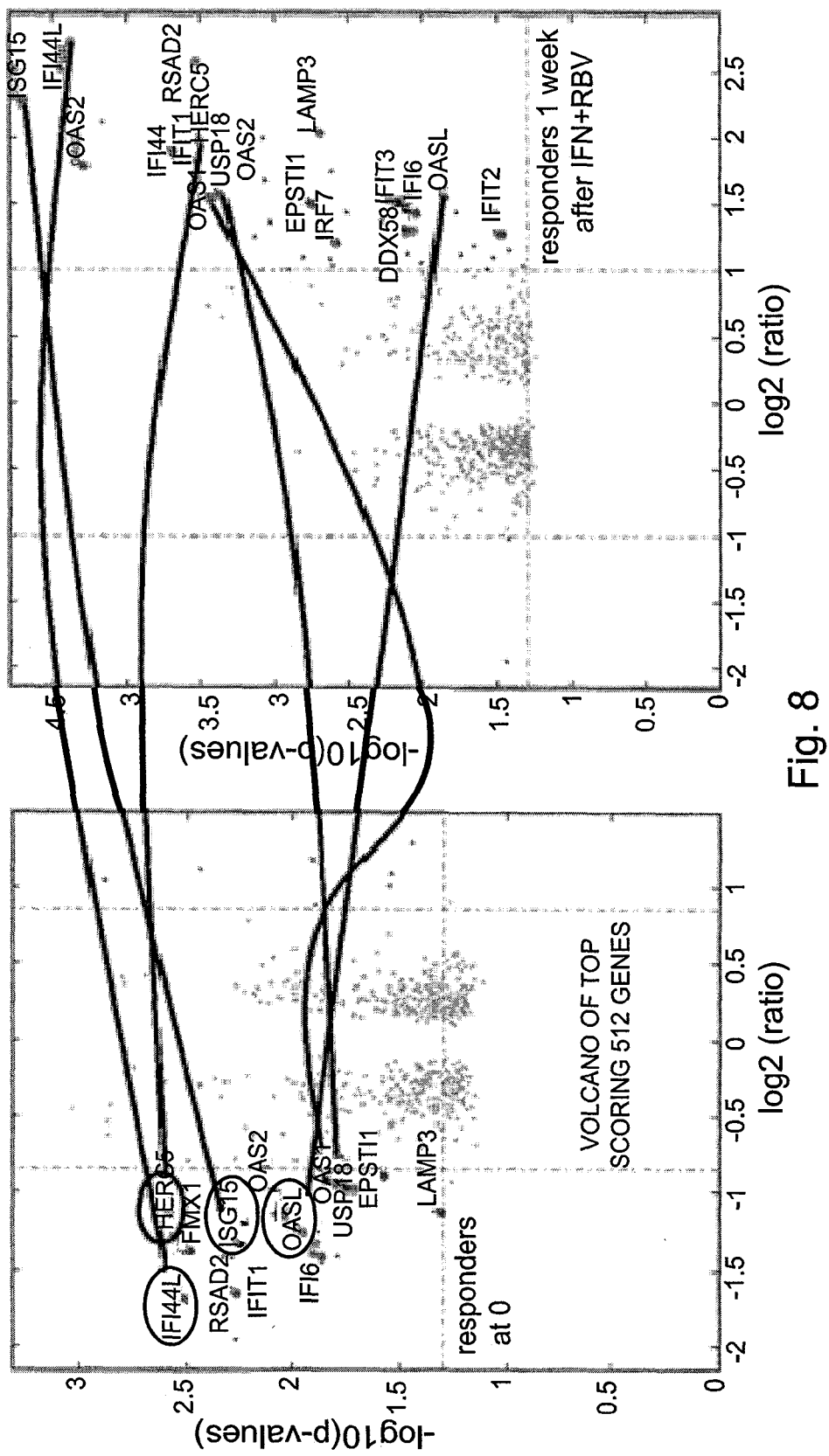
FIG. 8 is a volcano plot showing the significant changes in the expression level of different genes in liver biopsies of ten responders and ten non-responders HCV patients before treatment (left) and after one week of IFN and Rib treatment (right). Expression data was obtained from Gene Expression Omnibus Accession No. GSE17183. The "X"-axis represents log 2 of ratio between gene expression measured in responders vs. non-responders, the points present to the right of the right vertical line (shown at a value of 1 on the x-axis), represent genes that were up regulated by more than 2 folds whereas the points present to the left of the left vertical line (shown at a value of −0.75 on the x-axis), represent genes that were down regulated by more than 2 folds. The "Y" axis shows the p value assigned to each point. The horizontal line corresponds to p-value of 0.05, with points above this line correspond to a p values lower than 0.05 (namely, more significant).

The differential genetic expression in liver biopsies of responders and non-responders HCV patients after combined therapy is shown in FIG. 8. Specifically, the left hand side shows the ratio of expression level of genes in responders vs. non-responders at day 0 (namely, before treatment), whereas the right hand side shows the results obtained after one week following treatment of IFN and RBV. The results provide a representative set of genes having a low expression value before treatment in patients who are referred to as responders. One week after treatment, these genes were clearly up regulated in the responders group.

A non-limiting example is the results of ISG15 expression as specifically shown in Table 2. The initial ISG15 expression level in responders is low compared to non-responders. As shown by the Table, a week after treatment, a clear elevation in the expression of said gene appears in the responder group, whereas the non-responders show a clear reduction. Based on these results it may be suggested that the expression level of this gene in responders is close to its saturation level, and therefore interferon cannot induce elevation in the expression of these genes.

The same results were obtained for HERC5, USP18, OAS, IFIT and IFI44.

TABLE 2

Expression level of ISG15 in biopsies of ten responders and ten non-responders HCV patients before treatment and after one week of IFN and Rib treatment.

|  | non responders | responders |
|---|---|---|
| log2 expression before IFN | 9.016884851 | 7.682601881 |
| log2 change after 1 week of treatment | 0.399427605 | 2.694511557 |

The results obtained here are in accordance with previous results shown in International Patent Application WO10076788 that is a previous application by the inventor, which describes five signature genes that are up regulated before interferon treatment in patients that are considered non-responders to interferon treatment. Thus, based on the expression of the five signature genes before treatment, one can assess the probability to respond to treatment.

These finding were also repeated in additional data sets. Chen et al which gene expression from tissue taken from HCV patients before treatment in Gene Expression Omnibus Accession No. GSE 11190 provides data on tissue before and 4 hours after IFN injection. The same behavior as explained here was shown in these data sets.

Example 3B

MS Patients Treated with Interferon

Analysis of a cohort of 90 patients from PBMC samples of relapsing-remitting MS subjects and Clinically Isolated Demyelinating Syndrome (CIS) subjects.

Samples were selected at the first time point for each subject with multiple measurements based on an at least three months of treatment criteria Data was obtained Gene Expression Omnibus Accession No. GSE16214.

Figure 9:
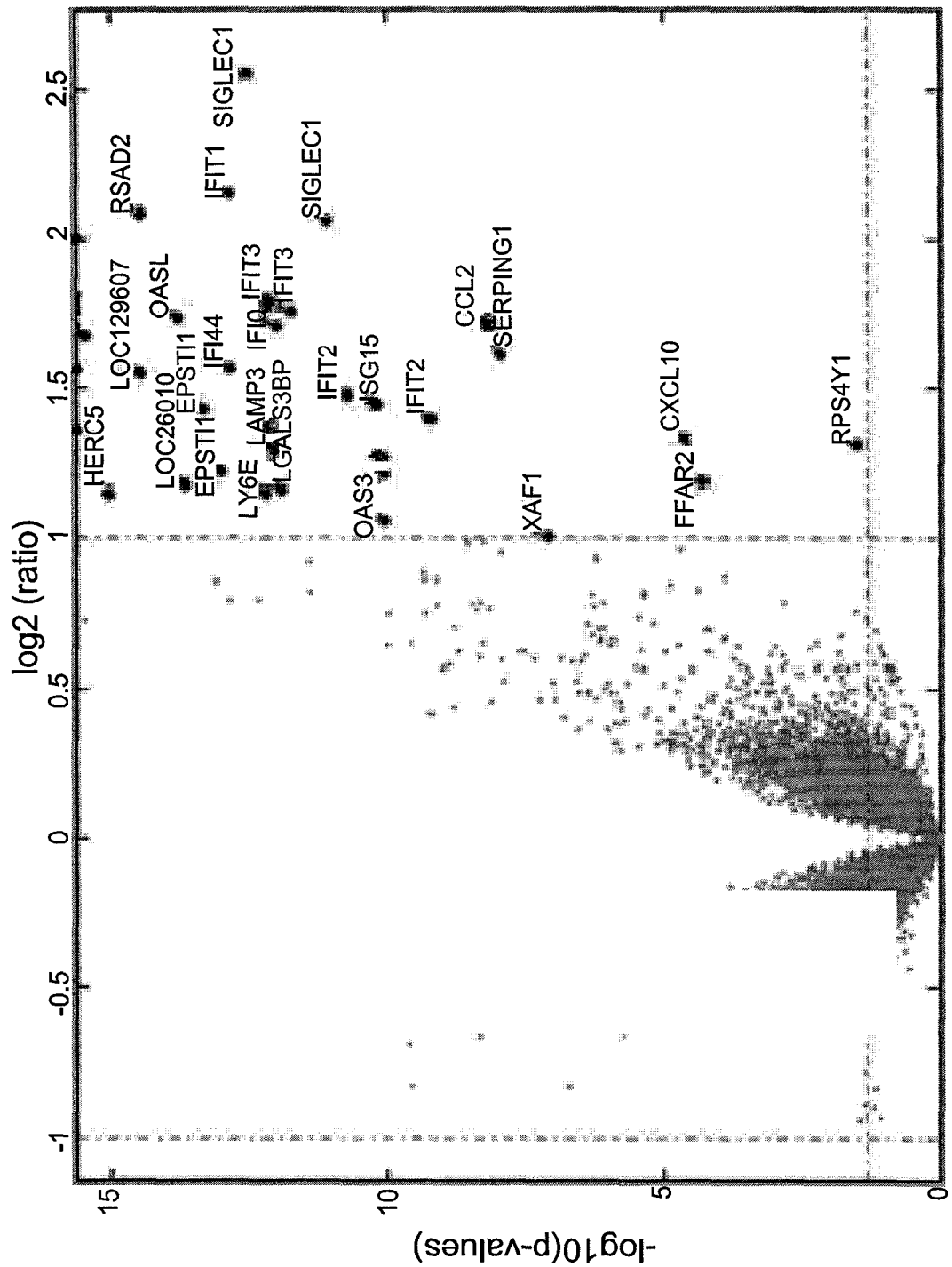
FIG. 9 is a volcano plot showing the significant changes in the expression level of different genes in MS patients three months after treatment with IFN-β. Expression data was obtained from Gene Expression Omnibus Accession No GSE16214. The "X"-axis represents log 2 of ratio between gene expression measured in after treatment, the points present to the right of the right vertical line (shown at a value of 1 on the x-axis), represent genes that were up regulated by more than 2 folds. The "Y" axis shows the p value assigned to each point. The horizontal line corresponds to p-value of 0.05, with points above this line correspond to a p values lower than 0.05 (namely, more significant).
Figure 10A:
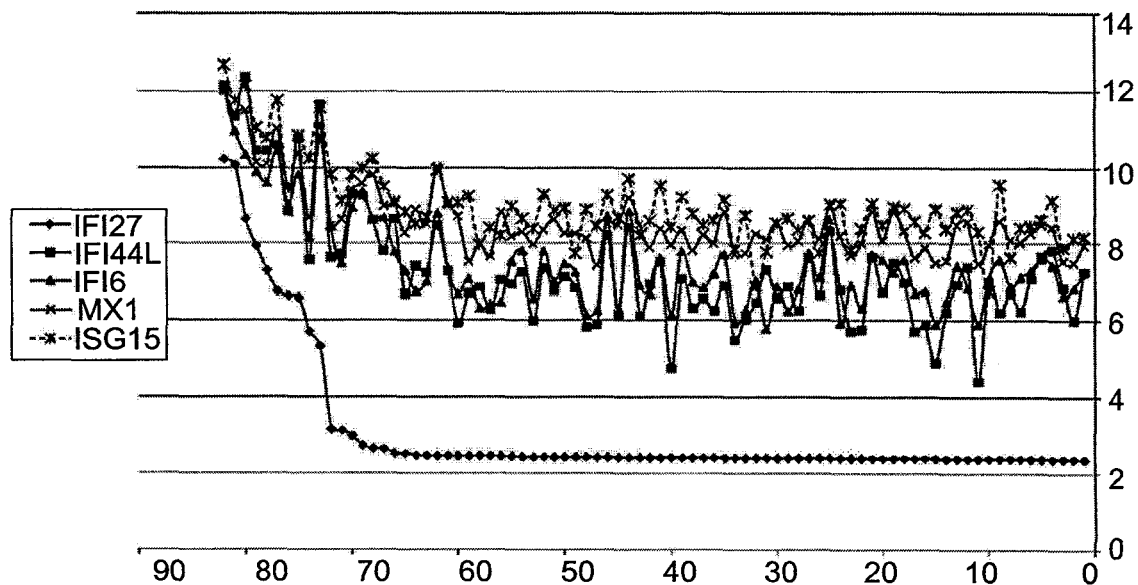
FIGS. 10A and 10B are graphs showing the expression of IFI27, IFI44L, IFI6, MX1 and ISG15 genes measured in PBMCs of MS patients before (FIG. 10A) and three month after treatment with interferon alpha (IFN-α) (FIG. 10B). Expression data was downloaded from Gene Expression Omnibus Accession No GSE16214. The "X"-axis represents the subject number and the "Y" axis represents the normalized expression level of the genes.
Figure 10B:
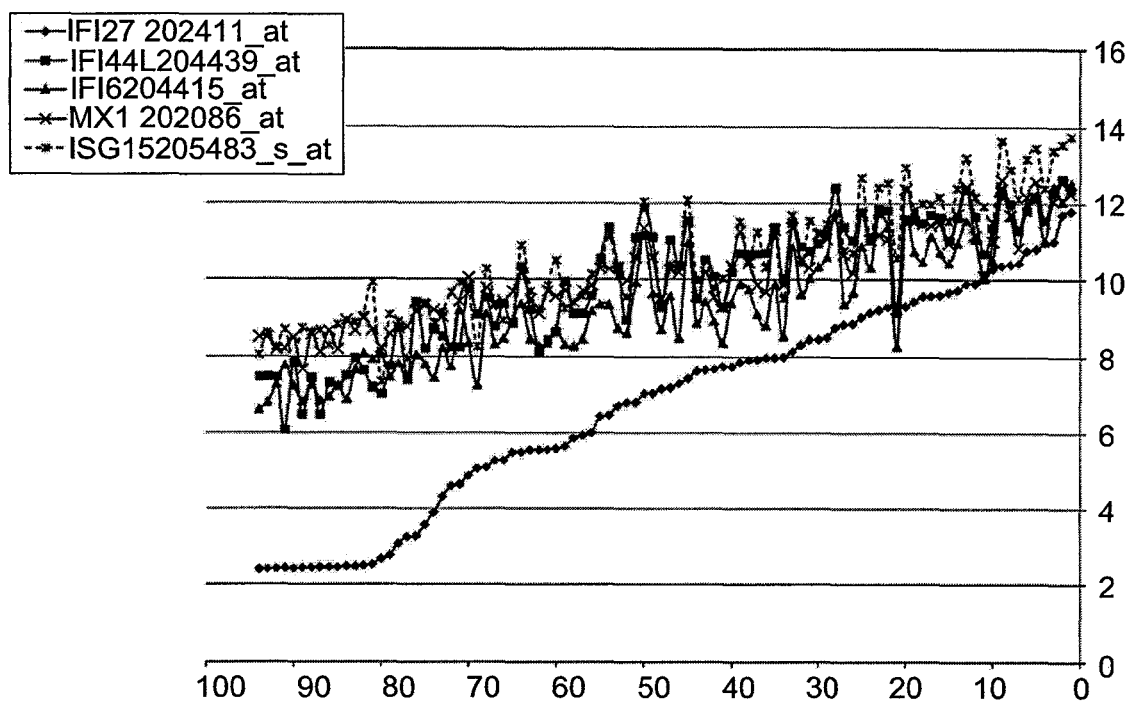

Both the volcano (FIG. 9) and the dynamic analysis disclosed in FIGS. 10A and 10B show the same observation of the determination of available dynamic range to predict the outcome of the treatment.

The volcano plot in FIG. 9 shows the genes are up regulated following treatment with IFN β compared to not-treated patients.

FIGS. 10A and 10B show the level of genes expression in MS patients before and after three month of treatment, respectively. The expression level of the genes is lower in most patients before treatment. Specifically, about 70 patients show low levels of expression and only about 20 patients show higher levels of expression (FIG. 10A). After treatment, as shown in FIG. 10B, patients who had a low gene expression before treatment (namely patients 1 to 70), show an increased expression after treatment, whereas those patients who had a high gene expression before treatment (namely patients 71 to 90), show a reduced expression after treatment.

The patients exhibiting an increase in the expression level may be considered as responders whereas the patients showing a decrease in the expression level or lack of elevation, may be considered as non-responders.

Example 3C

Gene Analysis in Poliovirus Infected Cells and Treated with Interferon

A human embryonic fibroblast cell line was synchronously infected with poliovirus in the absence or presence of interferon-α, or with vaccinia virus, a virus that is not inhibited by interferon. The samples were washed and incubated for another 4 to 16 h. Total RNA from three parallel cell cultures were used for each time point and compared with mock infected cells.

Interferon-alpha, at a concentration sufficient to inhibit poliovirus replication, was used to define genes that might be involved in viral defense.

Analysis of GSE 5549 database shows that the top genes of the Interferon are up regulated when Embryonic cells are injected with IFN (Table 3 shown 16h following injection), and Table 4, shows the elevation of gene expression at 16 hr after IFN was added to culture infected with polio virus (Table 4). Tables 3 and 4 show data from Grinde B, et al. (2007).

TABLE 3

| Name of gene | HE cells, interferon, 16 h |
|---|---|
| Interferon. alpha-inducible protein (clone IFI-15K) | 5.11 |
| Interferon. alpha-inducible protein (clone IFI-6-16) | 3.09 |
| Major histocompatibility complex. class I. C | 2.71 |
| Interferon induced transmembrane protein 2 (1-8D) | 2.63 |
| H300000271 | 2.6 |
| Lymphocyte antigen 6 complex. locus E | 2.56 |
| HLA class I histocompatibility antigen. A-3 alpha chain precursor (MHC class I antigen A*3). [Source:Uniprot/SWISSPROT:Acc:P04439] | 2.55 |
| Signal transducer and activator of transcription 1. 91 kDa | 2.483333 |
| Interferon-induced protein 44-like | 2.45 |
| Major histocompatibility complex. class I. B | 2.4 |
| Interferon-induced protein with tetratricopeptide repeats 3 | 2.29 |
| Tripartite motif-containing 22 | 2.2 |
| HLA-G histocompatibility antigen. class I. G | 2.145 |
| Ubiquitin-conjugating enzyme E2L 6 | 2.14 |
| HLA class I histocompatibility antigen. alpha chain G precursor (HLA G antigen). [Source:Uniprot/SWISSPROT:Acc:P17693] | 2.136667 |
| Major histocompatibility complex. class I. F | 2.12 |
| Beta-2-microglobulin | 2.08 |
| HLA class I histocompatibility antigen. B-7 alpha chain precursor (MHC class I antigen B*7). [Source:Uniprot/SWISSPROT:Acc:P01889] | 2.05 |
| Bone marrow stromal cell antigen 2 | 2.02 |
| Epithelial stromal interaction 1 (breast) | 2.01 |
| 2',5'-oligoadenylate synthetase 1. 40/46 kDa | 1.98 |

TABLE 4

| Name of gene | HE cells, interferon + poliovirus, 16 h |
|---|---|
| Interferon. alpha-inducible protein (clone IFI-15K) | 4.91 |
| Interferon. alpha-inducible protein (clone IFI-6-16) | 2.89 |
| Major histocompatibility complex. class I. C | 2.8 |
| Major histocompatibility complex. class I. C | 2.73 |
| Interferon induced transmembrane protein 2 (1-8D) | 2.71 |
| Interferon-induced protein 44-like | 2.7 |
| Signal transducer and activator of transcription 1. 91 kDa | 2.6 |
| Major histocompatibility complex. class I. C | 2.58 |
| Major histocompatibility complex. class I. B | 2.47 |
| Signal transducer and activator of transcription 1. 91 kDa | 2.44 |
| Major histocompatibility complex. class I. A | 2.43 |

TABLE 4-continued

| Name of gene | HE cells, interferon + poliovirus, 16 h |
|---|---|
| H300000271 | 2.38 |
| HLA class I histocompatibility antigen. B-7 alpha chain precursor (MHC class I antigen B*7). [Source:Uniprot/SWISSPROT:Acc:P01889] | 2.37 |
| major histocompatibility complex. class I. B | 2.35 |
| 2',5'-oligoadenylate synthetase 1. 40/46 kDa | 2.29 |
| Interferon-induced protein with tetratricopeptide repeats 3 | 2.28 |
| Signal transducer and activator of transcription 1. 91 kDa | 2.26 |
| HLA class I histocompatibility antigen. A-3 alpha chain precursor (MHC class I antigen A*3). [Source:Uniprot/SWISSPROT:Acc:P04439] | 2.25 |
| HLA-G histocompatibility antigen. class I. G | 2.19 |
| Tripartite motif-containing 22 | 2.18 |
| HLA-G histocompatibility antigen. class I. G | 2.16 |
| Beta-2-microglobulin | 2.15 |
| Ubiquitin-conjugating enzyme E2L 6 | 2.15 |

The results show that a set of genes can be detected in all the studied cases regardless of the viral origin, namely the set is reproducible and universal. In this connection, the M value, that reflects the ability of the specific individual to eliminate the disease symptoms (viral infection, for example), can be considered as a phenotype.

Taken together the results shown above suggest that there is a dynamic range for each gene that controls the extent to which a gene can be up regulated and down regulated. This dynamic range of a given gene is required and accordingly the protein encoded by said gene is recruited by the host for eliminating a variety of viral infections. For example, the more pathogenic virus H5N1 compared to H1N1, dengue virus in children and western Nile virus. This dynamic range varies between people as evident from the differences between responders and non responders and from the differences between people that mange to fight viral infection on their own and those who do not. The results presented herein clearly suggested that M as defined in the model above is a phenotypic properties of a specific individual.

Example 4

Figure 11:
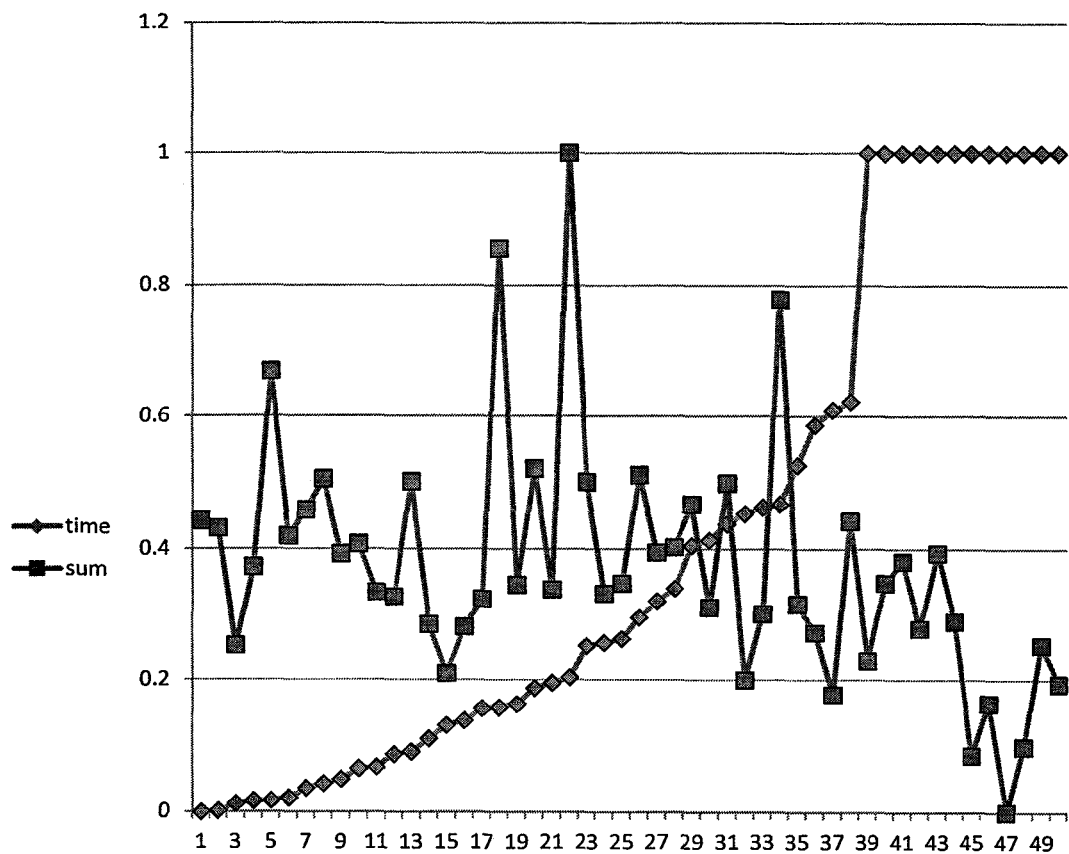
FIG. 11 is a graph showing the sum of the expression of the USP18, IFI44, MX1, IFI44L, OAS3, HERC5 and RSAD2 genes (square) and the relapse rate (diamond) of 50 MS patients (patients are indicated in the X-axis.

Inverse Correlation Between the Expression of the Genes of the Invention and Relapse in MS Patients The inventors used gene expression data of Gene Expression Omnibus Accession No. GSE15245, to determine whether the expression of the genes of the invention, namely, USP18, IFI44, MX1, IFI44L, OAS3, HERC5 and RSAD2, can distinguish between MS patients experiencing relapse and patients that respond to interferon treatment and therefore do not experience relapse. As shown in FIG. 11, sum of the expression values of these genes was inversely correlated with relapse rate of fifty MS patients. More specifically, patients 27 to 50 that displayed low initial expression level of the genes of the invention, showed no relapse, whereas patients exhibiting high expression level of the genes of the invention showed enhanced relapse rate.

The inventors have further analyzed data obtained from GSE5574 that provides gene expression data of MS patients treated with Avonex (β-interferon once a week). The expression of the ISG15, UPS18, UBE2L6 and HERC5 genes of the invention was examined before and during treatment (6 points including 2 reading nave prior to treatment, 2 readings 24 hr following first treatment, 2 readings 6 month following treatment and a week after last IFNB Avonex treatment. The expression level was compared with the following clinical parameters, wherein nonresponsive patients experienced clinical exacerbations including optic neuritis and ataxia requiring steroid treatment, none of the other patients reported any progression of symptoms during the course of the study. The non-responsive patients could not elevate the expression of the genes of the invention (data not shown). Therefore, follow-up of the expression of the signatory genes of the invention during treatment reflects the responsiveness of the patient.

Example 5

Determination of Treatment Regimen in Rheumatoid Arthritis (RA) Patients

B cell depletion therapy, for example, by using Rituximab, a chimeric monoclonal antibody against the protein CD20 which is primarily found on the surface of immune system B cells, is efficacious in rheumatoid arthritis (RA) patients that do not respond to tumor necrosis factor (TNF) blocking agents. However, approximately 40% to 50% of rituximab (RTX) treated RA patients display a poor response. The inventors therefore next explored the possibility of using the method of the invention as a tool for determining an appropriate treatment regimen for RA patients. More specifically, the invention provides for any specific individual, a molecular tool to determine whether a RTX treatment is appropriate, or alternatively, treatment with TNF blockers, such as Infliximab (INN; trade name Remicade), that is a chimeric monoclonal antibody specific for tumor necrosis factor alpha (TNF-α), may be more appropriate. Therefore, the inventors analyzed gene expression data provided by GSE 37107 and GEO 42296 that disclosed gene profiling of RA patients treated with RTX or infliximab, respectively.

More specifically, Gene Expression Omnibus Accession No. GSE 37107 provides expression profiling data of on whole peripheral blood RNA obtained from 14 RA patients treated with RTX. Expression data of 6 non responders were compared to 8 responders. Responsiveness has been determined 6 months after treatment, using disease activity score (ΔDAS28<1.2) and European League against Rheumatism (EULAR). The samples were obtained and examined prior to treatment.

Gene Expression Omnibus Accession No. GEO 42296 provides expression profiling data of whole peripheral blood RNA obtained from 29 individuals treated with infliximab and compares the gene expression profiling of 13 non-responders with 6 responders. The samples were obtained and examined prior to treatment.

The inventors have found that the genes presented in Table 5, are common to both groups and are differentially expressed in the RTX and the infliximab treatment. More specifically, the genes of Table 5, were found to be up-regulated in infliximab responders and down regulated in non-responders. In contrast, the very same genes were found to be down-regulated RTX responders, and up-regulated in RTX non-responders.

Figure 12:
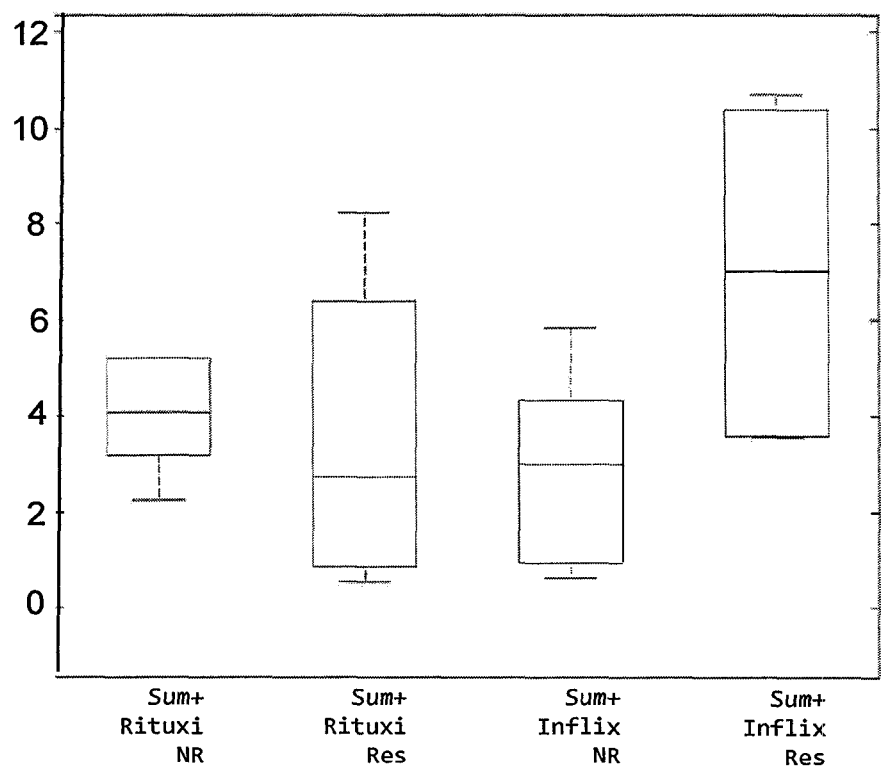
FIG. 12 is a graph illustrating the differential expression as calculated from the sum of the common genes, MX1, IFITM3, IFI44L, HERC5, IFI44, IFI6, OAS1, OAS3, RSAD2, IFIT1, IFIT3 and DDX58 in RA patients that are responders and non-responders to infliximab (influx) treatment, and responders and non-responders to RTX treatment (Rituxi=Rituximab).

FIG. 12 illustrates the differential expression as calculated from the sum of the common genes, indicating that an individual displaying a high initial expression of these genes will benefit infliximab treatment, whereas an individual displaying a low initial level of expression of these genes will benefit RTX treatment.

TABLE 5

| common signatory genes |
|---|
| MXI |
| IFITM3 |
| IFI44L |
| HERC5 |
| IFI44 |
| IFI6 |
| OAS1 |
| OAS3 |
| RSAD2 |
| IFIT1 |
| IFIT3 |
| DDX58 |

Example 6

Inverse Correlation Between the Expression of the Signatory Genes of the Invention and Responsiveness to HARRT Treatment of HIV Infected Patient To examine whether the signatory genes of the invention may have a predictive value on further viral infections and treatment of patients with other therapeutic agents, The inventors next examined whether the signatory genes of the invention, namely, IFI27, ISG15, IFIH1, IFI44L, OAS2, DDX58, IFIT1 and IFI6, may correlate with responsiveness of HIV infected patients to HAART treatment. More specifically, HIV infected patients that were treated with highly active antiviral therapies (HAART) that is a combination of multiple drugs that act on different viral targets, as reflected by the reduction in virus load.

The inventors used gene expression data of Gene Expression Omnibus Accession No. GSE18464 that provides gene expression data of high-density cDNA microarrays was performed on CD 14+ monocytes isolated from 55 subjects, 22 with HIV HVL, 22 with HIV LVL and 11 HIV seronegative controls. The examined patients were evaluated for virus load. The categorization of high or low viral load was based on clinical criteria with LVL <10,000 RNA copies/ml and HVL as >10,000 RNA copies/ml. Subjects in the study were males between 30 and 66 years of age and the cohort was comprised of white (62%), black (19%), Hispanic (12%), Asian (4%) and other (3%) individuals. At the time of the study individuals in the LVL group were on highly active antiretroviral therapies (HAART), while subjects with HVL fell into one of three categories: on HAART (15); scheduled treatment interruption (6) or HAART nave (1).

Figure 13:
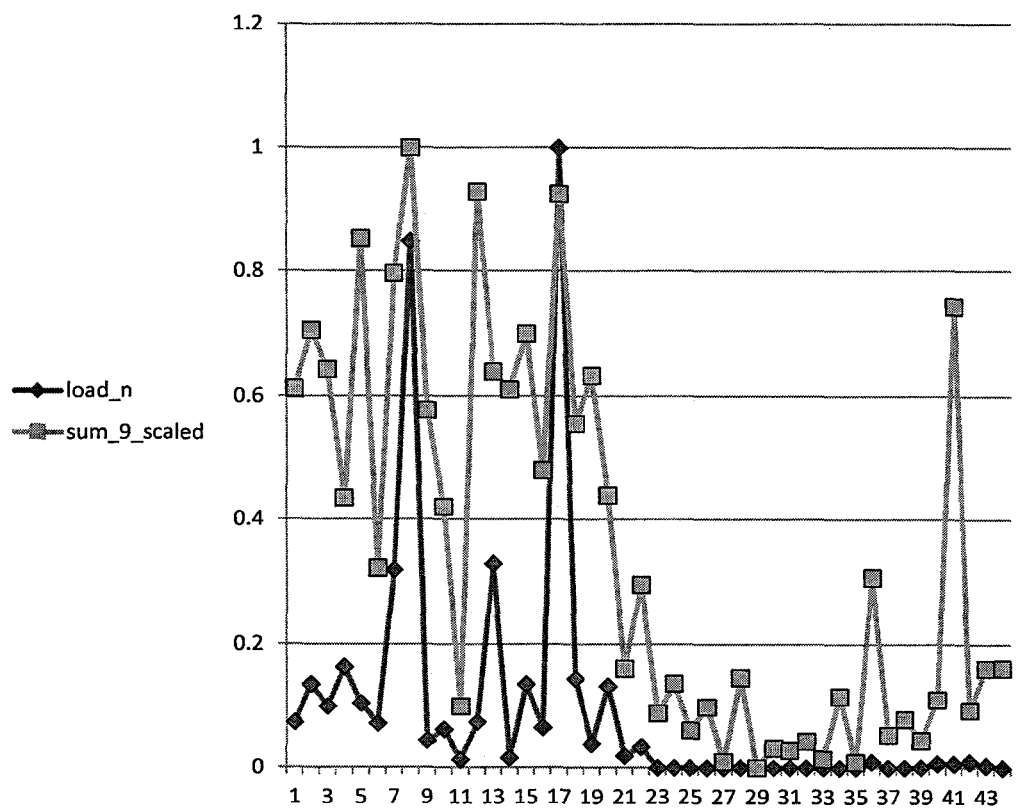
FIG. 13 is a graph showing the sum of expression of the IFI27, ISG15, IFIH1, IFI44L, OAS2, DDX58, IFIT1 and IFI6 genes in 44 HIV patients treated with HAART (squares) and the virus load (diamonds).

FIG. 13 presents the correlation between reduced virus load of the HIV patients and the initial expression of the genes of the invention in all 44 examined patients. As shown by the figure, a low expression rate of the genes of the invention is associated with a low virus load that reflects responsiveness to HAART treatment in patients 22-44 (that are the LVL group).

Example 7

In Vivo Adjuvant Activity in Ferrets Vaccinated Against Influenza Virus

Figure 14:
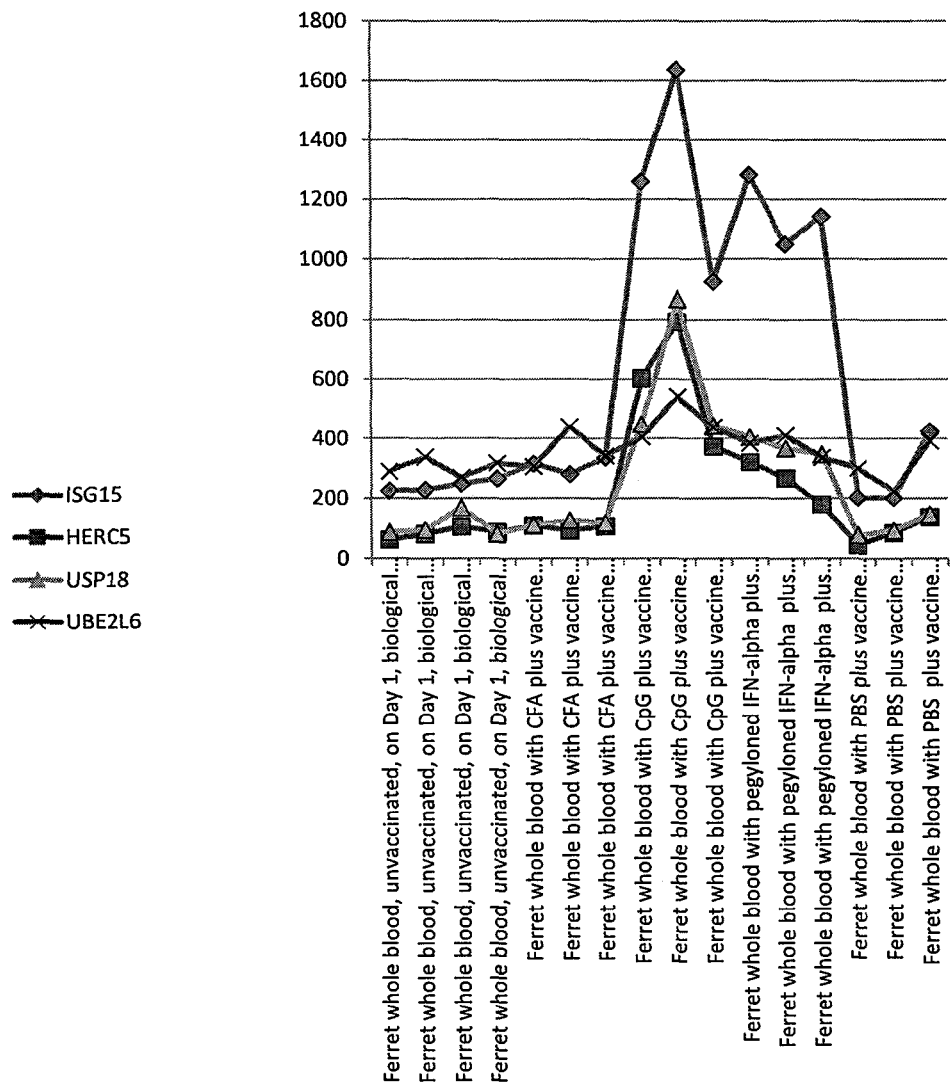
FIG. 14 is a graph showing the expression of the ISG15, HERC5, USP10 and UBE2L6 genes, in the ferret experimental groups as indicated therein.

To examine whether the signatory genes of the invention may be applicable for prediction of responsiveness in other mammals, the gene expression profile of Ferrets vaccinated against influenza virus was next analyzed. The inventors used gene expression data of Gene Expression Omnibus Accession No. GSE27248 that provides gene expression of Ferrets (3 ferrets in each group) immunized with different adjuvant human seasonal vaccines of CFA plus vaccine, CpG plus vaccine, pegylated IFN-alpha plus vaccine and vaccine alone (PBS plus vaccine). The control group comprised 4 ferrets received PBS only. The whole blood was collected for RNA extraction and subsequent gene expression analysis was performed with Affymetrix GeneChip Canine Genome 2.0 Array. The inventors analyzed the expression of the genes of the invention ISG15, HERC5, USP18 and UBE2L6, in all experimental groups. As shown in FIG. 14, a clear correlation of elevated expression of the genes of the invention is exhibited in response to treatment with CpG adjuvant. It should be noted that CpG clearly enhanced activation and antibody production, indicating that dynamic analysis of the expression of the genes of the invention may serve as a tool for evaluating successful treatment.

Example 8

Genetic Data Obtained from Healthy Populations

The purpose of these examples was to study variations of gene expression in peripheral blood leukocytes of healthy individuals and thus to obtain an individual specific finger printing.

Example 8A

PBL Samples of Healthy Individuals

Figure 15:
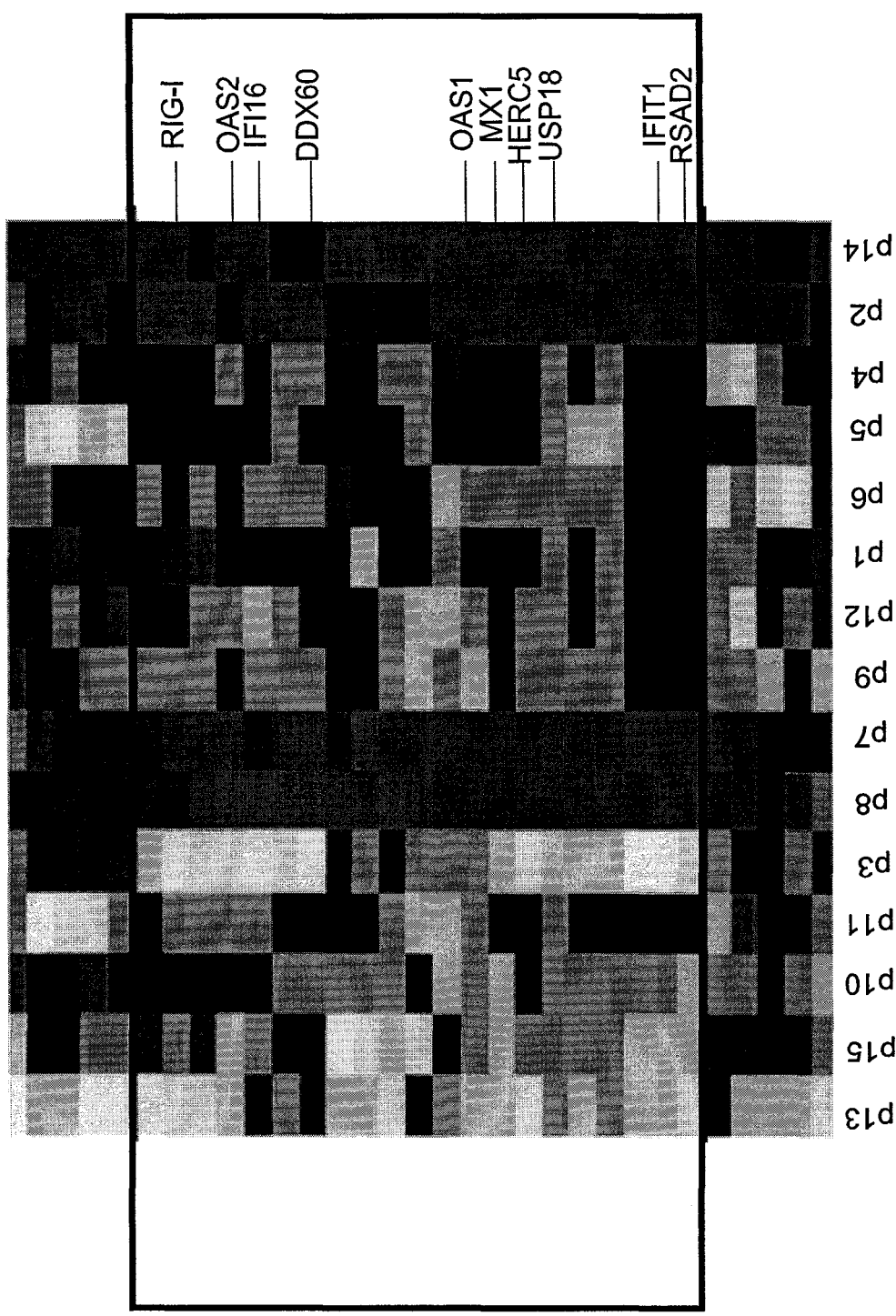
FIG. 15 is a graph showing the clustering of genes measured for a population of 15 healthy individuals. Expression data was downloaded from Gene Expression Omnibus Accession No GSE838. The "X" axis denotes the tested individual and the "Y" axis represents the measured genes.

The data used herein was obtained from peripheral blood leukocytes (PBL) of normal individuals sampled multiple times over periods ranging from several weeks up to 6 months. The genetic data obtained after the first reading for each individual was clustered using k-mean clustering algorithm. FIG. 15 shows the clustering results of the tested individuals, as can be seen, the genes that are clustered within one group include for example ISG15, HERC5, USP18 OAS and IFIT and their triggering elements RIG-I and DDX60. The expression of these genes is correlated and changes together in healthy individuals between high and low levels of expression.

The close ties between these genes can be better appreciated by looking at Table 5 showing the measured correlation to each of these genes.

TABLE 6 correlation between ISG15 and all other genes

| Column # | Column ID | r | p-value correlation | Lower CI | Upper CI | N |
|---|---|---|---|---|---|---|
| 3694 | FLJ11354 | 0.930123 | 5.11E−07 | 0.79815 | 0.976917 | 15 |
| 8622 | MX1 | 0.925057 | 7.95E−07 | 0.784585 | 0.9752 | 15 |
| 7251 | KPTN | 0.92249 | 9.83E−07 | 0.777762 | 0.974328 | 15 |
| 1522 | cig5 | 0.919924 | 1.21E−06 | 0.770975 | 0.973454 | 15 |
| 5764 | IFIT4 | 0.917704 | 1.43E−06 | 0.76513 | 0.972697 | 15 |
| 12247 | TREX1 | 0.903768 | 3.83E−06 | 0.72901 | 0.967918 | 15 |
| 2307 | DKFZp434J0310 | 0.893967 | 7.02E−06 | 0.704176 | 0.964529 | 15 |

TABLE 6-continued correlation between ISG15 and all other genes

| Column # | Column ID | r | p-value correlation | Lower CI | Upper CI | N |
|---|---|---|---|---|---|---|
| 12478 | USP18 | 0.893168 | 7.36E−06 | 0.702173 | 0.964252 | 15 |
| 8030 | LY6E | 0.891366 | 8.17E−06 | 0.697663 | 0.963625 | 15 |
| 6185 | KIAA0082 | 0.887221 | 1.03E−05 | 0.687348 | 0.962182 | 15 |
| 5763 | IFIT1 | 0.884509 | 1.20E−05 | 0.680644 | 0.961236 | 15 |
| 924 | BST2 | 0.883635 | 1.25E−05 | 0.67849 | 0.960931 | 15 |
| 12390 | UBE2L6 | 0.882725 | 1.31E−05 | 0.67625 | 0.960612 | 15 |
| 9071 | OAS1 | 0.871427 | 2.32E−05 | 0.648773 | 0.956645 | 15 |
| 7574 | LOC51191 | 0.870744 | 2.40E−05 | 0.647129 | 0.956404 | 15 |
| 9942 | PRKR | 0.868662 | 2.65E−05 | 0.642136 | 0.955669 | 15 |
| 8572 | MTAP44 | 0.86321 | 3.40E−05 | 0.629145 | 0.95374 | 15 |
| 5758 | IFI27 | 0.860744 | 3.80E−05 | 0.623314 | 0.952865 | 15 |
| 4966 | GS3686 | 0.855596 | 4.75E−05 | 0.611221 | 0.951032 | 15 |
| 5760 | IFI35 | 0.853527 | 5.18E−05 | 0.606915 | 0.950294 | 15 |
| 9158 | OS4 | 0.852918 | 5.32E−05 | 0.604976 | 0.950076 | 15 |
| 9131 | OR1F1 | 0.847821 | 6.55E−05 | 0.593175 | 0.948253 | 15 |
| 47 | ABCC1 | 0.828275 | 0.000137 | 0.548906 | 0.941196 | 15 |
| 7728 | LOC51667 | 0.827948 | 0.000138 | 0.548179 | 0.941077 | 15 |
| 10972 | SCO2 | 0.813388 | 0.000226 | 0.516209 | 0.935754 | 15 |
| 2505 | DKFZP586A0522 | 0.805792 | 0.000287 | 0.499852 | 0.932954 | 15 |
| 5654 | HSXIAPAF1 | 0.800053 | 0.000342 | 0.487637 | 0.930829 | 15 |
| 10571 | REC8 | 0.798916 | 0.000354 | 0.485213 | 0.930407 | 15 |
| 4554 | G1P3 | 0.794898 | 0.000398 | 0.47677 | 0.928913 | 15 |
| 3532 | FLJ10783 | 0.785073 | 0.000526 | 0.456321 | 0.92524 | 15 |
| 8997 | NRGN | 0.782342 | 0.000567 | 0.450698 | 0.924214 | 15 |
| 5961 | IRF7 | 0.781768 | 0.000576 | 0.44952 | 0.923999 | 15 |
| 3907 | FLJ20037 | 0.779139 | 0.000618 | 0.444136 | 0.923009 | 15 |
| 5509 | HSPC018 | 0.767953 | 0.000827 | 0.421502 | 0.918777 | 15 |
| 9558 | PIK3R2 | 0.765603 | 0.000878 | 0.416799 | 0.917883 | 15 |
| 3811 | FLJ13102 | 0.758369 | 0.00105 | 0.402444 | 0.915123 | 15 |
| 4012 | FLJ20281 | 0.755838 | 0.001116 | 0.397462 | 0.914154 | 15 |
| 6423 | KIAA0456 | 0.75358 | 0.001177 | 0.393035 | 0.913288 | 15 |
| 5970 | ISG20 | 0.749655 | 0.001291 | 0.385382 | 0.911779 | 15 |

Figure 16:
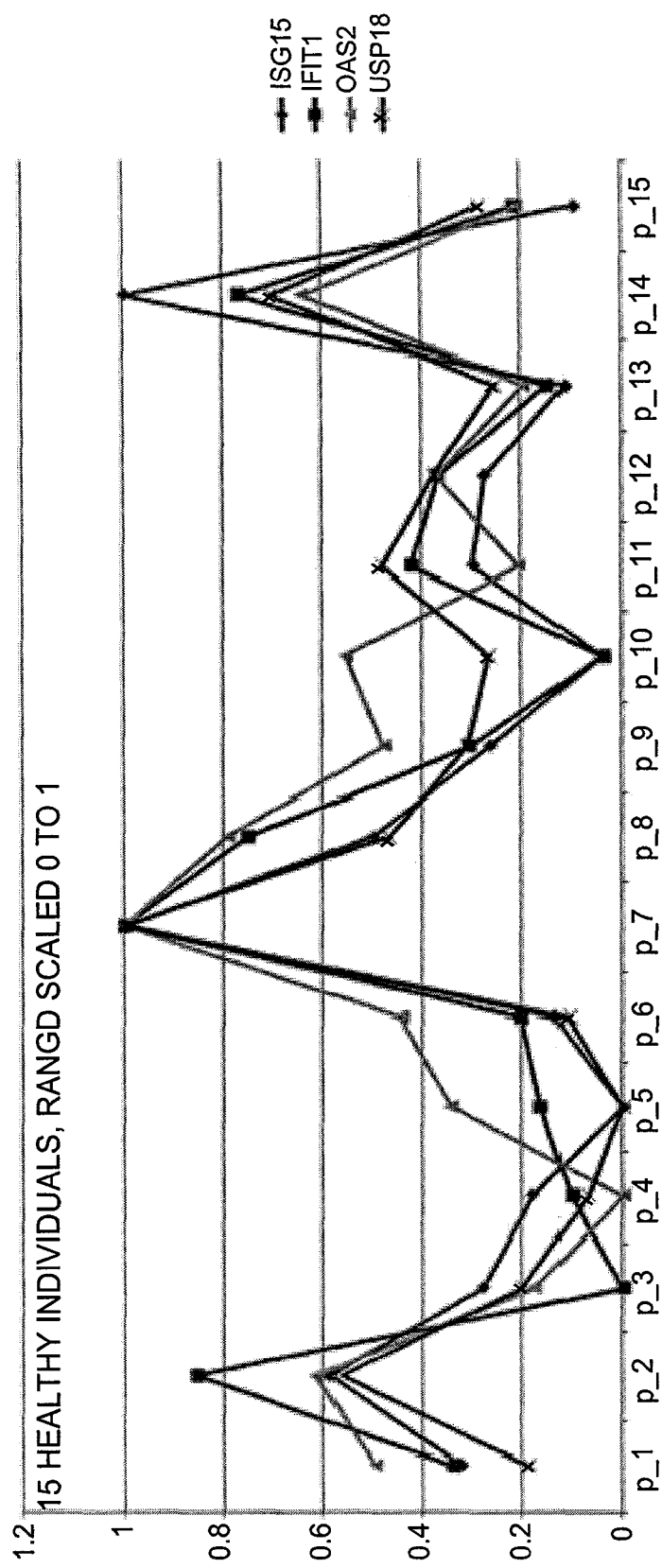
FIG. 16 is a graph showing the expression of IGS15, IFIT1, OAS2 and USP18 genes measured in healthy individuals. Expression data was downloaded from Gene Expression Omnibus Accession No GSE838 the "X"-axis represents the subject number (patients 1-15) and the "Y" axis represents the normalized expression level of the genes ranging from 0 to 1.

FIG. 16 shows the same expression but specially demonstrates the expression of IGS15, IFIT1, OAS2 and USP18 in the tested healthy individuals.

Using the clustering data (FIG. 15) and the specific genes expression graph (FIG. 16), it may be concluded that individuals 2, 7, 8 and 14 who express high levels of the genes at base line namely healthy individuals, will not benefit from IFN treatment if required.

The other individuals that are characterized by a low expression level would probably respond to IFN and in addition may have a better immune-response.

Example 8B

A similar approach was used to analyze a large cohort of 145 healthy individuals.

More specifically, a large dataset of 145 individuals was used to observe variation in gene expression patterns in blood, by using cDNA microarrays. Again in this group the correlated pattern of the IFN genes reappears as shown by the gene expression correlation in Table 7.

TABLE 7 correlation of genes with ISG15.

| Column # | Column ID | r | p-value (correlation) | Lower CI | Upper CI | N |
|---|---|---|---|---|---|---|
| 7036 | OAS3 | 0.744385 | 7.40E−27 | 0.661661 | 0.809205 | 145 |
| 4648 | IFIT1 | 0.72467 | 6.83E−25 | 0.636894 | 0.793899 | 145 |
| 8999 | SERPING1 | 0.708683 | 2.03E−23 | 0.616943 | 0.781422 | 145 |
| 4647 | IFI6 | 0.701859 | 8.06E−23 | 0.608461 | 0.776078 | 145 |
| 5868 | LY6E | 0.694095 | 3.69E−22 | 0.598839 | 0.769986 | 145 |
| 4646 | IFI44L | 0.693568 | 4.09E−22 | 0.598186 | 0.769572 | 145 |
| 7035 | OAS2 | 0.688079 | 1.16E−21 | 0.591402 | 0.765256 | 145 |
| 2079 | CMPK2 | 0.668012 | 4.39E−20 | 0.566711 | 0.749417 | 145 |
| 6487 | MX2 | 0.640268 | 4.28E−18 | 0.532872 | 0.727364 | 145 |
| 6486 | MX1 | 0.633634 | 1.20E−17 | 0.524832 | 0.722064 | 145 |
| 7202 | PARP14 | 0.625737 | 3.93E−17 | 0.515285 | 0.715741 | 145 |
| 3839 | GBP1 | 0.603309 | 9.68E−16 | 0.488322 | 0.697704 | 145 |
| 9739 | STAT1 | 0.593401 | 3.68E−15 | 0.47648 | 0.689698 | 145 |
| 9204 | SLC22A23 | 0.578805 | 2.43E−14 | 0.459111 | 0.67786 | 145 |
| 4649 | IFIT2 | 0.575336 | 3.76E−14 | 0.454997 | 0.675039 | 145 |
| 7209 | PARP9 | 0.560641 | 2.25E−13 | 0.437624 | 0.663056 | 145 |
| 6230 | MLC1 | 0.536979 | 3.34E−12 | 0.409841 | 0.643649 | 145 |
| 8743 | RTP4 | 0.526616 | 1.21E−11 | 0.397258 | 0.635454 | 144 |
| 3517 | FCGR1A | 0.520442 | 1.95E−11 | 0.390565 | 0.630006 | 145 |
| 3840 | GBP2 | 0.50984 | 5.76E−11 | 0.378266 | 0.621222 | 145 |

TABLE 7-continued correlation of genes with ISG15.

| Column # | Column ID | r | p-value (correlation) | Lower CI | Upper CI | N |
|---|---|---|---|---|---|---|
| 10725 | UBE2L6 | 0.503062 | 1.13E−10 | 0.370427 | 0.615592 | 145 |
| 4845 | ISG20 | 0.500953 | 1.39E−10 | 0.367991 | 0.613838 | 145 |
| 4651 | IFIT5 | 0.49784 | 1.88E−10 | 0.3644 | 0.611247 | 145 |
| 10495 | TRIM22 | 0.497346 | 1.97E−10 | 0.363831 | 0.610836 | 145 |
| 4644 | IFI35 | 0.494534 | 2.58E−10 | 0.360591 | 0.608492 | 145 |
| 1645 | CCR1 | 0.493976 | 2.72E−10 | 0.359949 | 0.608028 | 145 |
| 4640 | IFI16 | 0.492824 | 3.04E−10 | 0.358622 | 0.607066 | 145 |

Figure 17:
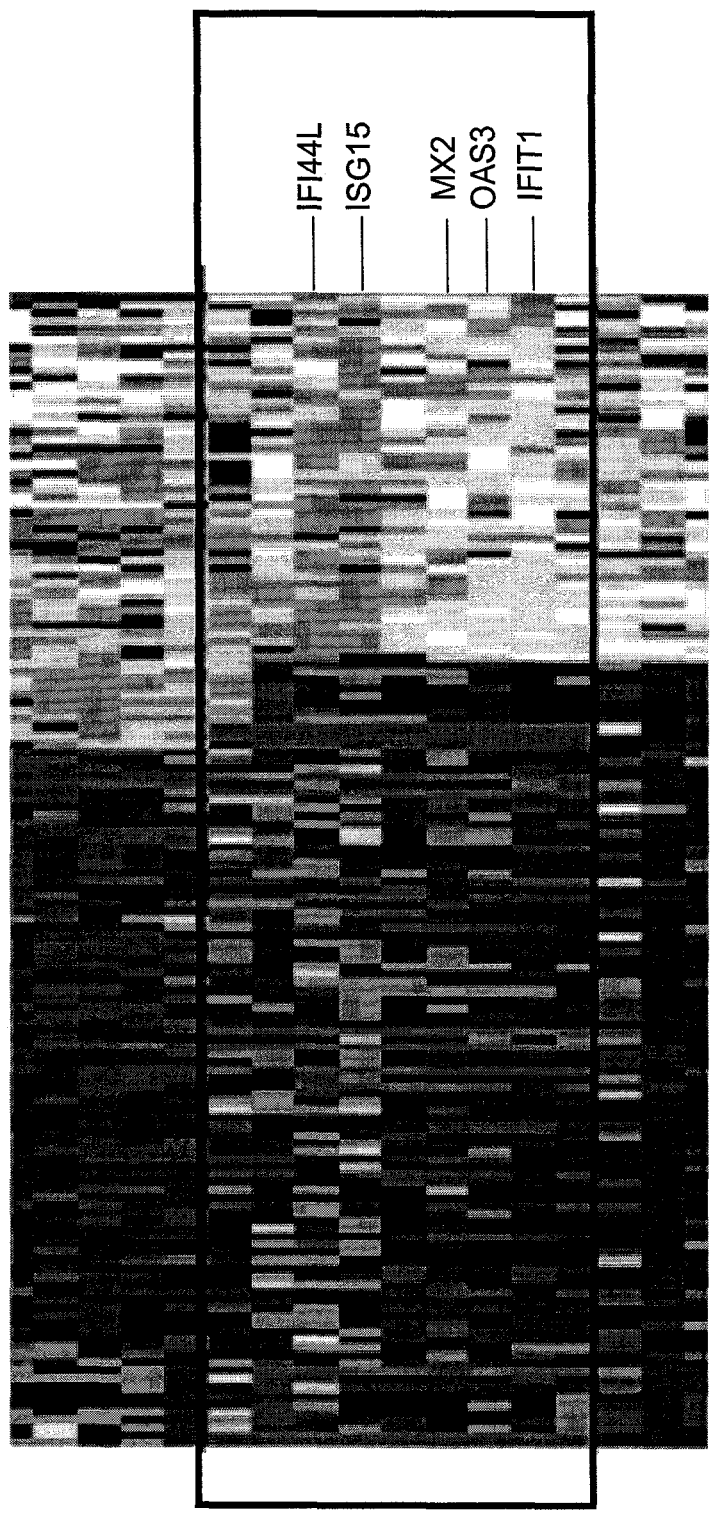
FIG. 17 is a graph showing the clustering of genes measured for a population of 145 healthy individuals. Expression data was downloaded from Gene Expression Omnibus Accession No GSE3649. The "X" axis denotes the tested individual and the "Y" axis represents the measured genes

Analysis of the data by clustering is shown in FIG. 17 demonstrating the genes clustering together in one group include for example LY6E, SLC22A23, IFI44L, ISG15, SERPING1, MX2, OAS3, IFIT1 and CMPK2.

Figure 18:
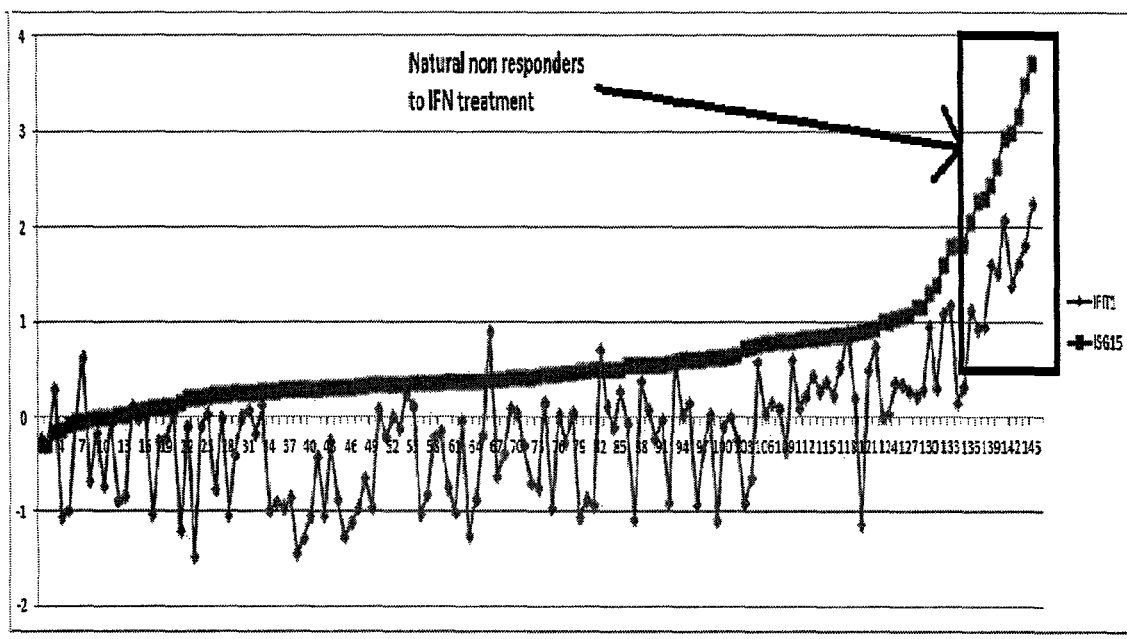
FIG. 18 is a graph showing the expression IGS15 and IFIT1 gene measured in healthy individuals. Expression data was downloaded from Gene Expression Omnibus Accession No. GSE3649. The "X"-axis represents the subject number and the "Y" axis represents the normalized expression level of the genes ranging from 0 to 1.

FIG. 18 shows an expression graph showing the expression level of ISG15 and IFIT1, where the individuals were sorted by the ISG15 expression level and not by the individual numbering. It can be suggested that the individuals in the right hand side of the graph (provided in the rectangular) would be non responsive to IFN as the initiation level of the genes is high before any treatment or pathological infection.

Example 9

Dynamic Analysis of Stimulated Healthy Individuals

As noted above, changes in the expression levels of genes are observed between cohorts of populations (healthy, infected but not treated yet and treated individuals) and well as between individuals that are responsive or non-responsive. One of the challenges was to quantify the dynamic range of a gene, namely what is the possible expression level a gene can exhibit.

In fact, it can be suggested that understanding and measuring this dynamic range of a set of known genes may help in determine the capabilities of an individual to use its own immune system in response to infection and/or the predicting if an individual will respond to interferon treatment, namely should interferon be administered to a patients as part of any medical treatment.

The data provided in Gene Expression Omnibus Accession No. Gse32862 provides information on the innate immune response in humans in response to synthetic double stranded RNA (poly ICLC), a ligand for TLR3 and MDA-5 cytosolic RNA helicase. poly ICLC is an immuno-stimulant and may be considered to have the same effect as interferon.

The study included transcriptional analysis of blood samples obtained from eight volunteers at different time points, after subcutaneous administration of poly ICLC.

Figure 19:
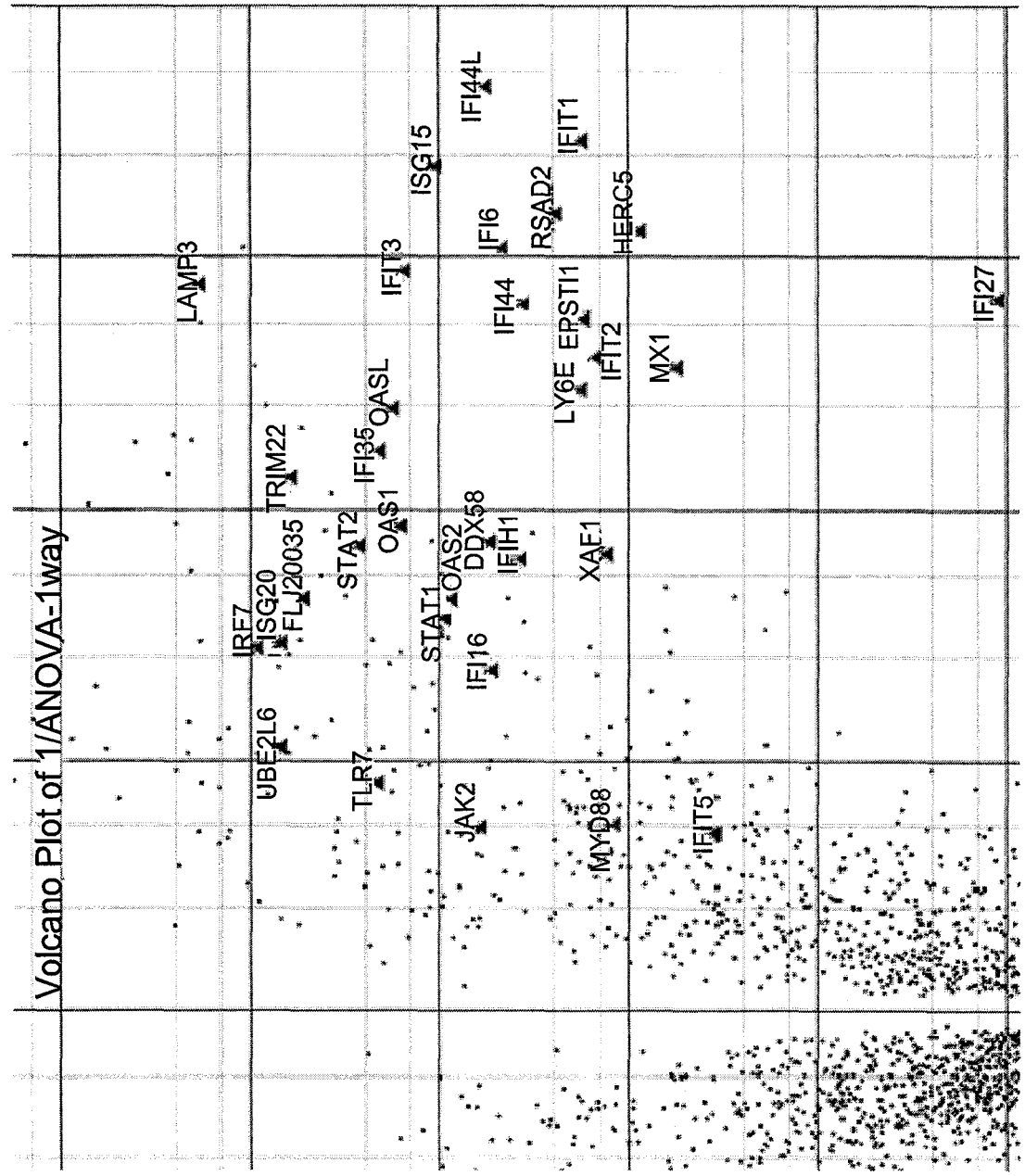
FIG. 19 is a volcano plot showing the significant changes in the expression level of different genes in healthy individuals 24 hours following injection of poly ICLC. Expression data was obtained from Gene Expression Omnibus Accession No GSE32862. The "X"-axis represents log 2 of ratio between gene expression measured 24 hours as compared to base line level before administration, the points present to the right of the right vertical line (shown at a value of 1 on the x-axis), represent genes that were up regulated by more than 2 folds. The "Y" axis shows the p value assigned to each point. Abbreviations: val. (value); rat. (ratio).
Figure 20:
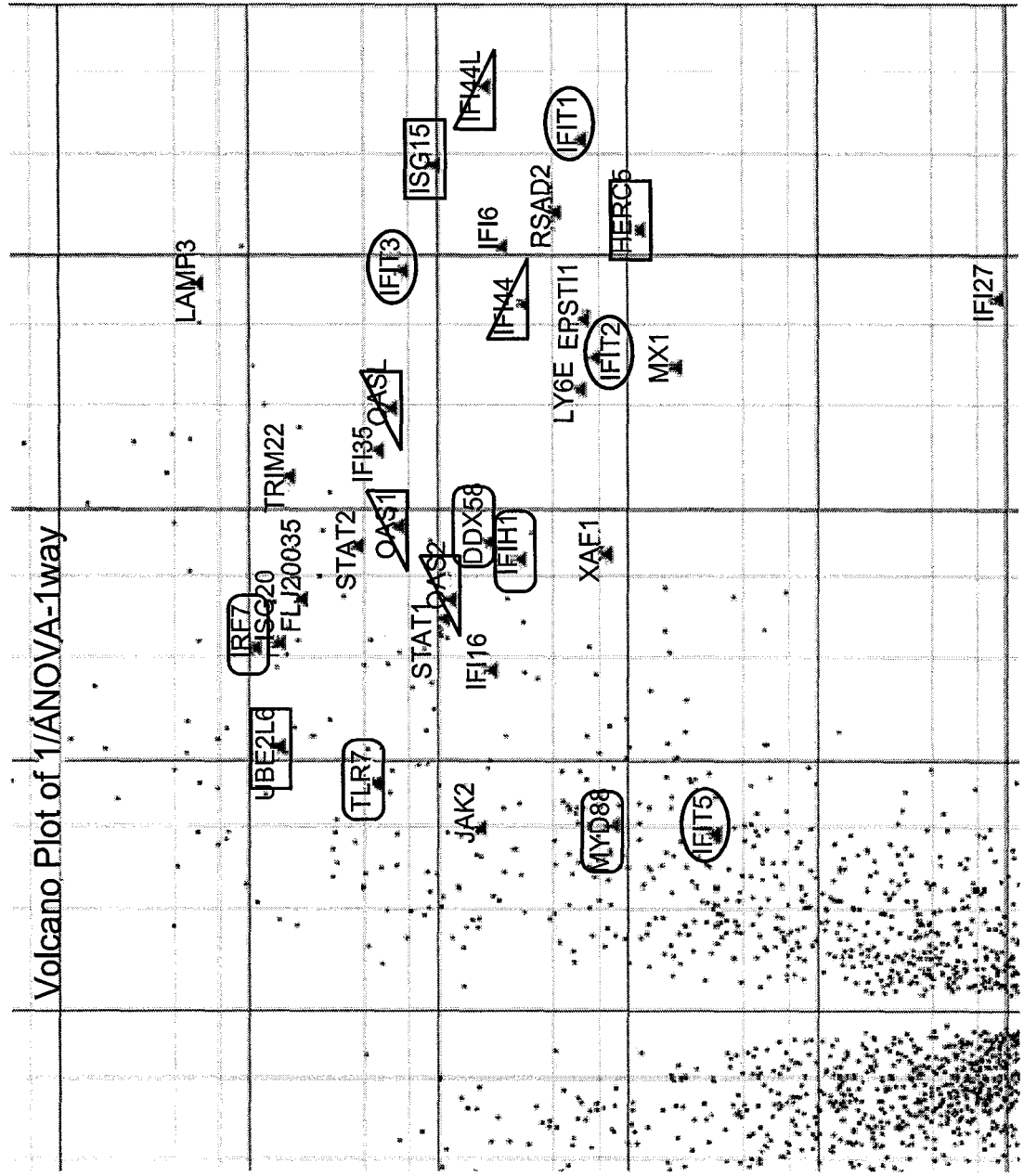
FIG. 20 is a volcano plot showing the significant changes in the expression level of different genes in healthy individuals 24 hours following injection of poly ICLC. Expression data was obtained from Gene Expression Omnibus Accession No GSE32862. The "X"-axis represents log 2 of ratio between gene expression measured 24 hours as compared to base line level before administration, the points present to the right of the right vertical line (shown at a value of 1 on the x-axis), represent genes that were up regulated by more than 2 folds. The "Y" axis shows the p value assigned to each point. Abbreviations: val. (value); rat. (ratio). The genes ISG15, HERC5 and UBE2L6 are given in squares, IFI44 set (in triangle pointing right), IFIT set (in circles), OAS set (in triangles pointing left), triggers DDX58, TLR7, IFIH1, MYd88.

The data analysis showed a peak in gene expression 24 hr following injection of poly ICLC (FIG. 19). FIG. 20 is a magnified volcano showing ISG15, IFIT1, IFI44, OASL and the triggering of IFIH1 and DDX58.

Figure 21:
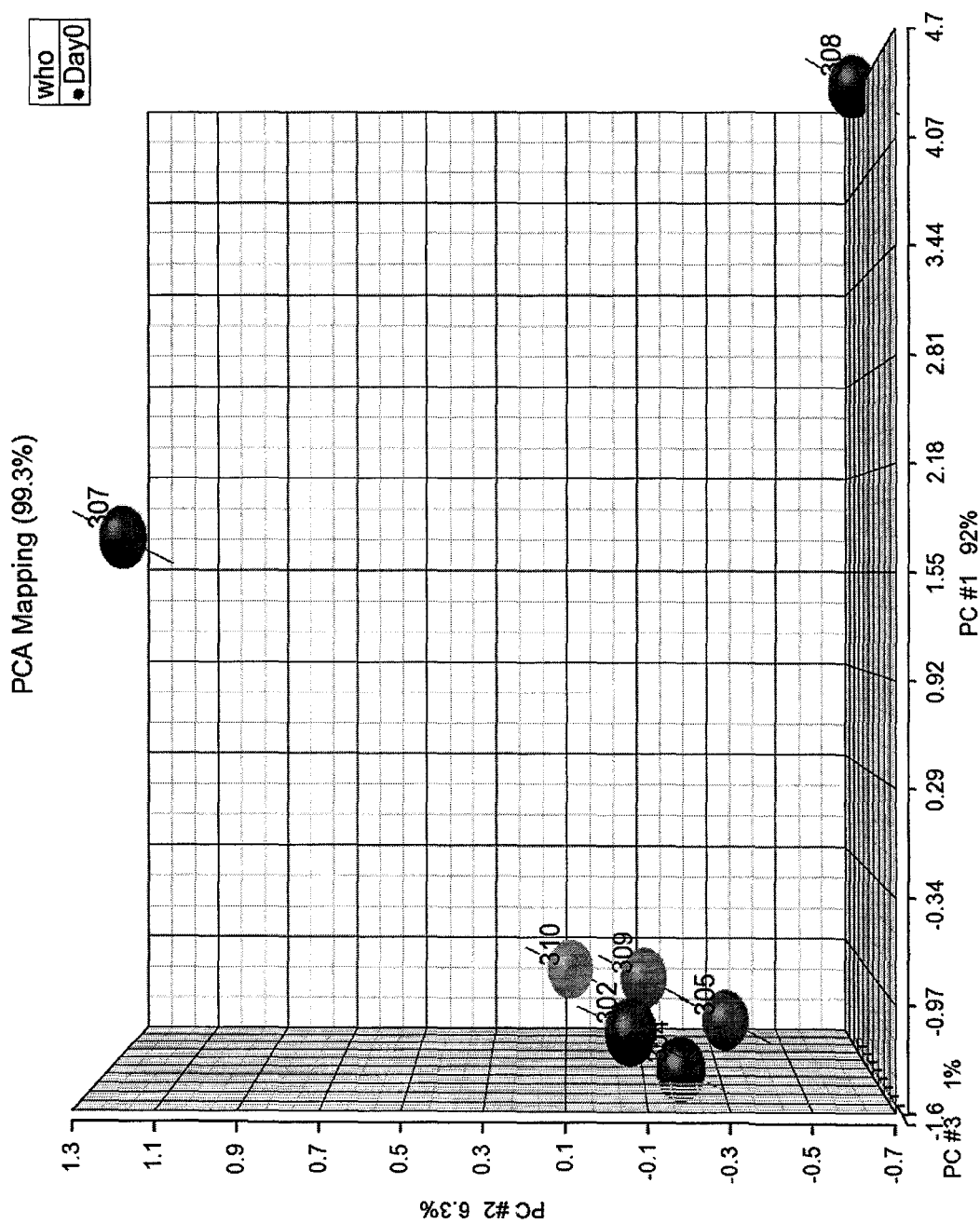
FIG. 21 is a graph showing principal component analysis (PCA) of the expression level of IFIT1, IFI44L, IFI6 and ISG15. The data was obtained from PBMC of healthy donors 24 hours after administration of poly ICLC as compared to baseline levels.

Principal component analysis (PCA) was applied using the data for ISG15, IFIT, IFI44, IFIT6 in order to evaluate the importance of the genes in predicting behavior of individuals and is shown in FIG. 21. As can be seen, three groups were obtained, one group including the majority of the individuals and two additional groups each one including one individual. It was suggested that the group with the majority of the individuals corresponds to responders or to individuals that will be able to fight the viral infection on their own. The two individuals were suggested to be non-responders.

Further, the volcano analysis shows that the up regulation following the poly ICLC mimics exactly the model simulation seen in all previous cases.

Figure 22:
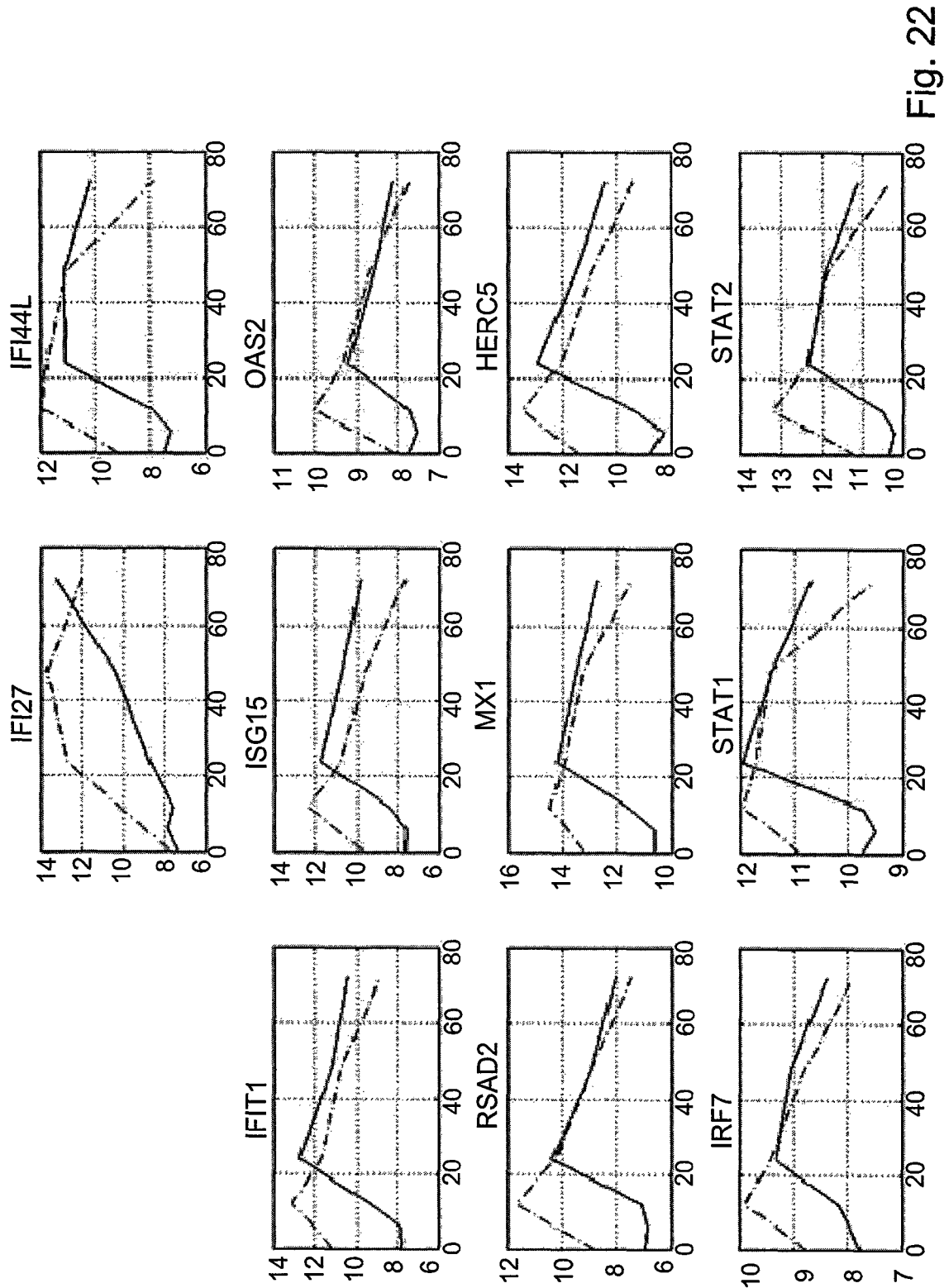
FIG. 22 are graphs showing timing of genes dynamics. Dashed lines correspond to non responders and full lines to responders. X-axis represents time and the Y-axis represents expression of the indicated genes.

FIG. 22 shows the dynamics of gene expression with time in responders and non-responders.

Figure 23:
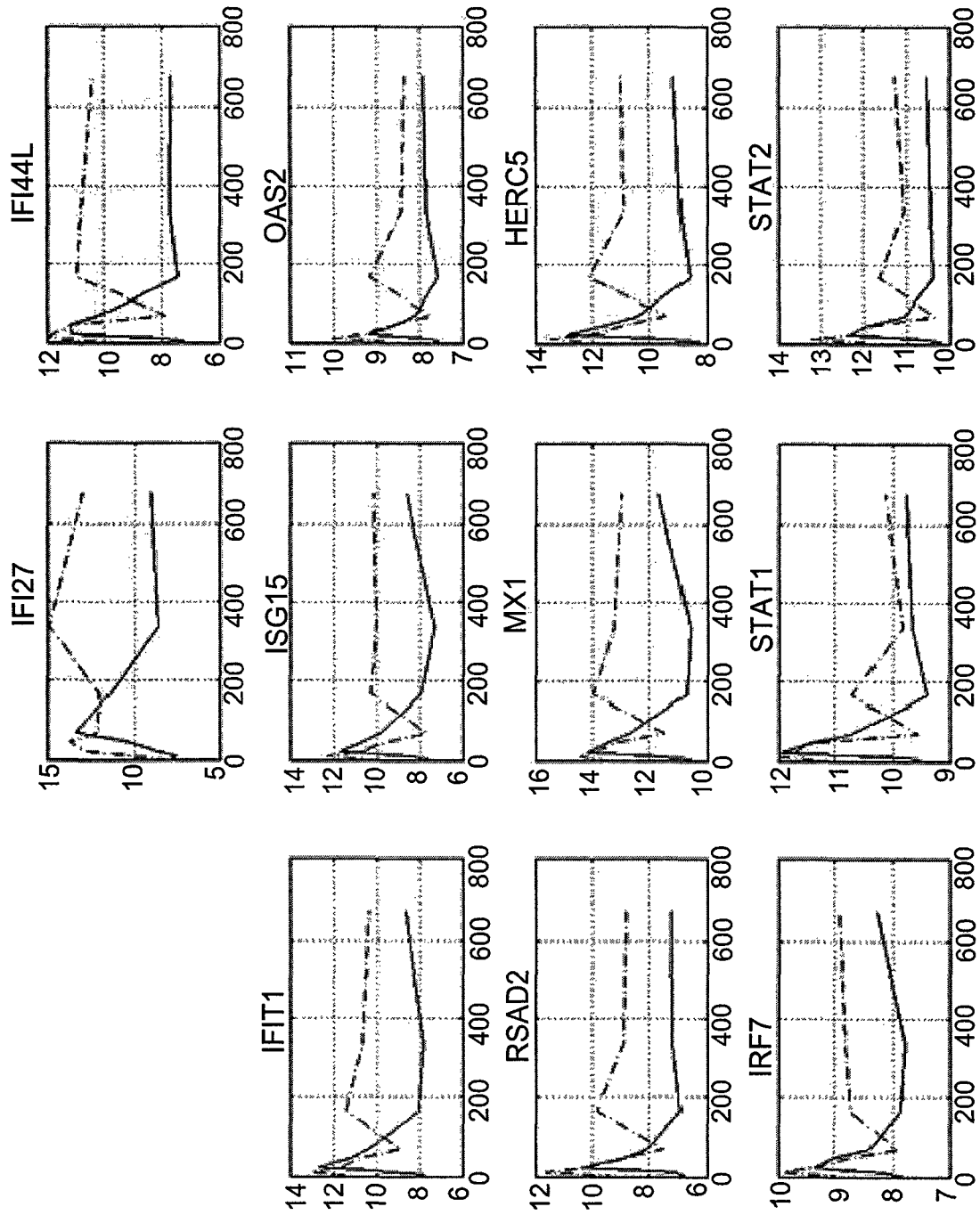
FIG. 23 are graphs showing timing of genes dynamics for longer periods. Dashed lines correspond to non responders and full lines to responders. X-axis represents time and the Y-axis represents expression of the indicated genes.

As can be seen in FIG. 22, the dynamics of the expression is different in responders and non-responders, specifically, the expression in the non responders (dashed line is high at the beginning (time "0"—healthy) and thus the magnitude of change in the expression is limited and narrow. The expression in the responders, on the other hand, is low at the beginning (time 0) and this enables a large change in their future expression. FIG. 23 shows the same results obtained in longer time intervals with the dashed line corresponding to data obtained from non responders.

Figure 24:
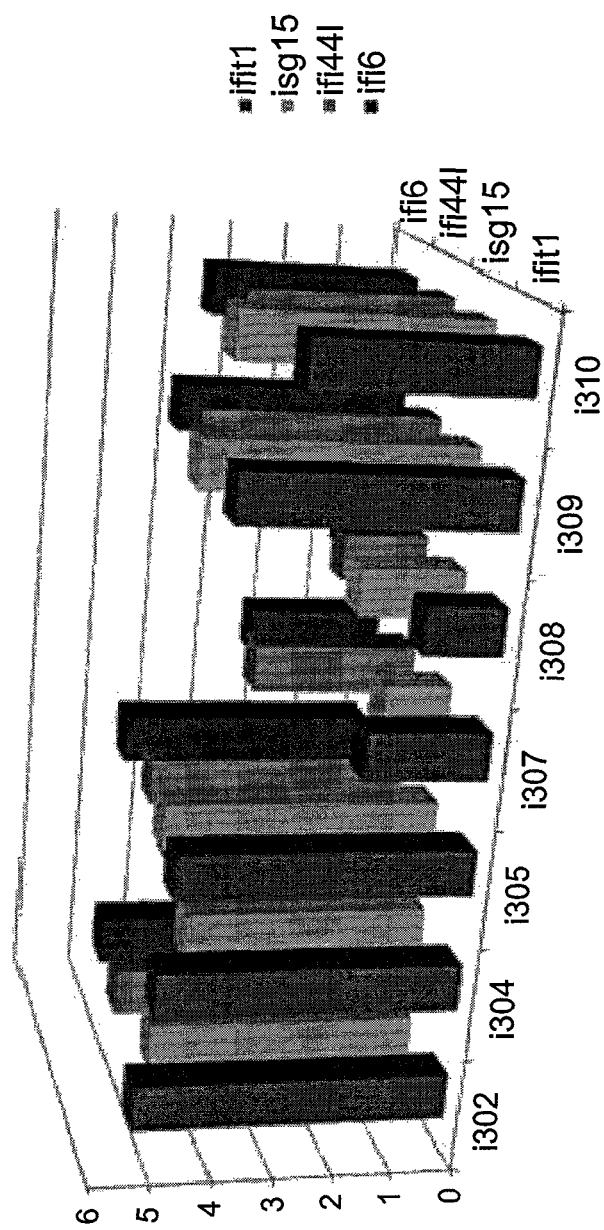
FIG. 24 is a histogram graph showing the changes in genes expression after 24 hours following PolyC treatment in healthy donors divided by baseline level of the same gene.

FIG. 24 shows the average increase in each gene expression as measured 24 hours after poly ICLC administration compared to baseline.

The fold increases are shown in Table 8.

TABLE 8 fold increase of genes

| Individual | IFIT1 | ISG15 | IFI44L | IFIT6 |
|---|---|---|---|---|
| i302 | 5.23 | 4.54 | 4.78 | 4.68 |
| i304 | 4.99 | 4.08 | 3.68 | 3.58 |
| i305 | 4.84 | 4.55 | 4.42 | 4.51 |
| i307 | 1.99 | 1.12 | 2.78 | 2.35 |
| i308 | 1.30 | 1.69 | 4.41 | 0.86 |
| i309 | 4.42 | 4.47 | 3.98 | 3.96 |
| i310 | 3.49 | 4.06 | 3.45 | 3.53 |

Since the observed changes in the expression level of the genes are a result of stimulation of the immune system, the results obtained here may be used to assess the capability of an immune system to react for example to a viral infection. In addition, these results may be also used to obtain information on the magnitude of possible changes in genes expression following interferon administration. Thus, taken together the magnitude of change observed in the expression level of the genes provides a range of the M values in the tested population. Namely, an individual having the highest increase in the expression, for example i302 is characterized with an M value of 1 and is expected to be able to use the immune system and to respond to treatment. On the contrary, an individual having the lowest increase in the expression, for example i308 is characterized with an M value of 0.2 and is expected to fail in inducing the immune system and not to respond to treatment.

Figure 25:
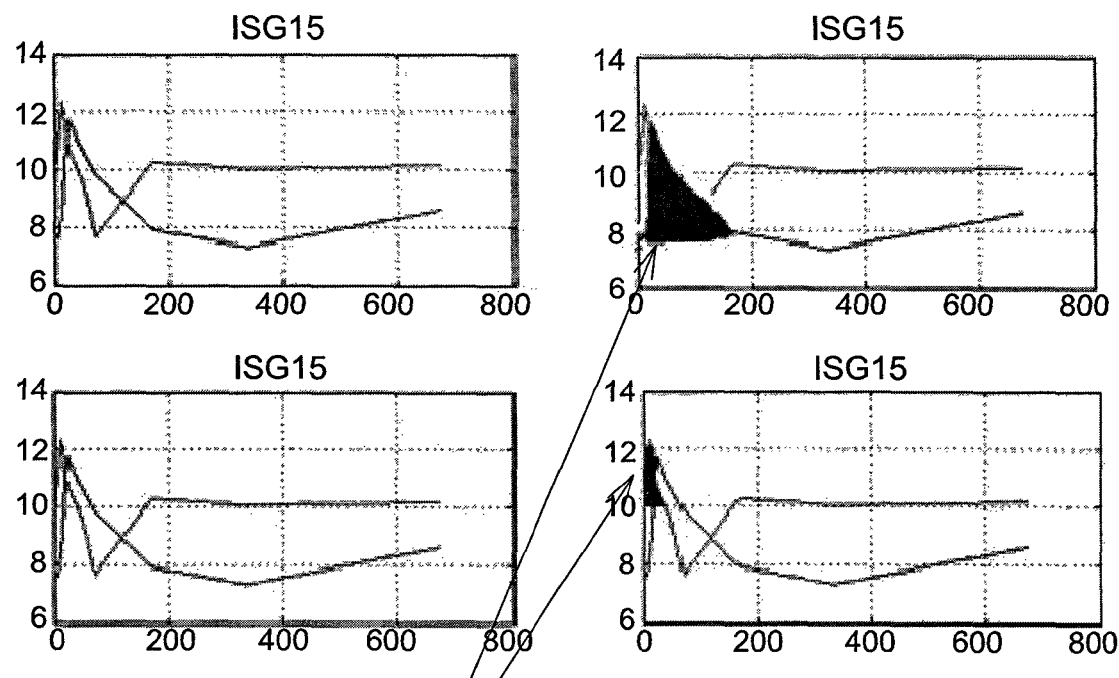
FIG. 25 is a graph showing the calculation of M from the model equations.

M may be calculated from the area under the curve from baseline to its peak (around 24 hr) and back to baseline should be calculated (FIG. 25). The area of the triangle represents added amount of the fighting gene used to combat the virus in the next cycle (−48 hr). Thus the maximal reached pick can represent M=1 and other M's can be derived from the ratio of the triangle area to this maximum triangle area.

Table 9 shows the change in gene expression obtained after administrating poly ICLC in vivo and in vitro. In vitro samples were obtained from PBMCs isolated from blood of healthy donors via density gradient centrifugation. In vivo samples were obtained from subjects randomized to either 1.6 mg poly ICLC or placebo (sterile saline) in a 2:1 ratio, administered S.C.

As can be seen, similar patterns are observed both in vivo and in vitro suggesting that in vitro data can be used to calculate M values.

TABLE 9 changes in gene expression after administrating poly ICLC in vivo and in vitro.

| Marker gene | logFC in vivo pICLC | logFC in vitro pIC |
| --- | --- | --- |
| IFIT3 | 4.473713385 | 4.741052 |
| IFIT1 | 4.384596081 | 5.420633 |
| IFI44L | 4.171223257 | 4.799476 |
| IFI6 | 4.016294707 | 2.691117 |
| HERC5 | 3.871166452 | 3.248894 |
| IFIT3 | 3.75211871 | 4.750157 |
| ISG15 | 3.726288606 | 4.480175 |
| IFIT2 | 3.702681715 | 4.218502 |
| RSAD2 | 3.628919044 | 4.957172 |
| MX1 | 3.440496672 | 2.968754 |
| IFIT3 | 3.438007383 | 2.896002 |
| OASL | 3.437579624 | 3.757009 |
| IFITM3 | 3.301297669 | 3.898404 |
| EPSTI1 | 3.288106942 | 3.001505 |
| IFI44 | 3.233595065 | 3.578491 |
| OAS1 | 3.122394636 | 3.803166 |
| LAMP3 | 2.958338552 | 1.798831 |
| MT2A | 2.951819567 | 1.502288 |
| HES4 | 2.904583684 | 2.542752 |
| GBP1 | 2.885817399 | 2.094531 |
| IRF7 | 2.818183268 | 2.601032 |
| FCGR1B | 2.815964332 | 0.34899 |
| OAS2 | 2.744736242 | 2.835379 |
| TNFSF10 | 2.708541769 | 3.520021 |
| GBP5 | 2.707972339 | 1.841636 |
| MT1A | 2.696990876 | 1.162177 |
| CXCL10 | 2.673387432 | 4.427627 |
| OAS1 | 2.669871256 | 3.51157 |
| IFI35 | 2.653402642 | 2.562161 |
| LAP3 | 2.647847669 | 1.792573 |
| SERPING1 | 2.629612763 | 2.03007 |
| XAF1 | 2.627899914 | 3.065335 |
| IFI27 | 2.616810145 | 3.207039 |
| LY6E | 2.578162512 | 2.557162 |
| ZBP1 | 2.572024498 | 1.786611 |

TABLE 9-continued changes in gene expression after administrating poly ICLC in vivo and in vitro.

| Marker gene | logFC in vivo pICLC | logFC in vitro pIC |
| --- | --- | --- |
| SAMD9L | 2.559958622 | 2.829755 |
| OASL | 2.488510388 | 2.512218 |

An exact pattern is shown by Gaucher et al in Gene Expression Omnibus Accession No. GSE13699, who examined the signature of the immune response to the yellow fever (YF) vaccine 17D (YF17D) in a cohort of forty volunteers.

Table 10 shows the top ranking genes in two tested in vivo vaccination studies in two different locations (Montreal, Canada and Lausanne, Switzerland). Both groups received YF17D (ratio measured 1 week after administration) and the polyI CLC, averaged on all participants.

TABLE 10

Top ranked genes expressed in poly ICLC administered individuals and in individuals administered with yellow fever (YF) vaccine 17D (YF17D) in two tested groups.

| polyc ratio 24 hr/baseline | Group A (yf Canada) ratio 1 week/baseline | Group B (yf Swiss) ratio 1 week/baseline |
| --- | --- | --- |
| RSAD2 | IFI44L | IFI44L |
| IFI44L | IFIT1 | RSAD2 |
| ISG15 | ISG15 | IFI44 |
| IFI44 | RSAD2 | ISG15 |
| OAS3 | HERC5 | IFI27 |
| HERC5 | IFITM3 | OAS3 |
| LY6E | IFI6 | IFIT3 |
| EPSTI1 | IFIT3 | EPSTI1 |
| IFI27 | LAMP3 | HES4 |
| IFITM3 | IFI27 | HERC5 |

Table 10 shows that there is a representative set of genes that is being regulated after administration of immune response stimulants. This suggests that the arsenal of observed genes may be regarded as the genes related to the M phenotype in a person.

Table 11 shows that among the cohort of individuals tested in Group A, a phenotype can be seen as provided in bold. The individuals that show a marked increase in the genes expression following stimulation of the immune response are suggested to correspond to individuals that will be able to use their immune system or to respond to therapy or both. The individuals that show a low increase in the genes expression are given in plain numbers and correspond to individuals that will not be able to use their own immune system, will not respond to treatment or both.

TABLE 11

Top ranking genes that are up regulated and extent of regulation.

| Marker gene | diff | diff | diff | diff | diff | diff | diff | diff | diff | diff | diff | avg |
| --- | --- | --- | --- | --- | --- | --- | --- | --- | --- | --- | --- | --- |
| IFI44L | 1.9 | 3.25 | 5.7 | 3.2 | 4.1 | 5.5 | 3.7 | 5.2 | 4.7 | 0.8 | 3 | 3.73 |
| RSAD2 | 1.9 | 3.47 | 5.6 | 3.4 | 4.2 | 4.5 | 3.9 | 5.4 | 3.9 | 1.2 | 3.5 | 3.72 |
| IFI44 | 2.1 | 2.79 | 5.4 | 3.8 | 3.6 | 5.1 | 3.7 | 4.8 | 4 | 0.7 | 3 | 3.55 |
| ISG15 | 1.8 | 3.16 | 4.6 | 2.5 | 3.5 | 4.2 | 3.3 | 4.4 | 3.2 | 1.3 | 2.7 | 3.16 |
| IFI27 | 5 | 3.39 | 2.7 | 2.6 | 3.2 | 4.7 | 4.5 | 3.8 | 3.1 | 0 |  | 2.96 |
| OAS3 | 1.2 | 2.22 | 4.6 | 2.2 | 3.2 | 3.5 | 2.8 | 4 | 2.5 | 0.4 | 2.4 | 2.64 |
| IFIT3 | 2.3 | 2.61 | 3.7 | 2.6 | 2.6 | 2.9 | 2.8 | 3.5 | 2.1 | 0.8 | 1.8 | 2.52 |
| EPSTI1 | 1.4 | 2.43 | 4 | 2.23 | 2.9 | 3.6 | 2.1 | 3.6 | 2.9 | 0.5 | 1.5 | 2.47 |
| HES4 | 1.7 | 3.2 | 3.3 | 2.02 | 2.1 | 3.1 | 2.9 | 3.5 | 1.9 | 0.5 | 2.2 | 2.4 |
| HERC5 | 0.9 | 2.03 | 3.7 | 1.53 | 2.7 | 3.2 | 2.4 | 3.4 | 1.6 | 1 | 2.4 | 2.26 |

FIG. 26 is a graph showing simulation of replication vs. immune defense, per different M. As can be seen for the same individual with an M value suitable for K=3, that is calculated as follows M=1−⅓=0.66 being infected by a variety of viruses with varying K (multiplication rate). FIG. 26A shows that at K rate higher than 3, the virus progresses. FIG. 26B shows situation where K smaller than M, attenuation of the virus is achieved.

FIGS. 27A-B is a graph showing simulation instructing how much PI is needed per each individuals M and virus K. The PI effectively increases the individuals M, FIG. 27A shows an individual with M=0.6, FIG. 27B shows an individual with M=0.8 both are affected by the same range of PI injections. The better M the quicker an individual to become a responder with the same PI. The results shown here suggest that if M is measured (as shown above) and K is known for each type of virus, a simulator may be used to guide any clinical decision on the frequency of treatment (by simulation that changes each point on the graph 2 days or 3 days instead of one week). In addition, such a simulator may also indicate if and how much further combined therapy, for example protease inhibitors (PI) is required.

Example 10

Correlation Between Virus Load and Induction of the Ubiquitin Genes Expression

Figure 28:
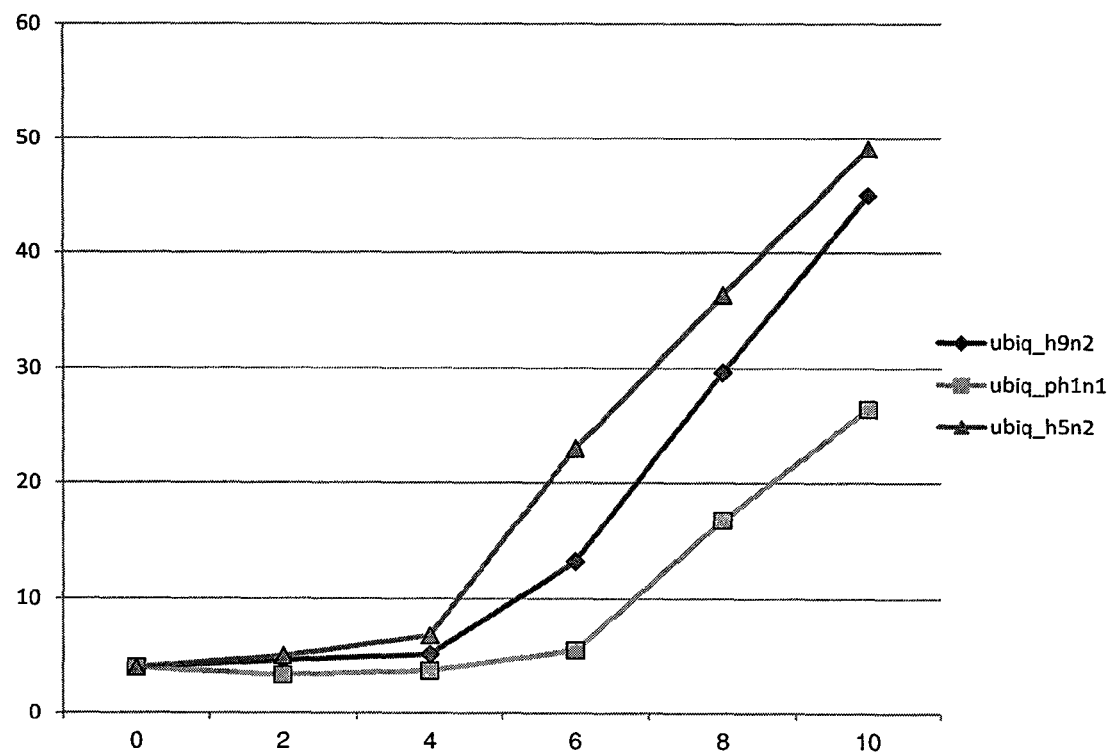
FIG. 28 is a graph showing sum of the expression of the ubiquitin genes, ISG15, USP18, HERC5, UBE2L6, as measured in A549 cells at 2, 4, 6, 8 and 10 hours post infection with the three different influenza strains.

As shown in Example 2B, infection of macrophages with influenza H1N1 and H5N1 strains, led to a significant elevation in the expression of the ubiquitin genes. The virulent strain, H5N1 showed a clear enhanced induction of the expression of said genes. To further establish the hypothesis that the virulence of the pathogen, as determined by measuring the increase in virus load, is correlated with the extent of the induced expression of the ubiquitin genes of the invention, specifically, ISG15, USP18, HERC5 and UBE2L6, the inventors have analyzed data of different host cells infected with three strains of influenza virus. Gene Expression Omnibus Accession No. GSE31518, GSE 31471 and GSE31472 provide gene expression data obtained at 2, 4, 6, 8 and 10 hours post infection of three different host cell lines (A549, MDCK and CEF) with three different Influenza A virus strains, pH1N1 (A/Singapore/478/2009), H9N2 and H5N2. Table 12, presents virus load (as indicated by measuring the vRNA copy number) of the three influenza strains 10 hr post infection of each of the three different host cell lines. FIG. 28 shows sum of the expression of the ubiquitin genes, ISG15, USP18, HERC5, UBE2L6, as measured in A549 cells at 2, 4, 6, 8 and 10 hours post infection with the three different influenza strains. A significant correlation between viral load in the infected A549 and the Ubiquitin genes sum expression is clearly observed.

The inventors have next examined the feasibility of using data of virus load and gene expression data to evaluate the ability of a specific individual (having a specific M value), to overcome an infection of a specific pathogen having a specific replication rate. Therefore, gene expression data of healthy human volunteers inoculated with intranasal influenza A H1N1 and H3N2 strains was analyzed by the inventors. Gene Expression Omnibus Accession No. GSE52428 provide gene expression data obtained from microarrays assay of peripheral blood at baseline and every 8 hours for 7 days following intranasal influenza A H1N1 or H3N2 inoculation in healthy volunteers.

Figure 29:
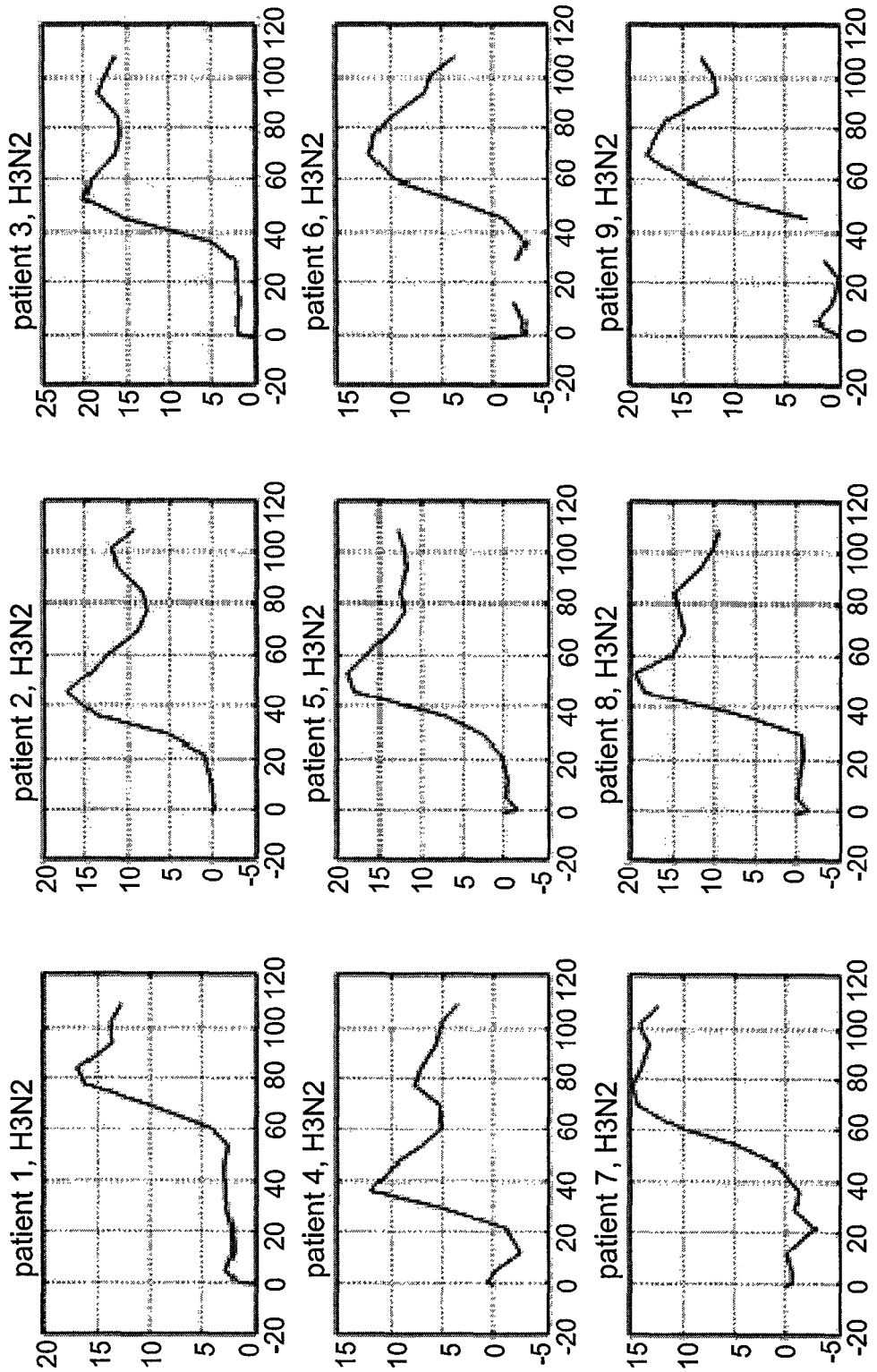
FIG. 29 is a graph showing the sum of the expression of the ubiquitin genes, ISG15, USP18, HERC5 and UBE2L6 in different time points up to 120 hr (X-axis) post infection of H3N2, in nine different individuals. Each individual is represented in one panel numbered 1 to 9.

FIG. 29 shows the sum of the expression of the 4 ubiquitin genes of the invention in different time points up to 120 hr post infection of H3N2 in all nine individuals (numbered as 1 to 9).

Simulation based on the model of the invention as described in Example 1 was performed using the data of all 9 infected individuals based on the calculated rate of induced expression of the ubiquitin genes, ISG15, USP18, HERC5 and UBE2L6.

Figure 30:
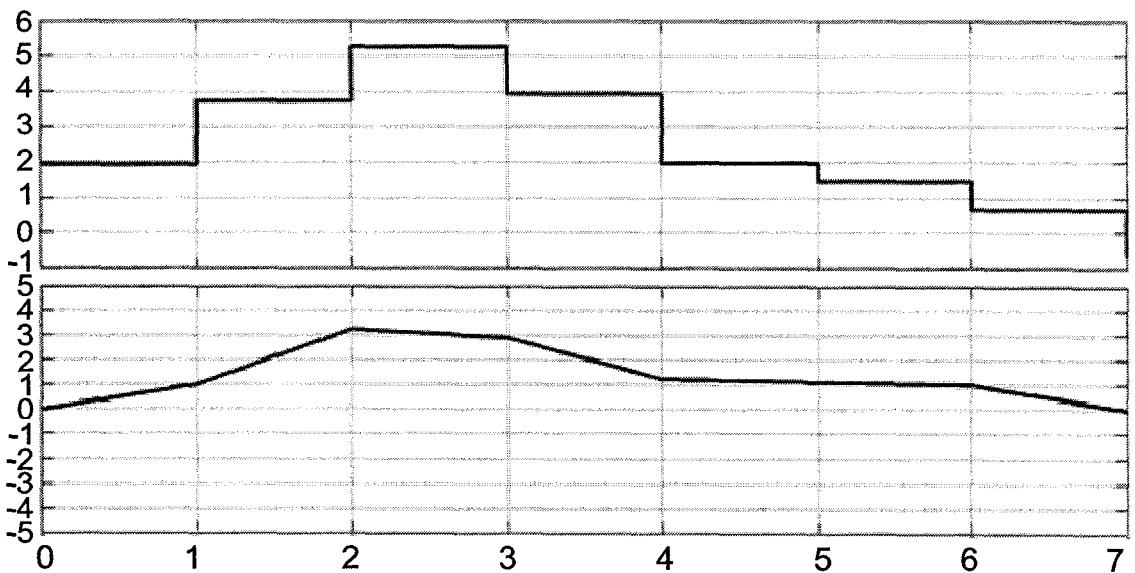
FIG. 30 is a graph showing the simulation results, in the upper panel the virus load of a virus having replication rate of 1.93, the lower panel shows the sum of the expression of the 4 genes, in individual 6 as presented in FIG. 29.
Figure 31:
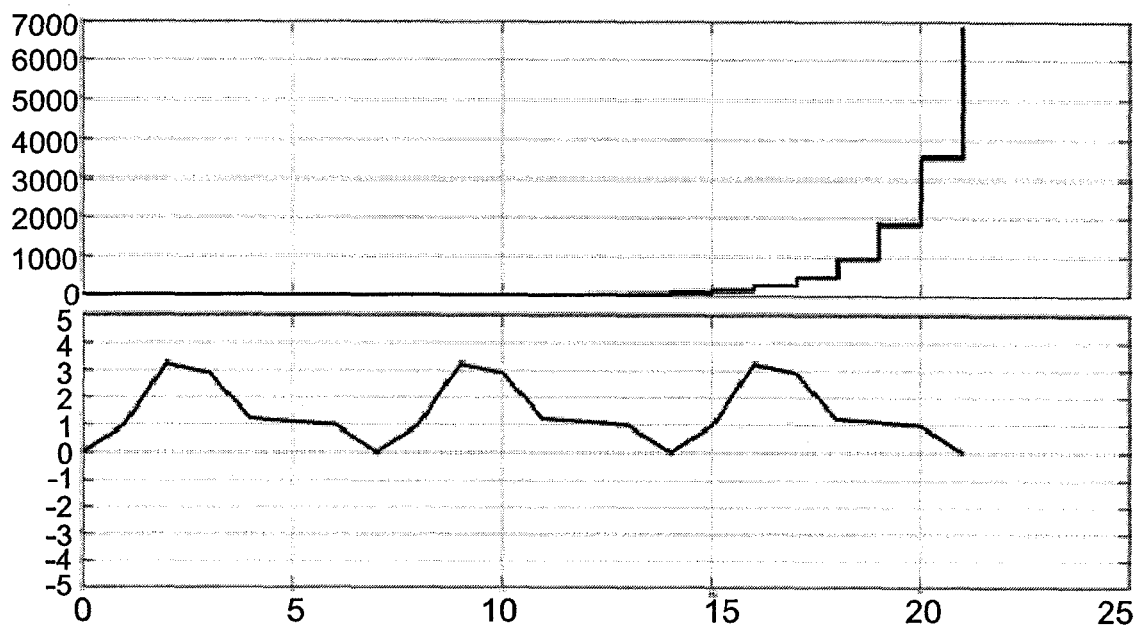
FIG. 31 is a graph showing the simulation results, in the upper panel the virus load of a virus having replication rate of 1.94, the lower panel shows the sum of the expression of the 4 genes, in individual 6 as presented in FIG. 29.

FIGS. 30 and 31, present the result of such simulation using the data of individual 6. Assuming that individual I is infected with a virus having a replication rate of 1.93 every 6 hrs, as presented in FIG. 30, the sum of the expression of the 4 genes, is maximal between 12 to 18 hrs post infection, and reduced after 36 hrs, as shown in the lower panel of the figure. The rate of expression of these genes is correlated to the replication of the virus, that is maximal between 12 to 18 hrs post infection and is significantly reduced after 36 hrs, indicating that the specific individual may successfully reduce the virus load of a virus having replication rate of 1.93, and therefore overcome the infection. FIG. 31 presents simulation of the same individual infected with a virus having a little higher replication rate, of 1.94. As clearly shown in the figure, the same individual, when confronted with said virus, shows increase in the gene expression of the signatory genes of the invention (bottom panel), however, 24 hrs post infection, the replication rate of the virus increases with no corresponding increase in the expression of the signatory genes, indicating that said individual may experience failure of overcoming an infection of virus having a rate of replication of 1.94 each 6 hrs. It should be appreciated that M as it is measured for the whole range (min to max) or alternatively, as it is made of the segmented parts measured for the individual.

This example clearly demonstrates the correlation between the expression of the signatory genes of the invention and the ability of the virus to propagate in a specific individual having a specific ability of increasing expression of the signatory genes, or in other words, having a specific M value.

TABLE 12

Comparison of the M gene vRNA levels at 10 hpi in influenza virus-infected A549, MDCK and CEF
vRNA (copy numbers)

| Virus | A549 | MDCK | CEF |
|---|---|---|---|
| H1N1 | 4.43 ± 0.07 | 5.74 ± 0.07 | 6.91 ± 0.05 |
| H9N2 | 1.71 ± 0.04 | 3.42 ± 0.08 | 7.34 ± 0.07 |
| H5N2(F118) | 5.71 ± 0.04 | 4.91 ± 0.02 | 7.47 ± 0.10 |
| H4N2(F189) | 5.70 ± 0.08 | 5.01 ± 0.20 | 7.28 ± 0.06 |
| H5N3 | 6.83 ± 0.04 | 5.93 ± 0.03 | 8.29 ± 0.06 |
| pH1N1/276 | 1.92 ± 0.06 | 2.11 ± 0.26 | 5.10 ± 0.52 |
| pH1N1/471 | 1.06 ± 0.09 | 2.69 ± 0.20 | 5.27 ± 0.11 |
| pH1N1/478 | 1.67 ± 0.12 | 2.53 ± 0.20 | 4.92 ± 0.33 |
| pH1N1/527 | 1.32 ± 0.11 | 2.46 ± 0.18 | 5.70 ± 0.21 |

Example 11

Prediction of Response to Treatment of IFN-α in Blood Samples and Liver Tissue of HCV Patients To further establish the model of the invention, the inventors next evaluated the ability of calculating the M parameter of an individual (that reflects the ability of a specific individual to overcome a pathologic disorder), infected by HCV in this case, from the measured data of the expression of the signatory genes of the invention, namely, UBE2L6, USP18, HERC5, OAS2 and ISG15, and the reduction in virus load as measured 4 weeks after treatment with Interferon alpha. Therefore, RT-PCR analysis of the genetic profile in Peripheral Blood Mononucleated Cell (PBMC) and liver tissue of HCV patients was performed on samples obtained before initiation of IFN-α treatment, and one month after.

The expression levels of the following genes: UBE2L6, USP18, HERC5, OAS2 and ISG1 (using 3 probes) in each patient was measured by RT-PCR and normalized to a control gene GAPDH. In addition, in each one of the eight patients, the virus load was determined before treatment and 4 weeks after treatment with IFN-α using commercial kits.

Based on the sum expression of the five genes, an experimental M was calculated as follows:

$$M = 1 - [(Ex_{samp} - Ex_{min})/(Ex_{max} - Ex_{min})].$$

Wherein $Ex_{max}$ is a maximal measured sum expression value of the five genes and $Ex_{min}$ is a minimal measured sum expression value of the five genes within a population and $Ex_{samp}$ is the measured sum expression value of the five genes for a specific patient within this population, to whom the M is calculated.

Based on the results of the change in virus load measured before treatment and after 4 weeks of treatment, two populations of HCV patients were defined: responders and non-responders.

A responder was considered as a patient that the amount of viral load was reduced by more than 100 within 4 weeks, (2 in log 10). A non-responder was considered as a patient that the amount of viral load was reduced by less than 100 within 4 weeks, (2 in log 10).

Experiments were conducted on different populations of HCV patients from samples obtained from PBMC and from liver tissue samples.

Figure 32:
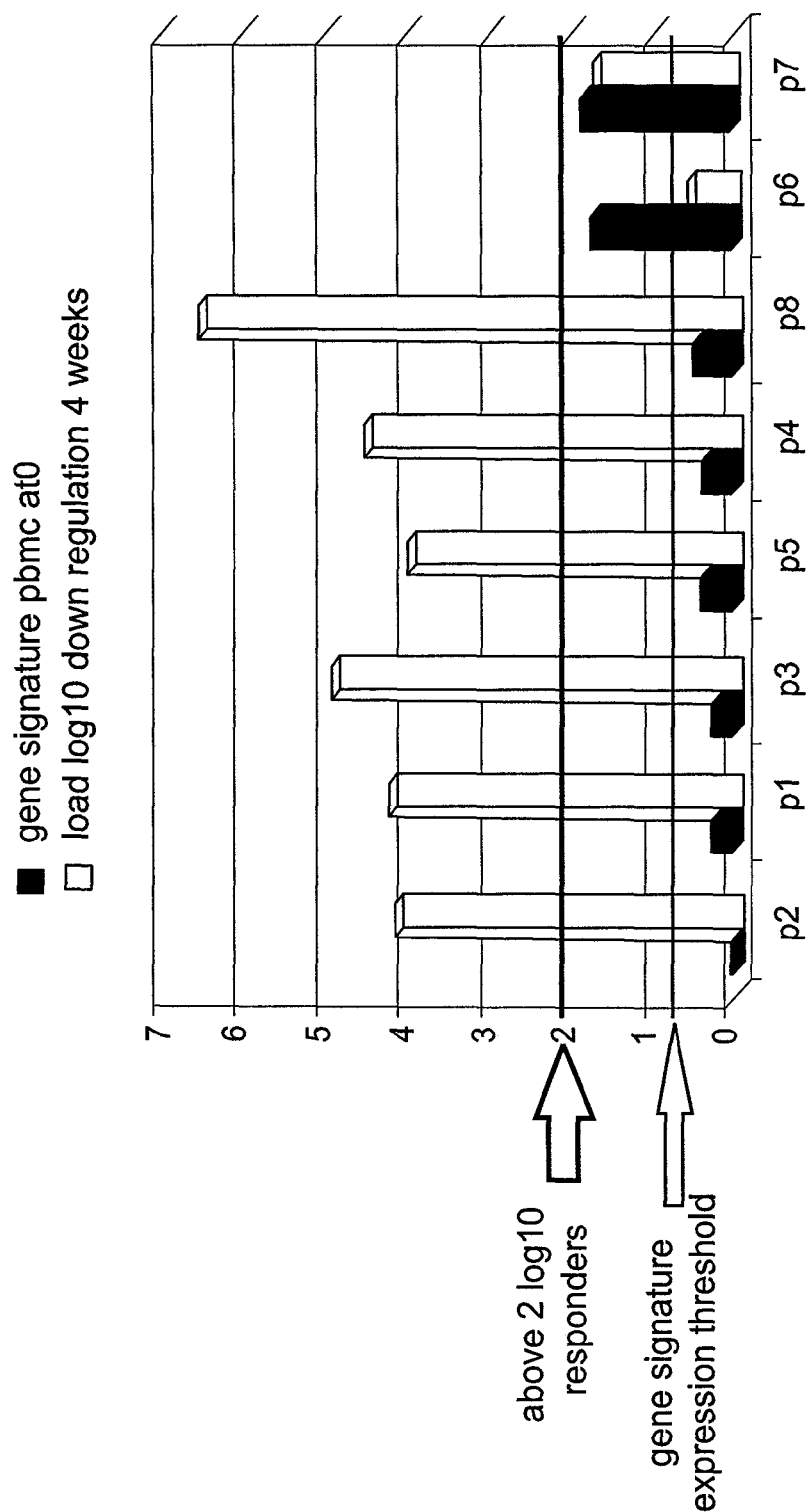
FIG. 32 is a bar graph showing the normalized and scaled sum expression of the genes UBE2L6, USP18, HERC5, OAS2 and ISG15 in each one of the tested patients and the amount of reduction in virus load.

Experiments on Blood Samples:

As can be seen in FIG. 32, the patients denoted as p2, p1, p3, p5, p4, and p8 experienced an amount of down regulation of virus load higher than 100 (observed as 2 in log 10 scale) and are thus considered responders to IFN-α treatment in line with the definition above.

In contrast, patients denoted as p6 and p7 experienced an amount of down regulation of virus load lower than 100 (observed as 2 in log 10 scale) and are thus considered non-responders to IFN-α treatment in line with the definition above.

The results in FIG. 32 demonstrated that the sum of normalized and scaled expression of the five genes UBE2L6, USP18, HERC5, OAS2 and ISG15 was significantly reduced in patients that were considered as responders (p2, p1, p3, p5, p4, and p8) compared to the expression in patients considered as non-responders (p6 and p7).

As indicated above, the virus load of these 8 HCV patients was recorded before and one month (4 injection cycles) after Pegylated Interferon-alpha Treatment. Gene signature of the UBE2L6, USP18, HERC5 and OAS2 genes expression was derived and scaled (0-1) before treatment. Simulation is carried out for different M values per 4 cycles of treatment.

Table 13 shows M values and their corresponding virus load decline in each of the 4 weeks of treatment with Peg Interferon as calculated by the model of the invention as described in Example 1.

TABLE 13

Simulation of calculated M values vs. reduction of virus load after treatment

| M value | treatment_w1 | treatment_w2 | treatment_w3 | treatment_w4 |
|---------|--------------|--------------|--------------|--------------|
| 0.87    | 1            | 1.538461538  | 2.366863905  | 3.641329085  |
| 0.88    | 1            | 1.666666667  | 2.777777778  | 4.62962963   |
| 0.89    | 1            | 1.818181818  | 3.305785124  | 0.89         |
| 0.9     | 1            | 2            | 4            | 8            |
| 0.91    | 1            | 2.222222222  | 4.938271605  | 10.9739369   |
| 0.92    | 1            | 2.5          | 6.25         | 15.625       |
| 0.93    | 1            | 2.857142857  | 8.163265306  | 23.32361516  |
| 0.94    | 1            | 3.333333333  | 11.11111111  | 37.03703704  |
| 0.95    | 1            | 4            | 16           | 64           |
| 0.96    | 1            | 5            | 25           | 125          |
| 0.97    | 1            | 6.666666667  | 44.44444444  | 296.2962963  |
| 0.98    | 1            | 10           | 100          | 1000         |
| 0.985   | 1            | 13.33333333  | 177.7777778  | 2370.37037   |
| 0.998   | 1            | 100          | 10000        | 1000000      |
| 0.999   | 1            | 200          | 40000        | 8000000      |

As shown by the table, assuming that the initial measured virus load is 1 (treatment w1), different calculated M values indicated in the table, result in the indicated reduction (folds of reduction) in virus load.

The virus load and expression values of the UBE2L6, USP18, HERC5 and OAS2 genes obtained for 7 of the HCV patients analyzed above, were now calculated using the simulation values of Table 13, and are presented in Table 14.

More specifically, Table 14 shows the correlation between the measured fold of virus load reduction after 1 month of interferon treatment (second column from left), and the measured expression of the 4 genes of the invention (the third column from left presents sum of the expression values of all 4 genes, each value scaled between 0 to 1).

TABLE 14

Calculated M values vs. reduction of measured HCV virus load after IFN treatment

| patient | fold decline in VL after 1 month | simulation M | scaled_expression | scaled_expression (0-1) | scaled simulation M (0_1) |
|---|---|---|---|---|---|
| p2 | 14535.3 | 0.9918 | 0 | 0 | 0.950819672 |
| p1 | 16760.7865 | 0.9921 | 0.96137233 | 0.251731718 | 0.953161593 |
| p3 | 51955.95 | 0.9948 | 1.032753453 | 0.270422596 | 0.974238876 |
| p4 | 20120.4 | 0.9928 | 1.144285694 | 0.299626892 | 0.958626073 |
| p8 | 2061843.2 | 0.9981 | 2.057379621 | 0.538717093 | 1 |
| p6 | 3.48570259 | 0.87 | 3.525351059 | 0.923099876 | 0 |
| p7 | 52.4136592 | 0.948 | 3.81903535 | 1 | 0.608899297 |

As shown in the table, for patient p1, for example, the measured reduction in virus load was about 16,000 folds, going back to the simulation of reduction in virus load as a parameter of M value, as presented in Table 13, an M value of about 0.992 is correlated with reduction of about 15,625 folds in the measured virus load. This predicted M value (shown in the second column from left), is correlated to a scaled expression value of 0.25. In contrast, patient p6 that showed only 3.48 folds reduction in virus load, was correlated with a scaled expression of 0.9, and a low M value of 0.87 (in the simulation Table 13, reduction of about 3.6 folds is correlated with an M value of 0.87). The right column of Table 14 shows scaled M values, of between 0 to 1, were the lowest M value, 0.87, was considered as 0 (as shown for patient p6), and the higher M value in the simulation, 0.9981, is considered as 1 (as shown for patient p8). When correlating to the scaled expression values (sum of the expression values of the 4 signatory genes), it seems that patients having scaled expression value of below 0.5, efficiently reduce the virus load and are therefore considered as responsive to interferon treatment, whereas patients presenting an initial scaled expression value of above 0.5, and a low M value, show poor response that is reflected in low ability to reduce virus load.

Figure 33:
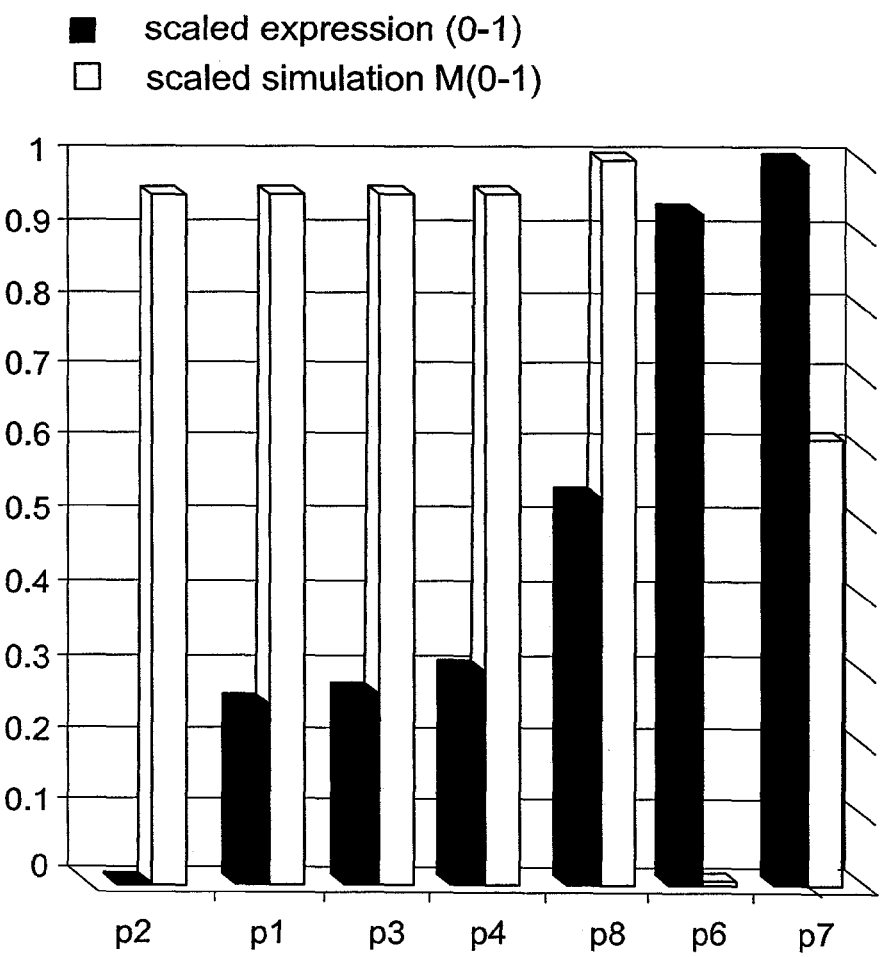
FIG. 33 is a bar graph showing the normalized and scaled (0-1) sum expression of the five genes UBE2L6, USP18, HERC5 and OAS2 in each one of the tested patients and the scaled M values of each patient as calculated using the simulation.

FIG. 33 clearly shows that the four responders have M values between 0.95 to 1 while their expression value of the signatory genes is below 0.5. The two non responders (p6 and p7 having low M values and a corresponding high levels of initial expression of the signature genes, of above 0.9.

This example clearly demonstrate the feasibility of using the measured initial expression of the signatory genes of the invention, before starting any treatment, to evaluate the personal M value that distinguish between responders and non-responders and also indicate the extent of predicted responsiveness of a specific individual. The method of the invention thereby provides a powerful tool for personalized medicine.

Figure 34A:
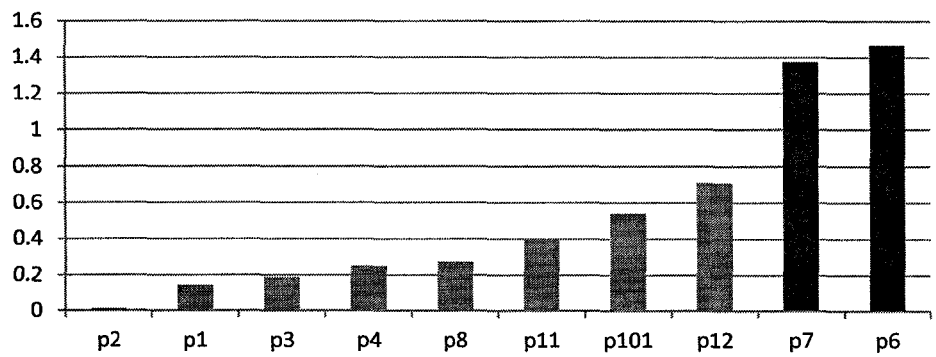
FIGS. 34A and 34B are bar graphs showing the sum expression of HERC5 and UBE2L6 genes (FIG. 34A) and the M value (FIG. 34B) in IFN responsive and non-responsive HCV patients. The data was obtained from PBMC of HCV patients.
Figure 34B:
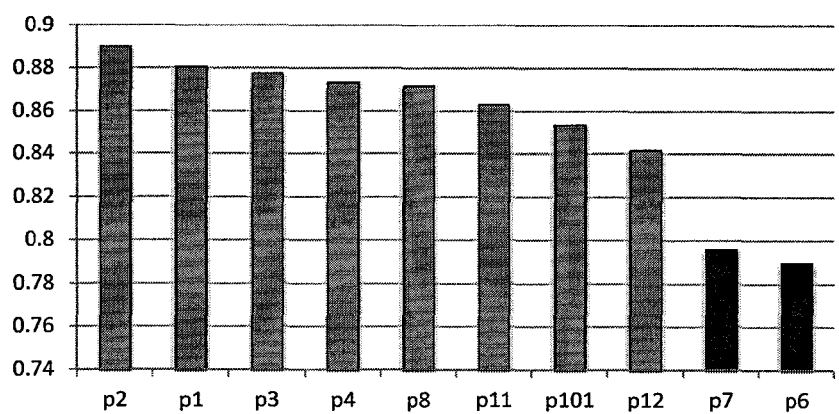

Further analysis of the sum of the expression of two genes, HERC5 and UBE2L6 in HCV patients is shown in FIGS. 34A and 34B. In the analysis shown in these figures, patients denoted as p2, p1, p3, p4, p8, p11, p101 and p12 experienced clear reduction of virus load that is more than by 100 (observed as 2 in log 10 scale) and are thus considered responders to IFN-α treatment in line with the definition above, whereas patients denoted as p6 and p7 experienced reduction of virus load lower than by 100 (observed as 2 in log 10 scale) and are thus considered non-responders to IFN-α treatment in line with the definition above.

Patient p12 experienced a reduction in virus load of 2.02 and thus theoretically should be considered as responder. However, in the following analysis, this patient was not categorized to any one of the groups since the value of 2.02 is in the border between responders and non-responders.

Analysis of the gene as described above is shown in FIG. 34A. As shown in FIG. 34A, a strong correlation was observed between the sum expression of the five genes and the patient's response to IFN treatment. A lower expression value was measured in patients p2, p1, p3, p4, p8, p11, p101 and p12 who were found responsive to IFN treatment. On the other hand, a high expression value was measured in patients p6 and p7 who were found not responsive.

Based on the experimental data of the expression of the two genes detailed above, the M value was calculated for each one of the patients. FIG. 34B shows the experimental M value calculated for each one of the tested patients presented in FIG. 34A.

As can be seen, a correlation exists between the M value and the patient's responsiveness to treatment. Patients having a high M value were found to be responsive to IFN treatment, whereas patients having a lower M value were found to be not responsive to treatment.

The effect of HCV in liver tissue may be considered different than the effect in blood samples. In HCV liver the battle is occurring inside hepatocytes and the inventor assume k=5 based on previous publications [Ruy M. Ribeiro et al., (2012)]. In PBMC the specificity of the cells is not as clear and the inventors assume its in a close range to the shaded amount transferred to the blood from the source hepatocytes.

The cutoff value may be calculated by using the following equation:

$$M_{cutoff} = 1 - 1/K$$

Thus for a virus characterized by a K value of 5, the theoretical $M_{cutoff}$ value is 0.8. As can be seen in FIG. 34B, the inventor assumes for this example the range of M to be between 7.9 to 8.9 and scaled M accordingly. Once more viral loads data points in time were received the final range for the group was narrower (0.815 to 0.862). It should be noted that there is an inverse correlation between the calculated M value and the sum of the genes expression.

Figure 35:
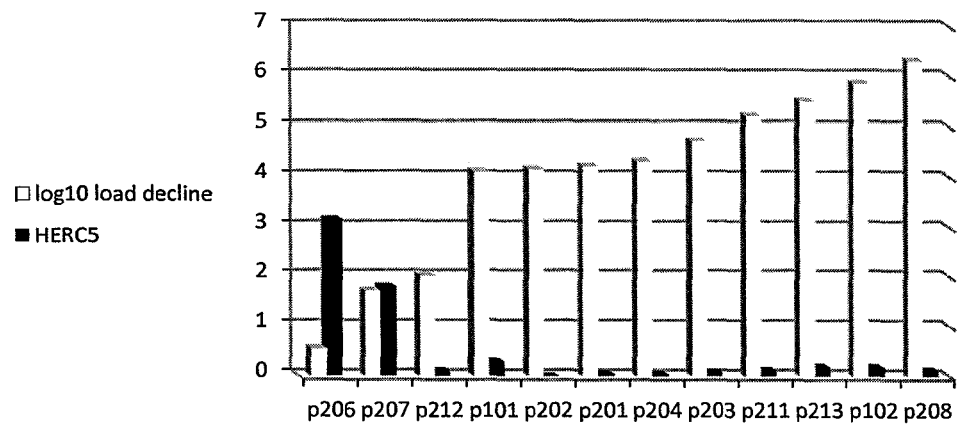
FIG. 35 is a bar graph showing the expression of HERC5 and the viral load in responsive and non-responsive HCV patients. The data was obtained from PBMC of HCV patients.

The inventors have also performed an analysis using the expression of a single gene, HERC5 which is considered as a predictive gene. FIG. 35 shows the patients denoted as p208, p213, p102, p201, p211, p203, p204, p202 and p101 experienced a reduction of virus load by more than 100 (observed as 2 in log 10 scale) and are thus considered responders to IFN-α treatment in line with the definition above.

In contrast, patients denoted as p206 and p207 experienced reduction of virus load that is lower than by 100 (observed as 2 in log 10 scale) and are thus considered non-responders to IFN-α treatment in line with the definition above.

Patient denoted as p212 experienced reduction regulation of virus load of 2.02 and is thus considered on the boarder between responder and non-responder to IFN-α treatment in line with the definition above.

The results in FIG. 35 demonstrated that the expression of the gene HERC5 was significantly reduced in patients that were considered as responders compared to the expression in patients considered as non-responders. Interestingly, the expression of the gene HERC5 was significantly reduced also in patient denoted as p212, which experienced a reduction of virus load by about 100 (observed as 2 in log 10 scale).

The inventors have used the virus load measured or each patient at the beginning and at the end of the experiment and used these parameters for the model simulation to obtain a value of M for each patient, taking into account that K for HCV in blood samples is 5 [Ruy M. Ribeiro et al., (2012)].

TABLE 15

The expression of HERC5 gene (arbitrary units $-2^\wedge$-dct rt-pcr_) and the calculated M for each one of the tested HCV patients.

| Patient # | Expression of HERC5 | M calculated from simulation assuming 4 weeks |
|---|---|---|
| p202 | 0.00144 | 0.8635 |
| p204 | 0.042563 | 0.863 |
| p201 | 0.047145 | 0.862 |
| p203 | 0.076972 | 0.867 |
| p212 | 0.100299 | 0.836 |
| p211 | 0.108098 | 0.872 |
| p208 | 0.111671 | 0.883 |
| p102 | 0.181633 | 0.8785 |
| p213 | 0.188302 | 0.875 |
| p101 | 0.28833 | 0.861 |
| p207 | 1.801784 | 0.832 |
| p206 | 3.157128 | 0.816 |

As shown in Table 15, the M values of all patients varied between 0.816 to 0.883.

Figure 36:
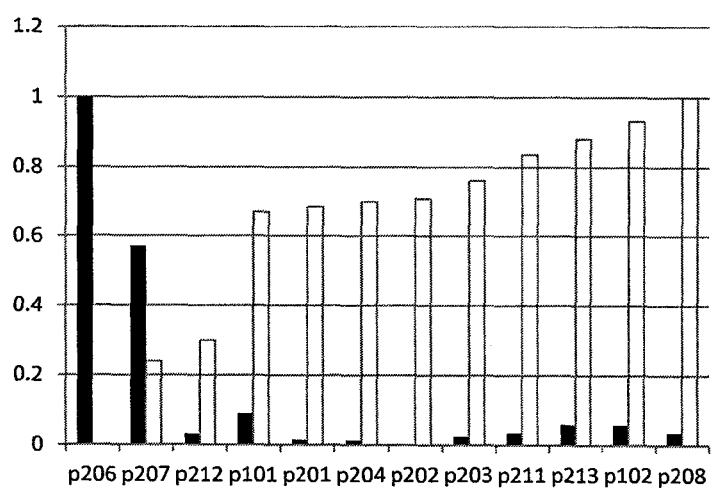
FIG. 36 is a bar graph showing the normalized expression of HERC5 gene (open box) and normalized M value (black box) obtained from model simulation using viral load data in responsive and non-responsive HCV patients. The data was obtained from PBMC of HCV patients.

The expression value of HERC5 and the M value obtained from the simulation were normalized with respect to the patient's population. FIG. 36, shows for each patient the normalized simulated M value (black box) and the normalized expression of HERC5 gene (open box). As can be seen, an inverse correlation is observed between the M value and the expression of HERC5 gene, with the patients being considered as responsive having considerably higher M value and the patients being considered as non-responsive having considerably lower M value.

Interestingly, the patient denoted as p212 that was considered on the boarder with respect to the virus load and responsive with respect to the HERC5 expression, has an intermediate M value. Simulation of the data of the patient denoted as p212 for a long time period of three month resulted in a M value correlating to responsiveness (data not shown).

Experiments on Tissue Samples

Figure 37A:
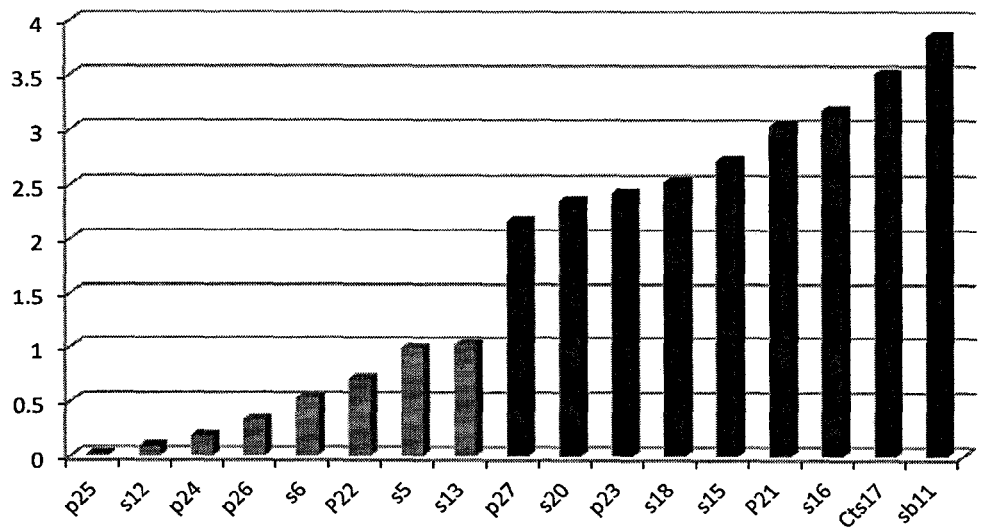
FIGS. 37A to 37C are graphs showing correlation between gene expression and M value, with FIG. 37A showing the sum of normalized and scaled expression of the five genes UBE2L6, USP18, HERC5, OAS2 and ISG15, FIG. 37B showing the M value calculated from the gene expression. The data was obtained from liver samples of HCV patients.
Figure 37B:
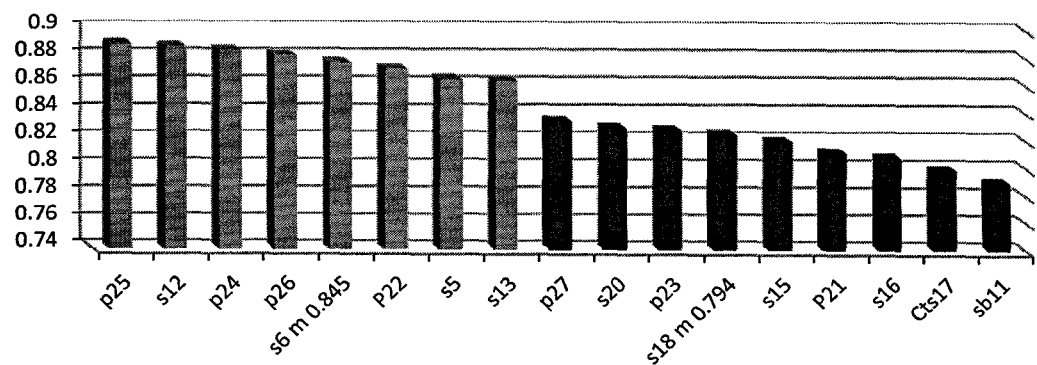

The data of liver tissue analysis of HCV patients is shown in FIGS. 37A and 37B. The patients denoted as p25, s12, p24, p26, s6, p22, s5 and s13 experienced reduction of virus load higher than by 100 (observed as 2 in log 10 scale) and are thus considered responders to IFN-α treatment in line with the definition above.

In contrast, patients denoted as p27, s20, p23, s18, s15, p21, s16, cts17 and sb11 experienced an amount of down regulation of virus load lower than 100 (observed as 2 in log 10 scale) and are thus considered non-responders to IFN-α treatment in line with the definition above.

The results presented in FIG. 37A demonstrate that the sum of normalized and scaled expression of the five genes UBE2L6, USP18, HERC5, OAS2 and ISG15 was significantly lower in patients that were considered as responders (patients p25, s12, p24, p26, s6, p22, s5 and s13) compared to the sum of the normalized expression in patients considered as non-responders (patients p25, s12, p24, p26, s6, p22, s5 and s13).

As indicated above, the M value was calculated for each patient using the experimental data obtained for the five genes. FIG. 37B shows the experimental M value for each one of the tested patients as in FIG. 37A.

As can be seen in FIG. 37B, there exists a strong correlation between the M value of a patient and the patient's response to treatment. The patients who were found to be responsive to IFN treatment (namely, patients p25, s12, p24, p26, s6, p22, s5 and s13) were characterized by a high M value (ranging between 0.86 to 0.88, whereas patients who were found to be non-responders to IFN treatment (namely, patients p25, s12, p24, p26, s6, p22, s5 and s13) were characterized by a low M value (ranges between 0.79 to 0.834).

As shown in FIG. 37B, the M value (that may be considered as a cut off to distinguish between responders and non-responders may range between 00.835 to 0.855. In this illustration example as in the PBMC case we assumed a distribution of M between 0.79 to 0.89.

Figure 37C:
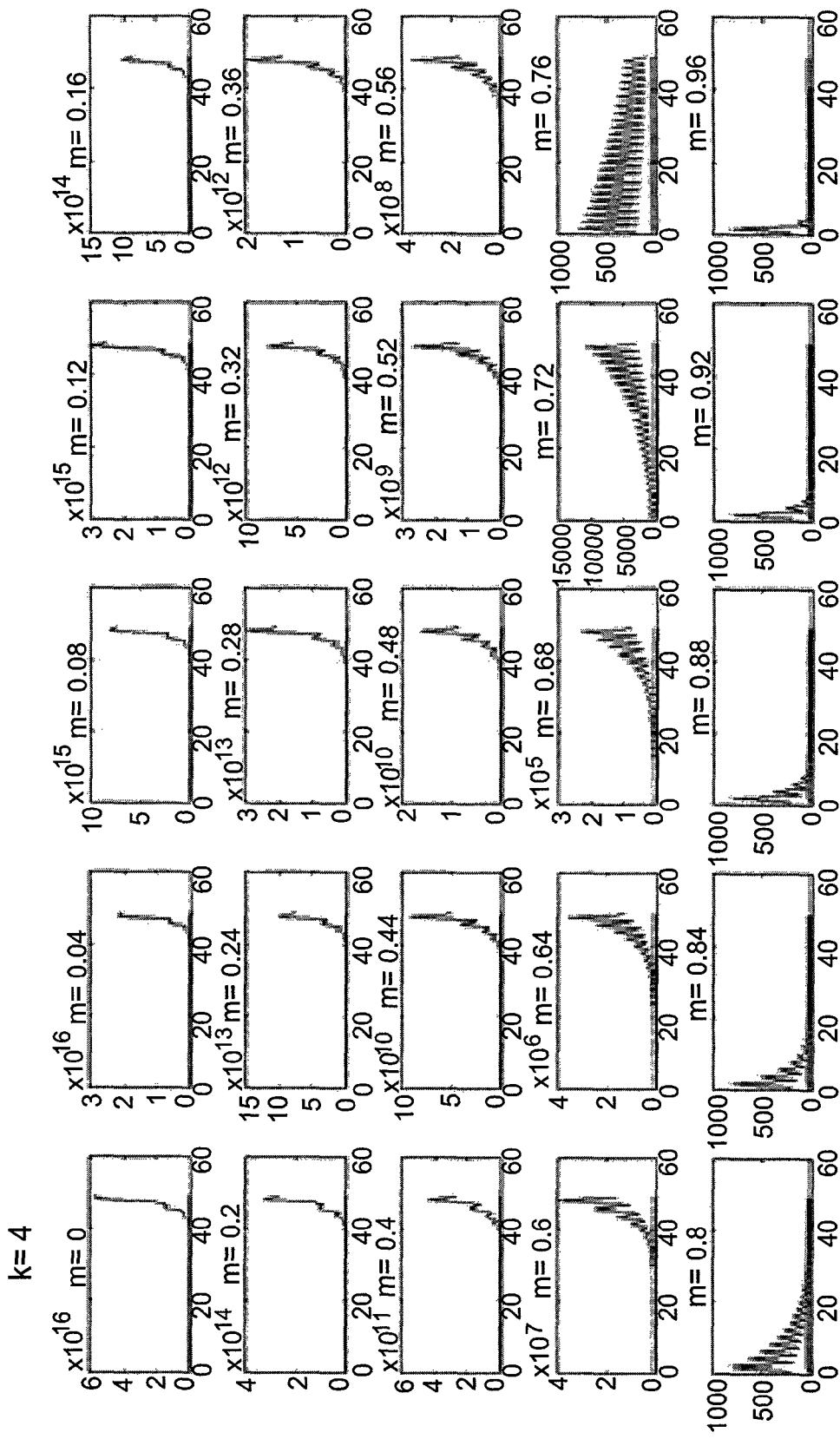

A clear link between the experimental data obtained from tissue samples and the mathematical model described herein indicate that there is a strong correlation between the simulation of M and the experimental data. HCV in tissue samples is characterized by a doubling time of 5, namely K=5. As shown herein in FIG. 37C, a simulations of the above model equations by taking K as 4, showed that at lower M values of 0 to 0.72, namely in those patients being characterized by M values of up to 0.72, the virus is capable of multiplying and hence the disease is progressing, as the immune system or IFN treatment fail to eradicate the virus.

An M value that is higher than 0.72, clearly reduce virus load thereby eliminating the disease caused by a virus with k=4. This may indicate that either the immune system or IFN treatment regimen or both succeed in eliminating the virus.

Similarly, HCV patients characterized by M values of above 0.8 will most likely be able to reduce or eliminate the disease.

These results clearly indicate that there is the model simulation of the invention predicts with a high accuracy a patient's behavior for a particular virus. Namely, for a given virus an accurate cutoff value of M can be determined, and such M value distinguishes patients that will be able to "fight" the disease by responding to treatment, and those who will still suffer from the disease, namely, patients that are not responsive to treatment.

Example 12

Calculation of M Using Model Simulation in HCV Patients Treated with Combination Therapy of IFN-α and Ribavirin (Rib)

Data from the publication by Honda M. et al. [Journal of Hepatology 53: 817-826 (2010)] was used for correlation analysis with the mathematical model. Superficially, the inventors used virus load measured in thirty HCV patients before and after administration of IFN-a 2b at different time points. In accordance with the response to treatment, Honda M. et al. have defined treatment outcomes according to as follows: sustained viral response (SVR)—clearance of HCV viremia at 24 weeks after initiation of therapy; transient response (TR)—no detectable HCV viremia at 24 weeks but relapse during the follow-up period; and non-response (NR).

Figure 38:
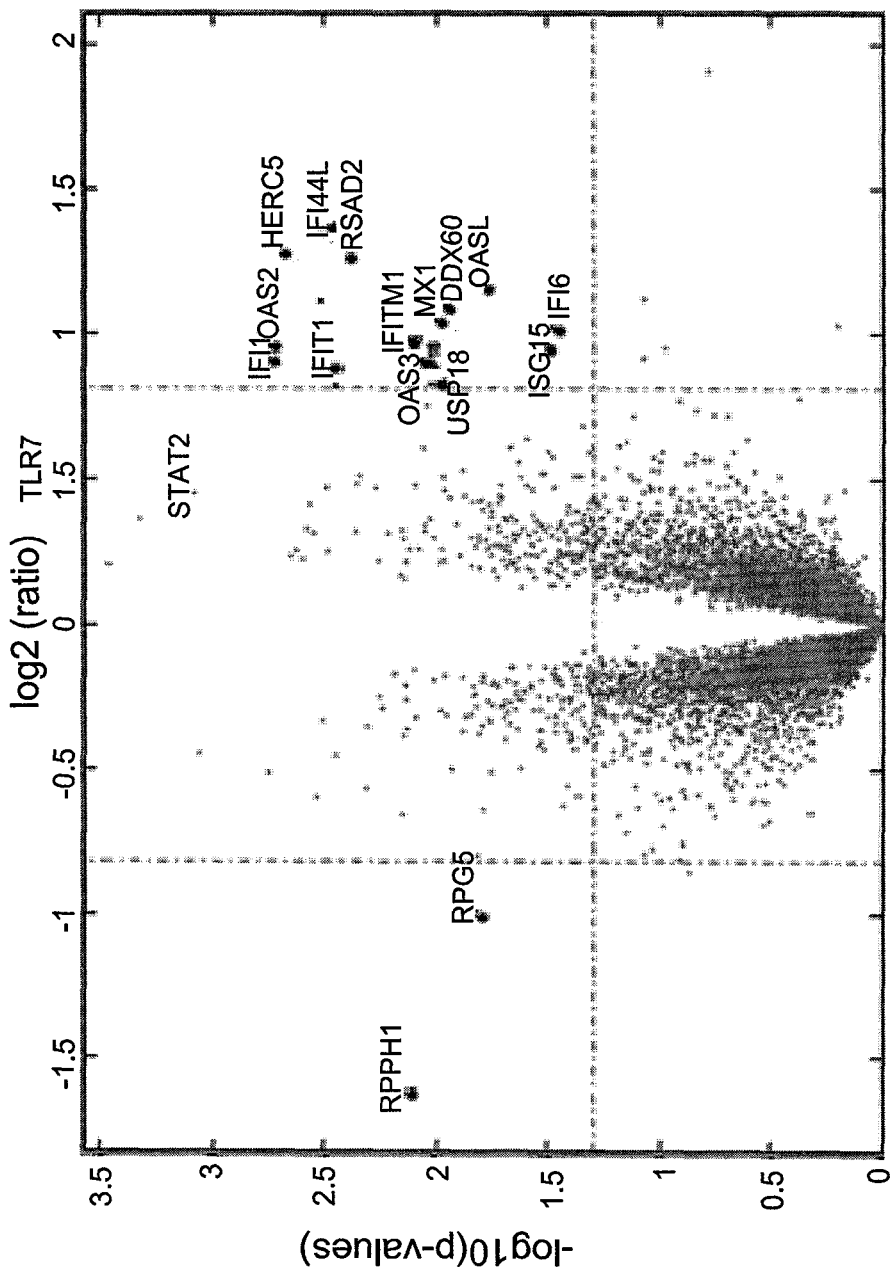
FIG. 38 is a volcano plot showing the significant changes in the expression level of different genes in liver biopsies in responders and non-responders HCV patients before treatment (left) and after one week of IFN and Rib treatment (right). Expression data was obtained from Masao H. et al. The "X"-axis represents log 2 of ratio between gene expression measured in responders vs. non-responders, the points present to the right of the right vertical line (shown at a value of 1 on the x-axis), represent genes that were up regulated by more than 2 folds whereas the points present to the left of the left vertical line (shown at a value of −0.75 on the x-axis), represent genes that were down regulated by more than 2 folds. The "Y" axis shows the p value assigned to each point. The horizontal line corresponds to p-value of 0.05, with points above this line correspond to a p values lower than 0.05 (namely, more significant).

FIG. 38 shows a differential genetic expression obtained in liver biopsies of responders and non-responders HCV patients after combined therapy as described in Masao H. et al. Specifically, the left hand side shows the ratio of expression level of genes in responders vs. non-responders at day 0 (namely, before treatment), whereas the right hand side shows the results obtained after one week following treatment of IFN and RBV. The results provide a representative set of genes having a low expression value before treatment in patients who are referred to as responders. One week after treatment, these genes were clearly up regulated in the responders group.

Figure 39A:
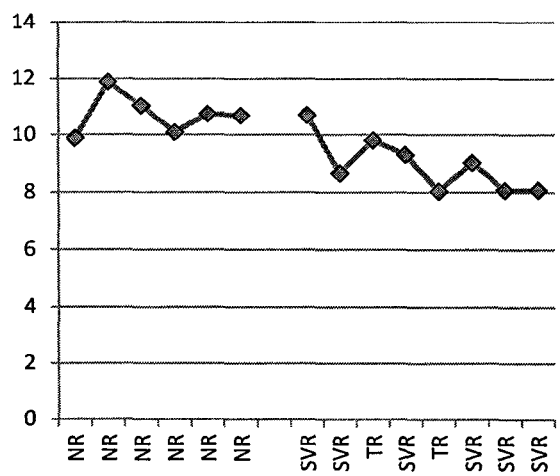
FIGS. 39A and 39B are graphs showing the expression of HERC5 gene expression before initiation of IFN and Rib treatment (FIG. 39A) and ratio between HERC5 gene expression measured after one week of treatment and a baseline level of the same gene measured before infection (FIG. 39B). The data was obtained from liver samples of HCV patients.
Figure 39B:
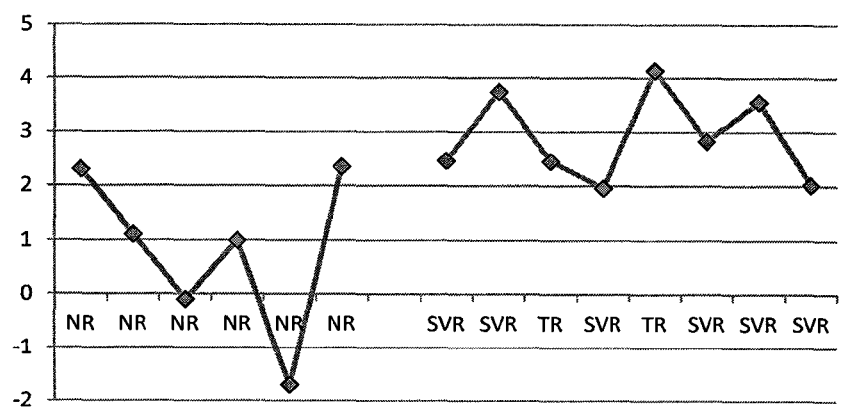

Among the genes shown in the volcano plot, the inventors have used the expression of HERC5 for further analysis as this gene was the predominant gene and obtained the best p-value in the analysis. FIG. 39A shows the expression of HERC5 before treatment and FIG. 39B shows the expression of HERC5 after one week of treatment relative to the expression before treatment.

The results in FIG. 39A show that the initial HERC5 expression level in responders (including the patients defined as TR is low compared to non-responders. As shown in FIG. 39B, a week after treatment, a clear elevation in the expression of HERC5 gene appears in the responder group (and in the patients defined as TR), whereas the non-responders show a clear reduction. Based on these results it may be suggested that the expression level of this gene in responders is close to its saturation level, and therefore interferon cannot induce elevation in the expression of these genes.

The inventors of the present application then used the virus load data measured for each patient at different time points in a model simulation as described herein to obtain an M value for each one of the tested patients (assuming that k is 5).

Figure 40:
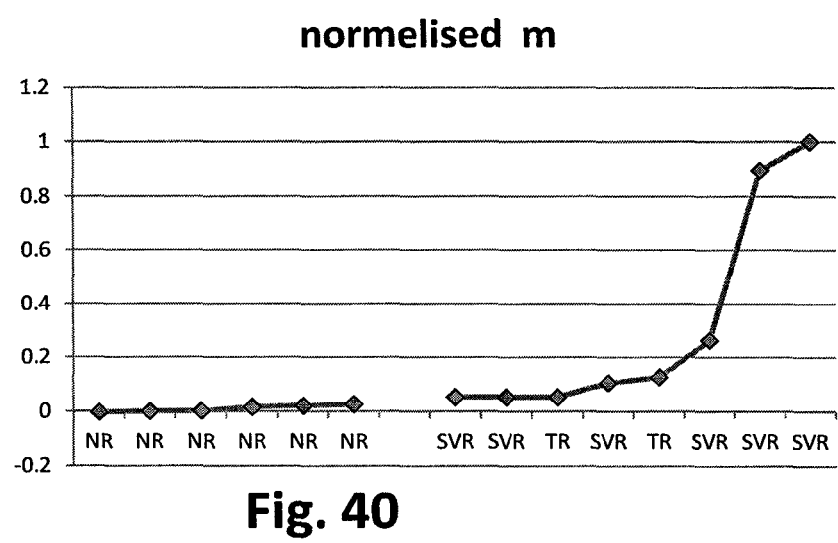
FIG. 40 is a graph showing normalized M value obtained from the model simulation for each one of the patients using the virus load data.

FIG. 40 show normalized M value obtained from the model simulation for each one of the patients. The results indicate that the patients being considered as non-responsive have considerably lower M values, whereas the patients that show response (defined as SVR or TR) have considerably higher M values.

Interestingly, in two of the responsive patients that were characterized with the heights M values in FIG. 40 (0.97 and 0.99), no virus was detected after 48 hours of treatment. These results suggest that for patients characterized with higher M value, a short treatment period is sufficient to reduce/eliminate the virus and there is no need to treat these patients using long-term treatment.

The M values calculated from the model simulation described herein were correlated to normalized expression of HERC5 in order to obtain a "calibration data" of M values.

Table 16 shows for each patient, the normalized expression of HERC5 before treatment and the model calculated M value. Such calibration data may be further used for derivation of M. The patients category NR, SVR or TR is as defined above.

TABLE 16

The expression of HERC5 gene and the simulated M for each one of the tested HCV patients.

| Patient category | Normalized Expression of HERC5 before treatment | Simulated M value |
|---|---|---|
| NR | 0.480499 | 0.7995 |
| NR | 1 | 0.8002 |
| NR | 0.780031 | 0.8004 |
| NR | 0.533021 | 0.803 |
| NR | 0.704628 | 0.804 |
| NR | 0.689028 | 0.805 |
| SVR | 0.694228 | 0.81 |
| SVR | 0.161206 | 0.81 |
| TR | 0.460218 | 0.81 |
| SVR | 0.330213 | 0.82 |
| TR | 0 | 0.824 |
| SVR | 0.25741 | 0.85 |
| SVR | 0.0078 | 0.97 |
| SVR | 0.01014 | 0.99 |

Example 13

Determining Treatment Duration by Calculating M Using Genetic Expression in HCV Patients Treated with IFN-α

Seventeen HCV patients were examined in this study as also presented in Example 11 and FIGS. 37A and 37B. The expression of HERC5 was determined for each one of the patients before initiation of treatment using RT-PCR.

Based on the response to treatment, the patients were categorized into responders or non-responders as shown in FIG. 37.

Using the calibration curve prepared in Example 12, the inventors have determined for each one of the patients, an M value based on the experimental normalized value of expression of HERC5. It should be noted that the inventor considers treatment with every day using IFN plus ribavirin, as the best way for calculating an accurate M and therefore approximates the treatment with PegIFN during the week.

Table 17 shows the normalized expression of HERC5 as measured by RT-PCT and the M value determined using the calibration data described above.

TABLE 17

The expression of HERC5 gene and the derived M (from the calibration data) for each one of the tested HCV patients.

| Patient category | Normalized Expression of HERC5 before treatment | derived M value |
|---|---|---|
| NR s18 | 0.40773 | 0.7995 |
| NR p21 | 0.413093 | 0.7995 |
| NR p23 | 0.448118 | 0.7995 |
| NR p27 | 0.494851 | 0.7995 |
| NR cts17 | 0.589386 | 0.803 |
| NR s20 | 0.654809 | 0.805 |
| NR s16 | 0.804371 | 0.8004 |
| NR s15 | 0.873918 | 0.8004 |
| NR sb11 | 1 | 0.8002 |

TABLE 17-continued

The expression of HERC5 gene and the derived M (from the calibration data) for each one of the tested HCV patients.

| Patient category | Normalized Expression of HERC5 before treatment | derived M value |
|---|---|---|
| Responsive p25 | 0 | 0.95 |
| Responsive p12 | 0.030833 | 0.95 |
| Responsive p26 | 0.076105 | 0.95 |
| Responsive p24 | 0.113371 | 0.84 |
| Responsive s6 | 0.120362 | 0.84 |
| Responsive p22 | 0.170882 | 0.84 |
| Responsive p13 | 0.250061 | 0.85 |
| Responsive s5 | 0.276657 | 0.85 |

These results show that the patients that were experimentally categorized as non-responders have lower M value compared with the patients that were experimentally categorized as responders. This suggest that measuring the expression of a single gene before treatment in a given patient and using this expression to obtain the corresponding M value for this patient, may predict if the patient will respond to treatment.

For prediction of treatment regimen, data from two patients were used denoted as s18 (non-responder) and p25 (responder). As shown in Table 17, using the initial virus load and the derived M for each one of these two patients, the viral load after 4 weeks was measured as presented in Table 18. The figure also discloses the normalized expression of HERC5 marker gene calculated for both patients.

TABLE 18 virus load and M values of HCV patients

| Patient | HERC5 expression | Derived M | Baseline virus load | Virus load after 4 weeks |
|---|---|---|---|---|
| S18 | 0.40773 | 0.7995 | 79986/07 | 168,162 |
| P25 | 0 | 0.95 | 4539 | HCV Not detected |

Figure 41A:
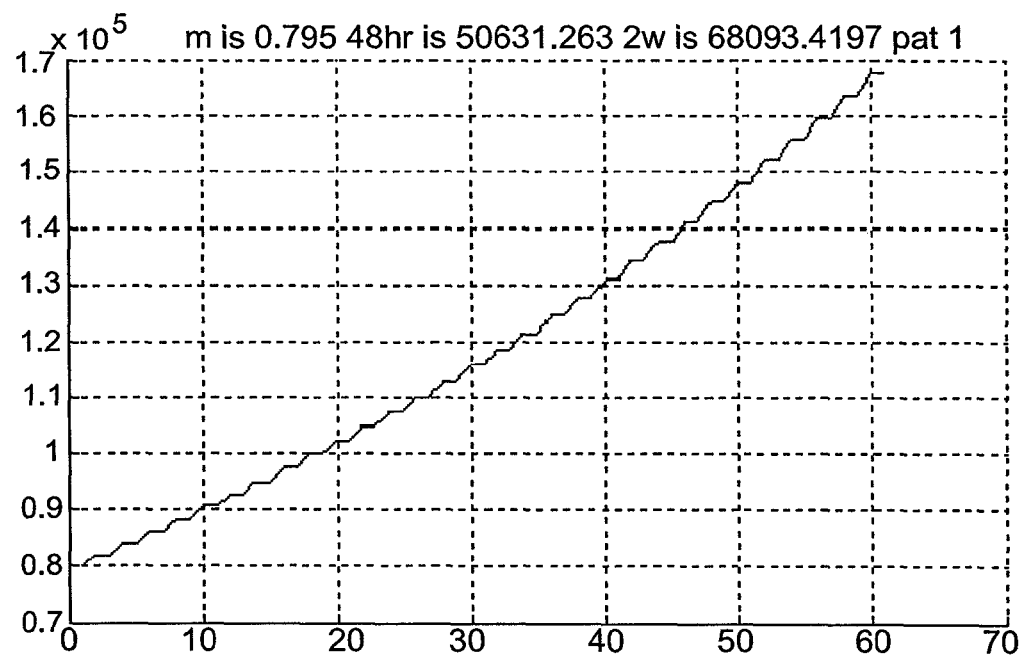
FIGS. 41A and 41B are model simulations predicting viral progression in a non responsive (FIG. 41A) and responsive (FIG. 41B) HCV patients.
Figure 41B:
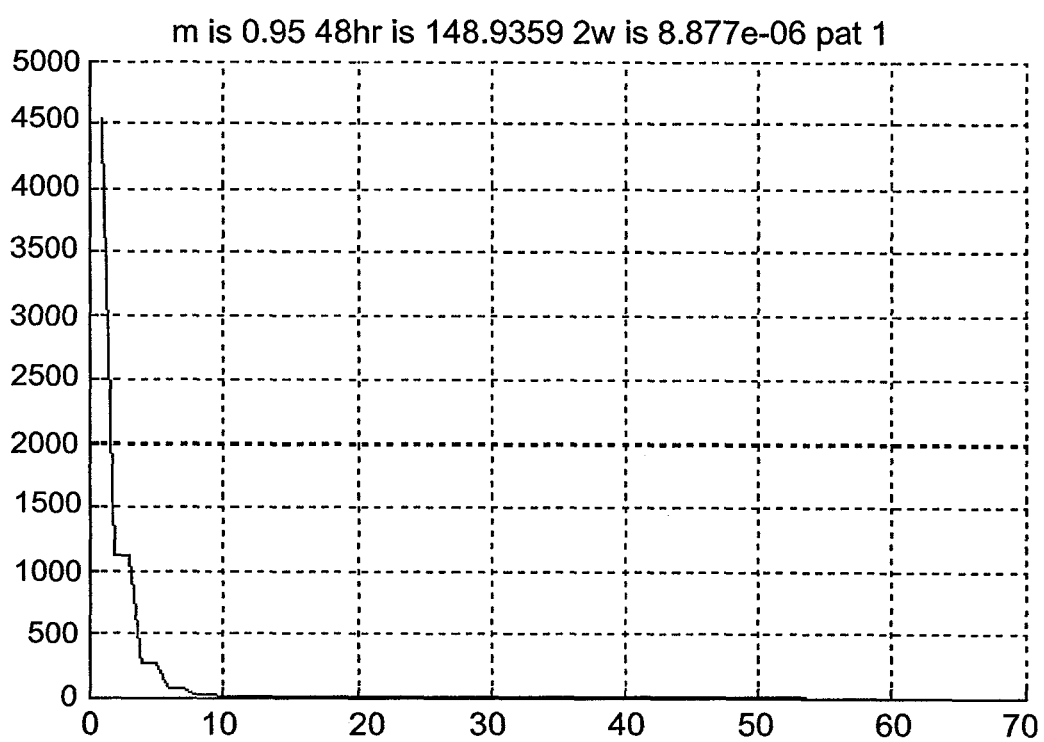

Based on the model described herein, FIGS. 41A and 41B show results of model simulation for s18 and p25, respectively providing calculated predicted virus load.

As shown in FIG. 41A, patient denoted as s18 having a measured initial virus load of 79986.07 (Table 18) and a calculated derived M value of 0.7995, exhibits an increase in virus load after a month up to a value of about 170,000. This simulation strongly correlates with the virus load measured in this patient after four weeks of treatment, which is about 168,162, as presented in Table 18.

In addition, as shown in FIG. 41B, patient denoted as p25 having an initial virus load of 4,539 and a derived M value of 0.95, exhibits a decrease in virus load after a month up to a value basically to baseline level. This strongly correlates with the fact that no virus load was measured in this patient after four weeks of treatment as presented in Table 18.

Thus, for a patient having an M value of 0.795 (p18), IFN treatment would not reduce viral load and therefore should be avoided. However, for a patient having an M value of about 0.95, eradication of the virus is achieved within several days (less than a week) of treatment. The data shown herein therefore also provide means to determine the treatment duration and also type of treatment.

Example 14

Predicting Treatment Regimen for Patient Suffering from HCV and HIV

Data from the publication of Murphya, Alison A. et al, *AIDS* 2011, 25:1179-1187 was used to study the ability of the model to predict treatment regimen. Specifically, the data of average virus load obtained from all patients at different time points was used in the simulation to obtain a M value of 0.82 (K was set at 5).

Figure 42:
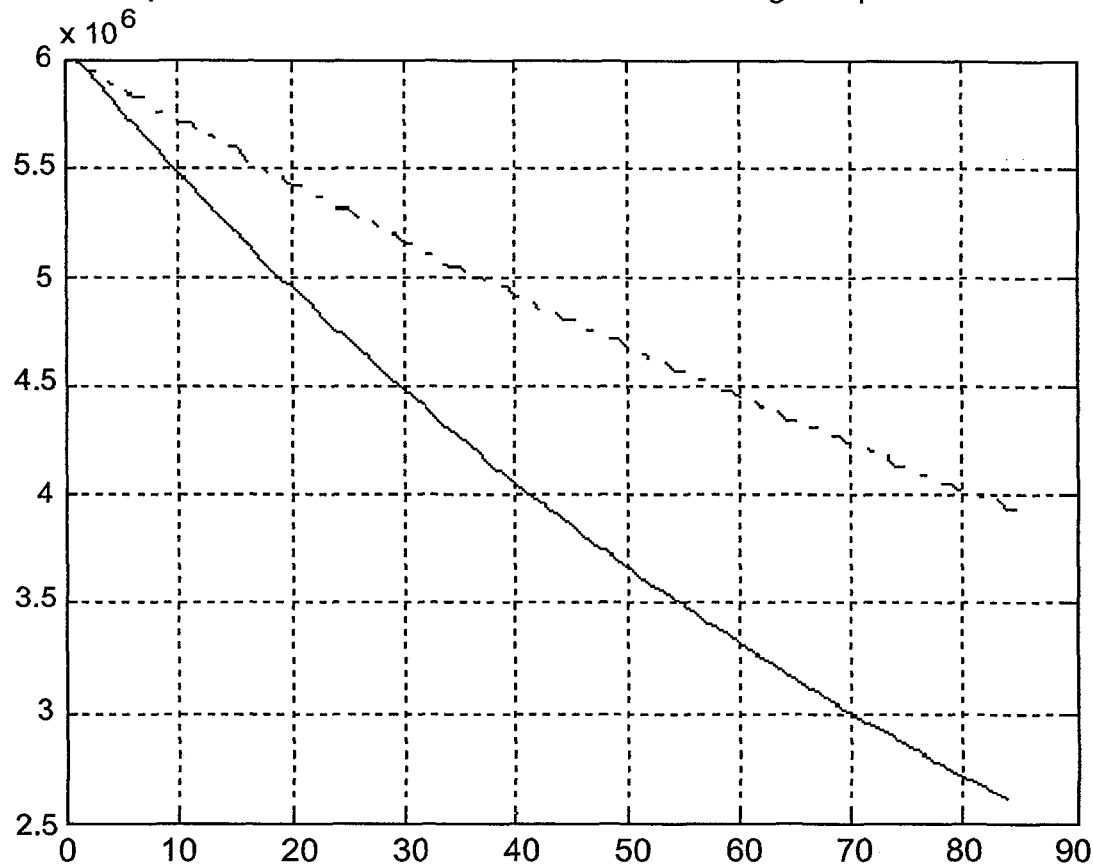
FIG. 42 is a model simulation predicting treatment regimen in HCV patients having an M value of 0.82.

FIG. 42 shows the model simulation (right curve) of the data providing a M value of 0.82.

The simulated M value (of 0.82) was then used together with the initial average virus load in a further simulation that used different dosing regimen, twice a week instead of once weekly. As can be seen in the left curve of FIG. 42, treatment twice a week was more efficient.

Figure 43:
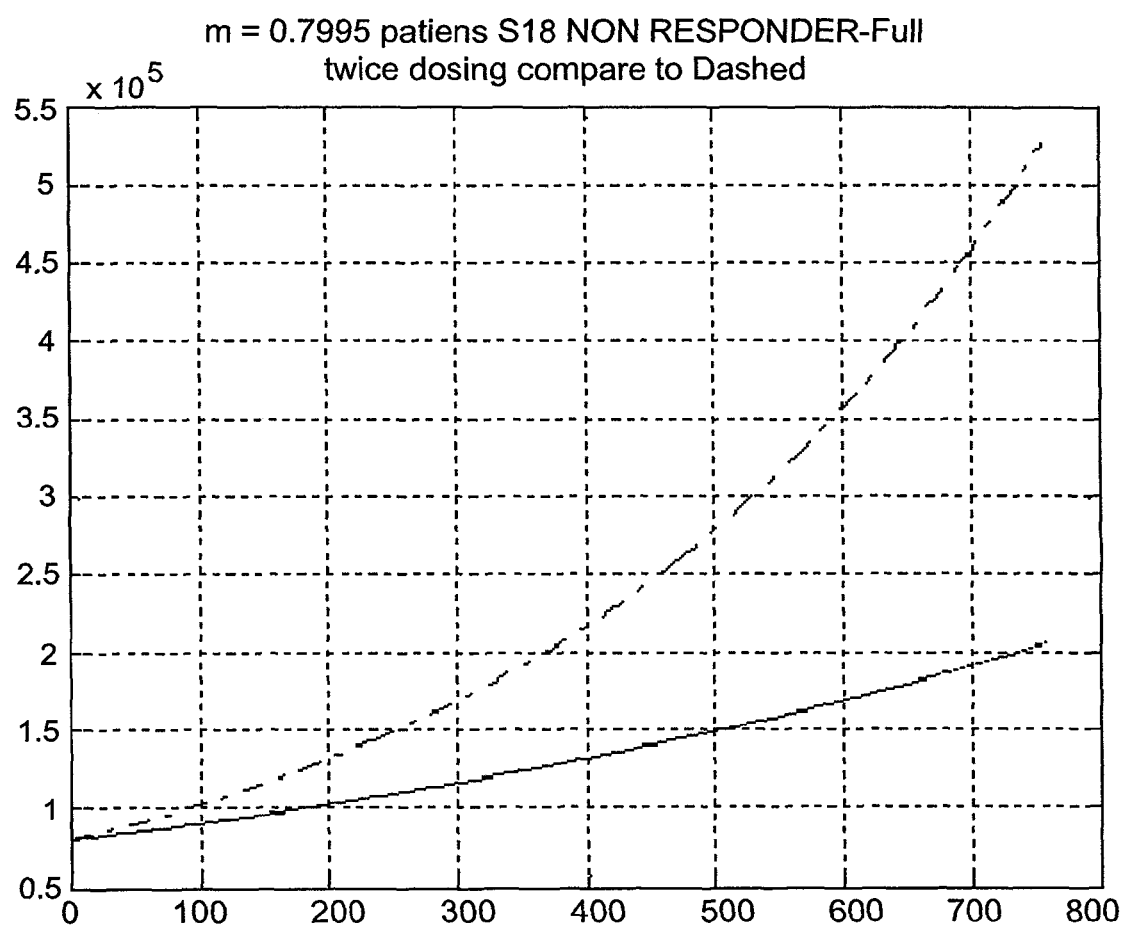
FIG. 43 is a model simulation predicting treatment regimen in HCV patient having an M value of 0.7995 (patient p18).

Further, the patient denoted as s18 (non responder) was further used in a model simulation of treatment regimen. Using the M value of 0.7995 and the initial virus load, the treatment outcome was simulated. As shown in the right curve in FIG. 43, there was an increase in virus load indicating that the patient was not responsive to treatment. Interestingly, as shown in left curve of FIG. 43, increasing the dosing regimen from once a week to twice a week did not result in a response to treatment. This data suggest that even treating this patient with higher amount and/or different regimen is not efficient and new medications need to be used.

TABLE 19

List of Sequences

| SEQ ID NO: | Details |
|---|---|
| 1 | DNA sequence of ISG15 ubiquitin-like modifier (ISG15) |
| 2 | Protein sequence of ISG15 ubiquitin-like modifier (ISG15) |
| 3 | DNA sequence of Interferon-induced protein with tetratricopeptide repeats 1 (IFIT1) |
| 4 | Protein sequence of Interferon-induced protein with tetratricopeptide repeats 1 (IFIT1) |
| 5 | DNA sequence of Interferon-induced protein with tetratricopeptide repeats 2 (IFIT2) |
| 6 | Protein sequence of Interferon-induced protein with tetratricopeptide repeats 2 (IFIT2) |
| 7 | DNA sequence of Interferon-induced protein with tetratricopeptide repeats 3 (IFIT3) |
| 8 | Protein sequence of Interferon-induced protein with tetratricopeptide repeats 3 (IFIT3) |
| 9 | DNA sequence of Interferon-induced protein with tetratricopeptide repeats 3 (IFIT3) |
| 10 | Protein sequence of Interferon-induced protein with tetratricopeptide repeats 3 (IFIT3) |
| 11 | DNA sequence of Interferon-induced protein with tetratricopeptide repeats 5 (IFIT5) |
| 12 | Protein sequence of Interferon-induced protein with tetratricopeptide repeats 5 (IFIT5) |
| 13 | DNA sequence of 2'-5'-oligoadenylate synthetase 1 (OAS1) |
| 14 | Protein sequence of 2'-5'-oligoadenylate synthetase 1 (OAS1) |
| 15 | DNA sequence of 2'-5'-oligoadenylate synthetase 1 (OAS1) |
| 16 | Protein sequence of 2'-5'-oligoadenylate synthetase 1 (OAS1) |
| 17 | DNA sequence of 2'-5'-oligoadenylate synthetase 1 (OAS1) |
| 18 | Protein sequence of 2'-5'-oligoadenylate synthetase 1 (OAS1) |
| 19 | DNA sequence of 2'-5'-oligoadenylate synthetase 2 (OAS2) |
| 20 | Protein sequence of 2'-5'-oligoadenylate synthetase 2 (OAS2) |
| 21 | DNA sequence of 2'-5'-oligoadenylate synthetase 2 (OAS2) |
| 22 | Protein sequence of 2'-5'-oligoadenylate synthetase 2 (OAS2) |
| 23 | DNA sequence of 2'-5'-oligoadenylate synthetase 2 (OAS2) |
| 24 | Protein sequence of 2'-5'-oligoadenylate synthetase 2 (OAS2) |
| 25 | DNA sequence of 2'-5'-oligoadenylate synthetase 3 (OAS3) |
| 26 | Protein sequence of 2'-5'-oligoadenylate synthetase 3 (OAS3) |

TABLE 19-continued

List of Sequences

| SEQ ID NO: | Details |
|---|---|
| 27 | DNA sequence of 2'-5'-oligoadenylate synthetase-like (OASL) |
| 28 | Protein sequence of 2'-5'-oligoadenylate synthetase-like (OASL) |
| 29 | DNA sequence of 2'-5'-oligoadenylate synthetase-like (OASL) |
| 30 | Protein sequence of 2'-5'-oligoadenylate synthetase-like (OASL) |
| 31 | DNA sequence of HECT and RLD domain containing E3 ubiquitin protein ligase 5 (HERC5) |
| 32 | Protein sequence of HECT and RLD domain containing E3 ubiquitin protein ligase 5 (HERC5) |
| 33 | DNA sequence of ubiquitin specific peptidase 18 (USP18) |
| 34 | Protein sequence of ubiquitin specific peptidase 18 (USP18) |
| 35 | DNA sequence of Radical S-adenosyl methionine domain containing 2 (RSAD2) |
| 36 | Protein sequence of Radical S-adenosyl methionine domain containing 2 (RSAD2) |
| 37 | DNA sequence of myxovirus (influenza virus) resistance 1 (MX1) |
| 38 | Protein sequence of myxovirus (influenza virus) resistance 1 (MX1) |
| 39 | DNA sequence of myxovirus (influenza virus) resistance 1 (MX1) |
| 40 | Protein sequence of myxovirus (influenza virus) resistance 1 (MX1) |
| 41 | DNA sequence of myxovirus (influenza virus) resistance 1 (MX1) |
| 42 | Protein sequence of myxovirus (influenza virus) resistance 1 (MX1) |
| 43 | DNA sequence of Interferon-induced protein 44-like (IFI44L) |
| 44 | Protein sequence of Interferon-induced protein 44-like (IFI44L) |
| 45 | DNA sequence of DEAD (Asp-Glu-Ala-Asp) box polypeptide 58 (DDX58) |
| 46 | Protein sequence of DEAD (Asp-Glu-Ala-Asp) box polypeptide 58 (DDX58) |
| 47 | DNA sequence of interferon alpha 1 |
| 48 | Protein sequence interferon alpha 1 |
| 49 | DNA sequence of interferon alpha 2 |
| 50 | Protein sequence of interferon alpha 2 |
| 51 | DNA sequence of Interferon alpha-4 |
| 52 | Protein sequence of Interferon alpha-4 |
| 53 | DNA sequence of Interferon alpha-5 |
| 54 | Protein sequence of Interferon alpha-5 |
| 55 | DNA sequence of Interferon alpha-6 |
| 56 | Protein sequence of Interferon alpha-6 |
| 57 | DNA sequence of Interferon alpha-7 |
| 58 | Protein sequence of Interferon alpha-7 |
| 59 | DNA sequence of Interferon alpha-8 |
| 60 | Protein sequence of Interferon alpha-8 |
| 61 | DNA sequence of Interferon alpha-10 |
| 62 | Protein sequence of Interferon alpha-10 |
| 63 | DNA sequence of Interferon alpha-1/13 |
| 64 | Protein sequence of Interferon alpha-1/13 |
| 65 | DNA sequence of Interferon alpha-14 |
| 66 | Protein sequence of Interferon alpha-14 |
| 67 | DNA sequence of Interferon alpha-16 |
| 68 | Protein sequence of Interferon alpha-16 |
| 69 | DNA sequence of Interferon alpha-17 |
| 70 | Protein sequence of Interferon alpha-17 |
| 71 | DNA sequence of Interferon alpha-21 |
| 72 | Protein sequence of Interferon alpha-21 |
| 73 | DNA sequence of Interferon, beta 1 |
| 74 | Protein sequence of Interferon, beta 1 |
| 75 | DNA sequence of Interferon omega-1 |
| 76 | Protein sequence of Interferon omega-1 |
| 77 | DNA sequence of Interferon-gamma |
| 78 | Protein sequence of Interferon-gamma |
| 79 | DNA sequence of E1-like ubiquitin-activating enzyme (UBE1L) |
| 80 | Protein sequence of E1-like ubiquitin-activating enzyme (UBE1L) |
| 81 | DNA sequence of Ubiquitin-conjugating enzyme E2L 6 (UBE2L6) |
| 82 | Protein sequence of Ubiquitin-conjugating enzyme E2L 6 (UBE2L6) |
| 83 | DNA sequence of Ubiquitin-conjugating enzyme E2L 6 (UBE2L6) |
| 84 | Protein sequence of Ubiquitin-conjugating enzyme E2L 6 (UBE2L6) |
| 85 | DNA sequence of Interferon alpha-inducible protein 27 (IFI27) |
| 86 | protein sequence of Interferon alpha-inducible protein 27 (IFI27) |
| 87 | DNA sequence of Interferon alpha-inducible protein 27 (IFI27) |
| 88 | Protein sequence of Interferon alpha-inducible protein 27 (IFI27) |
| 89 | DNA sequence of Interferon induced with helicase C domain 1 (IFIH1) |
| 90 | Protein sequence of Interferon induced with helicase C domain 1 (IFIH1) |
| 91 | DNA sequence of Toll-like receptor 7 (TLR-7) |
| 92 | Protein sequence of Toll-like receptor 7 (TLR-7) |
| 93 | DNA sequence of Interferon regulatory factor 7 (IRF7) |
| 94 | Protein sequence of Interferon regulatory factor 7 (IRF7) |
| 95 | DNA sequence of Interferon regulatory factor 7 (IRF7) |
| 96 | Protein sequence of Interferon regulatory factor 7 (IRF7) |
| 97 | DNA sequence of Interferon, alpha-inducible protein 6 (IFI6) |
| 98 | Protein sequence of Interferon, alpha-inducible protein 6 (IFI6) |
| 99 | DNA sequence of Interferon, alpha-inducible protein 6 (IFI6) |
| 100 | Protein sequence of Interferon, alpha-inducible protein 6 (IFI6) |
| 101 | DNA sequence of Interferon, alpha-inducible protein 6 (IFI6) |
| 102 | Protein sequence of Interferon, alpha-inducible protein 6 (IFI6) |
| 103 | DNA sequence of Signal transducer and activator of transcription 1 (STAT1) |
| 104 | DNA sequence of Signal transducer and activator of transcription 1 (STAT1) |
| 105 | Protein sequence of Signal transducer and activator of transcription 1 (STAT1) |
| 106 | Protein sequence of Signal transducer and activator of transcription 1 (STAT1) |
| 107 | DNA sequence of Interferon-induced protein 44 (IFI44) gene |
| 108 | Protein sequence of Interferon-induced protein 44 (IFI44) gene |
| 109 | DNA sequence of eukaryotic translation initiation factor 2-alpha kinase 2 (EIF2AK2) |
| 110 | Protein sequence of eukaryotic translation initiation factor 2-alpha kinase 2 (EIF2AK2) |
| 111 | DNA sequence of DEXH (Asp-Glu-X-His) box polypeptide 58 (DHX58) |
| 112 | Protein sequence of DEXH (Asp-Glu-X-His) box polypeptide 58 (DHX58) |

The invention claimed is:

1. A method for determining a personalized treatment regimen for a subject suffering from a Rheumatoid Arthritis (RA) and under treatment with i) a TNF blocker or ii) with a monoclonal antibody against the protein CD20, said method comprises the step of:

determining the level of expression of IFIT1, IFITM3, IFIT3, OAS1, OAS3, HERC5, RSAD2, MX1, IFI44L, IFI6, IFI44 and DDX58 genes, in a biological sample of said subject; wherein (i) up regulation of the determined genes, in the subject receiving TNF blocker, as compared to an untreated reference, indicates the subject is a responder, and down regulation of the determined genes indicates the subject is a non-responder to this treatment;

continuing to treat said subject indicated as a responder with TNF blocker; or discontinuing treatment with the TNF blocker of said subject if indicated as a non-responder;

(ii) down-regulation of the determined genes, in the subject receiving a monoclonal antibody against the protein CD20, as compared to an untreated reference, indicates the subject is a responder to this treatment and up regulation of the determined genes indicates the subject is a non-responder to this treatment;

continuing to treat said subject indicated as a responder with a monoclonal antibody against the protein CD20; or discontinuing treatment with the monoclonal antibody against the protein CD20 of said subject if indicated as a non-responder;

thereby determining the personalized treatment regimen for said subject.

2. The method according to claim 1, wherein the monoclonal antibody against the protein CD20 is rituximab.

3. The method according to claim 1, wherein the TNF blocker is Infliximab.

4. The method according to claim 1, wherein said determining the level of expression is performed by the step of contacting detecting molecules specific for said genes with a biological sample of said subject, or with any nucleic acid or protein product obtained therefrom, and wherein said detecting molecules are selected from isolated detecting nucleic acid molecules and isolated detecting amino acid molecules.

5. The method according to claim 4, wherein said nucleic acid detecting molecule comprises isolated oligonucleotide/s, each oligonucleotide specifically hybridizes to a nucleic acid sequence of each of said genes and optionally, to a control reference gene, and wherein said detecting molecule is at least one of a pair of primers, at least one primer, nucleotide probes or any combinations thereof.

* * * * *

SEQUENCE LISTING

```
<160> NUMBER OF SEQ ID NOS: 112

<210> SEQ ID NO 1
<211> LENGTH: 685
<212> TYPE: DNA
<213> ORGANISM: Homo sapiens

<400> SEQUENCE: 1
ataatagggc cggtgctgcc tgccgaagcc ggcggctgag aggcagcgaa ctcatctttg      60
ccagtacagg agcttgtgcc gtggcccaca gcccacagcc cacagccatg ggctgggacc     120
```

-continued

| | |
|---|---|
| tgacggtgaa gatgctggcg ggcaacgaat tccaggtgtc cctgagcagc tccatgtcgg | 180 |
| tgtcagagct gaaggcgcag atcacccaga agatcggcgt gcacgccttc cagcagcgtc | 240 |
| tggctgtcca cccgagcggt gtggcgctgc aggacagggt ccccccttgcc agccagggcc | 300 |
| tgggccccgg cagcacggtc ctgctggtgg tggacaaatg cgacgaacct ctgagcatcc | 360 |
| tggtgaggaa taacaagggc cgcagcagca cctacgaggt acggctgacg cagaccgtgg | 420 |
| cccacctgaa gcagcaagtg agcgggctgg agggtgtgca ggacgacctg ttctggctga | 480 |
| ccttcgaggg gaagcccctg gaggaccagc tcccgctggg ggagtacggc ctcaagcccc | 540 |
| tgagcaccgt gttcatgaat ctgcgcctgc ggggaggcgg cacagagcct ggcgggcgga | 600 |
| gctaagggcc tccaccagca tccgagcagg atcaagggcc ggaaataaag gctgttgtaa | 660 |
| agagaaaaaa aaaaaaaaaa aaaaa | 685 |

<210> SEQ ID NO 2
<211> LENGTH: 165
<212> TYPE: PRT
<213> ORGANISM: Homo sapiens

<400> SEQUENCE: 2

Met Gly Trp Asp Leu Thr Val Lys Met Leu Ala Gly Asn Glu Phe Gln
 1               5                  10                  15

Val Ser Leu Ser Ser Ser Met Ser Val Ser Glu Leu Lys Ala Gln Ile
            20                  25                  30

Thr Gln Lys Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
        115                 120                 125

Lys Pro Leu Glu Asp Gln Leu Pro Leu Gly Glu Tyr Gly Leu Lys Pro
    130                 135                 140

Leu Ser Thr Val Phe Met Asn Leu Arg Leu Arg Gly Gly Gly Thr Glu
145                 150                 155                 160

Pro Gly Gly Arg Ser
                165

<210> SEQ ID NO 3
<211> LENGTH: 4396
<212> TYPE: DNA
<213> ORGANISM: Homo sapiens

<400> SEQUENCE: 3

| | |
|---|---|
| gcaaggacac acccacagct tacaccattg gctgctgttt agctccctta tataacactg | 60 |
| tcttggggtt taaacgtaac tgaaaatcca caagacagaa tagccagatc tcagaggagc | 120 |
| ctggctaagc aaaaccctgc agaacggctg cctaatttac agcaaccatg agtacaaatg | 180 |
| gtgatgatca tcaggtcaag gatagtctgg agcaattgag atgtcacttt acatgggagt | 240 |
| tatccattga tgacgatgaa atgcctgatt tagaaaacag agtcttggat cagattgaat | 300 |

```
tcctagacac caaatacagt gtgggaatac acaacctact agcctatgtg aaacacctga    360
aaggccagaa tgaggaagcc ctgaagagct taaaagaagc tgaaaactta atgcaggaag    420
aacatgacaa ccaagcaaat gtgaggagtc tggtgacctg gggcaacttt gcctggatgt    480
attaccacat gggcagactg gcagaagccc agacttacct ggacaaggtg gagaacattt    540
gcaagaagct ttcaaatccc ttccgctata gaatggagtg tccagaaata gactgtgagg    600
aaggatgggc cttgctgaag tgtggaggaa aaaattatga acgggccaag gcctgctttg    660
aaaaggtgct tgaagtggac cctgaaaacc ctgaatccag cgctgggtat gcgatctctg    720
cctatcgcct ggatggcttt aaattagcca caaaaaatca caagccattt tctttgcttc    780
ccctaaggca ggctgtccgc ttaaatccag acaatggata tattaaggtt ctccttgccc    840
tgaagcttca ggatgaagga caggaagctg aaggagaaaa gtacattgaa gaagctctag    900
ccaacatgtc ctcacagacc tatgtctttc gatatgcagc caagttttac cgaagaaaag    960
gctctgtgga taaagctctt gagttattaa aaaaggcctt gcaggaaaca cccacttctg   1020
tcttactgca tcaccagata gggctttgct acaaggcaca aatgatccaa atcaaggagg   1080
ctacaaaagg gcagcctaga gggcagaaca gagaaaagct agacaaaatg ataagatcag   1140
ccatatttca ttttgaatct gcagtggaaa aaagcccac atttgaggtg gctcatctag   1200
acctggcaag aatgtatata gaagcaggca tcacagaaa agctgaagag aattttcaaa   1260
aattgttatg catgaaacca gtggtagaag aaacaatgca agacatacat ttccactatg   1320
gtcggtttca ggaatttcaa aagaaatctg acgtcaatgc aattatccat tatttaaaag   1380
ctataaaaat agaacaggca tcattaacaa gggataaaag tatcaattct ttgaagaaat   1440
tggtttttaag gaaacttcgg agaaaggcat tagatctgga aagcttgagc ctccttgggt   1500
tcgtctacaa attggaagga aatatgaatg aagcccctgga gtactatgag cgggccctga   1560
gactggctgc tgactttgag aactctgtga gacaaggtcc ttaggcaccc agatatcagc   1620
cactttcaca tttcatttca ttttatgcta acatttacta atcatctttt ctgcttactg   1680
ttttcagaaa cattataatt cactgtaatg atgtaattct tgaataataa atctgacaaa   1740
atattagttg tgttcaacaa ttagtgaaac agaatgtgtg tatgcatgta agaaagagaa   1800
atcatttgta tgagtgctat gtagtagaga aaaaatgtta gttaactttg taggaaataa   1860
aacattggac ttacactaaa tgtttaattc attcatttta ttgtgaaata aaaataaaat   1920
ccttagctcc tccaccaact gaacagaccc tcttggccaa ggagacccca gaaaccttaa   1980
aaactaagtt tcccaaccat gacaagatga gagatcattc acacctcatt atattccctc   2040
ccttgctaac tgccattgga cttttccac tgagttaaac agaaacccat ggaaaacaaa   2100
gaacagaaga ctcactcctt ggctgacttc acctagctca ctccacgtag cgccacagcc   2160
agactcccct cccctcttgc ggtttccaca tgacaactga tcagccttcc ctcctgataa   2220
gtgaccactg cccacagact ggttctggcc agtccatgga ggctgcacac agggtgcctc   2280
tatgtccttt gtttcacctt ttgatataga aaggctaatt ttgctgtatt ttaatgttaa   2340
gtctccacca cagagtgaac acagaatgca tgtgacatac atgtttacat accactattg   2400
tgtgactgcc cctcatgaat attcatagcc ccccataacc tgttaactat gtgtgtctag   2460
ccaatccacc aaccataaaa cttctgtaat accctcccott cctccaagag cctgcttttg   2520
gttgctgtgg taggctctgc ttcccaggct gcaggttgca ggagaggagg ctgcagtggc   2580
tcacgcctgt aatctcagca cttcgatggg acgaggcagg cagatcacct gaacccagga   2640
gttcgagagc agccttggca atggcaaaac caaccgtctc tacaaaaaat gcaaaaactt   2700
```

```
agctgggtgt ggtggcatgc acctgtagct tcagttccag ctactcagga ggctgaggtg    2760
agtggactgc tggagccagg gagttcgagg ctgcagtgtc gagatcttgc cactgcactc    2820
cattctggat gatagaacga gaccccatct caaaaaaaaa aaaagttctc tccaattgta    2880
tatagcttgt gattttatgt caacactatc aataaatagc tttcagtgca agaaaccaaa    2940
aatactgtaa taaacaggca catattcttc ccaaacctca tgcagtttac aatctagtga    3000
gagcacagag tagcagtaca gagtcaatta aaggttagtt ttcttcatga agatgtttta    3060 atttaattc aatgtgaaag ggttccaagg agtttatctt gttttatgcc attttatttg    3120
aagcactact tactaagtca tttgctgata ttaatctagt taaatcaaga aatattacat    3180
gaaaatgttg ctaaatcaga gatcatgggt aacaatcacc tttgattatg aataatcata    3240
ttttattgaa aggcaaggca caacaaataa taagaaggaa aaaataaata agcaatgtta    3300
ttgatctttc attctgtata tgttttgggg ggaatatact agtttctttt agtggctgta    3360
acaaattacc acaaacttgg tgacttaaaa tttcacagat ttactctttc ttacagttct    3420
ggaggtcaga agtctgaaat gggtttcaat gagccaaagt caaggtattg atgacgctac    3480
actcctccgg aggctctagg cagatagcct tttccagctt ccagaggctg cctgaattct    3540
ttcatccatc ttaaaaacca acagtgtagt agcctcaaat ctctctctct gcttccttct    3600
tcacatctcc ttctctcctc tgactctttt gcctctttct tctaaggacg caccaggtcc    3660
acctgcataa tccagaataa ttgccccatc cgcaaatcct taatttaata acatctgcaa    3720
agtccctttt gctatgtaaa gtagcatgtt cacaggttct ggagacttgg ccatggatac    3780
gattgcgggg ggggcattat tcttaccaca gagcacccca agaaaatctc caaattttgg    3840
gcttccaatc cattttgctt caattattta atattttac tccttccagt agatactgat    3900
ttcatccatt gcccttaaga aggtaggaca gagattatgg cacatctcac attaaatgct    3960
atattttcgt tggaaataca tttttttgctt caacttttat tttaaattca agggtacatg    4020
tgcaggatgt tcaggtttgt tacacaggta aacgtgtgcc atggcggttt gctgaacaga    4080
tcatcccatc accaacagat catcccattg agaggtgaag ccggctgggc ttctgggttg    4140
ggtggggact tggagaactt ttctgtctag ctaaagtatt gtaaaatgga ccagtcaaca    4200
ctctgtaaaa tggaccaatc agctctctgt aaaatggacc aatcagcagg atgtgggtgg    4260
ggccaagtaa gggaataaaa gcaggccacc cgagctggca gcggcaaccc gctcgggtcc    4320
ccttccatgc tgtggaagtt ttgttctttc gctctttcaa taaatcttgc tgctgctcaa    4380
aaaaaaaaaa aaaaaa                                                   4396
```

<210> SEQ ID NO 4
<211> LENGTH: 478
<212> TYPE: PRT
<213> ORGANISM: Homo sapiens

<400> SEQUENCE: 4

```
Met Ser Thr Asn Gly Asp Asp His Gln Val Lys Asp Ser Leu Glu Gln
1               5                   10                  15

Leu Arg Cys His Phe Thr Trp Glu Leu Ser Ile Asp Asp Asp Glu Met
            20                  25                  30

Pro Asp Leu Glu Asn Arg Val Leu Asp Gln Ile Glu Phe Leu Asp Thr
        35                  40                  45

Lys Tyr Ser Val Gly Ile His Asn Leu Leu Ala Tyr Val Lys His Leu
    50                  55                  60
```

```
Lys Gly Gln Asn Glu Glu Ala Leu Lys Ser Leu Lys Glu Ala Glu Asn
 65                  70                  75                  80

Leu Met Gln Glu Glu His Asp Asn Gln Ala Asn Val Arg Ser Leu Val
                 85                  90                  95

Thr Trp Gly Asn Phe Ala Trp Met Tyr Tyr His Met Gly Arg Leu Ala
            100                 105                 110

Glu Ala Gln Thr Tyr Leu Asp Lys Val Glu Asn Ile Cys Lys Lys Leu
        115                 120                 125

Ser Asn Pro Phe Arg Tyr Arg Met Glu Cys Pro Glu Ile Asp Cys Glu
130                 135                 140

Glu Gly Trp Ala Leu Leu Lys Cys Gly Gly Lys Asn Tyr Glu Arg Ala
145                 150                 155                 160

Lys Ala Cys Phe Glu Lys Val Leu Glu Val Asp Pro Glu Asn Pro Glu
                165                 170                 175

Ser Ser Ala Gly Tyr Ala Ile Ser Ala Tyr Arg Leu Asp Gly Phe Lys
            180                 185                 190

Leu Ala Thr Lys Asn His Lys Pro Phe Ser Leu Leu Pro Leu Arg Gln
        195                 200                 205

Ala Val Arg Leu Asn Pro Asp Asn Gly Tyr Ile Lys Val Leu Leu Ala
210                 215                 220

Leu Lys Leu Gln Asp Glu Gly Gln Glu Ala Glu Gly Glu Lys Tyr Ile
225                 230                 235                 240

Glu Glu Ala Leu Ala Asn Met Ser Ser Gln Thr Tyr Val Phe Arg Tyr
                245                 250                 255

Ala Ala Lys Phe Tyr Arg Arg Lys Gly Ser Val Asp Lys Ala Leu Glu
            260                 265                 270

Leu Leu Lys Lys Ala Leu Gln Glu Thr Pro Thr Ser Val Leu Leu His
        275                 280                 285

His Gln Ile Gly Leu Cys Tyr Lys Ala Gln Met Ile Gln Ile Lys Glu
            290                 295                 300

Ala Thr Lys Gly Gln Pro Arg Gly Gln Asn Arg Glu Lys Leu Asp Lys
305                 310                 315                 320

Met Ile Arg Ser Ala Ile Phe His Phe Glu Ser Ala Val Glu Lys Lys
                325                 330                 335

Pro Thr Phe Glu Val Ala His Leu Asp Leu Ala Arg Met Tyr Ile Glu
            340                 345                 350

Ala Gly Asn His Arg Lys Ala Glu Glu Asn Phe Gln Lys Leu Leu Cys
        355                 360                 365

Met Lys Pro Val Val Glu Glu Thr Met Gln Asp Ile His Phe His Tyr
370                 375                 380

Gly Arg Phe Gln Glu Phe Gln Lys Lys Ser Asp Val Asn Ala Ile Ile
385                 390                 395                 400

His Tyr Leu Lys Ala Ile Lys Ile Glu Gln Ala Ser Leu Thr Arg Asp
                405                 410                 415

Lys Ser Ile Asn Ser Leu Lys Lys Leu Val Leu Arg Lys Leu Arg Arg
            420                 425                 430

Lys Ala Leu Asp Leu Glu Ser Leu Ser Leu Leu Gly Phe Val Tyr Lys
        435                 440                 445

Leu Glu Gly Asn Met Asn Glu Ala Leu Glu Tyr Tyr Glu Arg Ala Leu
        450                 455                 460

Arg Leu Ala Ala Asp Phe Glu Asn Ser Val Arg Gln Gly Pro
465                 470                 475
```

```
<210> SEQ ID NO 5
<211> LENGTH: 3505
<212> TYPE: DNA
<213> ORGANISM: Homo sapiens

<400> SEQUENCE: 5
agtttcactt tcccttttgt aacgtcagct gaagggaaac aaacaaaaag gaaccagagg      60
ccacttgtat atataggtct cttcagcatt tattggtggc agaagaggaa gatttctgaa     120
gagtgcagct gcctgaaccg agccctgccg aacagctgag aattgcactg caaccatgag     180
tgagaacaat aagaattcct tggagagcag cctacggcaa ctaaaatgcc atttcacctg     240
gaacttgatg gagggagaaa actccttgga tgattttgaa gacaaagtat tttaccggac     300
tgagtttcag aatcgtgaat tcaaagccac aatgtgcaac ctactggcct atctaaagca     360
cctcaaaggg caaacgagg cagccctgga atgcttacgt aaagctgaag agttaatcca     420
gcaagagcat gctgaccagg cagaaatcag aagtctggtc acctgggaa actatgcctg     480 ggtctactat cacatgggcc gactctcaga cgttcagatt tatgtagaca aggtgaaaca     540
tgtctgtgag aagttttcca gtccctatag aattgagagt ccagagcttg actgtgagga     600
agggtggaca cggttaaagt gtggaggaaa ccaaaatgaa agagcgaagg tgtgctttga     660
gaaggctctg gaaaagaagc caaagaaccc agaattcacc tctggactgg caatagcaag     720
ctaccgtctg gacaactggc caccatctca gaacgccatt gaccctctga ggcaagccat     780
tcggctgaat cctgacaacc agtaccttaa gtcctcctg gctctgaagc ttcataagat     840
gcgtgaagaa ggtgaagagg aaggtgaagg agagaagtta gttgaagaag ccttggagaa     900
agccccaggt gtaacagatg ttcttcgcag tgcagccaag ttttatcgaa gaaaagatga     960
gccagacaaa gcgattgaac tgcttaaaaa ggctttagaa tacataccaa acaatgccta    1020
cctgcattgc caaattgggt gctgctatag ggcaaaagtc ttccaagtaa tgaatctaag    1080
agagaatgga atgtatggga aaagaaagtt actggaacta ataggacacg ctgtggctca    1140
tctgaagaaa gctgatgagg ccaatgataa tctcttccgt gtctgttcca ttcttgccag    1200
cctccatgct ctagcagatc agtatgaaga cgcagagtat tacttccaaa aggaattcag    1260
taaagagctt actcctgtag cgaaacaact gctccatctg cggtatggca actttcagct    1320
gtaccaaatg aagtgtgaag acaaggccat ccaccacttt atagagggtg taaaaataaa    1380
ccagaaatca agggagaaag aaaagatgaa agacaaactg caaaaaattg ccaaaatgcg    1440
actttctaaa aatggagcag attctgaggc tttgcatgtc ttggcattcc ttcaggagct    1500
gaatgaaaaa atgcaacaag cagatgaaga ctctgagagg ggtttggagt ctggaagcct    1560
catcccttca gcatcaagct ggaatgggga atgaagaata gagatgtggt gcccactagg    1620
ctactgctga aagggagctg aaattcctcc accaagttgg tattcaaaat atgtaatgac    1680
tggtatggca aaagattgga ctaagacact ggccatacca ctggacaggg ttatgttaac    1740
acctgaattg ctgggtcttg agagagccca aggagttctg ggagagggac agattgggg    1800 ggtaggtcca cgggcttggt gatagaatta tttctcgatt gacttcttga gtgcaatttg    1860
aactgtaaca tttgcttagt caccttttagt ggagtaatct actgggcttg tttctatatt    1920
tatataaagc agccaaatcc ttcatgtaat attgaagtcc attttgcaa tgttgttcca    1980 tacttggagt cattttgcat cccatagagg ttagtcctgc atagccagta atgtgctaag    2040
ttcatccaaa agctggcgga ccaaagtcta aatagggctc agtatccccc atcgcttatc    2100
tctgcctcct tcctcctcct tcccagtcta tcatcaacct tgagtattct acacaatgtg    2160
```

```
aattcaagtg cctgattaat tgaggtggca acatagtttg agacgagggc agagaacagg    2220
aagatacata gctagaagcg acgggtacaa aaagcaatgt gtacaagaag actttcagca    2280
agtatacaga gagttcacct ctactctgcc ctcctcatag tcataatgta gcaagtaaag    2340
aatgagaatg gattctgtac aatacactag aaaccaacat aatgtatttc tttaaaacct    2400
gtgtgaaaaa ataaatgttc caccagtagg gataggggaa aagtaaccaa aagagagaaa    2460
gagaaaggaa tgctggttta tctttgtaga ttgtaatcga atggagaaat ttgcagtatt    2520
ttagccacta ttaggaattt ttttttttg taaaatgaag actgaactct gttcaaatgc     2580
tttcatgaac ctggtttgag acggtaggaa agcaacaaaa cgtgggaacc tggtgactaa    2640
gggcctggtg caaggacttg ggaaatgtca ttgataatag atggtggggt tttccccccct   2700 ttagaaatgt tggatattaa gtgatataaa cacttctttt aactccgaaa atcttctgag    2760
aaatcacaaa attcacggta tgcttggaac gattgagatt ttctaggtag atgctgaata    2820
gcctagacat caaagttggt gtgaaccaaa atagagtcag ctgacccagc atcagccaca    2880
ctctgggttg gaaaatgttt gcctgttgga attaatttaa gcttaagtat atatcaacat    2940
tattttattg tgcaattaaa acaatacaaa ttcatggttt tttaaagtta aaaattctaa    3000
ccactgtaac aacagttttt gtgttatttt ctgtattaaa catcttgttg cacgcatttg    3060
aggtcatcag ggtgcaaaat ttgtattcct gaaaatgtca tatattttca ttaataaata    3120 acctaaaatat gataaaacat aaagcagtgt tctggttcat ctggaatttt gctgtacttt   3180
aaatctttca gactcagcta ctgataaatg aaacgttaca caggtgtgaa ccaaatccaa    3240
ataacctcga ctggtctact atcataatca cctgaacaga acaaaacttt ttcctcagct    3300
ttaagagtcc agggcttcgg ataacagctg ccatctgcca cctgctacca ttgacctacg    3360
tgaacacaga cattctgtct ccaccttgat ggtgggtggg ctgctcccct tttcttgtt     3420 aaattttgtg ctttcatcac attttctcta ttctgacctc tgttatgaga aataaaagtc    3480
actgattcca ttttaaaaaa aaaaa                                         3505
```

<210> SEQ ID NO 6
<211> LENGTH: 472
<212> TYPE: PRT
<213> ORGANISM: Homo sapiens

<400> SEQUENCE: 6

```
Met Ser Glu Asn Asn Lys Asn Ser Leu Glu Ser Ser Leu Arg Gln Leu
1               5                   10                  15

Lys Cys His Phe Thr Trp Asn Leu Met Glu Gly Glu Asn Ser Leu Asp
            20                  25                  30

Asp Phe Glu Asp Lys Val Phe Tyr Arg Thr Glu Phe Gln Asn Arg Glu
        35                  40                  45

Phe Lys Ala Thr Met Cys Asn Leu Leu Ala Tyr Leu Lys His Leu Lys
    50                  55                  60

Gly Gln Asn Glu Ala Ala Leu Glu Cys Leu Arg Lys Ala Glu Glu Leu
65                  70                  75                  80

Ile Gln Gln Glu His Ala Asp Gln Ala Glu Ile Arg Ser Leu Val Thr
                85                  90                  95

Trp Gly Asn Tyr Ala Trp Val Tyr Tyr His Met Gly Arg Leu Ser Asp
            100                 105                 110

Val Gln Ile Tyr Val Asp Lys Val Lys His Val Cys Glu Lys Phe Ser
        115                 120                 125

Ser Pro Tyr Arg Ile Glu Ser Pro Glu Leu Asp Cys Glu Glu Gly Trp
```

```
            130                 135                 140
Thr Arg Leu Lys Cys Gly Gly Asn Gln Asn Glu Arg Ala Lys Val Cys
145                 150                 155                 160

Phe Glu Lys Ala Leu Glu Lys Lys Pro Lys Asn Pro Glu Phe Thr Ser
                165                 170                 175

Gly Leu Ala Ile Ala Ser Tyr Arg Leu Asp Asn Trp Pro Pro Ser Gln
                180                 185                 190

Asn Ala Ile Asp Pro Leu Arg Gln Ala Ile Arg Leu Asn Pro Asp Asn
                195                 200                 205

Gln Tyr Leu Lys Val Leu Leu Ala Leu Lys Leu His Lys Met Arg Glu
210                 215                 220

Glu Gly Glu Glu Glu Gly Glu Gly Lys Leu Val Glu Ala Leu
225                 230                 235                 240

Glu Lys Ala Pro Gly Val Thr Asp Val Leu Arg Ser Ala Ala Lys Phe
                245                 250                 255

Tyr Arg Arg Lys Asp Glu Pro Asp Lys Ala Ile Glu Leu Leu Lys Lys
                260                 265                 270

Ala Leu Glu Tyr Ile Pro Asn Asn Ala Tyr Leu His Cys Gln Ile Gly
                275                 280                 285

Cys Cys Tyr Arg Ala Lys Val Phe Gln Val Met Asn Leu Arg Glu Asn
290                 295                 300

Gly Met Tyr Gly Lys Arg Lys Leu Leu Glu Leu Ile Gly His Ala Val
305                 310                 315                 320

Ala His Leu Lys Lys Ala Asp Glu Ala Asn Asp Asn Leu Phe Arg Val
                325                 330                 335

Cys Ser Ile Leu Ala Ser Leu His Ala Leu Ala Asp Gln Tyr Glu Asp
                340                 345                 350

Ala Glu Tyr Tyr Phe Gln Lys Glu Phe Ser Lys Glu Leu Thr Pro Val
                355                 360                 365

Ala Lys Gln Leu Leu His Leu Arg Tyr Gly Asn Phe Gln Leu Tyr Gln
370                 375                 380

Met Lys Cys Glu Asp Lys Ala Ile His His Phe Ile Glu Gly Val Lys
385                 390                 395                 400

Ile Asn Gln Lys Ser Arg Glu Lys Glu Lys Met Lys Asp Lys Leu Gln
                405                 410                 415

Lys Ile Ala Lys Met Arg Leu Ser Lys Asn Gly Ala Asp Ser Glu Ala
                420                 425                 430

Leu His Val Leu Ala Phe Leu Gln Glu Leu Asn Glu Lys Met Gln Gln
                435                 440                 445

Ala Asp Glu Asp Ser Glu Arg Gly Leu Glu Ser Gly Ser Leu Ile Pro
450                 455                 460

Ser Ala Ser Ser Trp Asn Gly Glu
465                 470
```

<210> SEQ ID NO 7
<211> LENGTH: 2464
<212> TYPE: DNA
<213> ORGANISM: Homo sapiens

<400> SEQUENCE: 7

```
actttccttt cccctttcat aaaagcacag acctaacagc accctgggtg gaaacctctt    60
cagcatttgc ttggaatcag taagctaaaa acaaaatcaa ccgggacccc agcttttcag   120
aactgcaggg aaacagccat catgagtgag gtcaccaaga ttccctgga gaaaatcctt   180
```

```
ccacagctga aatgccattt cacctggaac ttattcaagg aagacagtgt ctcaagggat      240
ctagaagata gagtgtgtaa ccagattgaa tttttaaaca ctgagttcaa agctacaatg      300
tacaacttgt tggcctacat aaaacaccta gatggtaaca acgaggcagc cctggaatgc      360
ttacggcaag ctgaagagtt aatccagcaa gaacatgctg accaagcaga atcagaagt       420
ctagtcactt ggggaaacta cgcctgggtc tactatcact tgggcagact ctcagatgct      480
cagatttatg tagataaggt gaaacaaacc tgcaagaaat tttcaaatcc atacagtatt      540
gagtattctg aacttgactg tgaggaaggg tggacacaac tgaagtgtgg aagaaatgaa      600
agggcgaagg tgtgttttga gaaggctctg aagaaaagc ccaacaaccc agaattctcc       660
tctggactgg caattgcgat gtaccatctg gataatcacc cagagaaaca gttctctact      720
gatgttttga agcaggccat tgagctgagt cctgataacc aatacgtcaa ggttctcttg      780
ggcctgaaac tgcagaagat gaataaagaa gctgaaggag agcagtttgt tgaagaagcc      840
ttggaaaagt ctccttgcca aacagatgtc ctccgcagtg cagccaaatt ttacagaaga      900
aaaggtgacc tagacaaagc tattgaactg tttcaacggg tgttggaatc cacaccaaac      960
aatggctacc tctatcacca gattgggtgc tgctacaagg caaaagtaag acaaatgcag     1020
aatacaggag aatctgaagc tagtggaaat aaagagatga ttgaagcact aaagcaatat     1080
gctatggact attcgaataa agctcttgag aagggactga atcctctgaa tgcatactcc     1140
gatctcgctg agttcctgga gacgaatgt tatcagacac cattcaataa ggaagtccct      1200
gatgctgaaa agcaacaatc ccatcagcgc tactgcaacc ttcagaaata taatgggaag     1260
tctgaagaca ctgctgtgca acatggttta gagggtttgt ccataagcaa aaaatcaact     1320
gacaaggaag agatcaaaga ccaaccacag aatgtatctg aaaatctgct tccacaaaat     1380
gcaccaaatt attggtatct tcaaggatta attcataagc agaatggaga tctgctgcaa     1440
gcagccaaat gttatgagaa ggaactgggc cgcctgctaa gggatgcccc ttcaggcata     1500
ggcagtattt tcctgtcagc atctgagctt gaggatggta gtgaggaaat gggccagggc     1560
gcagtcagct ccagtcccag agagctcctc tctaactcag agcaactgaa ctgagacaga     1620
ggaggaaaac agagcatcag aagcctgcag tggtggttgt gacgggtagg acgataggaa     1680
gacaggggc cccaacctgg gattgctgag cagggaagct ttgcatgttg ctctaaggta      1740
catttttaaa gagttgtttt ttggccgggc gcagtggctc atgcctgtaa tcccagcact     1800
tgggaggcc gaggtgggcg atcacgagg tctggagttt gagaccatcc tggctaacac       1860
agtgaaatcc cgtctctact aaaaatacaa aaaattagcc aggcgtggtg gctggcacct     1920
gtagtcccag ctacttggga ggctgaggca ggagaatggc gtgaacctgg aaggaagagg     1980
ttgcagtgag ccaagattgc gcccctgcac tccagcctgg gcaacagagc aagactccat     2040
ctcaaaaaaa aaaaaaaaa aaaaaagag ttgttttctc atgttcatta tagttcatta      2100
cagttacata gtccgaaggt cttacaacta atcactggta gcaataaatg cttcaggccc     2160
acatgatgct gattagttct cagttttcat tcagttcaca atataaccac cattcctgcc     2220
ctccctgcca agggtcataa atggtgactg cctaacaaca aaatttgcag tctcatctca     2280
ttttcatcca gacttctgga actcaaagat taacttttga ctaaccctgg aatatctctt     2340
atctcactta tagcttcagg catgtattta tatgtattct tgatagcaat accataatca     2400
atgtgtattc ctgatagtaa tgctacaata aatccaaaca tttcaactct gttaaaaaaa     2460
aaaa                                                                  2464
```

```
<210> SEQ ID NO 8
<211> LENGTH: 490
<212> TYPE: PRT
<213> ORGANISM: Homo sapiens

<400> SEQUENCE: 8

Met Ser Glu Val Thr Lys Asn Ser Leu Glu Lys Ile Leu Pro Gln Leu
1               5                   10                  15

Lys Cys His Phe Thr Trp Asn Leu Phe Lys Glu Asp Ser Val Ser Arg
            20                  25                  30

Asp Leu Glu Asp Arg Val Cys Asn Gln Ile Glu Phe Leu Asn Thr Glu
        35                  40                  45

Phe Lys Ala Thr Met Tyr Asn Leu Leu Ala Tyr Ile Lys His Leu Asp
    50                  55                  60

Gly Asn Asn Glu Ala Ala Leu Glu Cys Leu Arg Gln Ala Glu Glu Leu
65                  70                  75                  80

Ile Gln Gln Glu His Ala Asp Gln Ala Glu Ile Arg Ser Leu Val Thr
                85                  90                  95

Trp Gly Asn Tyr Ala Trp Val Tyr Tyr His Leu Gly Arg Leu Ser Asp
            100                 105                 110

Ala Gln Ile Tyr Val Asp Lys Val Lys Gln Thr Cys Lys Lys Phe Ser
        115                 120                 125

Asn Pro Tyr Ser Ile Glu Tyr Ser Glu Leu Asp Cys Glu Glu Gly Trp
    130                 135                 140

Thr Gln Leu Lys Cys Gly Arg Asn Glu Arg Ala Lys Val Cys Phe Glu
145                 150                 155                 160

Lys Ala Leu Glu Glu Lys Pro Asn Asn Pro Glu Phe Ser Ser Gly Leu
                165                 170                 175

Ala Ile Ala Met Tyr His Leu Asp Asn His Pro Glu Lys Gln Phe Ser
            180                 185                 190

Thr Asp Val Leu Lys Gln Ala Ile Glu Leu Ser Pro Asp Asn Gln Tyr
        195                 200                 205

Val Lys Val Leu Leu Gly Leu Lys Leu Gln Lys Met Asn Lys Glu Ala
    210                 215                 220

Glu Gly Glu Gln Phe Val Glu Glu Ala Leu Glu Lys Ser Pro Cys Gln
225                 230                 235                 240

Thr Asp Val Leu Arg Ser Ala Ala Lys Phe Tyr Arg Arg Lys Gly Asp
                245                 250                 255

Leu Asp Lys Ala Ile Glu Leu Phe Gln Arg Val Leu Glu Ser Thr Pro
            260                 265                 270

Asn Asn Gly Tyr Leu Tyr His Gln Ile Gly Cys Cys Tyr Lys Ala Lys
        275                 280                 285

Val Arg Gln Met Gln Asn Thr Gly Glu Ser Ala Ser Gly Asn Lys
    290                 295                 300

Glu Met Ile Glu Ala Leu Lys Gln Tyr Ala Met Asp Tyr Ser Asn Lys
305                 310                 315                 320

Ala Leu Glu Lys Gly Leu Asn Pro Leu Asn Ala Tyr Ser Asp Leu Ala
                325                 330                 335

Glu Phe Leu Glu Thr Glu Cys Tyr Gln Thr Pro Phe Asn Lys Glu Val
            340                 345                 350

Pro Asp Ala Glu Lys Gln Gln Ser His Gln Arg Tyr Cys Asn Leu Gln
        355                 360                 365

Lys Tyr Asn Gly Lys Ser Glu Asp Thr Ala Val Gln His Gly Leu Glu
    370                 375                 380
```

```
Gly Leu Ser Ile Ser Lys Lys Ser Thr Asp Lys Glu Ile Lys Asp
385                 390                 395                 400

Gln Pro Gln Asn Val Ser Glu Asn Leu Leu Pro Gln Asn Ala Pro Asn
                405                 410                 415

Tyr Trp Tyr Leu Gln Gly Leu Ile His Lys Gln Asn Gly Asp Leu Leu
            420                 425                 430

Gln Ala Ala Lys Cys Tyr Glu Lys Glu Leu Gly Arg Leu Leu Arg Asp
                435                 440                 445

Ala Pro Ser Gly Ile Gly Ser Ile Phe Leu Ser Ala Ser Glu Leu Glu
        450                 455                 460

Asp Gly Ser Glu Glu Met Gly Gln Gly Ala Val Ser Ser Ser Pro Arg
465                 470                 475                 480

Glu Leu Leu Ser Asn Ser Glu Gln Leu Asn
                485                 490

<210> SEQ ID NO 9
<211> LENGTH: 2552
<212> TYPE: DNA
<213> ORGANISM: Homo sapiens

<400> SEQUENCE: 9
attttcctcc tcccaacgat tttaaattag tttcactttc cagtttcctc ttccttcccc    60
taaaagcaat tactcaaaaa cggagaaaac atcagctgat gcgtgcccta ctctcccacc   120
cctttatata gttccttcag tatttacttg aggcagacag gaagacttct gaagaacaaa   180
tcagcctggt caccagcttt tcggaacagc agagacacag agggcagtca tgagtgaggt   240
caccaagaat tccctggaga aaatccttcc acagctgaaa tgccatttca cctggaactt   300
attcaaggaa gacagtgtct caagggatct agaagataga gtgtgtaacc agattgaatt   360
tttaaacact gagttcaaag ctacaatgta caacttgttg gcctacataa aacacctaga   420
tggtaacaac gaggcagccc tggaatgctt acggcaagct gaagagttaa tccagcaaga   480
acatgctgac caagcagaaa tcagaagtct agtcacttgg ggaaactacg cctgggtcta   540
ctatcacttg ggcagactct cagatgctca gatttatgta gataaggtga acaaacctg   600 caagaaattt tcaaatccat acagtattga gtattctgaa cttgactgtg aggaagggtg   660
gacacaactg aagtgtggaa gaaatgaaag ggcgaaggtg tgttttgaga aggctctgga   720
agaaaagccc aacaacccag aattctcctc tggactggca attgcgatgt accatctgga   780
taatcaccca gagaaacagt ctctactga tgttttgaag caggccattg agctgagtcc   840
tgataaccaa tacgtcaagg ttctcttggg cctgaaactg cagaagatga ataaagaagc   900
tgaaggagag cagtttgttg aagaagcctt ggaaaagtct ccttgccaaa cagatgtcct   960
ccgcagtgca gccaaatttt acagaagaaa aggtgaccta gacaaagcta ttgaactgtt  1020
tcaacgggtg ttggaatcca ccaaacaa tggctacctc tatcaccaga ttgggtgctg  1080
ctacaaggca aaagtaagac aaatgcagaa tacaggagaa tctgaagcta gtggaaataa  1140
agagatgatt gaagcactaa agcaatatgc tatggactat tcgaataaag ctcttgagaa  1200
gggactgaat cctctgaatg catactccga tctcgctgag ttcctggaga cggaatgtta  1260
tcagacacca ttcaataagg aagtccctga tgctgaaaag caacaatccc atcagcgcta  1320 ctgcaaccttt cagaaatata tgggaagtc tgaagacact gctgtgcaac atggtttaga  1380
gggtttgtcc ataagcaaaa aatcaactga caaggaagag atcaaagacc aaccacagaa  1440
tgtatctgaa aatctgcttc cacaaaatgc accaaattat tggtatcttc aaggattaat  1500
```

```
tcataagcag aatggagatc tgctgcaagc agccaaatgt tatgagaagg aactgggccg    1560
cctgctaagg gatgccccctt caggcatagg cagtatttc ctgtcagcat ctgagcttga    1620
ggatggtagt gaggaaatgg gccagggcgc agtcagctcc agtcccagag agctcctctc    1680
taactcagag caactgaact gagacagagg aggaaaacag agcatcagaa gcctgcagtg    1740
gtggttgtga cgggtaggac gataggaaga caggggggccc caacctggga ttgctgagca    1800
gggaagcttt gcatgttgct ctaaggtaca ttttaaaga gttgttttt ggccgggcgc    1860 agtggctcat gcctgtaatc ccagcacttt gggaggccga ggtgggcgga tcacgaggtc    1920
tggagtttga gaccatcctg gctaacacag tgaaatcccg tctctactaa aaatacaaaa    1980
aattagccag gcgtggtggc tggcacctgt agtcccagct acttgggagg ctgaggcagg    2040
agaatggcgt gaacctggaa ggaagaggtt gcagtgagcc aagattgcgc cctgcactc    2100 cagcctgggc aacagagcaa gactccatct caaaaaaaaa aaaaaaaaa aaaaagagtt    2160 gttttctcat gttcattata gttcattaca gttacatagt ccgaaggtct tacaactaat    2220
cactggtagc aataaatgct tcaggcccac atgatgctga ttagttctca gttttcattc    2280
agttcacaat ataaccacca ttcctgccct ccctgccaag ggtcataaat ggtgactgcc    2340
taacaacaaa atttgcagtc tcatctcatt ttcatccaga cttctggaac tcaaagatta    2400
acttttgact aaccctggaa tatctcttat ctcacttata gcttcaggca tgtatttata    2460
tgtattcttg atagcaatac cataatcaat gtgtattcct gatagtaatg ctacaataaa    2520
tccaaacatt tcaactctgt taaaaaaaaa aa                                 2552

<210> SEQ ID NO 10
<211> LENGTH: 490
<212> TYPE: PRT
<213> ORGANISM: Homo sapiens

<400> SEQUENCE: 10

Met Ser Glu Val Thr Lys Asn Ser Leu Glu Lys Ile Leu Pro Gln Leu
1               5                  10                  15

Lys Cys His Phe Thr Trp Asn Leu Phe Lys Glu Asp Ser Val Ser Arg
                20                  25                  30

Asp Leu Glu Asp Arg Val Cys Asn Gln Ile Glu Phe Leu Asn Thr Glu
            35                  40                  45

Phe Lys Ala Thr Met Tyr Asn Leu Leu Ala Tyr Ile Lys His Leu Asp
        50                  55                  60

Gly Asn Asn Glu Ala Ala Leu Glu Cys Leu Arg Gln Ala Glu Glu Leu
65                  70                  75                  80

Ile Gln Gln Glu His Ala Asp Gln Ala Glu Ile Arg Ser Leu Val Thr
                85                  90                  95

Trp Gly Asn Tyr Ala Trp Val Tyr Tyr His Leu Gly Arg Leu Ser Asp
            100                 105                 110

Ala Gln Ile Tyr Val Asp Lys Val Lys Gln Thr Cys Lys Lys Phe Ser
        115                 120                 125

Asn Pro Tyr Ser Ile Glu Tyr Ser Glu Leu Asp Cys Glu Glu Gly Trp
    130                 135                 140

Thr Gln Leu Lys Cys Gly Arg Asn Glu Arg Ala Lys Val Cys Phe Glu
145                 150                 155                 160

Lys Ala Leu Glu Glu Lys Pro Asn Asn Pro Glu Phe Ser Ser Gly Leu
                165                 170                 175

Ala Ile Ala Met Tyr His Leu Asp Asn His Pro Glu Lys Gln Phe Ser
            180                 185                 190
```

```
Thr Asp Val Leu Lys Gln Ala Ile Glu Leu Ser Pro Asp Asn Gln Tyr
        195                 200                 205

Val Lys Val Leu Leu Gly Leu Lys Leu Gln Lys Met Asn Lys Glu Ala
        210                 215                 220

Glu Gly Glu Gln Phe Val Glu Ala Leu Glu Lys Ser Pro Cys Gln
225                 230                 235                 240

Thr Asp Val Leu Arg Ser Ala Ala Lys Phe Tyr Arg Arg Lys Gly Asp
            245                 250                 255

Leu Asp Lys Ala Ile Glu Leu Phe Gln Arg Val Leu Glu Ser Thr Pro
            260                 265                 270

Asn Asn Gly Tyr Leu Tyr His Gln Ile Gly Cys Cys Tyr Lys Ala Lys
            275                 280                 285

Val Arg Gln Met Gln Asn Thr Gly Glu Ser Glu Ala Ser Gly Asn Lys
            290                 295                 300

Glu Met Ile Glu Ala Leu Lys Gln Tyr Ala Met Asp Tyr Ser Asn Lys
305                 310                 315                 320

Ala Leu Glu Lys Gly Leu Asn Pro Leu Asn Ala Tyr Ser Asp Leu Ala
            325                 330                 335

Glu Phe Leu Glu Thr Glu Cys Tyr Gln Thr Pro Phe Asn Lys Glu Val
            340                 345                 350

Pro Asp Ala Glu Lys Gln Gln Ser His Gln Arg Tyr Cys Asn Leu Gln
            355                 360                 365

Lys Tyr Asn Gly Lys Ser Glu Asp Thr Ala Val Gln His Gly Leu Glu
            370                 375                 380

Gly Leu Ser Ile Ser Lys Lys Ser Thr Asp Lys Glu Glu Ile Lys Asp
385                 390                 395                 400

Gln Pro Gln Asn Val Ser Glu Asn Leu Pro Gln Asn Ala Pro Asn
            405                 410                 415

Tyr Trp Tyr Leu Gln Gly Leu Ile His Lys Gln Asn Gly Asp Leu Leu
            420                 425                 430

Gln Ala Ala Lys Cys Tyr Glu Lys Glu Leu Gly Arg Leu Leu Arg Asp
            435                 440                 445

Ala Pro Ser Gly Ile Gly Ser Ile Phe Leu Ser Ala Ser Glu Leu Glu
            450                 455                 460

Asp Gly Ser Glu Glu Met Gly Gln Gly Ala Val Ser Ser Ser Pro Arg
465                 470                 475                 480

Glu Leu Leu Ser Asn Ser Glu Gln Leu Asn
            485                 490
```

<210> SEQ ID NO 11
<211> LENGTH: 4034
<212> TYPE: DNA
<213> ORGANISM: Homo sapiens

<400> SEQUENCE: 11

```
agtttctgag cgctcggcat ctgattcaat ctccagtttc ctgttcttgc tggggctggg      60
gtctctcctt taacaaagac acgccgcgcg gccgagtcca ggggctgcag aggcctggcg     120
cgcgcacgcg cacgcgcacg cccaccgcgc ggcttcccgc ggtccccggt gctgaggaga     180
gagcgatccg agggactgcg ccgcccggac ggcctgcaga gcgctgccat catgagtgaa     240
attcgtaagg acaccttgaa ggccattctg ttggagttag aatgtcattt tacatggaat     300
ttacttaagg aagacattga tctgtttgag gtagaagata caattgggca acagcttgaa     360
tttcttacca caaaatctag acttgctctt tataacctat ggcctatgt gaaacaccta     420
```

```
aaaggccaaa ataaagacgc ccttgagtgc ttggaacaag cagaagaaat aatccagcaa      480
gaacactcag acaaagaaga agtacgaagc ctggtcactt ggggaaacta tgcctgggtg      540
tattatcaca tggaccagct tgaagaagct cagaagtata caggtaagat agggaatgtc      600
tgtaagaaat tgtccagtcc ttctaactac aagttggagt gtcctgagac tgactgtgag      660
aaaggctggg cactcttgaa atttggagga aagtattatc aaaaggctaa agcggctttt      720
gagaaggctc tggaagtgga gcctgacaat ccagaattta acatcggcta tgctatcaca      780
gtgtatcggc tggatgattc tgatagagaa gggtctgtaa agagcttttc tctggggcct      840
ttgagaaagg ctgttaccct gaacccagat aacagctata ttaaggtttt tctggcactg      900
aagcttcaag atgtacatgc agaagctgaa ggggaaaagt atattgaaga atcctggac      960 caaatatcat cccagcctta cgtccttcgt tatgcagcca agttctatag gagaaaaat      1020 tcctggaaca aagctctcga acttttaaaa aaggccttgg aggtgacacc aacttcttct      1080
ttcctgcatc accagatggg actttgctac agggcacaaa tgatccaaat caagaaggcc      1140
acacacaaca gacctaaagg aaaggataaa ctaaaggttg atgagctgat tcatctgct      1200 atatttcatt tcaaagcagc catggaacga gactctatgt ttgcatttgc ctacacagac      1260
ctggccaaca tgtacgctga aggaggccag tatagcaatg ctgaggacat tttccggaaa      1320
gctcttcgtc tggagaacat aaccgatgat cacaaacatc agatccatta ccactatggc      1380
cgctttcagg aatttcaccg taaatcagaa atactgcca tccatcatta tttagaagcc      1440
ttaaaggtca aagacagatc accccttcgc accaaactga caagtgctct gaagaaattg      1500
tctaccaaga gactttgtca caatgcttta gatgtgcaga gtttaagtgc cctagggttt      1560
gtttacaagc tggaaggaga aaagaggcaa gctgctgagt actatgagaa ggcacaaaag      1620
atagatccag aaaatgcaga attcctgact gctctctgtg agctccgact ttccatttaa      1680
atacatactc taggaaatta gctctaagtt tttcccttca ttttgggttc tcctgtttgt      1740 tttttttta ttatttaat cccttgttta ttatagagct aatatttatt gaatagttat      1800
tgtgtaccaa gcattgtgct aaatacttta tatgcattat gatgaatctt gtgcggtttt      1860 cttctttt tctttttaa ttaaaatact ataatccatt gagaaatagc aatattctag      1920
ctattgtaac ttctaaaaat ggtatggcca ttagatctgt gcttttatc tctgctcttt      1980 gaatttctca tattatatag taaatatatt cctacgtaaa cctttgatac ctagatcagg      2040
aatactcttc caggagtaca aaattacatt attgatagtt aagctcttaa ttgtgtagct      2100
tgcaaaagac agcactttt agttacagat gttttgactt tgatgaggat atttagctat      2160
caatctaata gtcacctaaa atatcttttt tgttggaaaa aagtttataa taaaaaagtt      2220
tgtcatctct agtgacttca ataaagaaaa aactagaaga ggagaaaaag gatttcctca      2280
aattttaaat atgtaacttc agggattcaa tccccaaatg tttattaagt agctagaaat      2340
aattatgtgg aaaaaatga ataatggaaa atagtgagtc tcaaattgtt ctcttttttt      2400
ttttaactaa aacaaatctg caatgaatct agatgcaatt aattttattc cttccaacta      2460
aaattacaat atttttaggt taaaattatt gagatataaa gcagccattg ggaaattggg      2520
agaaatgata aacaaatgga aaagaagat gtccctaacc tacacccata gattaccaag      2580
gtttcagtgt actagttttg aatctgttct gaatggagtt tttataccct caatttctgg      2640
cctttggcta tttagcatt tcaaagtgac ttctatgaag cttttttttt aatgtgaaat      2700
tttcagaatg ttgtttttt catgtagata ctccaggaag agttaagcac tgctttcagt      2760
```

-continued

```
tttaatatcc accttgaggg gtcgctgctt gagggctctt atcccagggg acttttaat      2820 tcggatgtta cttaatgtgg cttctctaat gtagtttctt tgattaccga ctacacaatt      2880
atgtaccatc acagtattag tggaaaagta ccatgtgatt taattctcca ttcctccaat      2940
gtaactctta aaattattat gtatgtgtgt gtgttttact ttttgttttt tatcatcttt      3000
aaaatttcta ttatggtttg attattataa aaataatgaa ttctcactgt aaatttcaaa      3060
aaaaaattac aaaagtatgt gaatttaaaa atgagagcag tcctctcacc ctaccacagt      3120
tccacaccct caaggtaaac ttataactta taatttgata tgtaaacttc cagatctttt      3180
ttctatgcgt aatcagacat acatatatac tgcagtgtat ctcacgtatt aattttaaa      3240 aatcttttgt tttacttaat tctgtttta ttattattat tattttgttt gatctattaa      3300
ggaagaacaa ggaagggaat gatctttact caagaatttc agaaagtcag cactgaagtc      3360
ctgacctatc agtagacaca tttgtccctt tcagatattt taggatattc tagcaaagca      3420
ggccatttct cccacctgaa agtacataac ttctatcact tgccacataa ttaaaagaac      3480
tcacattaag cggttactca gacagttaat catagaaaag attatttgct tcatcagttc      3540
atagaaaaga ttatttgctt catcagttaa cttgttttta taaatcaggg ctgtgttcat      3600
acacagaagg ggcctgagat ttctgcactt taaacaagct cctcctaggt gaggatgctg      3660
tggctgttct aattacattt tgagtagtaa ggtctacagc attgttcctc aaacttggct      3720
acgtattgga atcacctaaa aagttaaaac aaaacatgga tgtctgggtc ccgccccata      3780
gagaatgact taattggcat ggggtgcagt ccaggcatca tgattttag atttcccagt      3840 tggaacttgt gcagcaaagt ttgggagcta ctgatggaca tgtgaaaagt aagtataaat      3900
ggaataaaat taattaggct aataggctta acccaggaaa tcctaagttc cttgaatatc      3960
cagtttgcat ttggactcct catcatatac ttggtatata atactctaat aaaagctgcc      4020
tgagttgaat tgta                                                        4034
```

<210> SEQ ID NO 12
<211> LENGTH: 482
<212> TYPE: PRT
<213> ORGANISM: Homo sapiens

<400> SEQUENCE: 12

```
Met Ser Glu Ile Arg Lys Asp Thr Leu Lys Ala Ile Leu Glu Leu
1               5                   10                  15

Glu Cys His Phe Thr Trp Asn Leu Leu Lys Glu Asp Ile Asp Leu Phe
            20                  25                  30

Glu Val Glu Asp Thr Ile Gly Gln Gln Leu Glu Phe Leu Thr Thr Lys
        35                  40                  45

Ser Arg Leu Ala Leu Tyr Asn Leu Leu Ala Tyr Val Lys His Leu Lys
    50                  55                  60

Gly Gln Asn Lys Asp Ala Leu Glu Cys Leu Glu Gln Ala Glu Glu Ile
65                  70                  75                  80

Ile Gln Gln Glu His Ser Asp Lys Glu Glu Val Arg Ser Leu Val Thr
                85                  90                  95

Trp Gly Asn Tyr Ala Trp Val Tyr Tyr His Met Asp Gln Leu Glu Glu
            100                 105                 110

Ala Gln Lys Tyr Thr Gly Lys Ile Gly Asn Val Cys Lys Lys Leu Ser
        115                 120                 125

Ser Pro Ser Asn Tyr Lys Leu Glu Cys Pro Glu Thr Asp Cys Glu Lys
    130                 135                 140
```

Gly Trp Ala Leu Leu Lys Phe Gly Gly Lys Tyr Gln Lys Ala Lys
145                 150                 155                 160

Ala Ala Phe Glu Lys Ala Leu Glu Val Glu Pro Asp Asn Pro Glu Phe
                165                 170                 175

Asn Ile Gly Tyr Ala Ile Thr Val Tyr Arg Leu Asp Asp Ser Asp Arg
            180                 185                 190

Glu Gly Ser Val Lys Ser Phe Ser Leu Gly Pro Leu Arg Lys Ala Val
        195                 200                 205

Thr Leu Asn Pro Asp Asn Ser Tyr Ile Lys Val Phe Leu Ala Leu Lys
210                 215                 220

Leu Gln Asp Val His Ala Glu Ala Glu Gly Lys Tyr Ile Glu Glu
225                 230                 235                 240

Ile Leu Asp Gln Ile Ser Ser Gln Pro Tyr Val Leu Arg Tyr Ala Ala
                245                 250                 255

Lys Phe Tyr Arg Arg Lys Asn Ser Trp Asn Lys Ala Leu Glu Leu Leu
            260                 265                 270

Lys Lys Ala Leu Glu Val Thr Pro Thr Ser Ser Phe Leu His His Gln
        275                 280                 285

Met Gly Leu Cys Tyr Arg Ala Gln Met Ile Gln Ile Lys Lys Ala Thr
290                 295                 300

His Asn Arg Pro Lys Gly Lys Asp Lys Leu Lys Val Asp Glu Leu Ile
305                 310                 315                 320

Ser Ser Ala Ile Phe His Phe Lys Ala Ala Met Glu Arg Asp Ser Met
                325                 330                 335

Phe Ala Phe Ala Tyr Thr Asp Leu Ala Asn Met Tyr Ala Glu Gly Gly
            340                 345                 350

Gln Tyr Ser Asn Ala Glu Asp Ile Phe Arg Lys Ala Leu Arg Leu Glu
        355                 360                 365

Asn Ile Thr Asp Asp His Lys His Gln Ile His Tyr His Tyr Gly Arg
370                 375                 380

Phe Gln Glu Phe His Arg Lys Ser Glu Asn Thr Ala Ile His His Tyr
385                 390                 395                 400

Leu Glu Ala Leu Lys Val Lys Asp Arg Ser Pro Leu Arg Thr Lys Leu
                405                 410                 415

Thr Ser Ala Leu Lys Lys Leu Ser Thr Lys Arg Leu Cys His Asn Ala
            420                 425                 430

Leu Asp Val Gln Ser Leu Ser Ala Leu Gly Phe Val Tyr Lys Leu Glu
        435                 440                 445

Gly Glu Lys Arg Gln Ala Ala Glu Tyr Tyr Lys Ala Gln Lys Ile
450                 455                 460

Asp Pro Glu Asn Ala Glu Phe Leu Thr Ala Leu Cys Glu Leu Arg Leu
465                 470                 475                 480

Ser Ile

<210> SEQ ID NO 13
<211> LENGTH: 1673
<212> TYPE: DNA
<213> ORGANISM: Homo sapiens

<400> SEQUENCE: 13
tcccttctga ggaaacgaaa ccaacagcag tccaagctca gtcagcagaa gagataaaag    60
caaacaggtc tgggaggcag ttctgttgcc actctctctc ctgtcaatga tggatctcag   120 aaataccca gccaaatctc tggacaagtt cattgaagac tatctcttgc cagacacgtg   180

```
tttccgcatg caaatcaacc atgccattga catcatctgt gggttcctga aggaaaggtg    240
cttccgaggt agctcctacc ctgtgtgtgt gtccaaggtg gtaaagggtg gctcctcagg    300
caagggcacc accctcagag gccgatctga cgctgacctg gttgtcttcc tcagtcctct    360
caccactttt caggatcagt taaatcgccg gggagagttc atccaggaaa ttaggagaca    420
gctggaagcc tgtcaaagag agagagcatt ttccgtgaag tttgaggtcc aggctccacg    480
ctggggcaac ccccgtgcgc tcagcttcgt actgagttcg ctccagctcg ggagggggt    540 ggagttcgat gtgctgcctg cctttgatgc cctgggtcag ttgactggcg gctataaacc    600 taaccccaa atctatgtca agctcatcga ggagtgcacc gacctgcaga agagggcga    660 gttctccacc tgcttcacag aactacagag agacttcctg aagcagcgcc ccaccaagct    720
caagagcctc atccgcctag tcaagcactg gtaccaaaat tgtaagaaga agcttgggaa    780
gctgccacct cagtatgccc tggagctcct gacggtctat gcttgggagc gagggagcat    840
gaaaacacat ttcaacacag cccagggatt tcggacggtc ttggaattag tcataaacta    900
ccagcaactc tgcatctact ggacaaagta ttatgacttt aaaaaccccca ttattgaaaa    960 gtacctgaga aggcagctca cgaaacccag gcctgtgatc ctggacccgg cggaccctac    1020
aggaaacttg ggtggtggag acccaaaggg ttggaggcag ctggcacaag aggctgaggc    1080
ctggctgaat tacccatgct ttaagaattg ggatgggtcc ccagtgagct cctggattct    1140
gctggctgaa agcaacagtg cagacgatga gaccgacgat cccaggaggt atcagaaata    1200
tggttacatt ggaacacatg gtaccctca tttctctcat agacccagca cactccaggc    1260
agcatccacc ccacaggcag aagaggactg gacctgcacc atcctctgaa tgccagtgca    1320
tcttggggga agggctcca gtgttatctg gaccagttcc ttcattttca ggtgggactc    1380
ttgatccaga gaggacaaag ctcctcagtg agctggtgta atatccagga cagaacccag    1440
gtctcctgac tcctggcctt ctatgccctc tatcctatca tagataacat tctccacagc    1500
ctcacttcat tccacctatt tctctgaaaat attccctgag agagaacaga gagatttaga    1560
taagagaatg aaattccagc cttgactttc ttctgtgcac ctgatgggag ggtaatgtct    1620
aatgtattat caataacaat aaaaataaag caaataccat taaaaaaaaa aaa           1673
```

<210> SEQ ID NO 14
<211> LENGTH: 400
<212> TYPE: PRT
<213> ORGANISM: Homo sapiens

<400> SEQUENCE: 14

```
Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110
```

```
Arg Ala Phe Ser Val Lys Phe Glu Val Gln Ala Pro Arg Trp Gly Asn
            115                 120                 125
Pro Arg Ala Leu Ser Phe Val Leu Ser Ser Leu Gln Leu Gly Glu Gly
        130                 135                 140
Val Glu Phe Asp Val Leu Pro Ala Phe Asp Ala Leu Gly Gln Leu Thr
145                 150                 155                 160
Gly Gly Tyr Lys Pro Asn Pro Gln Ile Tyr Val Lys Leu Ile Glu Glu
                165                 170                 175
Cys Thr Asp Leu Gln Lys Glu Gly Glu Phe Ser Thr Cys Phe Thr Glu
            180                 185                 190
Leu Gln Arg Asp Phe Leu Lys Gln Arg Pro Thr Lys Leu Lys Ser Leu
        195                 200                 205
Ile Arg Leu Val Lys His Trp Tyr Gln Asn Cys Lys Lys Lys Leu Gly
210                 215                 220
Lys Leu Pro Pro Gln Tyr Ala Leu Glu Leu Leu Thr Val Tyr Ala Trp
225                 230                 235                 240
Glu Arg Gly Ser Met Lys Thr His Phe Asn Thr Ala Gln Gly Phe Arg
                245                 250                 255
Thr Val Leu Glu Leu Val Ile Asn Tyr Gln Gln Leu Cys Ile Tyr Trp
            260                 265                 270
Thr Lys Tyr Tyr Asp Phe Lys Asn Pro Ile Ile Glu Lys Tyr Leu Arg
        275                 280                 285
Arg Gln Leu Thr Lys Pro Arg Pro Val Ile Leu Asp Pro Ala Asp Pro
    290                 295                 300
Thr Gly Asn Leu Gly Gly Gly Asp Pro Lys Gly Trp Arg Gln Leu Ala
305                 310                 315                 320
Gln Glu Ala Glu Ala Trp Leu Asn Tyr Pro Cys Phe Lys Asn Trp Asp
                325                 330                 335
Gly Ser Pro Val Ser Ser Trp Ile Leu Leu Ala Glu Ser Asn Ser Ala
            340                 345                 350
Asp Asp Glu Thr Asp Pro Arg Arg Tyr Gln Lys Tyr Gly Tyr Ile
        355                 360                 365
Gly Thr His Glu Tyr Pro His Phe Ser His Arg Pro Ser Thr Leu Gln
370                 375                 380
Ala Ala Ser Thr Pro Gln Ala Glu Glu Asp Trp Thr Cys Thr Ile Leu
385                 390                 395                 400

<210> SEQ ID NO 15
<211> LENGTH: 1470
<212> TYPE: DNA
<213> ORGANISM: Homo sapiens

<400> SEQUENCE: 15
tcccttctga ggaaacgaaa ccaacagcag tccaagctca gtcagcagaa gagataaaag      60
caaacaggtc tgggaggcag ttctgttgcc actctctctc ctgtcaatga tggatctcag     120 aaataccccá gccaaatctc tggacaagtt cattgaagac tatctcttgc agacacgtg     180 tttccgcatg caaatcaacc atgccattga catcatctgt gggttcctga ggaaaggtg     240 cttccgaggt agctcctacc ctgtgtgtgt gtccaaggtg gtaaagggtg gctcctcagg     300
caagggcacc accctcagag gccgatctga cgctgacctg gttgtcttcc tcagtcctct     360
caccactttt caggatcagt taaatcgccg gggagagttc atccaggaaa ttaggagaca     420
gctggaagcc tgtcaaagag agagagcatt ttccgtgaag tttgaggtcc aggctccacg     480
ctggggcaac ccccgtgcgc tcagcttcgt actgagttcg ctccagctcg ggagggggt     540
```

-continued

```
ggagttcgat gtgctgcctg cctttgatgc cctgggtcag ttgactggcg gctataaacc    600 taaccccaa atctatgtca agctcatcga ggagtgcacc gacctgcaga aagagggcga    660
gttctccacc tgcttcacag aactacagag agacttcctg aagcagcgcc ccaccaagct    720
caagagcctc atccgcctag tcaagcactg gtaccaaaat tgtaagaaga agcttgggaa    780
gctgccacct cagtatgccc tggagctcct gacggtctat gcttgggagc gagggagcat    840
gaaaacacat ttcaacacag cccagggatt tcggacggtc ttggaattag tcataaacta    900
ccagcaactc tgcatctact ggacaaagta ttatgacttt aaaaacccca ttattgaaaa    960
gtacctgaga aggcagctca cgaaacccag gcctgtgatc ctggacccgg cggaccctac   1020
aggaaacttg ggtggtggag acccaaaggg ttggaggcag ctggcacaag aggctgaggc   1080
ctggctgaat tacccatgct ttaagaattg ggatgggtcc ccagtgagct cctggattct   1140
gctggtgaga cctcctgctt cctccctgcc attcatccct gcccctctcc atgaagcttg   1200
agacatatag ctggagacca ttctttccaa agaacttacc tcttgccaaa ggccatttat   1260
attcatatag tgacaggctg tgctccatat tttacagtca ttttggtcac aatcgagggt   1320
ttctggaatt ttcacatccc ttgtccagaa ttcattcccc taagagtaat aataaataat   1380
ctctaacacc atttattgac tgtctgcttc gggctcaggt tctgtcctaa gcccctttaat  1440 atgcactctc tcattaaata gtcacaacaa                                    1470
```

<210> SEQ ID NO 16
<211> LENGTH: 364
<212> TYPE: PRT
<213> ORGANISM: Homo sapiens

<400> SEQUENCE: 16

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205
```

Ile Arg Leu Val Lys His Trp Tyr Gln Asn Cys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Val Arg Pro Pro Ala Ser
            340                 345                 350

Ser Leu Pro Phe Ile Pro Ala Pro Leu His Glu Ala
        355                 360

<210> SEQ ID NO 17
<211> LENGTH: 1575
<212> TYPE: DNA
<213> ORGANISM: Homo sapiens

<400> SEQUENCE: 17

| | | |
|---|---|---|
| tcccttctga ggaaacgaaa ccaacagcag tccaagctca gtcagcagaa gagataaaag | 60 |
| caaacaggtc tgggaggcag ttctgttgcc actctctctc ctgtcaatga tggatctcag | 120 |
| aaatacccca gccaaatctc tggacaagtt cattgaagac tatctcttgc agacacgtg | 180 |
| tttccgcatg caaatcaacc atgccattga catcatctgt gggttcctga ggaaaggtg | 240 |
| cttccgaggt agctcctacc ctgtgtgtgt gtccaaggtg gtaaagggtg gctcctcagg | 300 |
| caagggcacc accctcagag gccgatctga cgctgacctg gttgtcttcc tcagtcctct | 360 |
| caccactttt caggatcagt taaatcgccg gggagagttc atccaggaaa ttaggagaca | 420 |
| gctggaagcc tgtcaaagag agagagcatt tccgtgaag tttgaggtcc aggctccacg | 480 |
| ctggggcaac cccgtgcgc tcagcttcgt actgagttcg ctccagctcg ggagggggt | 540 |
| ggagttcgat gtgctgcctg cctttgatgc cctgggtcag ttgactggcg gctataaacc | 600 |
| taaccccca atctatgtca agctcatcga ggagtgcacc gacctgcaga agagggcga | 660 |
| gttctccacc tgcttcacag aactacagag agacttcctg aagcagcgcc ccaccaagct | 720 |
| caagagcctc atccgcctag tcaagcactg gtaccaaaat tgtaagaaga agcttgggaa | 780 |
| gctgccacct cagtatgccc tggagctcct gacggtctat gcttgggagc gagggagcat | 840 |
| gaaaacacat ttcaacacag cccagggatt tcggacggtc ttggaattag tcataaacta | 900 |
| ccagcaactc tgcatctact ggacaaagta ttatgacttt aaaaacccca ttattgaaaa | 960 |
| gtacctgaga aggcagctca cgaaaccag gcctgtgatc ctggacccgg cggaccctac | 1020 |
| aggaaacttg ggtggtggag acccaaaggg ttggaggcag ctggcacaag aggctgaggc | 1080 |
| ctggctgaat tacccatgct ttaagaattg ggatgggtcc ccagtgagct cctggattct | 1140 |
| gctgacccag cacactccag gcagcatcca ccccacaggc agaagaggac tggacctgca | 1200 |

```
ccatcctctg aatgccagtg catcttgggg gaaagggctc cagtgttatc tggaccagtt   1260
ccttcatttt caggtgggac tcttgatcca gagaggacaa agctcctcag tgagctggtg   1320
tataatccag acagaaccc aggtctcctg actcctggcc ttctatgccc tctatcctat   1380
catagataac attctccaca gcctcacttc attccaccta ttctctgaaa atattccctg   1440
agagagaaca gagagattta gataagagaa tgaaattcca gccttgactt tcttctgtgc   1500
acctgatggg agggtaatgt ctaatgtatt atcaataaca ataaaaataa agcaaatacc   1560
atttaaaaaa aaaaa                                                    1575
```

<210> SEQ ID NO 18
<211> LENGTH: 414
<212> TYPE: PRT
<213> ORGANISM: Homo sapiens

<400> SEQUENCE: 18

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300
```

```
Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Thr Gln His Thr Pro Gly
                340                 345                 350

Ser Ile His Pro Thr Gly Arg Arg Gly Leu Asp Leu His His Pro Leu
            355                 360                 365

Asn Ala Ser Ala Ser Trp Gly Lys Gly Leu Gln Cys Tyr Leu Asp Gln
        370                 375                 380

Phe Leu His Phe Gln Val Gly Leu Leu Ile Gln Arg Gly Gln Ser Ser
385                 390                 395                 400

Ser Val Ser Trp Cys Ile Ile Gln Asp Arg Thr Gln Val Ser
                405                 410

<210> SEQ ID NO 19
<211> LENGTH: 3539
<212> TYPE: DNA
<213> ORGANISM: Homo sapiens

<400> SEQUENCE: 19
caagagttgg taagctcgct gcagtgggtg gagagaggcc tctagacttc agtttcagtt      60
tcctggctct gggcagcagc aagaattcct ctgcctccca tcctaccatt cactgtcttg     120
ccggcagcca gctgagagca atgggaaatg gggagtccca gctgtcctcg gtgcctgctc     180
agaagctggg ttggtttatc caggaatacc tgaagcccta cgaagaatgt cagacactga     240
tcgacgagat ggtgaacacc atctgtgacg tcctgcagga acccgaacag ttcccctgg      300 tgcagggagt ggccataggt ggctcctatg acggaaaac agtcttaaga ggcaactccg      360
atggtaccct tgtcctcttc ttcagtgact taaaacaatt ccaggatcag aagagaagcc     420
aacgtgacat cctcgataaa actggggata agctgaagtt ctgtctgttc acgaagtggt     480
tgaaaaacaa tttcgagatc cagaagtccc ttgatgggtt caccatccag gtgttcacaa     540
aaaatcagag aatctctttc gaggtgctgg ccgccttcaa cgctctgagc ttaaatgata     600
atcccagccc ctggatctat cgagagctca aaagatcctt ggataagaca aatgccagtc     660
ctggtgagtt tgcagtctgc ttcactgaac tccagcagaa gttttttgac aaccgtcctg     720
gaaaactaaa ggatttgatc ctcttgataa agcactggca tcaacagtgc cagaaaaaaa     780
tcaaggattt accctcgctg tctccgtatg ccctggagct gcttacggtg tatgcctggg     840
aacagggtgt cagaaaagac aactttgaca ttgctgaagg cgtcagaacc gtactggagc     900
tgatcaaatg ccaggagaag ctgtgtatct attggatggt caactacaac tttgaagatg     960
agaccatcag gaacatcctg ctgcaccagc tccaatcagc gaggccagta atcttggatc    1020
cagttgaccc aaccaataat gtgagtggag ataaatatg ctggcaatgg ctgaaaaaag    1080
aagctcaaac ctggttgact ctcccaacc tggataatga gttacctgca ccatcttgga    1140
atgttctgcc tgcaccactc ttcacgaccc caggccacct tctggataag ttcatcaagg    1200
agtttctcca gcccaacaaa tgcttcctag agcagattga cagtgctgtt aacatcatcc    1260
gtacattcct taaagaaaac tgcttccgac aatcaacagc caagatccag attgtccggg    1320
gaggatcaac cgccaaggc acagctctga agactggctc tgatgccgat ctcgtcgtgt    1380
tccataactc acttaaaagc tacacctccc aaaaaaacga gcggcacaaa atcgtcaagg    1440
aaatccatga acagctgaaa gcctttttgga gggagaagga ggaggagctt gaagtcagct    1500
```

|                                                                              |      |
|------------------------------------------------------------------------------|------|
| ttgagcctcc caagtggaag gctcccaggg tgctgagctt ctctctgaaa tccaaagtcc            | 1560 |
| tcaacgaaag tgtcagcttt gatgtgcttc ctgcctttaa tgcactgggt cagctgagtt            | 1620 |
| ctggctccac acccagcccc gaggtttatg cagggctcat tgatctgtat aaatcctcgg            | 1680 |
| acctcccggg aggagagttt tctacctgtt tcacagtcct gcagcgaaac ttcattcgct            | 1740 |
| cccggcccac caaactaaag gatttaattc gcctggtgaa gcactggtac aaagagtgtg            | 1800 |
| aaaggaaact gaagccaaag gggtctttgc ccccaaagta tgccttggag ctgctcacca            | 1860 |
| tctatgcctg ggagcagggg agtggagtgc cggattttga cactgcagaa ggtttccgga            | 1920 |
| cagtcctgga gctggtcaca caatatcagc agctctgcat cttctggaag gtcaattaca            | 1980 |
| actttgaaga tgagaccgtg aggaagtttc tactgagcca gttgcagaaa accaggcctg            | 2040 |
| tgatcttgga cccagccgaa cccacaggtg acgtgggtgg aggggaccgt tggtgttggc            | 2100 |
| atcttctggc aaaagaagca aaggaatggt tatcctctcc ctgcttcaag gatgggactg            | 2160 |
| gaaacccaat accaccttgg aaagtgccga caatgcagac accaggaagt tgtggagcta            | 2220 |
| ggatccatcc tattgtcaat gagatgttct catccagaag ccatagaatc ctgaataata            | 2280 |
| attctaaaag aaacttctag agatcatctg gcaatcgctt ttaaagactc ggctcaccgt            | 2340 |
| gagaaagagt cactcacatc cattcttccc ttgatggtcc ctattcctcc ttcccttgct            | 2400 |
| tcttggactt cttgaaatca atcaagactg caaaccctt cataaagtct tgccttgctg             | 2460 |
| aactccctct ctgcaggcag cctgccttta aaaatagttg ctgtcatcca ctttatgtgc            | 2520 |
| atcttatttc tgtcaacttg tattttttt cttgtatttt tccaattagc tcctcctttt             | 2580 |
| tccttccagt ctaaaaaagg aatcctctgt gtcttcaaag caaagctctt tacttttccc            | 2640 |
| ttggttctca taactctgtg atcttgctct cggtgcttcc aactcatcca cgtcctgtct            | 2700 |
| gtttcctctg tatacaaaac cctttctgcc cctgctgaca cagacatcct ctatgccagc            | 2760 |
| agccagccaa cccttttcatt agaacttcaa gctctccaaa ggctcagatt ataactgttg           | 2820 |
| tcatatttat atgaggctgt tgtctttttcc ttctgagcct gcctttctcc ccccaccca            | 2880 |
| ggagtatcct cttgccaaat caaaagactt tttccttggg ctttagcctt aaagatactt            | 2940 |
| gaaggtctag gtgctttaac ctcacatacc ctcacttaaa cttttatcac tgttgcatat            | 3000 |
| accagttgtg atacaataaa gaatgtatct ggattttgtg cctagttcct agcacacagc            | 3060 |
| ttcaaaaatt ctagagtttc ctgataggag tgtcttttgt attcataaca agccctttc             | 3120 |
| acccatgcct gggtttatgc taacaaggtt acccatggtg ggcccttagt ttcaaggaag            | 3180 |
| gagttggcca agccagaaag accaagcatg tggttaaagc attggaattt tcagccccat            | 3240 |
| cccacccca atctccaagg aggtgatggg gctggaaatt gagttcaatt ttaacatggc             | 3300 |
| cagtgattta agcaatgctg cctatgtaaa gaaaccccaa taaaaactct ggacagtgag            | 3360 |
| gcttggggag cttcctgatt ggcagacatt ccaatgtact aggaaggtag cgcatcttga            | 3420 |
| ttccacaggg acaaaggctc ctgagctctg ggccttcca gtgcttgcca ccctacatac             | 3480 |
| tctttgtctg gctcttcatt tgtattcttt ataataaaat ggtgattgta agtagagca             | 3539 |

<210> SEQ ID NO 20
<211> LENGTH: 719
<212> TYPE: PRT
<213> ORGANISM: Homo sapiens

<400> SEQUENCE: 20

Met Gly Asn Gly Glu Ser Gln Leu Ser Ser Val Pro Ala Gln Lys Leu
1               5                   10                  15

-continued

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Leu Gln Glu Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140

Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
            180                 185                 190

Pro Gly Lys Leu Lys Asp Leu Ile Leu Leu Ile Lys His Trp His Gln
        195                 200                 205

Gln Cys Gln Lys Lys Ile Lys Asp Leu Pro Ser Leu Ser Pro Tyr Ala
    210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
                245                 250                 255

Cys Gln Glu Lys Leu Cys Ile Tyr Trp Met Val Asn Tyr Asn Phe Glu
            260                 265                 270

Asp Glu Thr Ile Arg Asn Ile Leu Leu His Gln Leu Gln Ser Ala Arg
        275                 280                 285

Pro Val Ile Leu Asp Pro Val Asp Pro Thr Asn Asn Val Ser Gly Asp
    290                 295                 300

Lys Ile Cys Trp Gln Trp Leu Lys Lys Glu Ala Gln Thr Trp Leu Thr
305                 310                 315                 320

Ser Pro Asn Leu Asp Asn Glu Leu Pro Ala Pro Ser Trp Asn Val Leu
                325                 330                 335

Pro Ala Pro Leu Phe Thr Thr Pro Gly His Leu Leu Asp Lys Phe Ile
            340                 345                 350

Lys Glu Phe Leu Gln Pro Asn Lys Cys Phe Leu Glu Gln Ile Asp Ser
        355                 360                 365

Ala Val Asn Ile Ile Arg Thr Phe Leu Lys Glu Asn Cys Phe Arg Gln
    370                 375                 380

Ser Thr Ala Lys Ile Gln Ile Val Arg Gly Gly Ser Thr Ala Lys Gly
385                 390                 395                 400

Thr Ala Leu Lys Thr Gly Ser Asp Ala Asp Leu Val Val Phe His Asn
                405                 410                 415

Ser Leu Lys Ser Tyr Thr Ser Gln Lys Asn Glu Arg His Lys Ile Val
            420                 425                 430

Lys Glu Ile His Glu Gln Leu Lys Ala Phe Trp Arg Glu Lys Glu Glu

-continued

```
                  435                 440                 445
Glu Leu Glu Val Ser Phe Glu Pro Pro Lys Trp Lys Ala Pro Arg Val
450                 455                 460
Leu Ser Phe Ser Leu Lys Ser Lys Val Leu Asn Glu Ser Val Ser Phe
465                 470                 475                 480
Asp Val Leu Pro Ala Phe Asn Ala Leu Gly Gln Leu Ser Ser Gly Ser
                485                 490                 495
Thr Pro Ser Pro Glu Val Tyr Ala Gly Leu Ile Asp Leu Tyr Lys Ser
            500                 505                 510
Ser Asp Leu Pro Gly Gly Glu Phe Ser Thr Cys Phe Thr Val Leu Gln
        515                 520                 525
Arg Asn Phe Ile Arg Ser Arg Pro Thr Lys Leu Lys Asp Leu Ile Arg
        530                 535                 540
Leu Val Lys His Trp Tyr Lys Glu Cys Glu Arg Lys Leu Lys Pro Lys
545                 550                 555                 560
Gly Ser Leu Pro Pro Lys Tyr Ala Leu Glu Leu Leu Thr Ile Tyr Ala
                565                 570                 575
Trp Glu Gln Gly Ser Gly Val Pro Asp Phe Asp Thr Ala Glu Gly Phe
            580                 585                 590
Arg Thr Val Leu Glu Leu Val Thr Gln Tyr Gln Gln Leu Cys Ile Phe
        595                 600                 605
Trp Lys Val Asn Tyr Asn Phe Glu Asp Glu Thr Val Arg Lys Phe Leu
610                 615                 620
Leu Ser Gln Leu Gln Lys Thr Arg Pro Val Ile Leu Asp Pro Ala Glu
625                 630                 635                 640
Pro Thr Gly Asp Val Gly Gly Asp Arg Trp Cys Trp His Leu Leu
                645                 650                 655
Ala Lys Glu Ala Lys Glu Trp Leu Ser Ser Pro Cys Phe Lys Asp Gly
            660                 665                 670
Thr Gly Asn Pro Ile Pro Pro Trp Lys Val Pro Thr Met Gln Thr Pro
        675                 680                 685
Gly Ser Cys Gly Ala Arg Ile His Pro Ile Val Asn Glu Met Phe Ser
690                 695                 700
Ser Arg Ser His Arg Ile Leu Asn Asn Asn Ser Lys Arg Asn Phe
705                 710                 715
```

<210> SEQ ID NO 21
<211> LENGTH: 3647
<212> TYPE: DNA
<213> ORGANISM: Homo sapiens

<400> SEQUENCE: 21

```
caagagttgg taagctcgct gcagtgggtg gagagaggcc tctagacttc agtttcagtt     60
tcctggctct gggcagcagc aagaattcct ctgcctccca tcctaccatt cactgtcttg    120
ccggcagcca gctgagagca atgggaaatg gggagtccca gctgtcctcg gtgcctgctc    180
agaagctggg ttggtttatc caggaatacc tgaagcccta cgaagaatgt cagacactga    240
tcgacgagat ggtgaacacc atctgtgacg tcctgcagga acccgaacag ttccccctgg    300
tgcagggagt ggccataggt ggctcctatg acggaaaaac agtcttaaga ggcaactccg    360
atggtaccct tgtcctcttc ttcagtgact aaaacaatt ccaggatcag aagagaagcc    420
aacgtgacat cctcgataaa actggggata agctgaagtt ctgtctgttc acgaagtggt    480
tgaaaaacaa tttcgagatc cagaagtccc ttgatgggtt caccatccag gtgttcacaa    540
```

```
aaaatcagag aatctctttc gaggtgctgg ccgccttcaa cgctctgagc ttaaatgata    600
atcccagccc ctggatctat cgagagctca aaagatcctt ggataagaca aatgccagtc    660
ctggtgagtt tgcagtctgc ttcactgaac tccagcagaa gttttttgac aaccgtcctg    720
gaaaactaaa ggatttgatc ctcttgataa agcactggca tcaacagtgc cagaaaaaaa    780
tcaaggattt accctcgctg tctccgtatg ccctggagct gcttacggtg tatgcctggg    840
aacaggggtg cagaaaagac aactttgaca ttgctgaagg cgtcagaacc gtactggagc    900
tgatcaaatg ccaggagaag ctgtgtatct attggatggt caactacaac tttgaagatg    960
agaccatcag gaacatcctg ctgcaccagc tccaatcagc gaggccagta atcttggatc   1020
cagttgaccc aaccaataat gtgagtggag ataaaatatg ctggcaatgg ctgaaaaaag   1080
aagctcaaac ctggttgact tctcccaacc tggataatga gttacctgca ccatcttgga   1140
atgttctgcc tgcaccactc ttcacgaccc caggccacct tctggataag ttcatcaagg   1200
agtttctcca gcccaacaaa tgcttcctag agcagattga cagtgctgtt aacatcatcc   1260
gtacattcct taaagaaaac tgcttccgac aatcaacagc caagatccag attgtccggg   1320
gaggatcaac cgccaaaggc acagctctga agactggctc tgatgccgat ctcgtcgtgt   1380
tccataactc acttaaaagc tacacctccc aaaaaaacga gcggcacaaa atcgtcaagg   1440
aaatccatga acagctgaaa gccttttgga gggagaagga ggaggagctt gaagtcagct   1500
ttgagcctcc caagtggaag gctcccaggg tgctgagctt ctctctgaaa tccaaagtcc   1560
tcaacgaaag tgtcagcttt gatgtgcttc ctgccttaaa tgcactgggt cagctgagtt   1620
ctggctccac acccagcccc gaggtttatg cagggctcat tgatctgtat aaatcctcgg   1680
acctcccggg aggagagttt tctacctgtt tcacagtcct gcagcgaaac ttcattcgct   1740
cccggccac caaactaaag gatttaattc gcctggtgaa gcactggtac aaagagtgtg   1800
aaggaaact gaagccaaag gggtctttgc ccccaaagta tgccttggag ctgctcacca   1860
tctatgcctg ggagcagggg agtggagtgc cggattttga cactgcagaa ggtttccgga   1920
cagtcctgga gctggtcaca caatatcagc agctctgcat cttctggaag gtcaattaca   1980
actttgaaga tgagaccgtg aggaagtttc tactgagcca gttgcagaaa accaggcctg   2040
tgatcttgga cccagccgaa cccacaggtg acgtgggtgg aggggaccgt tggtgttggc   2100
atcttctggc aaaagaagca aaggaatggt tatcctctcc ctgcttcaag gatgggactg   2160
gaaacccaat accaccttgg aaagtgccgg taaaagtcat ctaaaggagg cgttgtctgg   2220
aaatagccct gtaacaggct tgaatcaaag aacttctcct actgtagcaa cctgaaatta   2280
actcagacac aaataaagga aacccagctc acaggagctt aaacagctgg tcagccccct   2340
aagcccccac tacaagtgat cctcaggcag gtaaccccag attcatgcac gtagggtgc   2400
tgcgcagcat ccctagtctc tacccagtag atgccactag ccctcctctc ccagtgacaa   2460
ccaaaagtct tcagacattg tcaaacgttc ccctgggttc acagatcttt ctgccttttgg   2520
cttttggctc caccctcttt agctgttaat ttgagtactt atggccctga aagcggccac   2580
ggtgcctcca gatggcaggt ttgcaatcca agcaggaaga aggaaaagat acccaaaggt   2640
caagaacaca gtgattttat tagaagtttc atccgcaaat tttcttccat ttcattgctc   2700
agaaatgtca tgtggctacc tgtaacttga aggtggctac aaagatgact gtggacgtgg   2760
gttgcactgg ccacccaagg atgtctgcca cactctccaa aagccctccc tacctaccaa   2820
gatatacctg atatattcca ccaggatatc ctccctccag atatacttgg ttctctccac   2880
caggttcttt cttttaaagca ggatttctca actttgatac ttactcacat ttggggctag   2940
```

```
acagttcttt gtttggaggc tctcttgtgc attgtaggat gttgagcagc atctctggcc    3000
tgtacccagt agatgccacc cagttgtgac aattaaaagt gtcttgagac tttatcatgt    3060
gtcttctgcc ctaggtgaga acccttgcac tagaggaacc ctacacccca accctggggg    3120
gaatgtaggg aagaggtggc caagccaacc gtggggttag ctctaattat taagatatgc    3180
attataaata aataccaaaa aattgtctct ggcaatagtt accttcccag atacaggtcc    3240
cccctttttt cccctaactc ttttaagcaa tgattgtaac tattaggaga cattgctctc    3300
ccacgtatgt ttttcttttt agacaatgca gacaccagga agttgtggag ctaggatcca    3360
tcctattgtc aatgagatgt tctcatccag aagccataga atcctgaata ataattctaa    3420
aagaaacttc tagagatcat ctggcaatcg cttttaaaga ctcggctcac cgtgagaaag    3480
agtcactcac atccattctt cccttgatgg tccctattcc tccttccctt gcttcttgga    3540
cttcttgaaa tcaatcaaga ctgcaaaccc tttcataaag tcttgccttg ctgaactccc    3600
tctctgcagg cagcctgcct ttaaaaatag ttgctgtcat ccacttt                  3647
```

<210> SEQ ID NO 22
<211> LENGTH: 687
<212> TYPE: PRT
<213> ORGANISM: Homo sapiens

<400> SEQUENCE: 22

```
Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Leu Gln Glu Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140

Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
            180                 185                 190

Pro Gly Lys Leu Lys Asp Leu Ile Leu Leu Ile Lys His Trp His Gln
        195                 200                 205

Gln Cys Gln Lys Lys Ile Lys Asp Leu Pro Ser Leu Ser Pro Tyr Ala
    210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
```

```
                   245                 250                 255
          Cys Gln Glu Lys Leu Cys Ile Tyr Trp Met Val Asn Tyr Asn Phe Glu
                      260                 265                 270

Asp Glu Thr Ile Arg Asn Ile Leu Leu His Gln Leu Gln Ser Ala Arg
                      275                 280                 285

Pro Val Ile Leu Asp Pro Val Asp Pro Thr Asn Asn Val Ser Gly Asp
                      290                 295                 300

Lys Ile Cys Trp Gln Trp Leu Lys Lys Glu Ala Gln Thr Trp Leu Thr
          305                 310                 315                 320

Ser Pro Asn Leu Asp Asn Glu Leu Pro Ala Pro Ser Trp Asn Val Leu
                      325                 330                 335

Pro Ala Pro Leu Phe Thr Thr Pro Gly His Leu Leu Asp Lys Phe Ile
                      340                 345                 350

Lys Glu Phe Leu Gln Pro Asn Lys Cys Phe Leu Glu Gln Ile Asp Ser
                      355                 360                 365

Ala Val Asn Ile Ile Arg Thr Phe Leu Lys Glu Asn Cys Phe Arg Gln
                      370                 375                 380

Ser Thr Ala Lys Ile Gln Ile Val Arg Gly Gly Ser Thr Ala Lys Gly
          385                 390                 395                 400

Thr Ala Leu Lys Thr Gly Ser Asp Ala Asp Leu Val Val Phe His Asn
                      405                 410                 415

Ser Leu Lys Ser Tyr Thr Ser Gln Lys Asn Glu Arg His Lys Ile Val
                      420                 425                 430

Lys Glu Ile His Glu Gln Leu Lys Ala Phe Trp Arg Glu Lys Glu Glu
                      435                 440                 445

Glu Leu Glu Val Ser Phe Glu Pro Pro Lys Trp Lys Ala Pro Arg Val
                      450                 455                 460

Leu Ser Phe Ser Leu Lys Ser Lys Val Leu Asn Glu Ser Val Ser Phe
          465                 470                 475                 480

Asp Val Leu Pro Ala Phe Asn Ala Leu Gly Gln Leu Ser Ser Gly Ser
                      485                 490                 495

Thr Pro Ser Pro Glu Val Tyr Ala Gly Leu Ile Asp Leu Tyr Lys Ser
                      500                 505                 510

Ser Asp Leu Pro Gly Gly Glu Phe Ser Thr Cys Phe Thr Val Leu Gln
                      515                 520                 525

Arg Asn Phe Ile Arg Ser Arg Pro Thr Lys Leu Lys Asp Leu Ile Arg
                      530                 535                 540

Leu Val Lys His Trp Tyr Lys Glu Cys Glu Arg Lys Leu Lys Pro Lys
          545                 550                 555                 560

Gly Ser Leu Pro Pro Lys Tyr Ala Leu Glu Leu Leu Thr Ile Tyr Ala
                      565                 570                 575

Trp Glu Gln Gly Ser Gly Val Pro Asp Phe Asp Thr Ala Glu Gly Phe
                      580                 585                 590

Arg Thr Val Leu Glu Leu Val Thr Gln Tyr Gln Gln Leu Cys Ile Phe
                      595                 600                 605

Trp Lys Val Asn Tyr Asn Phe Glu Asp Glu Thr Val Arg Lys Phe Leu
                      610                 615                 620

Leu Ser Gln Leu Gln Lys Thr Arg Pro Val Ile Leu Asp Pro Ala Glu
          625                 630                 635                 640

Pro Thr Gly Asp Val Gly Gly Asp Arg Trp Cys Trp His Leu Leu
                      645                 650                 655

Ala Lys Glu Ala Lys Glu Trp Leu Ser Ser Pro Cys Phe Lys Asp Gly
                      660                 665                 670
```

Thr Gly Asn Pro Ile Pro Pro Trp Lys Val Pro Val Lys Val Ile
        675                 680                 685

<210> SEQ ID NO 23
<211> LENGTH: 2123
<212> TYPE: DNA
<213> ORGANISM: Homo sapiens

<400> SEQUENCE: 23

| | | | | | |
|---|---|---|---|---|---|
| caagagttgg | taagctcgct | gcagtgggtg | gagagaggcc | tctagacttc | agtttcagtt | 60 |
| tcctggctct | gggcagcagc | aagaattcct | ctgcctccca | tcctaccatt | cactgtcttg | 120 |
| ccggcagcca | gctgagagca | atgggaaatg | gggagtccca | gctgtcctcg | gtgcctgctc | 180 |
| agaagctggg | ttggtttatc | caggaatacc | tgaagcccta | cgaagaatgt | cagacactga | 240 |
| tcgacgagat | ggtgaacacc | atctgtgacg | tcctgcagga | acccgaacag | ttcccccctgg | 300 |
| tgcagggagt | ggccataggt | ggctcctatg | acggaaaaac | agtcttaaga | ggcaactccg | 360 |
| atggtaccct | tgtcctcttc | ttcagtgact | aaaacaatt | ccaggatcag | aagagaagcc | 420 |
| aacgtgacat | cctcgataaa | actggggata | agctgaagtt | ctgtctgttc | acgaagtggt | 480 |
| tgaaaaacaa | tttcgagatc | cagaagtccc | ttgatgggtt | caccatccag | gtgttcacaa | 540 |
| aaaatcagag | aatctctttc | gaggtgctgg | ccgccttcaa | cgctctgagt | aagcattgct | 600 |
| gggtgtcagg | agagaaaagc | caagaagcg | ggtgccagac | agctctgtgc | aacctctagg | 660 |
| ccatgagtgg | gatagatacc | actgctgctt | taaaaaatgg | agaccatag | accctcagga | 720 |
| gagaagaatc | ccttctaccc | tggactcgct | ctcttctctg | gaactaactt | ctcccccata | 780 |
| ccctgattgt | ctttggagaa | aatgttctgg | attctagaat | ctaaggcaga | gccttttaag | 840 |
| ccatactgta | cacataaatc | acctggaacc | ttgttaaaat | gcagatcctg | actcaggagg | 900 |
| tctgagttag | agcccaggat | ttcatatttc | tagccagctc | catgatgagc | tgctggtccg | 960 |
| cagatcatgc | ttgcaggttt | tgaccagagt | cagtgttggt | tagagtaaga | ggatgaggca | 1020 |
| gacatctggg | aaaagtccag | ctggggcaag | catttgaagt | ctgccttcct | accaggtcaa | 1080 |
| aatcaaggca | acgaccttcc | atagataact | atcaaagctt | gagggggtgc | cttgaaccca | 1140 |
| actcctaaat | ccctaagacc | tgcccacctc | ttgtgtctcc | tgtctcagca | acattccca | 1200 |
| cactcttgca | tattgttaaa | gtaacctctg | cttaccaggc | ttctggttta | ataaaagatg | 1260 |
| gctagagtga | ctccatctta | aagcaagtag | ctaggcactc | aaaaggaacc | tacaggctta | 1320 |
| atacttgggt | ctgaaaatag | ccacagtcta | agctgaccac | caattataat | tgcagaatat | 1380 |
| ttaaggccat | acaaaacatc | tcccactaag | cctacaaaat | gtccaggtgt | cctaaaagtt | 1440 |
| cagcccactt | aaaggcagca | ttaatgagca | ggtttaggtt | gaaggattaa | tggtcatcaa | 1500 |
| taccactgtt | aagaagaaaa | ttcttggcca | aattgaattt | aatggagttt | aactgagcag | 1560 |
| acaattcaca | aatctagaag | cctcctgagc | cagagtaggt | tcagagagtc | ttgaacacag | 1620 |
| ccacgtggtg | gaagaagatt | tatggacagg | aaaaggaaaa | tgatgtactg | aaaatgaaag | 1680 |
| tgaggtacag | aaacagccag | actggttata | gctcagcatt | ggccttattt | gaacgagatt | 1740 |
| tgaacagttg | gccacctttg | attggccgaa | actcagtgat | tggcacaaga | gtaggttgca | 1800 |
| gtctgtttac | acatcctttt | aggttatagt | tcaccatgta | cagagaaatt | ttaggccaaa | 1860 |
| cttaaaatat | gtaaggaggc | agctttaggc | taaacttgat | ttaacagcac | caatacccc | 1920 |
| tacctttagt | gagcacatct | gcacattcca | attttaatga | cagctcctta | gaatttctta | 1980 |
| tcaacgaaga | cactaacaaa | gaatggcgca | ttcctccttc | tcctttctga | ggatgcccta | 2040 |

```
cccctgtaaca aagtcgtttc taataaattt gcttctttca ccataaaaaa aaaaaaaaa      2100 aaaaaaaaaa aaaaaaaaaa aaa                                              2123
```

<210> SEQ ID NO 24
<211> LENGTH: 172
<212> TYPE: PRT
<213> ORGANISM: Homo sapiens

<400> SEQUENCE: 24

```
Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Leu Gln Glu Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140

Ala Phe Asn Ala Leu Ser Lys His Cys Trp Val Ser Gly Glu Lys Ser
145                 150                 155                 160

Gln Arg Ser Gly Cys Gln Thr Ala Leu Cys Asn Leu
                165                 170
```

<210> SEQ ID NO 25
<211> LENGTH: 6646
<212> TYPE: DNA
<213> ORGANISM: Homo sapiens

<400> SEQUENCE: 25

```
gttcggagag ccgggcggga aaacgaaacc agaaatccga aggccgcgcc agagccctgc      60 ttcccttgc acctgcgccg ggcggccatg gacttgtaca gcaccccggc cgctgcgctg      120
gacaggttcg tggccagaag gctgcagccg cggaaggagt tcgtagagaa ggcgcggcgc      180
gctctgggcg ccctggccgc tgccctgagg gagcgcgggg gccgcctcgg tgctgctgcc      240
ccgcgggtgc tgaaaactgt caagggaggc tcctcgggcc ggggcacagc tctcaagggt      300
ggctgtgatt ctgaacttgt catcttcctc gactgcttca agagctatgt ggaccagagg      360
gcccgccgtg cagagatcct cagtgagatg cgggcatcgc tggaatcctg gtggcagaac      420
ccagtccctg gtctgagact cacgtttcct gagcagagcg tgcctggggc cctgcagttc      480
cgcctgacat ccgtagatct tgaggactgg atgatgtta gctggtgcc tgccttcaat      540 gtcctgggtc aggccggctc cggcgtcaaa cccaagccac aagtctactc taccctcctc      600
aacagtggct gccaaggggg cgagcatgcg gcctgcttca cagagctgcg gaggaacttt      660
gtgaacattc gcccagccaa gttgaagaac ctaatcttgc tggtgaagca ctggtaccac      720
caggtgtgcc tacaggggtt gtggaaggag acgctgcccc ggtctatgc cctggaattg      780
```

```
ctgaccatct tcgcctggga gcagggctgt aagaaggatg ctttcagcct agccgaaggc    840
ctccgaactg tcctgggcct gatccaacag catcagcacc tgtgtgtttt ctggactgtc    900
aactatggct tcgaggaccc tgcagttggg cagttcttgc agcggcagct taagagaccc    960
aggcctgtga tcctggaccc agctgacccc acatgggacc tggggaatgg ggcagcctgg   1020
cactgggatt tgctagccca ggaggcagca tcctgctatg accacccatg ctttctgagg   1080
gggatggggg acccagtgca gtcttggaag gggccgggcc ttccacgtgc tggatgctca   1140
ggtttgggcc accccatcca gctagaccct aaccagaaga cccctgaaaa cagcaagagc   1200
ctcaatgctg tgtacccaag agcagggagc aaacctccct catgcccagc tcctggcccc   1260
actggggcag ccagcatcgt cccctctgtg ccgggaatgg ccttggacct gtctcagatc   1320
cccaccaagg agctggaccg cttcatccag gaccacctga agccgagccc ccagttccag   1380
gagcaggtga aaaaggccat cgacatcatc ttgcgctgcc tccatgagaa ctgtgttcac   1440
aaggcctcaa gagtcagtaa agggggctca tttggccggg gcacagacct aagggatggc   1500
tgtgatgttg aactcatcat cttcctcaac tgcttcacgg actacaagga ccaggggccc   1560
cgccgcgcag agatccttga tgagatgcga gcgcagctag aatcctggtg caggaccag    1620 gtgcccagcc tgagccttca gtttcctgag cagaatgtgc ctgaggctct gcagttccag   1680
ctggtgtcca cagccctgaa gagctggacg gatgttagcc tgctgcctgc cttcgatgct   1740
gtggggcagc tcagttctgg caccaaacca aatccccagg tctactcgag gctcctcacc   1800
agtggctgcc aggagggcga gcataaggcc tgcttcgcag agctgcggag gaacttcatg   1860
aacattcgcc ctgtcaagct gaagaacctg attctgctgg tgaagcactg gtaccgccag   1920
gttgcggctc agaacaaagg aaaaggacca gcccctgcct ctctgccccc agcctatgcc   1980
ctggagctcc tcaccatctt tgcctgggag cagggctgca ggcaggattg tttcaacatg   2040
gcccaaggct tccggacggt gctgggctc gtgcaacagc atcagcagct ctgtgtctac    2100
tggacggtca actatagcac tgaggaccca gccatgagaa tgcaccttct tggccagctt   2160
cgaaaaccca gacccctggt cctgaccccc gctgatccca cctggaacgt gggccacgt    2220 agctgggagc tgttggccca ggaagcagca gcgctgggga tgcaggcctg ctttctgagt   2280
agagacggga catctgtgca gccctgggat gtgatgccag ccctcctta ccaaacccca    2340 gctggggacc ttgacaagtt catcagtgaa tttctccagc ccaaccgcca gttcctggcc   2400
caggtgaaca aggccgttga taccatctgt tcattttga aggaaaactg cttccggaat    2460
tctcccatca aagtgatcaa ggtggtcaag ggtggctctt cagccaaagg cacagctctg   2520
cgaggccgct cagatgccga cctcgtggtg ttcctcagct gcttcagcca gttcactgag   2580
cagggcaaca agcgggccga gatcatctcc gagatccgag cccagctgga ggcatgtcaa   2640
caggagcggc agttcgaggt caagtttgaa gtctccaaat gggagaatcc ccgcgtgctg   2700
agcttctcac tgacatccca gacgatgctg accagagtg tggactttga tgtgctgcca   2760
gcctttgacg ccctaggcca gctggtctct ggctccaggc cagctctca gtctacgtc    2820 gacctcatcc acagctacag caatgcgggc gagtactcca cctgcttcac agagctacaa   2880
cgggacttca tcatctctcg ccctaccaag ctgaagagcc tgatccggct ggtgaagcac   2940
tggtaccagc agtgtaccaa gatctccaag gggagaggct ccctacccc acagcacggg    3000 ctggaactcc tgactgtgta tgcctgggag cagggcggga aggactccca gttcaacatg   3060
gctgagggct tccgcacggt cctggagctg gtcacccagt accgccagct ctgtatctac   3120
```

```
tggaccatca actacaacgc caaggacaag actgttggag acttcctgaa acagcagctt    3180
cagaagccca ggcctatcat cctggatccg gctgacccga caggcaacct gggccacaat    3240
gcccgctggg acctgctggc caaggaagct gcagcctgca catctgccct gtgctgcatg    3300
ggacggaatg gcatcccat ccagccatgg ccagtgaagg ctgctgtgtg aagttgagaa     3360
aatcagcggt cctactggat gaagagaaga tggacaccag ccctcagcat gaggaaattc    3420
agggtcccct accagatgag agagattgtg tacatgtgtg tgtgagcaca tgtgtgcatg    3480
tgtgtgcaca cgtgtgcatg tgtgtgtttt agtgaatctg ctctcccagc tcacacactc    3540
ccctgcctcc catggcttac acactaggat ccagactcca tggtttgaca ccagcctgcg    3600
tttgcagctt ctctgtcact tccatgactc tatcctcata ccaccactgc tgcttcccac    3660
ccagctgaga atgcccctc ctccctgact cctctctgcc catgcaaatt agctcacatc     3720
tttcctcctg ctgcaatcca tcccttcctc ccattggcct ctccttgcca aatctaaata    3780
gtttatatag ggatggcaga gagttcccat ctcatctgtc agccacagtc atttggtact    3840
ggctacctgg agccttatct tctgaagggt tttaaagaat ggccaattag ctgagaagaa    3900
ttatctaatc aattagtgat gtctgccatg gatgcagtag aggaaagtgg tggtacaagt    3960
gccatgattg attagcaatg tctgcactgg atacggaaaa aagaaggtgc ttgcaggttt    4020
acagtgtata tgtgggctat tgaagagccc tctgagctcg gttgctagca ggagagcatg    4080
cccatattgg cttactttgt ctgccacaga cacagacaga gggagttggg acatgcatgc    4140
tatggggacc ctcttgttgg acacctaatt ggatgcctct tcatgagagg cctccttttc    4200 ttcaccttt atgctgcact cctcccctag tttacacatc ttgatgctgt ggctcagttt    4260
gccttcctga atttttattg ggtccctgtt ttctctccta acatgctgag attctgcatc    4320
cccacagcct aaaactgagcc agtggccaaa caaccgtgct cagcctgttt ctctctgccc    4380
tctagagcaa ggcccaccag gtccatccag gaggctctcc tgacctcaag tccaacaaca    4440
gtgtccacac tagtcaaggt tcagcccaga aaacagaaag cactctagga atcttaggca    4500
gaaagggatt ttatctaaat cactggaaag gctggaggag cagaaggcag aggccaccac    4560
tggactattg gtttcaatat tagaccactg tagccgaatc agaggccaga gagcagccac    4620
tgctactgct aatgccacca ctaccctgc catcactgcc ccacatggac aaaactggag     4680
tcgagaccta ggttagattc ctgcaaccac aaacatccat cagggatggc cagctgccag    4740
agctgcggga agacggatcc cacctccctt tcttagcaga atctaaatta cagccagacc    4800
tctggctgca gaggagtctg agacatgtat gattgaatgg gtgccaagtg ccaggggcg     4860 gagtccccag cagatgcatc ctggccatct gttgcgtgga tgagggagtg ggtctatctc    4920
agaggaagga acaggaaaca aagaaaggaa gccactgaac atcccttctc tgctccacag    4980
gagtgcctta gacagcctga ctctccacaa accactgtta aaacttacct gctaggaatg    5040
ctagattgaa tgggatggga agagccttcc ctcattattg tcattcttgg agagaggtga    5100
gcaaccaagg gaagctcctc tgattcacct agaacctgtt ctctgccgtc tttggctcag    5160
cctacagaga ctagagtagg tgaagggaca gaggacaggg cttctaatac ctgtgccata    5220
ttgacagcct ccatccctgt ccccatctt ggtgctgaac caacgctaag ggcaccttct     5280
tagactcacc tcatcgatac tgcctggtaa tccaaagcta gaactctcag gaccccaaac    5340
tccacctctt ggattggccc tggctgctgc cacacacata tccaagagct cagggccagt    5400
tctggtgggc agcagagacc tgctctgcca agttgtccag cagcagagtg gccctggcct    5460
gggcatcaca agccagtgat gctcctggga agaccaggtg gcaggtcgca gttgggtacc    5520
```

```
ttccattccc accacacaga ctctgggcct ccccgcaaaa tggctccaga attagagtaa    5580
ttatgagatg gtgggaacca gagcaactca ggtgcatgat acaaggagag gttgtcatct    5640
gggtagggca gagaggaggg cttgctcatc tgaacagggg tgtatttcat tccaggccct    5700
cagtctttgg caatgccac cctggtgttg gcatattggc cccactgtaa cttttggggg    5760
cttcccggtc tagccacacc ctcggatgga aagacttgac tgcataaaga tgtcagttct    5820
ccctgagttg attgataggc ttaatggtca ccctaaaaac acccacatat gcttttcgat    5880
ggaaccaggt aagttgacgc taaagttctt atggaaaaat acacacgcaa tagctaggaa    5940
aacacaggga aagaagagtt ctgagcaggg cctagtctta gccaatatta aaacatacta    6000
tgaagcctct gatacttaaa cagcatggcg ctggtacgta aatagaccaa tgcagttagg    6060
tggctctttc caagactctg ggaaaaaag tagtaaaaag ctaaatgcaa tcaatcagca    6120
attgaaagct aagtgagaga gccagagggc ctccttggtg gtaaaagagg gttgcatttc    6180
ttgcagccag aaggcagaga agtgaagac caagtccaga actgaatcct aagaaatgca    6240
ggactgcaaa gaaattggtg tgtgtgtgtg tgtgtgtgtg tgtgtgtgtg tttaatttt    6300 aaaaagtttt tattgagata caagtcaata ccataaagct ctcacccttc taaagtgtac    6360
aattcagtgg tgtgagtata ttcataagat ttatacttgg tgtctattca taagacttat    6420
atccagcata ttcataacta gagccatatc acagatgcat tcatcataat aattccagac    6480 atttttcatca ccctaaaagg aaaccctgaa acccattagc agtcattccc cattcctcca    6540
acccattctc tccctaatcc ctagaaacca ccaatctgct gtgtatttca tctattgcca    6600
acatttcata taaatggcat catacaaaaa aaaaaaaaaa aaaaaa                   6646
```

<210> SEQ ID NO 26
<211> LENGTH: 1087
<212> TYPE: PRT
<213> ORGANISM: Homo sapiens

<400> SEQUENCE: 26

```
Met Asp Leu Tyr Ser Thr Pro Ala Ala Ala Leu Asp Arg Phe Val Ala
1               5                   10                  15

Arg Arg Leu Gln Pro Arg Lys Glu Phe Val Glu Lys Ala Arg Arg Ala
                20                  25                  30

Leu Gly Ala Leu Ala Ala Ala Leu Arg Glu Arg Gly Gly Arg Leu Gly
            35                  40                  45

Ala Ala Ala Pro Arg Val Leu Lys Thr Val Lys Gly Gly Ser Ser Gly
        50                  55                  60

Arg Gly Thr Ala Leu Lys Gly Gly Cys Asp Ser Glu Leu Val Ile Phe
65                  70                  75                  80

Leu Asp Cys Phe Lys Ser Tyr Val Asp Gln Arg Ala Arg Arg Ala Glu
                85                  90                  95

Ile Leu Ser Glu Met Arg Ala Ser Leu Glu Ser Trp Trp Gln Asn Pro
                100                 105                 110

Val Pro Gly Leu Arg Leu Thr Phe Pro Glu Gln Ser Val Pro Gly Ala
            115                 120                 125

Leu Gln Phe Arg Leu Thr Ser Val Asp Leu Glu Asp Trp Met Asp Val
        130                 135                 140

Ser Leu Val Pro Ala Phe Asn Val Leu Gly Gln Ala Gly Ser Gly Val
145                 150                 155                 160

Lys Pro Lys Pro Gln Val Tyr Ser Thr Leu Leu Asn Ser Gly Cys Gln
                165                 170                 175
```

```
Gly Gly Glu His Ala Ala Cys Phe Thr Glu Leu Arg Arg Asn Phe Val
            180                 185                 190

Asn Ile Arg Pro Ala Lys Leu Lys Asn Leu Ile Leu Leu Val Lys His
        195                 200                 205

Trp Tyr His Gln Val Cys Leu Gln Gly Leu Trp Lys Glu Thr Leu Pro
    210                 215                 220

Pro Val Tyr Ala Leu Glu Leu Leu Thr Ile Phe Ala Trp Glu Gln Gly
225                 230                 235                 240

Cys Lys Lys Asp Ala Phe Ser Leu Ala Glu Gly Leu Arg Thr Val Leu
                245                 250                 255

Gly Leu Ile Gln Gln His Gln His Leu Cys Val Phe Trp Thr Val Asn
            260                 265                 270

Tyr Gly Phe Glu Asp Pro Ala Val Gly Gln Phe Leu Gln Arg Gln Leu
        275                 280                 285

Lys Arg Pro Arg Pro Val Ile Leu Asp Pro Ala Asp Pro Thr Trp Asp
    290                 295                 300

Leu Gly Asn Gly Ala Ala Trp His Trp Asp Leu Leu Ala Gln Glu Ala
305                 310                 315                 320

Ala Ser Cys Tyr Asp His Pro Cys Phe Leu Arg Gly Met Gly Asp Pro
                325                 330                 335

Val Gln Ser Trp Lys Gly Pro Gly Leu Pro Arg Ala Gly Cys Ser Gly
            340                 345                 350

Leu Gly His Pro Ile Gln Leu Asp Pro Asn Gln Lys Thr Pro Glu Asn
        355                 360                 365

Ser Lys Ser Leu Asn Ala Val Tyr Pro Arg Ala Gly Ser Lys Pro Pro
    370                 375                 380

Ser Cys Pro Ala Pro Gly Pro Thr Gly Ala Ala Ser Ile Val Pro Ser
385                 390                 395                 400

Val Pro Gly Met Ala Leu Asp Leu Ser Gln Ile Pro Thr Lys Glu Leu
                405                 410                 415

Asp Arg Phe Ile Gln Asp His Leu Lys Pro Ser Pro Gln Phe Gln Glu
            420                 425                 430

Gln Val Lys Lys Ala Ile Asp Ile Ile Leu Arg Cys Leu His Glu Asn
        435                 440                 445

Cys Val His Lys Ala Ser Arg Val Ser Lys Gly Gly Ser Phe Gly Arg
    450                 455                 460

Gly Thr Asp Leu Arg Asp Gly Cys Asp Val Glu Leu Ile Ile Phe Leu
465                 470                 475                 480

Asn Cys Phe Thr Asp Tyr Lys Asp Gln Gly Pro Arg Ala Glu Ile
                485                 490                 495

Leu Asp Glu Met Arg Ala Gln Leu Glu Ser Trp Trp Gln Asp Gln Val
            500                 505                 510

Pro Ser Leu Ser Leu Gln Phe Pro Glu Gln Asn Val Pro Glu Ala Leu
        515                 520                 525

Gln Phe Gln Leu Val Ser Thr Ala Leu Lys Ser Trp Thr Asp Val Ser
    530                 535                 540

Leu Leu Pro Ala Phe Asp Ala Val Gly Gln Leu Ser Ser Gly Thr Lys
545                 550                 555                 560

Pro Asn Pro Gln Val Tyr Ser Arg Leu Leu Thr Ser Gly Cys Gln Glu
                565                 570                 575

Gly Glu His Lys Ala Cys Phe Ala Glu Leu Arg Arg Asn Phe Met Asn
            580                 585                 590
```

-continued

```
Ile Arg Pro Val Lys Leu Lys Asn Leu Ile Leu Leu Val Lys His Trp
            595                 600                 605
Tyr Arg Gln Val Ala Ala Gln Asn Lys Gly Lys Gly Pro Ala Pro Ala
        610                 615                 620
Ser Leu Pro Pro Ala Tyr Ala Leu Glu Leu Leu Thr Ile Phe Ala Trp
625                 630                 635                 640
Glu Gln Gly Cys Arg Gln Asp Cys Phe Asn Met Ala Gln Gly Phe Arg
                645                 650                 655
Thr Val Leu Gly Leu Val Gln Gln His Gln Gln Leu Cys Val Tyr Trp
            660                 665                 670
Thr Val Asn Tyr Ser Thr Glu Asp Pro Ala Met Arg Met His Leu Leu
        675                 680                 685
Gly Gln Leu Arg Lys Pro Arg Pro Leu Val Leu Asp Pro Ala Asp Pro
    690                 695                 700
Thr Trp Asn Val Gly His Gly Ser Trp Glu Leu Leu Ala Gln Glu Ala
705                 710                 715                 720
Ala Ala Leu Gly Met Gln Ala Cys Phe Leu Ser Arg Asp Gly Thr Ser
                725                 730                 735
Val Gln Pro Trp Asp Val Met Pro Ala Leu Leu Tyr Gln Thr Pro Ala
            740                 745                 750
Gly Asp Leu Asp Lys Phe Ile Ser Glu Phe Leu Gln Pro Asn Arg Gln
        755                 760                 765
Phe Leu Ala Gln Val Asn Lys Ala Val Asp Thr Ile Cys Ser Phe Leu
770                 775                 780
Lys Glu Asn Cys Phe Arg Asn Ser Pro Ile Lys Val Ile Lys Val Val
785                 790                 795                 800
Lys Gly Gly Ser Ser Ala Lys Gly Thr Ala Leu Arg Gly Arg Ser Asp
                805                 810                 815
Ala Asp Leu Val Val Phe Leu Ser Cys Phe Ser Gln Phe Thr Glu Gln
            820                 825                 830
Gly Asn Lys Arg Ala Glu Ile Ile Ser Glu Ile Arg Ala Gln Leu Glu
        835                 840                 845
Ala Cys Gln Gln Glu Arg Gln Phe Glu Val Lys Phe Glu Val Ser Lys
850                 855                 860
Trp Glu Asn Pro Arg Val Leu Ser Phe Ser Leu Thr Ser Gln Thr Met
865                 870                 875                 880
Leu Asp Gln Ser Val Asp Phe Asp Val Leu Pro Ala Phe Asp Ala Leu
                885                 890                 895
Gly Gln Leu Val Ser Gly Ser Arg Pro Ser Ser Gln Val Tyr Val Asp
            900                 905                 910
Leu Ile His Ser Tyr Ser Asn Ala Gly Glu Tyr Ser Thr Cys Phe Thr
        915                 920                 925
Glu Leu Gln Arg Asp Phe Ile Ile Ser Arg Pro Thr Lys Leu Lys Ser
    930                 935                 940
Leu Ile Arg Leu Val Lys His Trp Tyr Gln Gln Cys Thr Lys Ile Ser
945                 950                 955                 960
Lys Gly Arg Gly Ser Leu Pro Pro Gln His Gly Leu Glu Leu Leu Thr
                965                 970                 975
Val Tyr Ala Trp Glu Gln Gly Gly Lys Asp Ser Gln Phe Asn Met Ala
            980                 985                 990
Glu Gly Phe Arg Thr Val Leu Glu Leu Val Thr Gln Tyr Arg Gln Leu
        995                 1000                1005
Cys Ile Tyr Trp Thr Ile Asn Tyr Asn Ala Lys Asp Lys Thr Val
```

```
                1010                1015                1020
Gly Asp Phe Leu Lys Gln Gln Leu Gln Lys Pro Arg Pro Ile Ile
        1025                1030                1035
Leu Asp Pro Ala Asp Pro Thr Gly Asn Leu Gly His Asn Ala Arg
        1040                1045                1050
Trp Asp Leu Leu Ala Lys Glu Ala Ala Ala Cys Thr Ser Ala Leu
        1055                1060                1065
Cys Cys Met Gly Arg Asn Gly Ile Pro Ile Gln Pro Trp Pro Val
        1070                1075                1080
Lys Ala Ala Val
        1085

<210> SEQ ID NO 27
<211> LENGTH: 2103
<212> TYPE: DNA
<213> ORGANISM: Homo sapiens

<400> SEQUENCE: 27
tgactagacg gccagcctgt taaggtggcc ccagatattc cagcctcagc ccagagtcct      60
cctgtgcccc tactgcagca agggtgtctc caagaagggg gacctggagt cagcccgtca     120
cacctggttt cctctctgct agggtccctc ctcccacaga gcactggagg gcagctgagg     180
aggagctacc ttaaaaaagg aggtgtgtgc caggagctg ggtaggagcc tggctatata     240
tctgcccagc agcggtactc tcgggacaga gatggcactg atgcaggaac tgtatagcac     300
accagcctcc aggctggact ccttcgtggc tcagtggctg cagccccacc gggagtggaa     360
ggaagaggtg ctagacgctg tgcggaccgt ggaggagttt ctgaggcagg agcatttcca     420
ggggaagcgt gggctggacc aggatgtgcg ggtgctgaag gtagtcaagg tgggctcctt     480
cgggaatggc acggttctca ggagcaccag agaggtggag ctggtggcgt ttctgagctg     540
tttccacagc ttccaggagg cagccaagca tcacaaagat gttctgaggc tgatatggaa     600
aaccatgtgg caaagccagg acctgctgga cctcgggctc gaggacctga ggatggagca     660
gagagtcccc gatgctctcg tcttcaccat ccagaccagg gggactgcgg agcccatcac     720
ggtcaccatt gtgcctgcct acagagccct ggggccttct cttcccaact cccagccacc     780
ccctgaggtc tatgtgagcc tgatcaaggc ctgcggtggt cctggaaatt tctgcccatc     840
cttcagcgag ctgcagagaa atttcgtgaa acatcggcca actaagctga agagcctcct     900
gcgcctggtg aaacactggt accagcagta tgtgaaagcc aggtccccca gagccaatct     960
gccccctctc tatgctcttg aacttctaac catctatgcc tgggaaatgg gtactgaaga    1020
agacgagaat ttcatgttgg acgaaggctt caccactgtg atggacctgc tcctggagta    1080
tgaagtcatc tgtatctact ggaccaagta ctacacactc cacaatgcaa tcattgagga    1140
ttgtgtcaga aaacagctca aaaagagag gcccatcatc ctggatccgg ccgaccccac    1200
cctcaacgtg gcagaagggt acagatggga catcgttgct cagagggcct cccagtgcct    1260
gaaacaggac tgttgctatg acaacaggga gaaccccatc tccagctgga acgtgaagag    1320
ggcacgagac atccacttga cagtggagca gagggttac ccagatttca acctcatcgt    1380
gaacccttat gagcccataa ggaaggttaa agagaaaatc cggaggacca ggggctactc    1440
tggcctgcag cgtctgtcct tccaggttcc tggcagtgag aggcagcttc tcagcagcag    1500
gtgctcctta gccaaatatg ggatcttctc ccacactcac atctatctgc tggagaccat    1560
cccctccgag atccaggtct tcgtgaagaa tcctgatggt gggagctacg cctatgccat    1620
```

-continued

```
caacccccaac agcttcatcc tgggtctgaa gcagcagatt gaagaccagc aggggcttcc    1680
taaaaagcag cagcgctgg aattccaagg ccaagtcctg caggactggt tgggtctggg    1740
gatctatggc atccaagaca gtgacactct catcctctcg aagaagaaag gagaggctct    1800
gtttccagcc agttagtttt ctctgggaga cttctctgta catttctgcc atgtactcca    1860
gaactcatcc tgtcaatcac tctgtcccat tgtctactgg gaaggtccca ggtcttcacc    1920
agttttacaa tgagttatcc caggccagac gtggtagctc acacctgtaa tcccagaact    1980
ttgggaggcc gaggtgggag gagcgcttga gccgaggagt tcaagaccag cctgggtatc    2040
acagggagac cccgtctcta caaaataaaa aataattca ctgggaaaaa aaaaaaaaa    2100 aaa                                                                  2103
```

<210> SEQ ID NO 28
<211> LENGTH: 514
<212> TYPE: PRT
<213> ORGANISM: Homo sapiens

<400> SEQUENCE: 28

```
Met Ala Leu Met Gln Glu Leu Tyr Ser Thr Pro Ala Ser Arg Leu Asp
1               5                   10                  15

Ser Phe Val Ala Gln Trp Leu Gln Pro His Arg Glu Trp Lys Glu Glu
            20                  25                  30

Val Leu Asp Ala Val Arg Thr Val Glu Glu Phe Leu Arg Gln Glu His
        35                  40                  45

Phe Gln Gly Lys Arg Gly Leu Asp Gln Asp Val Arg Val Leu Lys Val
    50                  55                  60

Val Lys Val Gly Ser Phe Gly Asn Gly Thr Val Leu Arg Ser Thr Arg
65                  70                  75                  80

Glu Val Glu Leu Val Ala Phe Leu Ser Cys Phe His Ser Phe Gln Glu
                85                  90                  95

Ala Ala Lys His His Lys Asp Val Leu Arg Leu Ile Trp Lys Thr Met
            100                 105                 110

Trp Gln Ser Gln Asp Leu Leu Asp Leu Gly Leu Glu Asp Leu Arg Met
        115                 120                 125

Glu Gln Arg Val Pro Asp Ala Leu Val Phe Thr Ile Gln Thr Arg Gly
    130                 135                 140

Thr Ala Glu Pro Ile Thr Val Thr Ile Val Pro Ala Tyr Arg Ala Leu
145                 150                 155                 160

Gly Pro Ser Leu Pro Asn Ser Gln Pro Pro Glu Val Tyr Val Ser
                165                 170                 175

Leu Ile Lys Ala Cys Gly Gly Pro Gly Asn Phe Cys Pro Ser Phe Ser
            180                 185                 190

Glu Leu Gln Arg Asn Phe Val Lys His Arg Pro Thr Lys Leu Lys Ser
        195                 200                 205

Leu Leu Arg Leu Val Lys His Trp Tyr Gln Gln Tyr Val Lys Ala Arg
    210                 215                 220

Ser Pro Arg Ala Asn Leu Pro Pro Leu Tyr Ala Leu Glu Leu Leu Thr
225                 230                 235                 240

Ile Tyr Ala Trp Glu Met Gly Thr Glu Glu Asp Glu Asn Phe Met Leu
                245                 250                 255

Asp Glu Gly Phe Thr Thr Val Met Asp Leu Leu Glu Tyr Glu Val
            260                 265                 270

Ile Cys Ile Tyr Trp Thr Lys Tyr Tyr Thr Leu His Asn Ala Ile Ile
        275                 280                 285
```

```
Glu Asp Cys Val Arg Lys Gln Leu Lys Lys Glu Arg Pro Ile Ile Leu
    290                 295                 300
Asp Pro Ala Asp Pro Thr Leu Asn Val Ala Glu Gly Tyr Arg Trp Asp
305                 310                 315                 320
Ile Val Ala Gln Arg Ala Ser Gln Cys Leu Lys Gln Asp Cys Cys Tyr
                325                 330                 335
Asp Asn Arg Glu Asn Pro Ile Ser Ser Trp Asn Val Lys Arg Ala Arg
            340                 345                 350
Asp Ile His Leu Thr Val Glu Gln Arg Gly Tyr Pro Asp Phe Asn Leu
        355                 360                 365
Ile Val Asn Pro Tyr Glu Pro Ile Arg Lys Val Lys Glu Lys Ile Arg
    370                 375                 380
Arg Thr Arg Gly Tyr Ser Gly Leu Gln Arg Leu Ser Phe Gln Val Pro
385                 390                 395                 400
Gly Ser Glu Arg Gln Leu Leu Ser Ser Arg Cys Ser Leu Ala Lys Tyr
                405                 410                 415
Gly Ile Phe Ser His Thr His Ile Tyr Leu Leu Glu Thr Ile Pro Ser
            420                 425                 430
Glu Ile Gln Val Phe Val Lys Asn Pro Asp Gly Gly Ser Tyr Ala Tyr
        435                 440                 445
Ala Ile Asn Pro Asn Ser Phe Ile Leu Gly Leu Lys Gln Gln Ile Glu
    450                 455                 460
Asp Gln Gln Gly Leu Pro Lys Lys Gln Gln Leu Glu Phe Gln Gly
465                 470                 475                 480
Gln Val Leu Gln Asp Trp Leu Gly Leu Gly Ile Tyr Gly Ile Gln Asp
                485                 490                 495
Ser Asp Thr Leu Ile Leu Ser Lys Lys Lys Gly Glu Ala Leu Phe Pro
            500                 505                 510
Ala Ser
```

<210> SEQ ID NO 29
<211> LENGTH: 1861
<212> TYPE: DNA
<213> ORGANISM: Homo sapiens

<400> SEQUENCE: 29

```
tgactagacg gccagcctgt taaggtggcc ccagatattc cagcctcagc ccagagtcct    60
cctgtgcccc tactgcagca agggtgtctc caagaagggg gacctggagt cagcccgtca   120
cacctggttt cctctctgct agggtccctc ctcccacaga gcactggagg cagctgagg    180
aggagctacc ttaaaaaagg aggtgtgtgc cagggagctg ggtaggagcc tggctatata   240
tctgcccagc agcggtactc tcgggacaga gatggcactg atgcaggaac tgtatagcac   300
accagcctcc aggctggact ccttcgtggc tcagtggctg cagccccacc gggagtggaa   360
ggaagaggtg ctagacgctg tgcggaccgt ggaggagttt ctgaggcagg agcatttcca   420
ggggaagcgt gggctggacc aggatgtgcg ggtgctgaag gtagtcaagg tgggctcctt   480
cgggaatggc acggttctca ggagcaccag agaggtggag ctggtggcgt ttctgagctg   540
tttccacagc ttccaggagg cagccaagca tcacaaagat gttctgaggc tgatatggaa   600
aaccatgtgg caaagccagg acctgctgga cctcgggctc gaggacctga ggatggagca   660
gagagtcccc gatgctctcg tcttcaccat ccagaccagg gggactgcgg agcccatcac   720
ggtcaccatt gtgcctgcct acagagccct ggggccttct cttcccaact cccagccacc   780
```

```
cccctgaggtc tatgtgagcc tgatcaaggc ctgcggtggt cctggaaatt tctgcccatc    840
cttcagcgag ctgcagagaa atttcgtgaa acatcggcca actaagctga agagcctcct    900
gcgcctggtg aaacactggt accagcaggc ccatcatcct ggatccggcc gaccccaccc    960
tcaacgtggc agaagggtac agatgggaca tcgttgctca gagggcctcc cagtgcctga   1020
aacaggactg ttgctatgac aacagggaga accccatctc cagctggaac gtgaagaggg   1080
cacgagacat ccacttgaca gtggagcaga ggggttaccc agatttcaac ctcatcgtga   1140 accccttatga gcccataagg aaggttaaag agaaaatccg gaggaccagg ggctactctg   1200
gcctgcagcg tctgtccttc caggttcctg gcagtgagag cagcttctc agcagcaggt   1260 gctccttagc caaatatggg atcttctccc acactcacat ctatctgctg agaccatcc   1320 cctccgagat ccaggtcttc gtgaagaatc ctgatggtgg gagctacgcc tatgccatca   1380
accccaacag cttcatcctg ggtctgaagc agcagattga agaccagcag gggcttccta   1440
aaaagcagca gcagctggaa ttccaaggcc aagtcctgca ggactggttg ggtctgggga   1500
tctatggcat ccaagacagt gacactctca tcctctcgaa gaagaaagga gaggctctgt   1560
ttccagccag ttagttttct ctgggagact tctctgtaca tttctgccat gtactccaga   1620
actcatcctg tcaatcactc tgtcccattg tctactggga aggtcccagg tcttcaccag   1680
ttttacaatg agttatccca ggccagacgt ggtagctcac acctgtaatc ccagaacttt   1740
gggaggccga ggtgggagga gcgcttgagc cgaggagttc aagaccagcc tgggtatcac   1800
agggagaccc cgtctctaca aaataaaaaa ataattcact gggaaaaaaa aaaaaaaaa   1860 a                                                                   1861
```

<210> SEQ ID NO 30
<211> LENGTH: 255
<212> TYPE: PRT
<213> ORGANISM: Homo sapiens

<400> SEQUENCE: 30

```
Met Ala Leu Met Gln Glu Leu Tyr Ser Thr Pro Ala Ser Arg Leu Asp
1               5                   10                  15

Ser Phe Val Ala Gln Trp Leu Gln Pro His Arg Glu Trp Lys Glu Glu
            20                  25                  30

Val Leu Asp Ala Val Arg Thr Val Glu Glu Phe Leu Arg Gln Glu His
        35                  40                  45

Phe Gln Gly Lys Arg Gly Leu Asp Gln Asp Val Arg Val Leu Lys Val
    50                  55                  60

Val Lys Val Gly Ser Phe Gly Asn Gly Thr Val Leu Arg Ser Thr Arg
65                  70                  75                  80

Glu Val Glu Leu Val Ala Phe Leu Ser Cys Phe His Ser Phe Gln Glu
                85                  90                  95

Ala Ala Lys His His Lys Asp Val Leu Arg Leu Ile Trp Lys Thr Met
            100                 105                 110

Trp Gln Ser Gln Asp Leu Leu Asp Leu Gly Leu Glu Asp Leu Arg Met
        115                 120                 125

Glu Gln Arg Val Pro Asp Ala Leu Val Phe Thr Ile Gln Thr Arg Gly
    130                 135                 140

Thr Ala Glu Pro Ile Thr Val Thr Ile Val Pro Ala Tyr Arg Ala Leu
145                 150                 155                 160

Gly Pro Ser Leu Pro Asn Ser Gln Pro Pro Glu Val Tyr Val Ser
                165                 170                 175
```

| | | | | | | | | | | | |
|---|---|---|---|---|---|---|---|---|---|---|---|
|Leu|Ile|Lys|Ala|Cys|Gly|Gly|Pro|Gly|Asn|Phe|Cys|Pro|Ser|Phe|Ser|
| | | |180| | | |185| | | |190| | | | |
|Glu|Leu|Gln|Arg|Asn|Phe|Val|Lys|His|Arg|Pro|Thr|Lys|Leu|Lys|Ser|
| | | |195| | | |200| | | |205| | | | |
|Leu|Leu|Arg|Leu|Val|Lys|His|Trp|Tyr|Gln|Gln|Ala|His|His|Pro|Gly|
| |210| | | | |215| | | | |220| | | | |
|Ser|Gly|Arg|Pro|His|Pro|Gln|Arg|Gly|Arg|Arg|Val|Gln|Met|Gly|His|
|225| | | |230| | | | |235| | | | |240| |
|Arg|Cys|Ser|Glu|Gly|Leu|Pro|Val|Pro|Glu|Thr|Gly|Leu|Leu|Leu| |
| | | | |245| | | |250| | | | |255| | |

<210> SEQ ID NO 31
<211> LENGTH: 1240
<212> TYPE: DNA
<213> ORGANISM: Homo sapiens

<400> SEQUENCE: 31

```
ttatgggttt catttagtgg agaaattggg tatgacctcg aggagtcaa gaaagagttc      60
ttctactgtc tgtttgcaga gatgatccag ccggaatatg ggatgttcat gtatcctgaa    120
ggggcttcct gcatgtggtt tcctgtcaag cctaaatttg agaagaaaag atacttcttt    180
tttggggttc tatgtggact ttccctgttc aattgcaatg ttgccaacct tcctttccca    240
ctggcactgt ttaagaaact tttggaccaa atgccatcat ggaagacttg aaagaactc    300
agtcctgatt tgggaaagaa tttgcaaaca cttctggatg atgaaggtga taactttgag    360
gaagtatttt acatccattt taatgtgcac tgggacagaa acgacacaaa cttaattcct    420
aatggaagta gcataactgt caaccagact aacaagagag actatgtttc taagtatatc    480
aattacattt tcaacgactc tgtaaaggcg gtttatgaag aatttcggag aggattttat    540
aaaatgtgcg acgaagacat tatcaaatta ttccaccccg aagaactgaa ggatgtgatt    600
gttggaaata cagattatga ttggaaaaca tttgaaaaga atgcacgtta tgaaccagga    660
tataacagtt cacatcccac catagtgatg ttttggaagg cttccacaa attgactctg    720
gaagaaaaga aaaaattcct tgtatttctt acaggaactg acagactaca atgaaagat    780
ttaaataata tgaaaataac attttgctgt cctgaaagtt ggaatgaaag agaccctata    840
agagcactga catgtttcag tgtcctcttc ctccctaaat attctacaat ggaaacagtt    900
gaagaagcgc ttcaagaagc catcaacaac aacagaggat ttggctgacc agcttgcttg    960
tccaacagcc ttattttgtt gttgttatcg ttgttgttgt tgttgttgtt gttgtttctc   1020
tactttgttt tgtttaggc ttttagcagc ctgaagccat ggttttcat ttctgtctct    1080
agtgataagc aggaaagagg gatgaagaag agggttact ggccggttag aacccgtgac   1140
tgtattctct cccttggata ccctatgcc tacatcatat tccttacctc ttttgggaaa   1200
tatttttcaa aataaaata accgaaaaat taacataaaa                          1240
```

<210> SEQ ID NO 32
<211> LENGTH: 1024
<212> TYPE: PRT
<213> ORGANISM: Homo sapiens

<400> SEQUENCE: 32

| | | | | | | | | | | | | | | | |
|---|---|---|---|---|---|---|---|---|---|---|---|---|---|---|---|
|Met|Glu|Arg|Arg|Ser|Arg|Arg|Lys|Ser|Arg|Arg|Asn|Gly|Arg|Ser|Thr|
|1| | | |5| | | | |10| | | | |15| |
|Ala|Gly|Lys|Ala|Ala|Ala|Thr|Gln|Pro|Ala|Lys|Ser|Pro|Gly|Ala|Gln|
| | | |20| | | | |25| | | | |30| | |

-continued

```
Leu Trp Leu Phe Pro Ser Ala Ala Gly Leu His Arg Ala Leu Leu Arg
             35                  40                  45

Arg Val Glu Val Thr Arg Gln Leu Cys Cys Ser Pro Gly Arg Leu Ala
 50                  55                  60

Val Leu Glu Arg Gly Gly Ala Gly Val Gln Val His Gln Leu Leu Ala
 65                  70                  75                  80

Gly Ser Gly Gly Ala Arg Thr Pro Lys Cys Ile Lys Leu Gly Lys Asn
                 85                  90                  95

Met Lys Ile His Ser Val Asp Gln Gly Ala Glu His Met Leu Ile Leu
            100                 105                 110

Ser Ser Asp Gly Lys Pro Phe Glu Tyr Asp Asn Tyr Ser Met Lys His
            115                 120                 125

Leu Arg Phe Glu Ser Ile Leu Gln Glu Lys Lys Ile Ile Gln Ile Thr
        130                 135                 140

Cys Gly Asp Tyr His Ser Leu Ala Leu Ser Lys Gly Gly Glu Leu Phe
145                 150                 155                 160

Ala Trp Gly Gln Asn Leu His Gly Gln Leu Gly Val Gly Arg Lys Phe
                165                 170                 175

Pro Ser Thr Thr Thr Pro Gln Ile Val Glu His Leu Ala Gly Val Pro
            180                 185                 190

Leu Ala Gln Ile Ser Ala Gly Glu Ala His Ser Met Ala Leu Ser Met
        195                 200                 205

Ser Gly Asn Ile Tyr Ser Trp Gly Lys Asn Glu Cys Gly Gln Leu Gly
    210                 215                 220

Leu Gly His Thr Glu Ser Lys Asp Asp Pro Ser Leu Ile Glu Gly Leu
225                 230                 235                 240

Asp Asn Gln Lys Val Glu Phe Val Ala Cys Gly Gly Ser His Ser Ala
                245                 250                 255

Leu Leu Thr Gln Asp Gly Leu Leu Phe Thr Phe Gly Ala Gly Lys His
            260                 265                 270

Gly Gln Leu Gly His Asn Ser Thr Gln Asn Glu Leu Arg Pro Cys Leu
        275                 280                 285

Val Ala Glu Leu Val Gly Tyr Arg Val Thr Gln Ile Ala Cys Gly Arg
    290                 295                 300

Trp His Thr Leu Ala Tyr Val Ser Asp Leu Gly Lys Val Phe Ser Phe
305                 310                 315                 320

Gly Ser Gly Lys Asp Gly Gln Leu Gly Asn Gly Gly Thr Arg Asp Gln
                325                 330                 335

Leu Met Pro Leu Pro Val Lys Val Ser Ser Glu Glu Leu Lys Leu
            340                 345                 350

Glu Ser His Thr Ser Glu Lys Glu Leu Ile Met Ile Ala Gly Gly Asn
        355                 360                 365

Gln Ser Ile Leu Leu Trp Ile Lys Lys Glu Asn Ser Tyr Val Asn Leu
    370                 375                 380

Lys Arg Thr Ile Pro Thr Leu Asn Glu Gly Thr Val Lys Arg Trp Ile
385                 390                 395                 400

Ala Asp Val Glu Thr Lys Arg Trp Gln Ser Thr Lys Arg Glu Ile Gln
                405                 410                 415

Glu Ile Phe Ser Ser Pro Ala Cys Leu Thr Gly Ser Phe Leu Arg Lys
            420                 425                 430

Arg Arg Thr Thr Glu Met Met Pro Val Tyr Leu Asp Leu Asn Lys Ala
        435                 440                 445

Arg Asn Ile Phe Lys Glu Leu Thr Gln Lys Asp Trp Ile Thr Asn Met
```

-continued

```
                450                 455                 460
Ile Thr Thr Cys Leu Lys Asp Asn Leu Leu Lys Arg Leu Pro Phe His
465                 470                 475                 480

Ser Pro Pro Gln Glu Ala Leu Glu Ile Phe Phe Leu Leu Pro Glu Cys
                485                 490                 495

Pro Met Met His Ile Ser Asn Asn Trp Glu Ser Leu Val Val Pro Phe
            500                 505                 510

Ala Lys Val Val Cys Lys Met Ser Asp Gln Ser Ser Leu Val Leu Glu
            515                 520                 525

Glu Tyr Trp Ala Thr Leu Gln Glu Ser Thr Phe Ser Lys Leu Val Gln
            530                 535                 540

Met Phe Lys Thr Ala Val Ile Cys Gln Leu Asp Tyr Trp Asp Glu Ser
545                 550                 555                 560

Ala Glu Glu Asn Gly Asn Val Gln Ala Leu Leu Glu Met Leu Lys Lys
                565                 570                 575

Leu His Arg Val Asn Gln Val Lys Cys Gln Leu Pro Glu Ser Ile Phe
            580                 585                 590

Gln Val Asp Glu Leu Leu His Arg Leu Asn Phe Phe Val Glu Val Cys
            595                 600                 605

Arg Arg Tyr Leu Trp Lys Met Thr Val Asp Ala Ser Glu Asn Val Gln
610                 615                 620

Cys Cys Val Ile Phe Ser His Phe Pro Phe Ile Phe Asn Asn Leu Ser
625                 630                 635                 640

Lys Ile Lys Leu Leu His Thr Asp Thr Leu Leu Lys Ile Glu Ser Lys
                645                 650                 655

Lys His Lys Ala Tyr Leu Arg Ser Ala Ala Ile Glu Glu Arg Glu
                660                 665                 670

Ser Glu Phe Ala Leu Arg Pro Thr Phe Asp Leu Thr Val Arg Arg Asn
            675                 680                 685

His Leu Ile Glu Asp Val Leu Asn Gln Leu Ser Gln Phe Glu Asn Glu
            690                 695                 700

Asp Leu Arg Lys Glu Leu Trp Val Ser Phe Ser Gly Glu Ile Gly Tyr
705                 710                 715                 720

Asp Leu Gly Gly Val Lys Lys Glu Phe Phe Tyr Cys Leu Phe Ala Glu
                725                 730                 735

Met Ile Gln Pro Glu Tyr Gly Met Phe Met Tyr Pro Glu Gly Ala Ser
            740                 745                 750

Cys Met Trp Phe Pro Val Lys Pro Lys Phe Glu Lys Lys Arg Tyr Phe
            755                 760                 765

Phe Phe Gly Val Leu Cys Gly Leu Ser Leu Phe Asn Cys Asn Val Ala
            770                 775                 780

Asn Leu Pro Phe Pro Leu Ala Leu Phe Lys Lys Leu Leu Asp Gln Met
785                 790                 795                 800

Pro Ser Leu Glu Asp Leu Lys Glu Leu Ser Pro Asp Leu Gly Lys Asn
                805                 810                 815

Leu Gln Thr Leu Leu Asp Asp Glu Gly Asp Asn Phe Glu Glu Val Phe
                820                 825                 830

Tyr Ile His Phe Asn Val His Trp Asp Arg Asn Asp Thr Asn Leu Ile
            835                 840                 845

Pro Asn Gly Ser Ser Ile Thr Val Asn Gln Thr Asn Lys Arg Asp Tyr
            850                 855                 860

Val Ser Lys Tyr Ile Asn Tyr Ile Phe Asn Asp Ser Val Lys Ala Val
865                 870                 875                 880
```

Tyr Glu Glu Phe Arg Arg Gly Phe Tyr Lys Met Cys Asp Glu Asp Ile
            885                 890                 895

Ile Lys Leu Phe His Pro Glu Glu Leu Lys Asp Val Ile Val Gly Asn
        900                 905                 910

Thr Asp Tyr Asp Trp Lys Thr Phe Glu Lys Asn Ala Arg Tyr Glu Pro
            915                 920                 925

Gly Tyr Asn Ser Ser His Pro Thr Ile Val Met Phe Trp Lys Ala Phe
    930                 935                 940

His Lys Leu Thr Leu Glu Glu Lys Lys Lys Phe Leu Val Phe Leu Thr
945                 950                 955                 960

Gly Thr Asp Arg Leu Gln Met Lys Asp Leu Asn Met Lys Ile Thr
                965                 970                 975

Phe Cys Cys Pro Glu Ser Trp Asn Glu Arg Asp Pro Ile Arg Ala Leu
            980                 985                 990

Thr Cys Phe Ser Val Leu Phe Leu Pro Lys Tyr Ser Thr Met Glu Thr
            995                 1000                1005

Val Glu Glu Ala Leu Gln Glu Ala Ile Asn Asn Asn Arg Gly Phe
    1010                1015                1020

Gly

<210> SEQ ID NO 33
<211> LENGTH: 2037
<212> TYPE: DNA
<213> ORGANISM: Homo sapiens

<400> SEQUENCE: 33

```
gggaagctcg ggccggcagg gtttccccgc acgctggcgc ccagctcccg gcgcggaggc      60
cgctgtaagt ttcgctttcc attcagtgga aaacgaaagc tgggcggggt gccacgagcg     120
cggggccaga ccaaggcggg cccggagcgg aacttcggtc ccagctcggt ccccggctca     180
gtcccgacgt ggaactcagc agcggaggct ggacgcttgc atggcgcttg agagattcca     240
tcgtgcctgg ctcacataag cgcttcctgg aagtgaagtc gtgctgtcct gaacgcgggc     300
caggcagctg cggcctgggg gttttggagt gatcacgaat gagcaaggcg tttgggctcc     360
tgaggcaaat ctgtcagtcc atcctggctg agtcctcgca gtccccggca gatcttgaag     420
aaaagaagga agaagacagc aacatgaaga gagagcagcc cagagagcgt cccagggcct     480
gggactaccc tcatggcctg gttggtttac acaacattgg acagacctgc tgccttaact     540
ccttgattca ggtgttcgta atgaatgtgg acttcaccag gatattgaag aggatcacgg     600
tgcccagggg agctgacgag cagaggagaa gcgtccctt  ccagatgctt ctgctgctgg     660
agaagatgca ggacagccgg cagaaagcag tgcggcccct ggagctggcc tactgcctgc     720
agaagtgcaa cgtgcccttg tttgtccaac atgatgctgc ccaactgtac ctcaaactct     780
ggaacctgat taaggaccag atcactgatg tgcacttggt ggagactg caggccctgt     840
atacgatccg ggtgaaggac tccttgattt gcgttgactg tgccatggag agtagcagaa     900
acagcagcat gctcaccctc ccactttctc tttttgatgt ggactcaaag cccctgaaga     960
cactggagga cgccctgcac tgcttcttcc agcccaggga gttatcaagc aaaagcaagt    1020
gcttctgtga gaactgtggg aagaagaccc gtgggaaaca ggtcttgaag ctgacccatt    1080
tgccccagac cctgacaatc cacctcatgc gattctccat caggaattca cagacgagaa    1140
agatctgcca ctccctgtac ttcccccaga gcttggattt cagccagatc cttccaatga    1200
agcgagagtc ttgtgatgct gaggagcagt ctggagggca gtatgagctt tttgctgtga    1260
```

```
ttgcgcacgt gggaatggca gactccggtc attactgtgt ctacatccgg aatgctgtgg   1320
atggaaaatg gttctgcttc aatgactcca atatttgctt ggtgtcctgg aagacatcc   1380 agtgtaccta cggaaatcct aactaccact ggcaggaaac tgcatatctt ctggtttaca   1440
tgaagatgga gtgctaatgg aaatgcccaa aaccttcaga gattgacacg ctgtcatttt   1500
ccatttccgt tcctggatct acggagtctt ctaagagatt ttgcaatgag gagaagcatt   1560
gttttcaaac tatataactg agccttattt ataattaggg atattatcaa aatatgtaac   1620
catgaggccc ctcaggtcct gatcagtcag aatggatgct tcaccagca gacccggcca    1680 tgtggctgct cggtcctggg tgctcgctgc tgtgcaagac attagccctt tagttatgag   1740
cctgtgggaa cttcaggggt tcccagtggg gagagcagtg gcagtgggag gcatctgggg   1800
gccaaaggtc agtggcaggg ggtatttcag tattatacaa ctgctgtgac cagacttgta   1860
tactggctga atatcagtgc tgtttgtaat ttttcacttt gagaaccaac attaattcca   1920
tatgaatcaa gtgttttgta actgctattc atttattcag caaatattta ttgatcatct   1980
cttctccata agatagtgtg ataaacacag tcatgaataa agttattttc cacaaaa      2037
```

<210> SEQ ID NO 34
<211> LENGTH: 372
<212> TYPE: PRT
<213> ORGANISM: Homo sapiens

<400> SEQUENCE: 34

```
Met Ser Lys Ala Phe Gly Leu Leu Arg Gln Ile Cys Gln Ser Ile Leu
1               5                   10                  15

Ala Glu Ser Ser Gln Ser Pro Ala Asp Leu Glu Glu Lys Lys Glu Glu
                20                  25                  30

Asp Ser Asn Met Lys Arg Glu Gln Pro Arg Glu Arg Pro Arg Ala Trp
            35                  40                  45

Asp Tyr Pro His Gly Leu Val Gly Leu His Asn Ile Gly Gln Thr Cys
        50                  55                  60

Cys Leu Asn Ser Leu Ile Gln Val Phe Val Met Asn Val Asp Phe Thr
65                  70                  75                  80

Arg Ile Leu Lys Arg Ile Thr Val Pro Arg Gly Ala Asp Glu Gln Arg
                85                  90                  95

Arg Ser Val Pro Phe Gln Met Leu Leu Leu Glu Lys Met Gln Asp
                100                 105                 110

Ser Arg Gln Lys Ala Val Arg Pro Leu Glu Leu Ala Tyr Cys Leu Gln
            115                 120                 125

Lys Cys Asn Val Pro Leu Phe Val Gln His Asp Ala Ala Gln Leu Tyr
        130                 135                 140

Leu Lys Leu Trp Asn Leu Ile Lys Asp Gln Ile Thr Asp Val His Leu
145                 150                 155                 160

Val Glu Arg Leu Gln Ala Leu Tyr Thr Ile Arg Val Lys Asp Ser Leu
                165                 170                 175

Ile Cys Val Asp Cys Ala Met Glu Ser Ser Arg Asn Ser Ser Met Leu
            180                 185                 190

Thr Leu Pro Leu Ser Leu Phe Asp Val Asp Ser Lys Pro Leu Lys Thr
        195                 200                 205

Leu Glu Asp Ala Leu His Cys Phe Phe Gln Pro Arg Glu Leu Ser Ser
    210                 215                 220

Lys Ser Lys Cys Phe Cys Glu Asn Cys Gly Lys Lys Thr Arg Gly Lys
225                 230                 235                 240
```

```
Gln Val Leu Lys Leu Thr His Leu Pro Gln Thr Leu Thr Ile His Leu
                245                 250                 255

Met Arg Phe Ser Ile Arg Asn Ser Gln Thr Arg Lys Ile Cys His Ser
            260                 265                 270

Leu Tyr Phe Pro Gln Ser Leu Asp Phe Ser Gln Ile Leu Pro Met Lys
        275                 280                 285

Arg Glu Ser Cys Asp Ala Glu Glu Gln Ser Gly Gly Gln Tyr Glu Leu
    290                 295                 300

Phe Ala Val Ile Ala His Val Gly Met Ala Asp Ser Gly His Tyr Cys
305                 310                 315                 320

Val Tyr Ile Arg Asn Ala Val Asp Gly Lys Trp Phe Cys Phe Asn Asp
                325                 330                 335

Ser Asn Ile Cys Leu Val Ser Trp Glu Asp Ile Gln Cys Thr Tyr Gly
            340                 345                 350

Asn Pro Asn Tyr His Trp Gln Glu Thr Ala Tyr Leu Leu Val Tyr Met
        355                 360                 365

Lys Met Glu Cys
    370

<210> SEQ ID NO 35
<211> LENGTH: 3512
<212> TYPE: DNA
<213> ORGANISM: Homo sapiens

<400> SEQUENCE: 35
aactcagctg agtgttagtc aaagaaggtg tgtcctgctc cccaatgaca ggttgctcag      60
agactgctga tttccatccc tatataaaga gagtccctgg catacagaga ctgctctgct    120
ccaggcatct gccacaatgt gggtgcttac acctgctgct tttgctggga agctcttgag    180
tgtgttcagg caacctctga gctctctgtg gaggagcctg gtcccgctgt tctgctggct    240
gagggcaacc ttctggctgc tagctaccaa gaggagaaag cagcagctgg tcctgagagg    300
gccagatgag accaaagagg aggaagagga ccctcctctg cccaccaccc caaccagcgt    360
caactatcac ttcactcgcc agtgcaacta caaatgcggc ttctgtttcc acacagccaa    420
aacatccttt gtgctgcccc ttgaggaagc aaagagagga ttgcttttgc ttaaggaagc    480
tggtatggag aagatcaact tttcaggtgg agagccattt cttcaagacc ggggagaata    540
cctgggcaag ttggtgaggt tctgcaaagt agagttgcgg ctgcccagcg tgagcatcgt    600
gagcaatgga agcctgatcc gggagaggtg gttccagaat tatggtgagt atttggacat    660
tctcgctatc tcctgtgaca gctttgacga ggaagtcaat gtccttattg gccgtggcca    720
aggaaagaag aaccatgtgg aaaaccttca aaagctgagg aggtggtgta gggattatag    780
agtcgctttc aagataaatt ctgtcattaa tcgtttcaac gtggaagagg acatgacgga    840
acagatcaaa gcactaaacc ctgtccgctg gaaagtgttc cagtgcctct taattgaggg    900
tgagaattgt ggagaagatg ctctaagaga agcagaaaga tttgttattg gtgatgaaga    960
atttgaaaga ttcttggagc gccacaaaga agtgtcctgc ttggtgcctg aatctaacca   1020
gaagatgaaa gactcctacc ttattctgga tgaatatatg cgctttctga actgtagaaa   1080
gggacggaag gacccttcca agtccatcct ggatgttggt gtagaagaag ctataaaatt   1140
cagtggattt gatgaaaaga tgtttctgaa gcgaggagga aaatacatat ggagtaaggc   1200
tgatctgaag ctggattggt agagcggaaa gtggaacgag acttcaacac accagtggga   1260
aaactcctag agtaactgcc attgtctgca atactatccc gttggtattt cccagtggct   1320
```

```
gaaaacctga ttttctgctg cacgtggcat ctgattacct gtggtcactg aacacacgaa      1380
taacttggat agcaaatcct gagacaatgg aaaaccatta actttacttc attggcttat      1440
aaccttgttg ttattgaaac agcacttctg tttttgagtt tgttttagct aaaaagaagg      1500
aatacacaca ggaataatga ccccaaaaat gcttagaataa ggcccctata caccaggacct      1560 gacatttagc tcaatgatgc gtttgtaaga aataagctct agtgatatct gtggggcaa       1620 aatttaattt ggatttgatt ttttaaaaca atgtttactg cgatttctat atttccattt      1680
tgaaactatt tcttgttcca ggtttgttca tttgacagag tcagtatttt ttgccaaata      1740
tccagataac cagttttcac atctgagaca ttacaaagta tctgcctcaa ttatttctgc      1800
tggttataat gctttttttt ttttgccttt atgccattgc agtcttgtac tttttactgt      1860
gatgtacaga aatagtcaac agatgtttcc aagaacatat gatatgataa tcctaccaat     1920
tttcaagaag tctctagaaa gagataacac atggaaagac ggtgtggtgc agcccagccc     1980
acggtggctg ttccatgaat gctggctacc tatgtgtgtg gtacctgttg tgtcccttt c    2040 tcttcaaaga tcctgagcaa acaaagata cgctttccat ttgatgatgg agttgacatg      2100
gaggcagtgc ttgcattgct ttgttcgcct atcatctggc cacatgaggc tgtcaagcaa     2160
aagaatagga gtgtagttga gtagctggtt ggccctacat ctctgagaag tgacggcaca    2220
ctgggttggc ataagatatc ctaaaatcac gctggaacct tgggcaagga agaatgtgag     2280
caagagtaga gagagtgcct ggatttcatg tcagtgaagc caagtcacca tatcatattt     2340
ttgaatgaac tctgagtcag ttgaaatagg gtaccatcta ggtcagtta agaagagtca      2400 gctcagagaa agcaagcata agggaaaatg tcacgtaaac tagatcaggg aacaaaatcc    2460
tctccttgtg gaaatatccc atgcagtttg ttgatacaac ttagtatctt attgcctaaa     2520
aaaaaatttc ttatcattgt ttcaaaaaag caaaatcatg gaaaattttt gttgtccagg     2580
caaataaaag gtcattttaa tttagctgca atttcagtgt tcctcactag gtggcattta    2640
aatgtcgcct gatgtcatta agcaccatcc aaaaagtctg cttcataatc tattttcaag    2700
acttggtgat tctgaaagtt ttggtttttg tgactttgtt tctcaggaaa aaaaatattc     2760
ctacttaaat tttaagtcta taattcaatt taaatatgtg tgtgtctcat ccaggatagg     2820
ataggttgtc ttctatttt c catttttacct attttacttt tttgtaagaa aagagaaaaa    2880
tgaattctaa agatgttccc catgggtttt gattgtgtct aagctatgat gaccttcata     2940
taatcagcat aaacataaaa caattttttt acttaacatg agtgcacttt actaatcctc     3000
atggcacagt ggctcacgcc tgtaatccca gcacttggga ggacaatgtg ggtggatcac    3060
gaggtcagga gttcgagaac agcctggcca acatggtgaa accccgtctc cactaaaaat     3120
acaaaaatta gccaggcatg gtggcgtaca cttgtaattc cagctactca agaggctgag     3180
gcaggaggat tgcttgaacc ctgaaggcag aggttacaga gccaagatag cgccactgca     3240
ctccagcctg gatgacagag caagactccg tctcaaaaaa aaaaaaaaaa aaagcaaga      3300 gagttcaact aagaaaggtc acatatgtga aagcccaagg acactgtttg atatacagca    3360
ggtattcaat cagtgttatt tgaaaccaaa tctgaatttg aagtttgaat cttctgagtt     3420
ggaatgaatt ttttctagc tgagggaaac tgtatttttc tttccccaaa gaggaatgta    3480
atgtaaagtg aaataaaaact ataagctatg tt                                 3512
```

<210> SEQ ID NO 36
<211> LENGTH: 361
<212> TYPE: PRT

<213> ORGANISM: Homo sapiens

<400> SEQUENCE: 36

```
Met Trp Val Leu Thr Pro Ala Ala Phe Ala Gly Lys Leu Leu Ser Val
1               5                   10                  15

Phe Arg Gln Pro Leu Ser Ser Leu Trp Arg Ser Leu Val Pro Leu Phe
            20                  25                  30

Cys Trp Leu Arg Ala Thr Phe Trp Leu Leu Ala Thr Lys Arg Arg Lys
        35                  40                  45

Gln Gln Leu Val Leu Arg Gly Pro Asp Glu Thr Lys Glu Glu Glu Glu
    50                  55                  60

Asp Pro Pro Leu Pro Thr Thr Pro Thr Ser Val Asn Tyr His Phe Thr
65                  70                  75                  80

Arg Gln Cys Asn Tyr Lys Cys Gly Phe Cys Phe His Thr Ala Lys Thr
                85                  90                  95

Ser Phe Val Leu Pro Leu Glu Glu Ala Lys Arg Gly Leu Leu Leu Leu
            100                 105                 110

Lys Glu Ala Gly Met Glu Lys Ile Asn Phe Ser Gly Gly Glu Pro Phe
        115                 120                 125

Leu Gln Asp Arg Gly Glu Tyr Leu Gly Lys Leu Val Arg Phe Cys Lys
    130                 135                 140

Val Glu Leu Arg Leu Pro Ser Val Ser Ile Val Ser Asn Gly Ser Leu
145                 150                 155                 160

Ile Arg Glu Arg Trp Phe Gln Asn Tyr Gly Glu Tyr Leu Asp Ile Leu
                165                 170                 175

Ala Ile Ser Cys Asp Ser Phe Asp Glu Glu Val Asn Val Leu Ile Gly
            180                 185                 190

Arg Gly Gln Gly Lys Lys Asn His Val Glu Asn Leu Gln Lys Leu Arg
        195                 200                 205

Arg Trp Cys Arg Asp Tyr Arg Val Ala Phe Lys Ile Asn Ser Val Ile
    210                 215                 220

Asn Arg Phe Asn Val Glu Glu Asp Met Thr Glu Gln Ile Lys Ala Leu
225                 230                 235                 240

Asn Pro Val Arg Trp Lys Val Phe Gln Cys Leu Leu Ile Glu Gly Glu
                245                 250                 255

Asn Cys Gly Glu Asp Ala Leu Arg Glu Ala Glu Arg Phe Val Ile Gly
            260                 265                 270

Asp Glu Glu Phe Glu Arg Phe Leu Glu Arg His Lys Glu Val Ser Cys
        275                 280                 285

Leu Val Pro Glu Ser Asn Gln Lys Met Lys Asp Ser Tyr Leu Ile Leu
    290                 295                 300

Asp Glu Tyr Met Arg Phe Leu Asn Cys Arg Lys Gly Arg Lys Asp Pro
305                 310                 315                 320

Ser Lys Ser Ile Leu Asp Val Gly Val Glu Glu Ala Ile Lys Phe Ser
                325                 330                 335

Gly Phe Asp Glu Lys Met Phe Leu Lys Arg Gly Gly Lys Tyr Ile Trp
            340                 345                 350

Ser Lys Ala Asp Leu Lys Leu Asp Trp
        355                 360
```

<210> SEQ ID NO 37
<211> LENGTH: 2983
<212> TYPE: DNA
<213> ORGANISM: Homo sapiens

<400> SEQUENCE: 37

```
gttcgggccc gagaacctgc gtctcccgcg agttcccgcg aggcaagtgc tgcaggtgcg     60
gggccaggag ctaggtttcg tttctgcgcc cggagccgcc ctcagcacag ggtctgtgag    120
tttcatttct tcgcggcgcg gggcggggct gggcgcgggg tgaaagaggc gaagcgagag    180
cggaggccgc actccagcac tgcgcaggga ccgccttgga ccgcagttgc cggccaggaa    240
tcccagtgtc acggtggaca cgcctccctc gcgcccttgc cgcccacctg ctcacccagc    300
tcagggcctt tggaattctg tggccacact gcgaggagat cggttctggg tcggaggcta    360
caggaagact cccactccct gaaatctgga gtgaagaacg ccgccatcca gccaccattc    420
caaggaggtg caggagaaca gctctgtgat accatttaac ttgttgacat tacttttatt    480
tgaaggaacg tatattagag cttactttgc aaagaaggaa gatggttgtt ccgaagtgg     540
acatcgcaaa agctgatcca gctgctgcat cccaccctct attactgaat ggagatgcta    600
ctgtggccca gaaaaatcca ggctcggtgg ctgagaacaa cctgtgcagc cagtatgagg    660
agaaggtgcg cccctgcatc gacctcattg actccctgcg ggctctaggt gtggagcagg    720
acctggccct gccagccatc gccgtcatcg ggaccagag ctcgggcaag agctccgtgt    780
tggaggcact gtcaggagtt gcccttccca gaggcagcgg gatcgtgacc agatgcccgc    840
tggtgctgaa actgaagaaa cttgtgaacg aagataagtg gagaggcaag gtcagttacc    900
aggactacga gattgagatt tcggatgctt cagaggtaga aaaggaaatt aataaagccc    960
agaatgccat cgccggggaa ggaatgggaa tcagtcatga gctaatcacc ctggagatca   1020
gctcccgaga tgtcccggat ctgactctaa tagaccttcc tggcataacc agagtggctg   1080
tgggcaatca gcctgctgac attgggtata agatcaagac actcatcaag aagtacatcc   1140
agaggcagga gacaatcagc ctggtggtgg tcccccagtaa tgtggacatc gccaccacag   1200
aggctctcag catggcccag gaggtggacc ccgagggaga caggaccatc ggaatcttga   1260
cgaagcctga tctggtggac aaaggaactg aagacaaggt tgtggacgtg gtgcggaacc   1320
tcgtgttcca cctgaagaag ggttacatga ttgtcaagtg ccggggccag caggagatcc   1380
aggaccagct gagcctgtcc gaagccctgc agagagagaa gatcttcttt gagaaccacc   1440
catatttcag ggatctgctg gaggaaggaa aggccacggt tccctgcctg gcagaaaaac   1500
ttaccagcga gctcatcaca catatctgta aatctctgcc cctgttagaa atcaaatca    1560
aggagactca ccagagaata acagaggagc tacaaaagta tggtgtcgac ataccggaag   1620
acgaaaatga aaaaatgttc ttcctgatag ataaagttaa tgcctttaat caggacatca   1680
ctgctctcat gcaaggagag gaaactgtag gggaggaaga cattcggctg tttaccagac   1740
tccgacacga gttccacaaa tggagtacaa taattgaaaa caattttcaa gaaggccata   1800
aaattttgag tagaaaaatc cagaaatttg aaaatcagta tcgtggtaga gagctgccag   1860
gctttgtgaa ttacaggaca tttgagacaa tcgtgaaaca gcaaatcaag gcactggaag   1920
agccggctgt ggatatgcta cacaccgtga cggatatggt ccggcttgct ttcacagatg   1980
tttcgataaa aaattttgaa gagttttttta acctccacag aaccgccaag tccaaaattg   2040
aagacattag agcagaacaa gagagagaag gtgagaagct gatccgcctc cacttccaga   2100
tggaacagat tgtctactgc caggaccagg tatacagggg tgcattgcag aaggtcagag   2160
agaaggagct ggaagaagaa aagaagaaga atcctgggga ttttgggggct ttccagtcca   2220
gctcggcaac agactcttcc atggaggaga tctttcagca cctgatgcc tatcaccagg   2280
aggccagcaa gcgcatctcc agccacatcc ctttgatcat ccagttcttc atgctccaga   2340
```

-continued

```
cgtacggcca gcagcttcag aaggccatgc tgcagctcct gcaggacaag gacacctaca    2400
gctggctcct gaaggagcgg agcgacacca gcgacaagcg gaagttcctg aaggagcggc    2460
ttgcacggct gacgcaggct cggcgccggc ttgcccagtt ccccggttaa ccacactctg    2520
tccagccccg tagacgtgca cgcacactgt ctgcccccgt tcccgggtag ccactggact    2580
gacgacttga gtgctcagta gtcagactgg atagtccgtc tctgcttatc cgttagccgt    2640
ggtgatttag caggaagctg tgagagcagt ttggtttcta gcatgaagac agagccccac    2700
cctcagatgc acatgagctg gcgggattga aggatgctgt cttcgtactg ggaaagggat    2760
tttcagccct cagaatcgct ccaccttgca gctctcccct tctctgtatt cctagaaact    2820
gacacatgct gaacatcaca gcttatttcc tcattttat aatgtccctt cacaaaccca    2880 gtgtttttagg agcatgagtg ccgtgtgtgt gcgtcctgtc ggagccctgt ctcctctctc    2940
tgtaataaac tcatttctag cagacaaaaa aaaaaaaaaa aaa              2983
```

<210> SEQ ID NO 38
<211> LENGTH: 662
<212> TYPE: PRT
<213> ORGANISM: Homo sapiens

<400> SEQUENCE: 38

```
Met Val Ser Glu Val Asp Ile Ala Lys Ala Asp Pro Ala Ala Ala
1               5                   10                  15

Ser His Pro Leu Leu Asn Gly Asp Ala Thr Val Ala Gln Lys Asn
            20                  25                  30

Pro Gly Ser Val Ala Glu Asn Asn Leu Cys Ser Gln Tyr Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255
```

```
Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
        355                 360                 365

Asn Glu Lys Met Phe Phe Leu Ile Asp Lys Val Asn Ala Phe Asn Gln
    370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly His Lys Ile Leu Ser Arg Lys
            420                 425                 430

Ile Gln Lys Phe Glu Asn Gln Tyr Arg Gly Arg Glu Leu Pro Gly Phe
        435                 440                 445

Val Asn Tyr Arg Thr Phe Glu Thr Ile Val Lys Gln Gln Ile Lys Ala
    450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
            500                 505                 510

Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
    530                 535                 540

Val Arg Glu Lys Glu Leu Glu Glu Lys Lys Lys Ser Trp Asp
545                 550                 555                 560

Phe Gly Ala Phe Gln Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
        595                 600                 605

Gly Gln Gln Leu Gln Lys Ala Met Leu Gln Leu Gln Asp Lys Asp
    610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660
```

```
<210> SEQ ID NO 39
<211> LENGTH: 2683
<212> TYPE: DNA
<213> ORGANISM: Homo sapiens

<400> SEQUENCE: 39
tttcttcgcg gcgcggggcg gggctgggcg cggggtgaaa gaggcgaagc gagagcggag      60
gccgcactcc agcactgcgc agggaccgga attctgtggc cacactgcga ggagatcggt     120
tctgggtcgg aggctacagg aagactccca ctccctgaaa tctggagtga agaacgccgc     180
catccagcca ccattccaag cttactttgc aaagaaggaa gatggttgtt ccgaagtgg      240 acatcgcaaa agctgatcca gctgctgcat cccaccctct attactgaat ggagatgcta     300
ctgtggccca gaaaaatcca ggctcggtgg ctgagaacaa cctgtgcagc cagtatgagg     360
agaaggtgcg cccctgcatc gacctcattg actccctgcg ggctctaggt gtggagcagg     420
acctggccct gccagccatc gccgtcatcg ggaccagag ctcgggcaag agctccgtgt      480
tggaggcact gtcaggagtt gcccttccca gaggcagcgg gatcgtgacc agatgcccgc     540
tggtgctgaa actgaagaaa cttgtgaacg aagataagtg gagaggcaag gtcagttacc     600
aggactacga gattgagatt tcggatgctt cagaggtaga aaaggaaatt aataaagccc     660
agaatgccat cgccggggaa ggaatgggaa tcagtcatga gctaatcacc ctggagatca     720
gctcccgaga tgtcccggat ctgactctaa tagaccttcc tggcataacc agagtggctg     780
tgggcaatca gcctgctgac attgggtata agatcaagac actcatcaag aagtacatcc     840
agaggcagga gacaatcagc ctggtggtgg tcccccagtaa tgtggacatc gccaccacag     900
aggctctcag catggcccag gaggtggacc ccgagggaga caggaccatc ggaatcttga     960
cgaagcctga tctggtggac aaaggaactg aagacaaggt tgtggacgtg gtgcggaacc    1020
tcgtgttcca cctgaagaag ggttacatga ttgtcaagtg ccggggccag caggagatcc    1080
aggaccagct gagcctgtcc gaagccctgc agagagagaa gatcttcttt gagaaccacc    1140
catatttcag ggatctgctg gaggaaggaa aggccacggt tccctgcctg gcagaaaaac    1200
ttaccagcga gctcatcaca catatctgta aatctctgcc cctgttagaa atcaaaatca    1260
aggagactca ccagagaata acagaggagc tacaaaagta tggtgtcgac ataccggaag    1320
acgaaaatga aaaatgttc ttcctgatag ataaagttaa tgcctttaat caggacatca    1380
ctgctctcat gcaaggagag gaaactgtag gggaggaaga cattcggctg tttaccagac    1440
tccgacacga gttccacaaa tggagtacaa taattgaaaa caattttcaa gaaggccata    1500 aaatttgag tagaaaaatc cagaaatttg aaaatcagta tcgtggtaga gagctgccag    1560
gctttgtgaa ttacaggaca tttgagacaa tcgtgaaaca gcaaatcaag gcactggaag    1620
agccggctgt ggatatgcta cacaccgtga cggatatggt ccggcttgct ttcacagatg    1680
tttcgataaa aaattttgaa gagttttta acctccacag aaccgccaag tccaaaattg    1740
aagacattag agcagaacaa gagagagaag gtgagaagct gatccgcctc cacttccaga    1800
tggaacagat tgtctactgc caggaccagg tatacagggg tgcattgcag aaggtcagag    1860
agaaggagct ggaagaagaa aagaagaaga atcctgggga tttgggggct ttccagtcca    1920
gctcggcaac agactcttcc atggaggaga tctttcagca cctgatgcc tatcaccagg    1980 aggccagcaa gcgcatctcc agccacatcc ctttgatcat ccagttcttc atgctccaga    2040
cgtacgccca gcagcttcag aaggccatgc tgcagctcct gcaggacaag gacacctaca    2100
gctggctcct gaaggagcgg agcgacacca gcgacaagcg gaagttcctg aaggagcggc    2160
```

```
ttgcacggct gacgcaggct cggcgccggc ttgcccagtt ccccggttaa ccacactctg    2220
tccagccccg tagacgtgca cgcacactgt ctgcccccgt tcccgggtag ccactggact    2280
gacgacttga gtgctcagta gtcagactgg atagtccgtc tctgcttatc cgttagccgt    2340
ggtgatttag caggaagctg tgagagcagt ttggtttcta gcatgaagac agagccccac    2400
cctcagatgc acatgagctg gcgggattga aggatgctgt cttcgtactg ggaaagggat    2460
tttcagccct cagaatcgct ccaccttgca gctctcccct tctctgtatt cctagaaact    2520
gacacatgct gaacatcaca gcttatttcc tcattttat aatgtccctt cacaaaccca     2580
gtgtttyagg agcatgagtg ccgtgtgtgt gcgtcctgtc ggagccctgt ctcctctctc    2640
tgtaataaac tcatttctag cagacaaaaa aaaaaaaaa aaa                       2683
```

<210> SEQ ID NO 40
<211> LENGTH: 662
<212> TYPE: PRT
<213> ORGANISM: Homo sapiens

<400> SEQUENCE: 40

```
Met Val Val Ser Glu Val Asp Ile Ala Lys Ala Asp Pro Ala Ala
1               5                   10                  15

Ser His Pro Leu Leu Asn Gly Asp Ala Thr Val Ala Gln Lys Asn
            20                  25                  30

Pro Gly Ser Val Ala Glu Asn Asn Leu Cys Ser Gln Tyr Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285
```

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
                340                 345                 350

Ile Thr Glu Glu Leu Gln Lys Tyr Gly Val Asp Ile Pro Glu Asp Glu
            355                 360                 365

Asn Glu Lys Met Phe Phe Leu Ile Asp Lys Val Asn Ala Phe Asn Gln
370                 375                 380

Asp Ile Thr Ala Leu Met Gln Gly Glu Thr Val Gly Glu Glu Asp
385                 390                 395                 400

Ile Arg Leu Phe Thr Arg Leu Arg His Glu Phe His Lys Trp Ser Thr
            405                 410                 415

Ile Ile Glu Asn Asn Phe Gln Glu Gly His Lys Ile Leu Ser Arg Lys
                420                 425                 430

Ile Gln Lys Phe Glu Asn Gln Tyr Arg Gly Arg Glu Leu Pro Gly Phe
            435                 440                 445

Val Asn Tyr Arg Thr Phe Glu Thr Ile Val Lys Gln Gln Ile Lys Ala
450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
                500                 505                 510

Gln Glu Arg Glu Gly Glu Lys Leu Ile Arg Leu His Phe Gln Met Glu
            515                 520                 525

Gln Ile Val Tyr Cys Gln Asp Gln Val Tyr Arg Gly Ala Leu Gln Lys
530                 535                 540

Val Arg Glu Lys Glu Leu Glu Glu Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
            595                 600                 605

Gly Gln Gln Leu Gln Lys Ala Met Leu Gln Leu Leu Gln Asp Lys Asp
610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
                660

<210> SEQ ID NO 41
<211> LENGTH: 3409
<212> TYPE: DNA
<213> ORGANISM: Homo sapiens

<400> SEQUENCE: 41

```
aaattcgcgg tggggggcgga gagcgcaggg agaagtaagc ccagtgcagg atcctgaggc    60
ccgtgtttgc aggaccaggg ccggccttcc gattccccat tcattccaga agcaccgaac   120
cacgctgtgc ccggatccca agtgcagcgg cacccagcgt gggcctgggg ttgccggttg   180
acccggtcct cagcctggta gcagaggcca ggccagtgcc acaaggcacc taagtccacc   240
tgggcctgga gcaggacagg ttgcaaaaga aaatatctcg gaccccccaa actccttatg   300
ctaagggaaa catcgagcct gggaactgag ccatcaacgc tgccattctt tttcccaaac   360
agaaccctgt tgtcagaggt acacccagag caactccaca ccgggtgcat gccacagcaa   420
ctccatctta aataggagct ggtaaaacga ggctgatacc tactgggctg cattcccaga   480
cggcatagcg aggaggtgct gaagagcgca ggtttggaga atgatcacct ggattggaac   540
catagctcta ccaatatgga acccagctcc ttaggcctcg gtcttctcat ggagaacatg   600
gtgtgataat cctactcctc tgggagggtg gctgttaagc cttggaccgc agttgccggc   660
caggaatccc agtgtcacgg tggacacgcc tccctcgcgc ccttgccgcc cacctgctca   720
cccagctcag gggctttgga attctgtggc cacactgcga ggagatcggt tctgggtcgg   780
aggctacagg aagactccca ctccctgaaa tctggagtga agaacgccgc catccagcca   840
ccattccaag gaggtgcagg agaacagctc tgtgatacca tttaacttgt tgacattact   900
tttatttgaa ggaacgtata ttagagctta ctttgcaaag aaggaagatg gttgtttccg   960
aagtggacat cgcaaaagct gatccagctg ctgcatccca ccctctatta ctgaatggag  1020
atgctactgt ggcccagaaa aatccaggct cggtggctga gaacaacctg tgcagccagt  1080
atgaggagaa ggtgcgcccc tgcatcgacc tcattgactc cctgcgggct ctaggtgtgg  1140
agcaggacct ggccctgcca gccatcgccg tcatcgggga ccagagctcg ggcaagagct  1200
ccgtgttgga ggcactgtca ggagttgccc ttcccagagg cagcgggatc gtgaccagat  1260
gcccgctggt gctgaaactg aagaaacttg tgaacgaaga taagtggaga ggcaaggtca  1320
gttaccagga ctacgagatt gagatttcgg atgcttcaga ggtagaaaag gaaattaata  1380
aagcccagaa tgccatcgcc ggggaaggaa tgggaatcag tcatgagcta atcaccctgg  1440
agatcagctc ccgagatgtc ccggatctga ctctaataga ccttcctggc ataaccagag  1500
tggctgtggg caatcagcct gctgacattg ggtataagat caagacactc atcaagaagt  1560
acatccagag gcaggagaca atcagcctgg tggtggtccc cagtaatgtg gacatcgcca  1620
ccacagaggc tctcagcatg gcccaggagg tggaccccga gggagacagg accatcggaa  1680
tcttgacgaa gcctgatctg gtggacaaag gaactgaaga caaggttgtg gacgtggtgc  1740
ggaacctcgt gttccacctg aagaagggtt acatgattgt caagtgccgg ggccagcagg  1800
agatccagga ccagctgagc ctgtccgaag ccctgcagag agagaagatc ttctttgaga  1860
accacccata tttcagggat ctgctggagg aaggaaaggc cacggttccc tgcctggcag  1920
aaaaacttac cagcgagctc atcacacata tctgtaaatc tctgccccctg ttagaaaatc  1980
aaatcaagga gactcaccag agaataacag aggagctaca aaagtatggt gtcgacatac  2040
cggaagacga aaatgaaaaa atgttcttcc tgatagataa agttaatgcc tttaatcagg  2100
acatcactgc tctcatgcaa ggagaggaaa ctgtagggga ggaagacatt cggctgttta  2160
ccagactccg acacgagttc cacaaatgga gtacaataat tgaaaacaat ttcaagaag   2220
gccataaaat tttgagtaga aaaatccaga aatttgaaaa tcagtatcgt ggtagagagc  2280
tgccaggctt tgtgaattac aggacatttg agacaatcgt gaaacagcaa atcaaggcac  2340
```

```
tggaagagcc ggctgtggat atgctacaca ccgtgacgga tatggtccgg cttgctttca    2400
cagatgtttc gataaaaaat tttgaagagt tttttaacct ccacagaacc gccaagtcca    2460
aaattgaaga cattagagca gaacaagaga gagaaggtga gaagctgatc cgcctccact    2520
tccagatgga acagattgtc tactgccagg accaggtata caggggtgca ttgcagaagg    2580
tcagagagaa ggagctggaa gaagaaaaga agaagaaatc ctgggatttt ggggctttcc    2640
agtccagctc ggcaacagac tcttccatgg aggagatctt tcagcacctg atggcctatc    2700
accaggaggc cagcaagcgc atctccagcc acatcccttt gatcatccag ttcttcatgc    2760
tccagacgta cggccagcag cttcagaagg ccatgctgca gctcctgcag gacaaggaca    2820
cctacagctg gctcctgaag gagcggagcg acaccagcga caagcggaag ttcctgaagg    2880
agcggcttgc acggctgacg caggctcggc gccggcttgc ccagttcccc ggttaaccac    2940
actctgtcca gccccgtaga cgtgcacgca cactgtctgc ccccgttccc gggtagccac    3000
tggactgacg acttgagtgc tcagtagtca gactggatag tccgtctctg cttatccgtt    3060
agccgtggtg atttagcagg aagctgtgag agcagtttgg tttctagcat gaagacagag    3120 cccaccctc agatgcacat gagctggcgg gattgaagga tgctgtcttc gtactgggaa    3180
agggattttc agccctcaga atcgctccac cttgcagctc tcccttctc tgtattccta    3240 gaaactgaca catgctgaac atcacagctt atttcctcat ttttataatg tcccttcaca    3300
aacccagtgt tttaggagca tgagtgccgt gtgtgtgcgt cctgtcggag ccctgtctcc    3360
tctctctgta ataaactcat ttctagcaga caaaaaaaaa aaaaaaaa                 3409
```

<210> SEQ ID NO 42
<211> LENGTH: 662
<212> TYPE: PRT
<213> ORGANISM: Homo sapiens

<400> SEQUENCE: 42

```
Met Val Val Ser Glu Val Asp Ile Ala Lys Ala Asp Pro Ala Ala Ala
1               5                   10                  15

Ser His Pro Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
```

```
            180                 185                 190
Asp Ile Gly Tyr Lys Ile Lys Thr Leu Ile Lys Lys Tyr Ile Gln Arg
            195                 200                 205
Gln Glu Thr Ile Ser Leu Val Val Pro Ser Asn Val Asp Ile Ala
    210                 215                 220
Thr Thr Glu Ala Leu Ser Met Ala Gln Glu Val Asp Pro Glu Gly Asp
225                 230                 235                 240
Arg Thr Ile Gly Ile Leu Thr Lys Pro Asp Leu Val Asp Lys Gly Thr
                245                 250                 255
Glu Asp Lys Val Val Asp Val Val Arg Asn Leu Val Phe His Leu Lys
            260                 265                 270
Lys Gly Tyr Met Ile Val Lys Cys Arg Gly Gln Gln Glu Ile Gln Asp
            275                 280                 285
Gln Leu Ser Leu Ser Glu Ala Leu Gln Arg Glu Lys Ile Phe Phe Glu
            290                 295                 300
Asn His Pro Tyr Phe Arg Asp Leu Leu Glu Glu Gly Lys Ala Thr Val
305                 310                 315                 320
Pro Cys Leu Ala Glu Lys Leu Thr Ser Glu Leu Ile Thr His Ile Cys
                325                 330                 335
Lys Ser Leu Pro Leu Leu Glu Asn Gln Ile Lys Glu Thr His Gln Arg
                340                 345                 350
Ile Thr Glu Glu Leu Gln Lys Tyr Gly Val Asp Ile Pro Glu Asp Glu
            355                 360                 365
Asn Glu Lys Met Phe Phe Leu Ile Asp Lys Val Asn Ala Phe Asn Gln
    370                 375                 380
Asp Ile Thr Ala Leu Met Gln Gly Glu Glu Thr Val Gly Glu Glu Asp
385                 390                 395                 400
Ile Arg Leu Phe Thr Arg Leu Arg His Glu Phe His Lys Trp Ser Thr
                405                 410                 415
Ile Ile Glu Asn Asn Phe Gln Glu Gly His Lys Ile Leu Ser Arg Lys
                420                 425                 430
Ile Gln Lys Phe Glu Asn Gln Tyr Arg Gly Arg Glu Leu Pro Gly Phe
            435                 440                 445
Val Asn Tyr Arg Thr Phe Glu Thr Ile Val Lys Gln Gln Ile Lys Ala
    450                 455                 460
Leu Glu Glu Pro Ala Val Asp Met Leu His Thr Val Thr Asp Met Val
465                 470                 475                 480
Arg Leu Ala Phe Thr Asp Val Ser Ile Lys Asn Phe Glu Glu Phe Phe
                485                 490                 495
Asn Leu His Arg Thr Ala Lys Ser Lys Ile Glu Asp Ile Arg Ala Glu
            500                 505                 510
Gln Glu Arg Glu Gly Glu Lys Leu Ile Arg Leu His Phe Gln Met Glu
            515                 520                 525
Gln Ile Val Tyr Cys Gln Asp Gln Val Tyr Arg Gly Ala Leu Gln Lys
    530                 535                 540
Val Arg Glu Lys Glu Leu Glu Glu Lys Lys Lys Lys Ser Trp Asp
545                 550                 555                 560
Phe Gly Ala Phe Gln Ser Ser Ala Thr Asp Ser Ser Met Glu Glu
                565                 570                 575
Ile Phe Gln His Leu Met Ala Tyr His Gln Glu Ala Ser Lys Arg Ile
            580                 585                 590
Ser Ser His Ile Pro Leu Ile Ile Gln Phe Phe Met Leu Gln Thr Tyr
            595                 600                 605
```

```
Gly Gln Gln Leu Gln Lys Ala Met Leu Gln Leu Leu Gln Asp Lys Asp
    610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660

<210> SEQ ID NO 43
<211> LENGTH: 5889
<212> TYPE: DNA
<213> ORGANISM: Homo sapiens

<400> SEQUENCE: 43
```

| | | | | | |
|---|---|---|---|---|---|
| gctgccagct | gagttttttt | gctgctttga | gtctcagttt | tctttctttc | ctagagtctc | 60 |
| tgaagccaca | gatctcttaa | gaactttctg | tctccaaacc | gtggctgctc | gataaatcag | 120 |
| acagaacagt | taatcctcaa | tttaagcctg | atctaacccc | tagaaacaga | tatagaacaa | 180 |
| tggaagtgac | aacaagattg | acatggaatg | atgaaaatca | tctgcgcaag | ctgcttggaa | 240 |
| atgtttcttt | gagtcttctc | tataagtcta | gtgttcatgg | aggtagcatt | gaagatatgg | 300 |
| ttgaaagatg | cagccgtcag | ggatgtacta | aacaatggc | ttacattgat | tacaatatga | 360 |
| ttgtagcctt | tatgcttgga | aattatatta | atttacatga | aagttctaca | gagccaaatg | 420 |
| attccctatg | gttttcactt | caaaagaaaa | atgacaccac | tgaaatagaa | actttactct | 480 |
| taaatacagc | accaaaaatt | attgatgagc | aactggtgtg | tcgtttatcg | aaaacggata | 540 |
| ttttcattat | atgtcgagat | aataaaattt | atctagataa | aatgataaca | agaaacttga | 600 |
| aactaaggtt | ttatggccac | cgtcagtatt | tggaatgtga | agttttcga | gttgaaggaa | 660 |
| ttaaggataa | cctagacgac | ataaagagga | taattaaagc | cagagagcac | agaaataggc | 720 |
| ttctagcaga | catcagagac | tataggccct | atgcagactt | ggtttcagaa | attcgtattc | 780 |
| ttttggtggg | tccagttggg | tctggaaagt | ccagtttttt | caattcagtc | aagtctattt | 840 |
| ttcatggcca | tgtgactggc | caagccgtag | tggggtctga | tatcaccagc | ataaccgagc | 900 |
| ggtataggat | atattctgtt | aaagatggaa | aaaatggaaa | atctctgcca | tttatgttgt | 960 |
| gtgacactat | ggggctagat | ggggcagaag | gagcaggact | gtgcatggat | gacattcccc | 1020 |
| acatcttaaa | aggttgtatg | ccagacagat | atcagtttaa | ttcccgtaaa | ccaattacac | 1080 |
| ctgagcattc | tactttatc | acctctccat | ctctgaagga | caggattcac | tgtgtggctt | 1140 |
| atgtcttaga | catcaactct | attgacaatc | tctactctaa | aatgttggca | aaagtgaagc | 1200 |
| aagttcacaa | agaagtatta | aactgtggta | tagcatatgt | ggccttgctt | actaaagtgg | 1260 |
| atgattgcag | tgaggttctt | caagacaact | ttttaaacat | gagtagatct | atgacttctc | 1320 |
| aaaagccggt | catgaatgtc | cataaaatgc | taggcattcc | tatttccaat | attttgatgg | 1380 |
| ttggaaacta | tgcttcagat | ttggaactgg | accccatgaa | ggatattctc | atcctctctg | 1440 |
| cactgaggca | gatgctgcgg | gctgcagatg | attttttaga | agatttgcct | cttgaggaaa | 1500 |
| ctggtgcaat | tgagagagcg | ttacagccct | gcatttgaga | taagttgcct | tgattctgac | 1560 |
| atttggccca | gcctgtactg | gtgtgccgca | atgagagtca | atctctattg | acagcctgct | 1620 |
| tcagattttg | cttttgttcg | ttttgccttc | tgtccttgga | acagtcatat | ctcaagttca | 1680 |
| aaggccaaaa | cctgagaagc | ggtgggctaa | gataggtcct | actgcaaacc | accctccat | 1740 |

```
atttccgtac catttacaat tcagtttctg tgacatcttt ttaaaccact ggaggaaaaa    1800
tgagatattc tctaatttat tcttctataa cactctatat agagctatgt gagtactaat    1860
cacattgaat aatagttata aaattattgt atagacatct gcttcttaaa cagattgtga    1920
gttctttgag aaacagcgtg gattttactt atctgtgtat tcacagagct tagcacagtg    1980
cctggtaatg agcaagcata cttgccatta cttttccttc ccactctctc caacatcaca    2040
ttcactttaa attttctgt atatagaaag gaaaactagc ctgggcaaca tgatgaaacc    2100
ccatctccac tgcaaaaaaa aaaaaaaaa ataagaaaga acaaacaaa ccccacaaaa       2160 attagctggg tatgatggca cgtgcctgta gtcccagtta ctcaggatga ttgattgagc    2220
cttggaggtg gaggctacag tgagctgaga ttgtgccact gtactctagc cagggagaaa    2280
gagtgagatc ctggctcaaa aaaccaaat aaacaaaac aaacaaacga aaacagaaa         2340 ggaagactga aagagaatga aaagctgggg agggaaata aaaataaaga aggaagagtg     2400
tttcatttat atctgaatga aaatatgaat gactctaagt aattgaatta attaaaatga    2460
gccaactttt tttaacaat ttacatttta tttctatggg aaaaaataaa tattcctctt     2520
ctaacaaacc catgcttgat tttcattaat tgaattccaa atcatcctag ccatgtgtcc    2580
ttccatttag gttactgggg caaatcagta agaaagttct tatatttatg ctccaaataa    2640
ttctgaagtc ctcttactag ctgtgaaagc tagtactatt aagaaagaaa acaaaattcc    2700
caaaagatag ctttcacttt ttttttttcct taaagacttc ctaattctct tctccaaatt   2760
cttagtcttc ttcaaaataa tatgctttgg ttcaatagtt atccacattc tgacagtcta    2820
atttagtttt aatcagaatt atactcatct tttgggtagt catagatatt aagaaagcaa    2880
gagtttctta tgtccagtta tggaatattt cctaaagcaa ggctgcaggt gaagttgtgc    2940
tcaagtgaat gttcaggaga cacaattcag tggaagaaat taagtcttta aaaaagacct    3000
aggaatagga gaaccatgga aattgaggag gtaggcctac aagtagatat tgggaacaaa    3060
attagagagg caaccagaaa aagttatttt aggctcacca gagttgttct tattgcacag    3120
taacacacca atataccaaa acagcaggta ttgcagtaga gaaagagttt aataattgaa    3180
tggcagaaaa atgaggaagg ttgaggaaac ctcaaatcta cctccctgct gagtctaagt    3240
ttaggatttt taagagaaag gcaggtaagg tgctgaaggt ctggagctgc tgatttgttg    3300
gggtataggg aatgaaatga aacatacaga gatgaaaact ggaagttttt ttttgtttgt    3360
tttgtttttt ttttgttgtt gtttttttt tttttgttt tttgctgag tcaattcctt        3420 ggagggggtc ttcagactga ctggtgtcag cagacccatg ggattccaag atctggaaaa    3480
ctttttagat agaaacttga tgtttcttaa cgttacatat attatcttat agaaataact    3540 aaggaagtt agtgccttgt gaccacatct atgtgacttt taggcagtaa gaaactataa     3600
ggaaaggagc taacagtcat gctgtaagta gctacaggga attggcttaa agggcaagtt    3660
ggttagtact tagctgtgtt tttattcaaa gtctacattt tatgtagtgg ttaatgtttg    3720
ctgttcatta ggatggtttc acagttacca tacaaatgta gaagcaacag gtccaaaaag    3780
tagggcatga ttttctccat gtaatccagg gagaaaacaa gccatgacca ttgttggttg    3840
ggagactgaa ggtgattgaa ggttcaccat catcctcacc aacttttggg ccataattca    3900
cccaacccct tggtggagcc tgaaaaaaat ctgggcagaa tgtaggactt ctttatttttg   3960 tttaaggggg taacacagag tgcccttatg aaggagttgg agatcctgca aggaagagaa    4020
ggagtgaagg agagatcaag agagagaaac aatgaggaac atttcatttg acccaacatc    4080 cttttaggagc ataaatgttg acactaagtt atccctttttg tgctaaaatg gacagtattg  4140
```

-continued

```
gcaaaatgat accacaactt cttattctct ggctctatat tgctttggaa acacttaaac    4200
atcaaatgga gttaaataca tatttgaaat ttaggttagg aaatattggt gaggaggcct    4260
caaaaagggg gaaacatctt ttgtctggga ggatattttc cattttgtgg atttccctga    4320
tcttttcta ccaccctgag gggtggtggg aattatcatt ttgctacatt ttagaggtca     4380
tccaggattt ttgaaacttt acattcttta cggttaagca agatgtacag ctcagtcaaa    4440
gacactaaat tcttcttaga aaatagtgc taaggagtat agcagatgac ctatatgtgt     4500
gttggctggg agaatatcat cttaaagtga gagtgatgtt gtggagacag ttgaaatgtc    4560
aatgctagac cctctgtggt gtgaatgggc acgttaggtt gttgcattag aaagtgactg    4620
tttctgacag aaatttgtag ctttgtgcaa actcacccac catctacctc aataaaatat    4680
agagaaaaga aaaatagagc agtttgagtt ctatgaggta tgcaggccca gagagacata    4740
agtatgttcc tttagtcttg cttcctgtgt gccacactgc ccctccacaa ccatagctgg    4800
gggcaattgt ttaaagtcat tttgttcccg actagctgcc ttgcacatta tcttcatttt    4860
cctggaattt gatacagaga gcaatttata gccaattgat agcttatgct gtttcaatgt    4920
aaattcgtgg taaataactt aggaactgcc tcttctttt ctttgaaaac ctacttataa     4980
ctgttgctaa taagaatgtg tattgttcag acaacttgt ctccatacag ttgggttgta    5040
accctcatgc ttggcccaaa taactctct acttatatca gttttcctaa cacttcttcc     5100
ttttaggtca acaataccaa gaggggttac tgtgctgggt aatgtgtaaa cttgtgtctt    5160
gtttagaaag ataaatttaa agactatcac attgcttttt cataaaacaa gacaggtcta    5220
caattaattt attttgacgc aaattgatag gggggccaag taagccccat atgcttaatg    5280
atcagctgat gaataatcat ctcctagcaa cataactcaa tctaatgcta aggtaccccac   5340
aagatggcaa ggctgatcaa agtcgtcatg gaatcctgca accaaaagcc atgggaattt    5400
ggaagccctc aaatcccatt cctaatctga tgagtctatg gaccaatttg tggaggacag    5460
tagattaaat agatctgatt tttgccatca atgtaaggag gataaaaact tgcataccaa    5520
ttgtacaccc ttgcaaaatc tttctctgat gttggagaaa atgggccagt gagatcatgg    5580
atatagaagt acagtcaatg ttcagctgta ccctcccaca atcccacttc cttcctcaac    5640
acaattcaaa caaatagact cagactgttt caggctccag gacaggaagt gcagtgtagg    5700
caaaattgca aaaattgagg gcacaggggt ggaggtgggg gggttgaata acaagctgtg    5760
ctaaataatt acgtgtaaat atatttttc attttaaaa attgatttct tttgcacatt      5820
ccatgacaat atatgtcaca tttttaaaat aaatgcaaag aagcatacat ccaaaaaaaa    5880
aaaaaaaaa                                                            5889
```

<210> SEQ ID NO 44
<211> LENGTH: 452
<212> TYPE: PRT
<213> ORGANISM: Homo sapiens

<400> SEQUENCE: 44

```
Met Glu Val Thr Thr Arg Leu Thr Trp Asn Asp Glu Asn His Leu Arg
1               5                   10                  15

Lys Leu Leu Gly Asn Val Ser Leu Ser Leu Leu Tyr Lys Ser Ser Val
            20                  25                  30

His Gly Gly Ser Ile Glu Asp Met Val Glu Arg Cys Ser Arg Gln Gly
        35                  40                  45

Cys Thr Ile Thr Met Ala Tyr Ile Asp Tyr Asn Met Ile Val Ala Phe
```

```
                50                  55                  60
Met Leu Gly Asn Tyr Ile Asn Leu His Glu Ser Ser Thr Glu Pro Asn
 65                  70                  75                  80

Asp Ser Leu Trp Phe Ser Leu Gln Lys Lys Asn Asp Thr Thr Glu Ile
                     85                  90                  95

Glu Thr Leu Leu Leu Asn Thr Ala Pro Lys Ile Ile Asp Glu Gln Leu
                100                 105                 110

Val Cys Arg Leu Ser Lys Thr Asp Ile Phe Ile Cys Arg Asp Asn
                115                 120                 125

Lys Ile Tyr Leu Asp Lys Met Ile Thr Arg Asn Leu Lys Leu Arg Phe
            130                 135                 140

Tyr Gly His Arg Gln Tyr Leu Glu Cys Glu Val Phe Arg Val Glu Gly
145                 150                 155                 160

Ile Lys Asp Asn Leu Asp Asp Ile Lys Arg Ile Lys Ala Arg Glu
                    165                 170                 175

His Arg Asn Arg Leu Leu Ala Asp Ile Arg Asp Tyr Arg Pro Tyr Ala
                180                 185                 190

Asp Leu Val Ser Glu Ile Arg Ile Leu Leu Val Gly Pro Val Gly Ser
                195                 200                 205

Gly Lys Ser Ser Phe Phe Asn Ser Val Lys Ser Ile Phe His Gly His
                210                 215                 220

Val Thr Gly Gln Ala Val Val Gly Ser Asp Ile Thr Ser Ile Thr Glu
225                 230                 235                 240

Arg Tyr Arg Ile Tyr Ser Val Lys Asp Gly Lys Asn Gly Lys Ser Leu
                    245                 250                 255

Pro Phe Met Leu Cys Asp Thr Met Gly Leu Asp Gly Ala Glu Gly Ala
                260                 265                 270

Gly Leu Cys Met Asp Asp Ile Pro His Ile Leu Lys Gly Cys Met Pro
                275                 280                 285

Asp Arg Tyr Gln Phe Asn Ser Arg Lys Pro Ile Thr Pro Glu His Ser
                290                 295                 300

Thr Phe Ile Thr Ser Pro Ser Leu Lys Asp Arg Ile His Cys Val Ala
305                 310                 315                 320

Tyr Val Leu Asp Ile Asn Ser Ile Asp Asn Leu Tyr Ser Lys Met Leu
                    325                 330                 335

Ala Lys Val Lys Gln Val His Lys Glu Val Leu Asn Cys Gly Ile Ala
                340                 345                 350

Tyr Val Ala Leu Leu Thr Lys Val Asp Asp Cys Ser Glu Val Leu Gln
                355                 360                 365

Asp Asn Phe Leu Asn Met Ser Arg Ser Met Thr Ser Gln Ser Arg Val
                370                 375                 380

Met Asn Val His Lys Met Leu Gly Ile Pro Ile Ser Asn Ile Leu Met
385                 390                 395                 400

Val Gly Asn Tyr Ala Ser Asp Leu Glu Leu Asp Pro Met Lys Asp Ile
                    405                 410                 415

Leu Ile Leu Ser Ala Leu Arg Gln Met Leu Arg Ala Ala Asp Asp Phe
                420                 425                 430

Leu Glu Asp Leu Pro Leu Glu Glu Thr Gly Ala Ile Glu Arg Ala Leu
                435                 440                 445

Gln Pro Cys Ile
450

<210> SEQ ID NO 45
```

<211> LENGTH: 4759
<212> TYPE: DNA
<213> ORGANISM: Homo sapiens

<400> SEQUENCE: 45

```
tagttattaa agttcctatg cagctccgcc tcgcgtccgg cctcatttcc tcggaaaatc      60
cctgctttcc ccgctcgcca cgccctcctc ctacccggct ttaaagctag tgaggcacag     120
cctgcgggga acgtagctag ctgcaagcag aggccggcat gaccaccgag cagcgacgca     180
gcctgcaagc cttccaggat tatatccgga agaccctgga ccctacctac atcctgagct     240
acatggcccc ctggtttagg gaggaagagg tgcagtatat tcaggctgag aaaaacaaca     300
agggcccaat ggaggctgcc acactttttc tcaagttcct gttggagctc caggaggaag     360
gctggttccg tggcttttg gatgccctag accatgcagg ttattctgga ctttatgaag     420
ccattgaaag ttgggatttc aaaaaaattg aaaagttgga ggagtataga ttacttttaa     480
aacgtttaca accagaattt aaaaccagaa ttatcccaac cgatatcatt tctgatctgt     540
ctgaatgttt aattaatcag gaatgtgaag aaattctaca gatttgctct actaagggga     600
tgatggcagg tgcagagaaa ttggtggaat gccttctcag atcagacaag gaaaactggc     660
ccaaaacttt gaaacttgct ttggagaaag aaaggaacaa gttcagtgaa ctgtggattg     720
tagagaaagg tataaaagat gttgaaacag aagatcttga ggataagatg gaaacttctg     780
acatacagat tttctaccaa gaagatccag aatgccagaa tcttagtgag aattcatgtc     840
cacctttcaga agtgtctgat acaaacttgt acagcccatt taaaccaaga aattaccaat     900
tagagcttgc tttgcctgct atgaaaggaa aaaacacaat aatatgtgct cctacaggtt     960
gtggaaaaac ctttgtttca ctgcttatat gtgaacatca tcttaaaaaa ttcccacaag    1020
gacaaaaggg gaaagttgtc tttttgcga atcagatccc agtgtatgaa cagcagaaat    1080
ctgtattctc aaaatacttt gaaagacatg gtatagagt tacaggcatt tctggagcaa    1140
cagctgagaa tgtcccagtg aacagattg ttgagaacaa tgacatcatc atttaactc    1200
cacagattct tgtgaacaac cttaaaaagg gaacgattcc atcactatcc atctttactt    1260
tgatgatatt tgatgaatgc cacaacacta gtaaacaaca cccgtacaat atgatcatgt    1320
ttaattatct agatcagaaa cttggaggat cttcaggccc actgccccag gtcattgggc    1380
tgactgcctc ggttggtgtt ggggatgcca aaaacacaga tgaagccttg gattatatct    1440
gcaagctgtg tgcttctctt gatgcgtcag tgatagcaac agtcaaacac aatctggagg    1500
aactggagca agttgtttat aagccccaga gttttttcag gaaagtggaa tcacggatta    1560
gcgacaaatt taaatacatc atagctcagc tgatgaggga cacagagagt ctggcaaaga    1620
gaatctgcaa agacctcgaa aacttatctc aaattcaaaa tagggaattt ggaacacaga    1680
aatatgaaca atggattgtt acagttcaga aagcatgcat ggtgttccag atgccagaca    1740
aagatgaaga gagcaggatt tgtaaagccc tgtttttata cacttcacat ttgcggaaat    1800
ataatgatgc cctcattatc agtgagcatg cacgaatgaa agatgctctg gattacttga    1860
aagacttctt cagcaatgtc cgagcagcag gattcgatga gattgagcaa gatcttactc    1920
agagatttga agaaaagctg caggaactag aaagtgtttc cagggatccc agcaatgaga    1980
atcctaaact tgaagacctc tgcttcatct acaagaaga gtaccactta aacccagaga    2040
caataacaat tctctttgtg aaaaccagag cacttgtgga cgctttaaaa aattggattg    2100
aaggaaatcc taaactcagt tttctaaaac ctggcatatt gactgacgt ggcaaaacaa    2160
atcagaacac aggaatgacc ctcccggcac agaagtgtat attggatgca ttcaaagcca    2220
```

```
gtggagatca caatattctg attgccacct cagttgctga tgaaggcatt gacattgcac    2280
agtgcaatct tgtcatcctt tatgagtatg tgggcaatgt catcaaaatg atccaaacca    2340
gaggcagagg aagagcaaga ggtagcaagt gcttccttct gactagtaat gctggtgtaa    2400
ttgaaaaaga acaaataaac atgtacaaag aaaaaatgat gaatgactct attttacgcc    2460
ttcagacatg ggacgaagca gtatttaggg aaaagattct gcatatacag actcatgaaa    2520
aattcatcag agatagtcaa gaaaaaccaa aacctgtacc tgataaggaa aataaaaaac    2580
tgctctgcag aaagtgcaaa gccttggcat gttacacagc tgacgtaaga gtgatagagg    2640
aatgccatta cactgtgctt ggagatgctt ttaaggaatg ctttgtgagt agaccacatc    2700
ccaagccaaa gcagttttca agttttgaaa aaagagcaaa gatattctgt gcccgacaga    2760
actgcagcca tgactgggga atccatgtga agtacaagac atttgagatt ccagttataa    2820
aaattgaaag ttttgtggtg gaggatattg caactggagt tcagacactg tactcgaagt    2880
ggaaggactt tcattttgag aagataccat ttgatccagc agaaatgtcc aaatgatatc    2940
aggtcctcaa tcttcagcta cagggaatga gtaactttga gtggagaaga aacaaacata    3000
gtgggtataa tcatggatcg cttgtacccc tgtgaaaata tatttttttaa aaatatcttt    3060
agcagtttgt actatattat atatgcaaag cacaaatgag tgaatcacag cactgagtat    3120
tttgtaggcc aacagagctc atagtacttg ggaaaaatta aaaagcctca tttctagcct    3180
tcttttttaga gtcaactgcc aacaaacaca cagtaatcac tctgtacaca ctgggataga    3240
tgaatgaatg gaatgttggg aattttttatc tcccttttgtc tccttaacct actgtaaact    3300
ggcttttgcc cttaacaatc tactgaaatt gttcttttga aggttaccag tgactctggt    3360
tgccaaatcc actgggcact tcttaacctt ctatttgacc tctgcgcatt tggccctgtt    3420
gagcactctt cttgaagctc tccctgggct tctctctctt ctagttctat tctagtcttt    3480
ttttattgag tcctcctctt tgctgatccc ttccaagggt tcaatatata tacatgtata    3540
tactgtacat atgtatatgt aactaatata catacataca ggtatgtata tgtaatggtt    3600
atatgtactc atgttcctgg tgtagcaacg tgtggtatgg ctacacagag aacatgagaa    3660
cataaagcca ttttttatgct tactactaaa agctgtccac tgtagagttg ctgtatgtag    3720
caatgtgtat ccactctaca gtggtcagct tttagtagag agcataaaaa tgataaaata    3780
cttcttgaaa acttagttta ctatacatct tgccctatta atatgttctc ttaacgtgtg    3840
ccattgttct ctttgaccat tttcctataa tgatgttgat gttcaacacc tggactgaat    3900
gtctgttctc agatcccttg gatgttacag atgaggcagt ctgactgtcc tttctacttg    3960
aaagattaga atatgtatcc aaatggcatt cacgtgtcac ttagcaaggt ttgctgatgc    4020
ttcaaagagc ttagtttgcg gtttcctgga cgtggaaaca agtatctgag ttccctggag    4080
atcaacggga tgaggtgtta cagctgcctc cctcttcatg caatctggtg agcagtggtg    4140
caggcgggga gccagagaaa cttgccagtt atataacttc tctttggctt ttcttcatct    4200
gtaaaacaag gataatactg aactgtaagg gttagtggag agttttttaat taaaagaatg    4260
tgtgaaaagt acatgacaca gtagttgctt gataatagtt actagtagta gtattcttac    4320
taagacccaa tacaaatgga ttatttaaac caagtttatg agttggtttt ttttcatttt    4380
ctatttgtat tttattaaga gtgtctttctc ttatgtgatt tttttttaatt gctatttgat    4440
atggtttggc tatatgtccc cacccaaatc tcatcttgaa ttataatccc catgtgtcaa    4500
gggagggacc tgacgggagg tgattggatc acgggggcag ttgtccccat gctgttcttg    4560
```

```
ggatagtgag ttagttctca tgagatctga tggttttata agtgtttgac aattcctcct    4620
ttacacacac tctctctctc atctgctgcc atgtaagact tgcctgcttc cccttctgcc    4680
atgattgtaa gtttcctgag gcctcctcag ccatgtggaa ctgtgaatct attaagcctc    4740
ttttctttat aaatgaaaa                                                  4759
```

<210> SEQ ID NO 46
<211> LENGTH: 925
<212> TYPE: PRT
<213> ORGANISM: Homo sapiens

<400> SEQUENCE: 46

```
Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65                  70                  75                  80

Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Leu Lys Arg Leu Gln Pro
            100                 105                 110

Glu Phe Lys Thr Arg Ile Ile Pro Thr Asp Ile Ile Ser Asp Leu Ser
        115                 120                 125

Glu Cys Leu Ile Asn Gln Glu Cys Glu Glu Ile Leu Gln Ile Cys Ser
    130                 135                 140

Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Glu Lys Gly Ile
            180                 185                 190

Lys Asp Val Glu Thr Glu Asp Leu Glu Asp Lys Met Glu Thr Ser Asp
        195                 200                 205

Ile Gln Ile Phe Tyr Gln Glu Asp Pro Glu Cys Gln Asn Leu Ser Glu
    210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
                245                 250                 255

Gly Lys Asn Thr Ile Ile Cys Ala Pro Thr Gly Cys Gly Lys Thr Phe
            260                 265                 270

Val Ser Leu Leu Ile Cys Glu His Leu Lys Lys Phe Pro Gln Gly
        275                 280                 285

Gln Lys Gly Lys Val Phe Phe Ala Asn Gln Ile Pro Val Tyr Glu
    290                 295                 300

Gln Gln Lys Ser Val Phe Ser Lys Tyr Phe Glu Arg His Gly Tyr Arg
305                 310                 315                 320

Val Thr Gly Ile Ser Gly Ala Thr Ala Glu Asn Val Pro Val Glu Gln
                325                 330                 335
```

```
Ile Val Glu Asn Asn Asp Ile Ile Ile Leu Thr Pro Gln Ile Leu Val
            340                 345                 350

Asn Asn Leu Lys Lys Gly Thr Ile Pro Ser Leu Ser Ile Phe Thr Leu
            355                 360                 365

Met Ile Phe Asp Glu Cys His Asn Thr Ser Lys Gln His Pro Tyr Asn
    370                 375                 380

Met Ile Met Phe Asn Tyr Leu Asp Gln Lys Leu Gly Ser Ser Gly
385                 390                 395                 400

Pro Leu Pro Gln Val Ile Gly Leu Thr Ala Ser Val Gly Val Gly Asp
                    405                 410                 415

Ala Lys Asn Thr Asp Glu Ala Leu Asp Tyr Ile Cys Lys Leu Cys Ala
                420                 425                 430

Ser Leu Asp Ala Ser Val Ile Ala Thr Val Lys His Asn Leu Glu Glu
                435                 440                 445

Leu Glu Gln Val Val Tyr Lys Pro Gln Lys Phe Phe Arg Lys Val Glu
            450                 455                 460

Ser Arg Ile Ser Asp Lys Phe Lys Tyr Ile Ile Ala Gln Leu Met Arg
465                 470                 475                 480

Asp Thr Glu Ser Leu Ala Lys Arg Ile Cys Lys Asp Leu Glu Asn Leu
                485                 490                 495

Ser Gln Ile Gln Asn Arg Glu Phe Gly Thr Gln Lys Tyr Glu Gln Trp
            500                 505                 510

Ile Val Thr Val Gln Lys Ala Cys Met Val Phe Gln Met Pro Asp Lys
            515                 520                 525

Asp Glu Glu Ser Arg Ile Cys Lys Ala Leu Phe Leu Tyr Thr Ser His
530                 535                 540

Leu Arg Lys Tyr Asn Asp Ala Leu Ile Ile Ser Glu His Ala Arg Met
545                 550                 555                 560

Lys Asp Ala Leu Asp Tyr Leu Lys Asp Phe Phe Ser Asn Val Arg Ala
                565                 570                 575

Ala Gly Phe Asp Glu Ile Glu Gln Asp Leu Thr Gln Arg Phe Glu Glu
                580                 585                 590

Lys Leu Gln Glu Leu Glu Ser Val Ser Arg Asp Pro Ser Asn Glu Asn
            595                 600                 605

Pro Lys Leu Glu Asp Leu Cys Phe Ile Leu Gln Glu Glu Tyr His Leu
            610                 615                 620

Asn Pro Glu Thr Ile Thr Ile Leu Phe Val Lys Thr Arg Ala Leu Val
625                 630                 635                 640

Asp Ala Leu Lys Asn Trp Ile Glu Gly Asn Pro Lys Leu Ser Phe Leu
                645                 650                 655

Lys Pro Gly Ile Leu Thr Gly Arg Gly Lys Thr Asn Gln Asn Thr Gly
                660                 665                 670

Met Thr Leu Pro Ala Gln Lys Cys Ile Leu Asp Ala Phe Lys Ala Ser
            675                 680                 685

Gly Asp His Asn Ile Leu Ile Ala Thr Ser Val Ala Asp Glu Gly Ile
                690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
                740                 745                 750

Ile Asn Met Tyr Lys Glu Lys Met Met Asn Asp Ser Ile Leu Arg Leu
```

755                 760                 765
Gln Thr Trp Asp Glu Ala Val Phe Arg Glu Lys Ile Leu His Ile Gln
        770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
            820                 825                 830

Val Leu Gly Asp Ala Phe Lys Glu Cys Phe Val Ser Arg Pro His Pro
        835                 840                 845

Lys Pro Lys Gln Phe Ser Ser Phe Glu Lys Arg Ala Lys Ile Phe Cys
850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
                885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
        915                 920                 925

<210> SEQ ID NO 47
<211> LENGTH: 863
<212> TYPE: DNA
<213> ORGANISM: Homo sapiens

<400> SEQUENCE: 47
caaggttcag agtcacccat ctcagcaagc ccagaagtat ctgcaatatc tacgatggcc      60
tcgcccttg  ctttactgat ggtcctggtg gtgctcagct gcaagtcaag ctgctctctg     120
ggctgtgatc tccctgagac ccacagcctg ataacagga ggaccttgat gctcctggca     180
caaatgagca gaatctctcc ttcctcctgt ctgatggaca acatgacttt ggatttccc     240
caggaggagt tgatggcaa ccagttccag aaggctccag ccatctctgt cctccatgag     300
ctgatccagc agatcttcaa cctctttacc acaaaagatt catctgctgc ttgggatgag     360
gacctcctag acaaattctg caccgaactc taccagcagc tgaatgactt ggaagcctgt     420
gtgatgcagg aggagggt gggagaaact cccctgatga atgcggactc catcttggct     480
gtgaagaaat acttccgaag aatcactctc tatctgacag agaagaaata cagcccttgt     540
gcctgggagg ttgtcagagc agaaatcatg agatccctct ctttatcaac aaacttgcaa     600
gaaagattaa ggaggaagga ataacatctg gtccaacatg aaaacaattc ttattgactc     660
atacaccagg tcacgctttc atgaattctg tcatttcaaa gactctcacc cctgctataa     720
ctatgaccat gctgataaac tgatttatct atttaaatat ttatttaact attcataaga     780
tttaaattat ttttgttcat ataacgtcat gtgcacctt  acactgtggt tagtgtaata     840
aaacatgttc cttatattta ctc                                             863

<210> SEQ ID NO 48
<211> LENGTH: 189
<212> TYPE: PRT
<213> ORGANISM: Homo sapiens

<400> SEQUENCE: 48

Met Ala Ser Pro Phe Ala Leu Leu Met Val Leu Val Val Leu Ser Cys

```
            1               5                  10                  15
          Lys Ser Ser Cys Ser Leu Gly Cys Asp Leu Pro Glu Thr His Ser Leu
                        20                  25                  30

Asp Asn Arg Arg Thr Leu Met Leu Leu Ala Gln Met Ser Arg Ile Ser
                        35                  40                  45

Pro Ser Ser Cys Leu Met Asp Arg His Asp Phe Gly Phe Pro Gln Glu
                        50                  55                  60

Glu Phe Asp Gly Asn Gln Phe Gln Lys Ala Pro Ala Ile Ser Val Leu
           65                  70                  75                  80

His Glu Leu Ile Gln Gln Ile Phe Asn Leu Phe Thr Thr Lys Asp Ser
                        85                  90                  95

Ser Ala Ala Trp Asp Glu Asp Leu Leu Asp Lys Phe Cys Thr Glu Leu
                        100                 105                 110

Tyr Gln Gln Leu Asn Asp Leu Glu Ala Cys Val Met Gln Glu Glu Arg
                        115                 120                 125

Val Gly Glu Thr Pro Leu Met Asn Ala Asp Ser Ile Leu Ala Val Lys
                        130                 135                 140

Lys Tyr Phe Arg Arg Ile Thr Leu Tyr Leu Thr Glu Lys Lys Tyr Ser
          145                 150                 155                 160

Pro Cys Ala Trp Glu Val Val Arg Ala Glu Ile Met Arg Ser Leu Ser
                        165                 170                 175

Leu Ser Thr Asn Leu Gln Glu Arg Leu Arg Arg Lys Glu
                        180                 185
```

<210> SEQ ID NO 49
<211> LENGTH: 1143
<212> TYPE: DNA
<213> ORGANISM: Homo sapiens

<400> SEQUENCE: 49

```
gagaacctgg agcctaaggt ttaggctcac ccatttcaac cagtctagca gcatctgcaa    60
catctacaat ggccttgacc tttgctttac tggtggccct cctggtgctc agctgcaagt   120
caagctgctc tgtgggctgt gatctgcctc aaacccacag cctgggtagc aggaggacct   180
tgatgctcct ggcacagatg aggagaatct ctcttttctc ctgcttgaag acagacatg    240
actttggatt tccccaggag gagtttggca accagttcca aaaggctgaa accatccctg   300
tcctccatga gatgatccag cagatcttca atctcttcag cacaaaggac tcatctgctg   360
cttgggatga gaccctccta gacaaattct acactgaact ctaccagcag ctgaatgacc   420
tggaagcctg tgtgatacag gggtgggggt gacagagac tcccctgatg aaggaggact   480
ccattctggc tgtgaggaaa tacttccaaa gaatcactct ctatctgaaa gagaagaaat   540
acagcccttg tgcctgggag gttgtcagag cagaaatcat gagatctttt tctttgtcaa   600
caaacttgca agaaagttta agaagtaagg aatgaaaact ggttcaacat ggaaatgatt   660
ttcattgatt cgtatgccag ctcaccttt tatgatctgc catttcaaag actcatgttt    720
ctgctatgac catgacacga tttaaatctt ttcaaatgtt tttaggagta ttaatcaaca   780
ttgtattcag ctcttaaggc actagtccct tacagaggac catgctgact gatccattat   840
ctatttaaat attttaaaa tattatttat ttaactattt ataaacaac ttattttgt     900
tcatattatg tcatgtgcac ctttgcacag tggttaatgt aataaaatat gttctttgta   960
tttggtaaat ttattttgtg ttgttcattg aactttgct atggaaactt ttgtacttgt   1020
ttattctta aaatgaaatt ccaagcctaa ttgtgcaacc tgattacaga ataactggta   1080
```

```
cacttcattt atccatcaat attatattca agatataagt aaaaataaac tttctgtaaa    1140
cca                                                                 1143

<210> SEQ ID NO 50
<211> LENGTH: 188
<212> TYPE: PRT
<213> ORGANISM: Homo sapiens

<400> SEQUENCE: 50

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 51
<211> LENGTH: 982
<212> TYPE: DNA
<213> ORGANISM: Homo sapiens

<400> SEQUENCE: 51
agaaaaccta gaggccgaag ttcaaggtta tccatctcaa gtagcctagc aatatttgca     60
acatcccaat ggccctgtcc ttttctttac tgatggccgt gctggtgctc agctacaaat    120
ccatctgttc tctgggctgt gatctgcctc agacccacag cctgggtaat aggagggcct    180
tgatactcct ggcacaaatg gaagaatct ctcatttctc ctgcctgaag acagacatg      240 atttcggatt ccccgaggag gagtttgatg ccaccagtt ccagaaggct caagccatct    300
ctgtcctcca tgagatgatc cagcagacct tcaatctctt cagcacagag gactcatctg    360
ctgcttggga acagagcctc ctagaaaaat tttccactga actttaccag caactgaatg    420
acctggaagc atgtgtgata caggaggttg ggtggaaga gactcccctg atgaatgagg    480
actccatcct ggctgtgagg aaatacttcc aaagaatcac tctttatcta acagagaaga    540
aatacagccc ttgtgcctgg gaggttgtca gagcagaaat catgagatcc ctctcgtttt    600
caacaaactt gcaaaaaga ttaaggagga aggattgaaa cctggttcaa catggaaatg     660
atcctgattg actaatacat tatctcacac tttcatgagt tcttccattt caaagactca    720
```

```
cttctataac caccacgagt tgaatcaaaa ttttcaaatg ttttcagcag tgtgaagaag    780
cttggtgtat acctgtgcag gcactagtcc tttacagatg acaatgctga tgtctctgtt    840
catctattta tttaaatatt tatttatttt taaaatttaa attatttttt atgtgatatc    900
atgagtacct ttacattgtg gtgaatgtaa caatatatgt tcttcatatt tagccaatat    960
attaatttcc tttttcatta aa                                             982

<210> SEQ ID NO 52
<211> LENGTH: 189
<212> TYPE: PRT
<213> ORGANISM: Homo sapiens

<400> SEQUENCE: 52

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 53
<211> LENGTH: 700
<212> TYPE: DNA
<213> ORGANISM: Homo sapiens

<400> SEQUENCE: 53
gcccaaggtt cagggtcact caatctcaac agcccagaag catctgcaac ctccccaatg     60
gccttgccct ttgttttact gatggccctg gtggtgctca actgcaagtc aatctgttct    120
ctgggctgtg atctgcctca gacccacagc ctgagtaaca ggaggacttt gatgataatg    180
gcacaaatgg gaagaatctc tcctttctcc tgcctgaagg acagacatga ctttggattt    240
cctcaggagg agtttgatgg caaccagttc cagaaggctc aagccatctc tgtcctccat    300
gagatgatcc agcagacctt caatctcttc agcacaaagg actcatctgc tacttgggat    360
gagacacttc tagacaaatt ctacactgaa ctttaccagc agctgaatga cctggaagcc    420
tgtatgatgc aggaggttgg agtggaagac actcctctga tgaatgtgga ctctatcctg    480
```

```
actgtgagaa aatactttca aagaatcacc ctctatctga cagagaagaa atacagccct    540
tgtgcatggg aggttgtcag agcagaaatc atgagatcct tctctttatc agcaaacttg    600
caagaaagat taaggaggaa ggaatgaaaa ctggttcaac atcgaaatga ttctcattga    660
ctagtacacc atttcacact tcttgagttc tgccgtttca                          700
```

<210> SEQ ID NO 54
<211> LENGTH: 189
<212> TYPE: PRT
<213> ORGANISM: Homo sapiens

<400> SEQUENCE: 54

```
Met Ala Leu Pro Phe Val Leu Leu Met Ala Leu Val Val Leu Asn Cys
1               5                   10                  15

Lys Ser Ile Cys Ser Leu Gly Cys Asp Leu Pro Gln Thr His Ser Leu
            20                  25                  30

Ser Asn Arg Arg Thr Leu Met Ile Met Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Asp Glu Thr Leu Leu Asp Lys Phe Tyr Thr Glu Leu
            100                 105                 110

Tyr Gln Gln Leu Asn Asp Leu Glu Ala Cys Met Met Gln Glu Val Gly
        115                 120                 125

Val Glu Asp Thr Pro Leu Met Asn Val Asp Ser Ile Leu Thr Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Ala Asn Leu Gln Glu Arg Leu Arg Arg Lys Glu
            180                 185
```

<210> SEQ ID NO 55
<211> LENGTH: 570
<212> TYPE: DNA
<213> ORGANISM: Homo sapiens

<400> SEQUENCE: 55

```
atggctttgc cttttgcttt actgatggcc ctggtggtgc tcagctgcaa gtcaagctgc     60
tctctggact gtgatctgcc tcagacccac agcctgggtc acaggaggac catgatgctc    120
ctggcacaaa tgaggagaat ctctcttttc tcctgtctga aggacagaca tgacttcaga    180
tttccccagg aggagtttga tggcaaccag ttccagaagg ctgaagccat ctctgtcctc    240
catgaggtga ttcagcagac cttcaacctc ttcagcacaa aggactcatc tgttgcttgg    300
gatgagaggc ttctagacaa actctatact gaactttacc agcagctgaa tgacctggaa    360
gcctgtgtga tgcaggaggt gtgggtggga gggactcccc tgatgaatga ggactccatc    420
ctggctgtga aaaatacttt ccaaagaatc actctctacc tgacagagaa aaagtacagc    480
ccttgtgcct gggaggttgt cagagcagaa atcatgagat ccttctcttc atcaagaaac    540
ttgcaagaaa ggttaaggag gaaggaataa                                     570
```

<210> SEQ ID NO 56
<211> LENGTH: 189
<212> TYPE: PRT
<213> ORGANISM: Homo sapiens

<400> SEQUENCE: 56

```
Met Ala Leu Pro Phe Ala Leu Leu Met Ala Leu Val Val Leu Ser Cys
1               5                   10                  15

Lys Ser Ser Cys Ser Leu Asp Cys Asp Leu Pro Gln Thr His Ser Leu
            20                  25                  30

Gly His Arg Arg Thr Met Met Leu Leu Ala Gln Met Arg Arg Ile Ser
        35                  40                  45

Leu Phe Ser Cys Leu Lys Asp Arg His Asp Phe Arg Phe Pro Gln Glu
    50                  55                  60

Glu Phe Asp Gly Asn Gln Phe Gln Lys Ala Glu Ala Ile Ser Val Leu
65                  70                  75                  80

His Glu Val Ile Gln Gln Thr Phe Asn Leu Phe Ser Thr Lys Asp Ser
                85                  90                  95

Ser Val Ala Trp Asp Glu Arg Leu Leu Asp Lys Leu Tyr Thr Glu Leu
            100                 105                 110

Tyr Gln Gln Leu Asn Asp Leu Glu Ala Cys Val Met Gln Glu Val Trp
        115                 120                 125

Val Gly Gly Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Ser Ser Arg Asn Leu Gln Glu Arg Leu Arg Arg Lys Glu
            180                 185
```

<210> SEQ ID NO 57
<211> LENGTH: 736
<212> TYPE: DNA
<213> ORGANISM: Homo sapiens

<400> SEQUENCE: 57

| | | |
|---|---|---|
| tacccacctc aggtagccta gtgatatttg caaaatccca atggcccggt ccttttcttt | 60 |
| actgatggtc gtgctggtac tcagctacaa atccatctgc tctctgggct gtgatctgcc | 120 |
| tcagacccac agcctgcgta ataggagggc cttgatactc ctggcacaaa tgggaagaat | 180 |
| ctctcctttc tcctgcttga aggacagaca tgaattcaga ttcccagagg aggagtttga | 240 |
| tggccaccag ttccagaaga ctcaagccat ctctgtcctc catgagatga tccagcagac | 300 |
| cttcaatctc ttcagcacag aggactcatc tgctgcttgg aacagagcc tcctagaaaa | 360 |
| attttccact gaactttacc agcaactgaa tgacctggaa gcatgtgtga tacaggaggt | 420 |
| tgggtggaa gagactcccc tgatgaatga ggacttcatc ctggctgtga ggaaatactt | 480 |
| ccaaagaatc actctttatc taatggagaa gaaatacagc ccttgtgcct gggaggttgt | 540 |
| cagagcagaa atcatgagat ccttctcttt ttcaacaaac ttgaaaaaag gattaaggag | 600 |
| gaaggattga aaactggttc atcatggaaa tgattctcat tgactaatgc atcatctcac | 660 |
| actttcatga gttcttccat ttcaaagact cacttctata accaccacaa gttaatcaaa | 720 |
| attccaaat gttttc | 736 |

<210> SEQ ID NO 58
<211> LENGTH: 189
<212> TYPE: PRT
<213> ORGANISM: Homo sapiens

<400> SEQUENCE: 58

Met Ala Arg Ser Phe Ser Leu Leu Met Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Phe Ile Leu Ala Val Arg
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Lys Lys Gly Leu Arg Arg Lys Asp
            180                 185

<210> SEQ ID NO 59
<211> LENGTH: 1039
<212> TYPE: DNA
<213> ORGANISM: Homo sapiens

<400> SEQUENCE: 59
accagctcag cagcatccac aacatctaca atggccttga cttttttattt actggtggcc      60 ctagtggtgc tcagctacaa gtcattcagc tctctgggct gtgatctgcc tcagactcac     120
agcctgggta acaggagggc cttgatactc ctggcacaaa tgcgaagaat ctctcctttc     180
tcctgcctga aggacagaca tgactttgaa ttcccccagg aggagtttga tgataaacag     240
ttccagaagg ctcaagccat ctctgtcctc catgagatga tccagcagac cttcaacctc     300
ttcagcacaa aggactcatc tgctgctttg gatgagaccc ttctagatga attctacatc     360
gaacttgacc agcagctgaa tgacctggag tcctgtgtga tgcaggaagt gggggtgata     420
gagtctcccc tgatgtacga ggactccatc ctggctgtga ggaaatactt ccaaagaatc     480
actctatatc tgacagagaa gaaatacagc tcttgtgcct gggaggttgt cagagcagaa     540
atcatgagat ccttctcttt atcaatcaac ttgcaaaaaa gattgaagag taaggaatga     600
gacctggtac aacacggaaa tgattcttat agactaatac agcagctcac acttcgacaa     660
gttgtgctct ttcaaagacc cttgtttctg ccaaaaccat gctatgaatt gaatcaaatg     720
tgtcaagtgt tttcaggagt gttaagcaac atcctgttca gctgtatggg cactagtccc     780
ttacagatga ccatgctgat ggatctattc atctatttat ttaaatcttt atttagttaa     840

```
ctatctatag ggcttaaatt agttttgttc atattatatt atgtgaactt ttacattgtg    900
aattgtgtaa caaaaacatg ttctttatat ttattatttt gccttgttta ttaaattttt    960
actatagaaa aattctttat ttattccttta aaattgaact ccaaccctga ttgtgcaaac   1020
tgattaaaga atggatggt                                                 1039
```

<210> SEQ ID NO 60
<211> LENGTH: 189
<212> TYPE: PRT
<213> ORGANISM: Homo sapiens

<400> SEQUENCE: 60

Met Ala Leu Thr Phe Tyr Leu Leu Val Ala Leu Val Val Leu Ser Tyr
1               5                   10                  15

Lys Ser Phe Ser Ser Leu Gly Cys Asp Leu Pro Gln Thr His Ser Leu
            20                  25                  30

Gly Asn Arg Arg Ala Leu Ile Leu Leu Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Asp Lys Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 61
<211> LENGTH: 963
<212> TYPE: DNA
<213> ORGANISM: Homo sapiens

<400> SEQUENCE: 61

```
caaggttatc catctcaagt agcctagcaa tatttgcaac atcccaatgg ccctgtcctt     60
ttctttactt atggccgtgc tggtgctcag ctacaaatcc atctgttctc tgggctgtga    120
tctgcctcag acccacagcc tcggtaatag gagggccttg atactcctgg acaaatggg    180 aagaatctct cctttctcct gcctgaagga cagacatgat ttccgaatcc cccaggagga    240
gtttgatggc aaccagttcc agaaggctca agccatctct gtcctccatg agatgatcca    300
gcagaccttc aatctcttca gcacagagga ctcatctgct gcttgggaac agagcctcct    360
agaaaaattt tccactgaac tttaccagca actgaatgac ctggaagcat gtgtgataca    420
ggaggttggg gtggaagaga ctccccctgat gaatgaggac tccatcctgg ctgtgaggaa    480
atacttccaa agaatcactc tttatctaat agagaggaaa tacagccctt gtgcctggga    540
```

-continued

```
ggttgtcaga gcagaaatca tgagatccct ctcgttttca acaaacttgc aaaaaagatt      600
aaggaggaag gattgaaaac tggttcaaca tggcaatgat cctgattgac taatacatta      660
tctcacactt tcatgagttc ttccatttca aagactcact tctataacca cgacgcgttg      720
aatcaaaatt ttcaaatgtt ttcagcagtg taaagaagtg tcgtgtatac ctgtgcaggc      780
actagtcctt tacagatgac cattctgatg tctctgttca tcttttgttt aaatatttat      840
ttaattattt ttaaaattta tgtaaatatca tgagtcgctt tacattgtgg ttaatgtaac      900
aatatatgtt cttcatattt agccaatata ttaatttcct ttttcattaa attttttacta     960 tac                                                                    963
```

<210> SEQ ID NO 62
<211> LENGTH: 189
<212> TYPE: PRT
<213> ORGANISM: Homo sapiens

<400> SEQUENCE: 62

```
Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Gly Gln Met Gly Arg Ile Ser
        35                  40                  45

Pro Phe Ser Cys Leu Lys Asp Arg His Asp Phe Arg Ile Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 63
<211> LENGTH: 705
<212> TYPE: DNA
<213> ORGANISM: Homo sapiens

<400> SEQUENCE: 63

```
agagaaccta gagcccaagg ttcagagtca cccatctcag caagcccaga agcatctgca      60
atatctatga tggcctcgcc ctttgcttta ctgatggccc tggtggtgct cagctgcaag     120
tcaagctgct ctctgggctg tgatctccct gagacccaca gcctggataa caggaggacc     180
ttgatgctcc tggcacaaat gagcagaatc tctccttcct cctgtctgat ggacagacat     240
gactttggat ttccccagga ggagtttgat ggcaaccagt tccagaaggc tcagccatc      300 tctgtcctcc atgagctgat ccagcagatc ttcaacctct ttaccacaaa agattcatct     360
```

```
gctgcttggg atgaggacct cctagacaaa ttctgcaccg aactctacca gcagctgaat      420
gacttggaag cctgtgtgat gcaggaggag agggtgggag aaactcccct gatgaatgcg      480
gactccatct tggctgtgaa gaaatacttc cgaagaatca ctctctatct gacagagaag      540
aaatacagcc cttgtgcctg ggaggttgtc agagcagaaa tcatgagatc cctctcttta      600
tcaacaaact tgcaagaaag attaaggagg aaggaataac acctggtcca acatgaaaca      660
attcttattg actcatatac caggtcacgc tttcatgaat tctgc                     705
```

<210> SEQ ID NO 64
<211> LENGTH: 190
<212> TYPE: PRT
<213> ORGANISM: Homo sapiens

<400> SEQUENCE: 64

```
Met Met Ala Ser Pro Phe Ala Leu Leu Met Ala Leu Val Val Leu Ser
1               5                   10                  15

Cys Lys Ser Ser Cys Ser Leu Gly Cys Asp Leu Pro Glu Thr His Ser
            20                  25                  30

Leu Asp Asn Arg Arg Thr Leu Met Leu Leu Ala Gln Met Ser Arg Ile
        35                  40                  45

Ser Pro Ser Ser Cys Leu Met Asp Arg His Asp Phe Gly Phe Pro Gln
    50                  55                  60

Glu Glu Phe Asp Gly Asn Gln Phe Gln Lys Ala Pro Ala Ile Ser Val
65                  70                  75                  80

Leu His Glu Leu Ile Gln Gln Ile Phe Asn Leu Phe Thr Thr Lys Asp
                85                  90                  95

Ser Ser Ala Ala Trp Asp Glu Asp Leu Leu Asp Lys Phe Cys Thr Glu
            100                 105                 110

Leu Tyr Gln Gln Leu Asn Asp Leu Glu Ala Cys Val Met Gln Glu Glu
        115                 120                 125

Arg Val Gly Glu Thr Pro Leu Met Asn Ala Asp Ser Ile Leu Ala Val
    130                 135                 140

Lys Lys Tyr Phe Arg Arg Ile Thr Leu Tyr Leu Thr Glu Lys Lys Tyr
145                 150                 155                 160

Ser Pro Cys Ala Trp Glu Val Val Arg Ala Glu Ile Met Arg Ser Leu
                165                 170                 175

Ser Leu Ser Thr Asn Leu Gln Glu Arg Leu Arg Arg Lys Glu
            180                 185                 190
```

<210> SEQ ID NO 65
<211> LENGTH: 778
<212> TYPE: DNA
<213> ORGANISM: Homo sapiens

<400> SEQUENCE: 65

```
gttacccctc atcaaccagc ccagcagcat cttcgggatt cccaatggca ttgccctttg       60
ctttaatgat ggccctggtg gtgctcagct gcaagtcaag ctgctctctg ggctgtaatc      120
tgtctcaaac ccacagcctg aataacagga ggactttgat gctcatggca caaatgagga      180
gaatctctcc tttctcctgc ctgaaggaca gacatgagtt tgaatttccc caggaggaat      240
ttgatggcaa ccagttccag aaagctcaag ccatctctgt cctccatgag atgatgcagc      300
agaccttcaa tctcttcagc acaaagaact catctgctgc ttgggatgag accctcctag      360
aaaaattcta cattgaactt ttccagcaaa tgaatgacct ggaagcctgt gtgatacagg      420
```

```
aggttggggt ggaagagact ccctgatga atgaggactc catcctggct gtgaagaaat    480
acttccaaag aatcactctt tatctgatgg agaagaaata cagcccttgt gcctgggagg    540
ttgtcagagc agaaatcatg agatccctct cttttcaac aaacttgcaa aaagattaa     600 ggaggaagga ttgaaaactg gttcatcatg gaaatgattc tcattgacta atacatcatc    660
tcacactttc atgagttctt ccatttcaaa gactcacttc tcctataacc accacaagtt    720
gaatcaaaat tttcaaatgt tttcaggagt gtaaagaagc atcatgtata cctgtgca      778
```

<210> SEQ ID NO 66
<211> LENGTH: 189
<212> TYPE: PRT
<213> ORGANISM: Homo sapiens

<400> SEQUENCE: 66

```
Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

<210> SEQ ID NO 67
<211> LENGTH: 939
<212> TYPE: DNA
<213> ORGANISM: Homo sapiens

<400> SEQUENCE: 67

```
atcccaatgg ccctgtcctt ttctttactg atggccgtgc tggtgctcag ctacaaatcc     60
atctgttctc tgggctgtga tctgcctcag actcacagcc tgggtaatag gagggccttg    120
atactcctgg cacaaatggg aagaatctct catttctcct gcctgaagga cagatatgat    180
ttcggattcc cccaggaggt gtttgatggc aaccagttcc agaaggctca agccatctct    240
gccttccatg agatgatcca gcagaccttc aatctcttca gcacaaagga ttcatctgct    300
gcttgggatg agaccctcct agacaaattc tacattgaac ttttccagca actgaatgac    360
ctagaagcct gtgtgacaca ggaggttggg gtggaagaga ttgccctgat gaatgaggac    420
tccatcctgg ctgtgaggaa atactttcaa agaatcactc tttatctgat ggggaagaaa    480
```

```
tacagccctt gtgcctggga ggttgtcaga gcagaaatca tgagatcctt ctcttttca      540 acaaacttgc aaaaggatt aagaaggaag gattgaaaac tcattcaaca tggaaatgat      600
cctcattgat taatacatca tctcacactt tcatgagttc ttccatttca aagactcact      660
tctataacca ccacaagttg aatcaaaatt tcaaaatgtt ttcaggagtg taaagaagca      720
tcgtgtttac ctgtgcaggc actagtcctt tacagatgac catgctgatg tctctattca      780
tctatttatt taaatatta tttatttaac tatttttaag gtttaaatca tgttttatgt      840
aatatcatgt gtacctttac attttgctta atgtaacaat atatgttctt catatttagt      900
taatatatta acttccttt cattaaattt ttactatac                             939
```

```
<210> SEQ ID NO 68
<211> LENGTH: 189
<212> TYPE: PRT
<213> ORGANISM: Homo sapiens

<400> SEQUENCE: 68

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg Tyr Asp Phe Gly Phe Pro Gln Glu
    50                  55                  60

Val Phe Asp Gly Asn Gln Phe Gln Lys Ala Gln Ala Ile Ser Ala Phe
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Thr Gln Glu Val Gly
        115                 120                 125

Val Glu Glu Ile Ala Leu Met Asn Glu Asp Ser Ile Leu Ala Val Arg
    130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
            180                 185
```

```
<210> SEQ ID NO 69
<211> LENGTH: 980
<212> TYPE: DNA
<213> ORGANISM: Homo sapiens

<400> SEQUENCE: 69
gttcaaggtt acccatctca agtagcctag caacatttgc aacatcccaa tggccctgtc      60
cttttcttta ctgatggccg tgctggtgct cagctacaaa tccatctgtt ctctaggctg     120
tgatctgcct cagacccaca gcctgggtaa taggagggcc ttgatactcc tggcacaaat     180
gggaagaatc tctcctttct cctgcctgaa ggacagacat gacttggac ttccccagga     240 ggagtttgat ggcaaccagt tccagaagac tcaagccatc tctgtcctcc atgagatgat     300
```

```
ccagcagacc ttcaatctct tcagcacaga ggactcatct gctgcttggg aacagagcct      360
cctagaaaaa ttttccactg aactttacca gcaactgaat aacctggaag catgtgtgat      420
acaggaggtt gggatggaag agactcccct gatgaatgag gactccatcc tggctgtgag      480
gaaatacttc caaagaatca ctctttatct aacagagaag aaatacagcc cttgtgcctg      540
ggaggttgtc agagcagaaa tcatgagatc tctctctttt tcaacaaact tgcaaaaaat      600
attaaggagg aaggattgaa aactggttca acatggcaat gatcctgatt gactaataca      660
ttatctcaca ctttcatgag ttcctccatt tcaaagactc acttctataa ccaccacgag      720
ttgaatcaaa attttcaaat gttttcagca gtgtaaagaa gcgtcgtgta tacctgtgca      780
ggcactagta ctttacagat gaccatgctg atgtctctgt tcatctattt atttaaatat      840
ttatttaatt attttttaaga tttaaattat tttttttatgt aatatcatgt gtacctttac      900
attgtggtga atgtaacaat atatgttctt catatttagc caatatatta atttcctttt      960
tcattaaatt tttactatac                                                  980

<210> SEQ ID NO 70
<211> LENGTH: 189
<212> TYPE: PRT
<213> ORGANISM: Homo sapiens

<400> SEQUENCE: 70

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Leu Pro Gln Glu
    50                  55                  60

Glu Phe Asp Gly Asn Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asn Leu Glu Ala Cys Val Ile Gln Glu Val Gly
        115                 120                 125

Met Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
            180                 185

<210> SEQ ID NO 71
<211> LENGTH: 1024
<212> TYPE: DNA
<213> ORGANISM: Homo sapiens

<400> SEQUENCE: 71
ttcaaggtta cccatctcaa gtagcctagc aatattggca acatcccaat ggccctgtcc       60
ttttctttac tgatggccgt gctggtgctc agctacaaat ccatctgttc tctgggctgt      120
```

```
gatctgcctc agacccacag cctgggtaat aggagggcct tgatactcct ggcacaaatg      180
ggaagaatct ctcctttctc ctgcctgaag gacagacatg actttggatt cccccaggag      240
gagtttgatg caaccagtt ccagaaggct caagccatct ctgtcctcca tgagatgatc       300
cagcagacct tcaatctctt cagcacaaag gactcatctg ctacttggga acagagcctc      360
ctagaaaaat tttccactga acttaaccag cagctgaatg acctggaagc ctgcgtgata      420
caggaggttg gggtggaaga gactcccctg atgaatgtgg actccatcct ggctgtgaag      480
aaatacttcc aaagaatcac tctttatctg acagagaaga atacagccc ttgtgcctgg      540 gaggttgtca gagcagaaat catgagatcc ttctctttat caaaaatttt tcaagaaaga      600
ttaaggagga aggaatgaaa cctgtttcaa catggaaatg atctgtattg actaatacac      660
cagtccacac ttctatgact tctgccattt caaagactca tttctcctat aaccaccgca      720
tgagttgaat caaaattttc agatcttttc aggagtgtaa ggaaacatca tgtttacctg      780
tgcaggcact agtcctttac agatgaccat gctgatagat ctaattatct atctattgaa      840
atatttattt atttattaga tttaaattat ttttgtccat gtaatattat gtgtacttt       900 acattgtgtt atatcaaaat atgttattta tatttagtca atatattatt ttctttttat      960
taatttttac tattaaaact tcttatatta tttgtttatt ctttaataaa gaaataccaa     1020
gccc                                                                  1024

<210> SEQ ID NO 72
<211> LENGTH: 189
<212> TYPE: PRT
<213> ORGANISM: Homo sapiens

<400> SEQUENCE: 72

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
            100                 105                 110

Asn Gln Gln Leu Asn Asp Leu Glu Ala Cys Val Ile Gln Glu Val Gly
        115                 120                 125

Val Glu Glu Thr Pro Leu Met Asn Val Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
            180                 185

<210> SEQ ID NO 73
```

```
<211> LENGTH: 840
<212> TYPE: DNA
<213> ORGANISM: Homo sapiens

<400> SEQUENCE: 73
acattctaac tgcaaccttt cgaagccttt gctctggcac aacaggtagt aggcgacact      60
gttcgtgttg tcaacatgac caacaagtgt ctcctccaaa ttgctctcct gttgtgcttc     120
tccactacag ctcttccat gagctacaac ttgcttggat tcctacaaag aagcagcaat     180
tttcagtgtc agaagctcct gtggcaattg aatgggaggc ttgaatactg cctcaaggac     240
aggatgaact ttgacatccc tgaggagatt aagcagctgc agcagttcca gaaggaggac     300
gccgcattga ccatctatga gatgctccag aacatctttg ctattttcag acaagattca     360
tctagcactg gctggaatga gactattgtt gagaacctcc tggctaatgt ctatcatcag     420
ataaaccatc tgaagacagt cctggaagaa aaactggaga agaagatttt caccagggga     480
aaactcatga gcagtctgca cctgaaaaga tattatggga ggattctgca ttacctgaag     540
gccaaggagt acagtcactg tgcctggacc atagtcagat ggaaatcct aaggaacttt     600 tacttcatta acagacttac aggttacctc cgaaactgaa gatctcctag cctgtgcctc     660
tgggactgga caattgcttc aagcattctt caaccagcag atgctgttta agtgactgat     720
ggctaatgta ctgcatatga aaggacacta aagattttg aaatttttat taaattatga     780 gttatttta tttattaaa ttttattttg aaaataaat tattttggt gcaaaagtca     840

<210> SEQ ID NO 74
<211> LENGTH: 187
<212> TYPE: PRT
<213> ORGANISM: Homo sapiens

<400> SEQUENCE: 74

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185
```

<210> SEQ ID NO 75
<211> LENGTH: 1514
<212> TYPE: DNA
<213> ORGANISM: Homo sapiens

<400> SEQUENCE: 75

```
gatctggtaa acctgaagca aatatagaaa cctatagggc ctgacttcct acataaagta    60
aggagggtaa aaatggaggc tagaataagg gttaaaattt tgcttctaga acagagaaaa   120
tgatttttt  catatatata tgaatatata ttatatatac acatatatac atatattcac   180
tatagtgtgt atacataaat ataatatata tatattgtta gtgtagtgtg tgtctgatta   240
tttacatgca tatagtatat acacttatga ctttagtacc cagacgtttt tcatttgatt   300
aagcattcat ttgtattgac acagctgaag tttactggag tttagctgaa gtctaatgca   360
aaattaatag attgttgtca tcctcttaag gtcataggga gaacacacaa atgaaaacag   420
taaaagaaac tgaaagtaca gagaaatgtt cagaaaatga aaaccatgtg tttcctatta   480
aaagccatgc atacaagcaa tgtcttcaga aaacctaggg tccaaggtta agccatatcc   540
cagctcagta aagccaggag catcctcatt tcccaatggc cctcctgttc cctctactgg   600
cagcccagt  gatgaccagc tatagccctg ttggatctct gggctgtgat ctgcctcaga   660
accatggcct acttagcagg aacaccttgg tgcttctgca ccaaatgagg agaatctccc   720
ctttcttgtg tctcaaggac agaagagact tcaggttccc ccaggagatg gtaaagggga   780
gccagttgca gaaggcccat gtcatgtctg tcctccatga gatgctgcag cagatcttca   840
gcctcttcca cacagagcgc tcctctgctg cctggaacat gaccctccta gaccaactcc   900
acactggact tcatcagcaa ctgcaacacc tggagacctg cttgctgcag gtagtgggag   960
aaggagaatc tgctggggca attagcagcc ctgcactgac cttgaggagg tacttccagg  1020
gaatccgtgt ctacctgaaa gagaagaaat acagcgactg tgcctgggaa gttgtcagaa  1080
tggaaatcat gaaatccttg ttcttatcaa caaacatgca agaaagactg agaagtaaag  1140
atagagacct gggctcatct tgaaatgatt ctcattgatt aatttgccat ataacacttg  1200
cacatgtgac tctggtcaat tcaaaagact cttatttcgg cttttaatcac agaattgact  1260
gaattagttc tgcaaatact ttgtcggtat attaagccag tatatgttaa aaagacttag  1320
gttcaggggc atcagtccct aagatgttat ttattttac  tcatttattt attcttacat  1380
tttatcatat ttatactatt tatattctta tataacaaat gtttgccttt acattgtatt  1440
aagataacaa aacatgttca gctttccatt tggttaaata ttgtattttg ttatttatta  1500
aattatttc  aaac                                                    1514
```

<210> SEQ ID NO 76
<211> LENGTH: 195
<212> TYPE: PRT
<213> ORGANISM: Homo sapiens

<400> SEQUENCE: 76

```
Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60
```

```
Met Val Lys Gly Ser Gln Leu Gln Lys Ala His Val Met Ser Val Leu
 65                  70                  75                  80

His Glu Met Leu Gln Gln Ile Phe Ser Leu Phe His Thr Glu Arg Ser
                 85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
                180                 185                 190

Gly Ser Ser
        195

<210> SEQ ID NO 77
<211> LENGTH: 1240
<212> TYPE: DNA
<213> ORGANISM: Homo sapiens

<400> SEQUENCE: 77
cacattgttc tgatcatctg aagatcagct attagaagag aaagatcagt taagtccttt    60
ggacctgatc agcttgatac aagaactact gatttcaact tctttggctt aattctctcg   120
gaaacgatga atatacaag ttatatcttg gcttttcagc tctgcatcgt tttgggttct    180
cttggctgtt actgccagga cccatatgta aaagaagcag aaaaccttaa gaaatatttt   240
aatgcaggtc attcagatgt agcggataat ggaactcttt tcttaggcat tttgaagaat   300
tggaaagagg agagtgacag aaaaataatg cagagccaaa ttgtctcctt ttacttcaaa   360 cttttaaaa actttaaaga tgaccagagc atccaaaaga gtgtggagac catcaaggaa    420
gacatgaatg tcaagttttt caatagcaac aaaaagaaac gagatgactt cgaaaagctg   480
actaattatt cggtaactga cttgaatgtc aacgcaaag caatacatga actcatccaa    540
gtgatggctg aactgtcgcc agcagctaaa cagggaagc gaaaaggag tcagatgctg    600 tttcgaggtc gaagagcatc ccagtaatgg ttgtcctgcc tgcaatattt gaattttaaa   660
tctaaatcta tttattaata tttaacatta tttatgggg aatatatttt tagactcat    720 caatcaaata gtatttata atagcaactt ttgtgtaatg aaaatgaata tctattaata   780
tatgtattat ttataattcc tatatcctgt gactgtctca cttaatcctt tgttttctga   840
ctaattaggc aaggctatgt gattacaagg ctttatctca ggggccaact aggcagccaa   900
cctaagcaag atcccatggg ttgtgtgttt atttcacttg atgatacaat gaacacttat   960
aagtgaagtg atactatcca gttactgccg gtttgaaaat atgcctgcaa tctgagccag  1020
tgctttaatg gcatgtcaga cagaacttga atgtgtcagg tgaccctgat gaaaacatag  1080
catctcagga gatttcatgc ctggtgcttc caaatattgt tgacaactgt gactgtaccc  1140
aaatggaaag taactcattt gttaaaatta tcaatatcta atatatatga ataaagtgta  1200
agttcacaac aaaaaaaaaa aaaaaaaaa aaaaaaaaa                          1240

<210> SEQ ID NO 78
```

```
<211> LENGTH: 166
<212> TYPE: PRT
<213> ORGANISM: Homo sapiens

<400> SEQUENCE: 78

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 79
<211> LENGTH: 12979
<212> TYPE: DNA
<213> ORGANISM: Homo sapiens
<220> FEATURE:
<221> NAME/KEY: misc_feature
<222> LOCATION: (5427)..(5427)
<223> OTHER INFORMATION: n is a, c, g, or t
<220> FEATURE:
<221> NAME/KEY: misc_feature
<222> LOCATION: (5460)..(5461)
<223> OTHER INFORMATION: n is a, c, g, or t
<220> FEATURE:
<221> NAME/KEY: misc_feature
<222> LOCATION: (12190)..(12190)
<223> OTHER INFORMATION: n is a, c, g, or t
<220> FEATURE:
<221> NAME/KEY: misc_feature
<222> LOCATION: (12192)..(12192)
<223> OTHER INFORMATION: n is a, c, g, or t
<220> FEATURE:
<221> NAME/KEY: misc_feature
<222> LOCATION: (12237)..(12240)
<223> OTHER INFORMATION: n is a, c, g, or t

<400> SEQUENCE: 79
gaattccttg agcccaggaa gctgcagtga gccacgtttg taccattgca ctccagcttg    60
ggagatagag tgagaccctg tctcaaaaaa aaaaaaaaa aaaaaaagaa aaatttattt   120
ggcttacaga tgtctgggct gtacaagaag tgtggcagca gcatctgctt ccagtgaagg   180
cattaggctc cttctactca gcagaagaca acatgcagct ggcatgtgca gagaccacat   240
ggtaagagaa gaagccaatg ggggaatgca atgggggac ggggagacac acactttttt    300
tttttttttt gagatggagt ctcgctctgt cacccaggct ggagtgcagt ggcgcgatct   360
```

| | |
|---|---|
| cggctcactg caagctctgc ctcccgggtt cacgccattc tcctgcctca gccgcccgag | 420 |
| tagctgggac tacaggtgcc caccaccacg ccccgctgat tttttgtatt tttagtagag | 480 |
| atggggtttc accatgttag ccaggatggt ctcgatctcc tgacctcgtg atctgcctgc | 540 |
| cttggcttcc caaagtgctg ggattacagg catgagccac catgcctgtc cctttttttt | 600 |
| ttttttttt tgagacaggg gctgtcaccc aggctggagt gcactggcgt ggtcatggct | 660 |
| cattgcacct ttcacctcag gctcaagaga ccctcctacc tcagcctcct cagtagctgg | 720 |
| gactaaggaa gtacaccacc atgcccagct aattattttt tttaagatgc aatctcactc | 780 |
| tgttgcccag gctgcactgc agtggtacaa tctcagctca ctgcaacctc cgcctcctgg | 840 |
| gttcaagcga ttctcttgct tcagcctcct gagtagctgg gattacagat gcctgccacc | 900 |
| aggcccggct aattttttgta ttttttagtag atacagggtt tcgccatgtt ggccaggctg | 960 |
| gtctcgaact cctaacctaa ggtgatccgc ccatctcggc ctcccaaagt gctgggatta | 1020 |
| caggcatgag ccaccgtgcc tggcccatgc ccagctaagt taaaaaaatt tttggctggg | 1080 |
| caaggtgatt catacctgta attccaacaa tttgggaagc taaggcaggc agatcccatt | 1140 |
| tgagctcagg aattggagac catcttggac aatatggcga aatcctgtct ctacaaaata | 1200 |
| tacaaaaatt agctgggtgt ggtggcgctg tgcctgtagt cccagctact ccagaggctg | 1260 |
| aggtgggagg atggcttgag cccgggaggc agaggttgca gtgagccaaa atggtgacat | 1320 |
| tgcactccag cctgggcaac agagccgac cctgtctcaa aaaaaaaaa aaaaagctct | 1380 |
| aaaaatagat agtggtgata gttagttaca caacattgtg aatgtactta aatgtcactg | 1440 |
| aattatacac ttaaatgttt aaatggtaaa ttctatctta tgtatatttt accacaattt | 1500 |
| aaaaatttta tctatttcta ttttaatgag agttttaaaa agcaggaatg gatattgaat | 1560 |
| ttccttaaat actctttgga gtctattaaa gatagcattt tacttcaaaa tccagccctg | 1620 |
| gtttctgtac ctagtacttc tgtcacacca gtaaatgtta ttgaatgaaa acaaacaaaa | 1680 |
| gaccataaag acatacctct tcacgttcac taggattggt gtcatttttt taaaaaaagg | 1740 |
| aaagaaaaat aaccagtatt ggcaacagtg tggatatata gaaattttg tatattgctg | 1800 |
| gtaggaatat aaaatagggga aaacggtttg gtggttcctc aaaaagttca acataaaccc | 1860 |
| aggcgcggtg gctcatgcct gtaatcctag cactttggga ggctgaggtg ggagaactgt | 1920 |
| ttgatcccag gagtttgaga ccagcctagg caatatggtg agacctcatc tctacaaaaa | 1980 |
| attagctagg catggtggcg catgcctgta gtcccagcta cctgggaggc taagacagaa | 2040 |
| agatcacttg agcctggaag ggagtttgag gctgcagtga gcccagattg cgccactgca | 2100 |
| ctccagcctg ggtgacagag tgatatcctg tctcaaaata aataaataaa taataaacaa | 2160 |
| acacagaatt accatatgac ccagcaactc tactcctgtg tatatgccca aaaaagctga | 2220 |
| aagcccaggc actgtggctt acacctgtaa tcccagcact ttaggaggcc gaggcacttg | 2280 |
| accccaggat tttgagacca gcctgggcaa catagtactt gttcaagaat caggctgggc | 2340 |
| atggtggctc acacctgtaa tcccagcact ttgggagggc aaggtgggag gatcacttga | 2400 |
| ggccaggcat tcgagaccag cctgggcaag atagcaatac ccacccccaa tctctacaaa | 2460 |
| agcaagtaat taattaggaa attagccaaa gccaggtgcg gtggctcacg cctgtagtcc | 2520 |
| cagcactttg ggaggctgag gtgggcagat tgcttgagtc cagagattcg agaccagcct | 2580 |
| aggcaacata tcaaaacccc gtctctacta aaagtaaaaa aagaaaaatt gcactttggg | 2640 |
| aggccaaggc ggggggatca cctgatgtca ggagttcaag accagcctgg ccaacatggt | 2700 |
| gaaacccat ctctacaaaa atacaaaagt tagccgggca tgatggcagt gtctgtaatc | 2760 |

```
ccagctactc aggaggctgg gtcggaagaa tcatttgaat ccaggaggcg gaggttgcag    2820
tgaaccaaga ttgtgccatt gcattccagc ctgggtgaca gagcaagcct ccgtctcaaa    2880
aaaaaaaaaa aaagaaaaa ttagccagat gtggtggtgc atgcctgtgg tcccagctac    2940
tcaggaggct gtggtgggag gattgcttga gcccaagaca ctgaggctgc agtgagccat    3000
gatcacacca ctgcactcca gcctaggcaa ccagagtgag accctgtctc aaaaacaaac    3060
aaacaaacaa aaaccacttt aacagggtat ggtggtgcac acctctagtc ccagctactt    3120
gggaggttga ggcagccgga tcacttgacc ccaggagatc gaggctgcag tccagcctgg    3180
gcaaccgagt gagactgtct caaaagaaa aaaaaaaaa aaaggacata gcagcactat     3240
tcacaaatcc aaaagttaga ataactcag atgtccatca acagatgaat ggataaacga     3300
attgtggtat atacatataa tggactatta ttcagccatt aaaaggaatg aaatattgat    3360
acaggctata aactctatga acattgaaaa cattctaagt gaaggaaat agacataaga     3420 ggtcacattt tgcaattctt ttttttttt tttttttttt tgagactgag tctcactctg    3480
ttgcccaggc tggagcgcag tggctcgatc tcagctcact gcaacctcca tctcccgaat    3540
tcaagcaatt cttctgcctc agcctcccga gtagctggga ttacatgtag gcatgcacca    3600
ccatgcctgg ctaattttttg tacttttagt agagatgggg tttcaccatg ttggtcaggc    3660
tggtcttgaa ctccagacct caggtggtcc acccgcctttg gcctcccaaa gtgctaggat    3720
tacaggtgtg agccaccatg cccggccaca tgtatggtaa ttattgaatg tgtttggtat    3780
gttcgttgtg ggtgatgaaa tattttggaa ctagatagac gtgatggttg aacaacactg    3840
tggatgcact aaatgccact gaattgtaca ctttaaaatt gttaacttta tgttacatga    3900
atttcaccta aattaacaac aacaacaaaa aagaacttaa gacagcactt ggtttggcta    3960
ttacgtagtt tcgtgacaaa cagtggtcca tctcccagag aactggcccc aggttcctaa    4020
gaaggcaaaa ggagacacag gacctctctg cactattttt tttgcaactt cttatgagtc    4080
tataattatt tcaaaataaa agtctaaaag gaaaataaga acatgtgtga atgtggctgc    4140
cccatgcctc ccaccctcag gtctgacact cagagactga tcacctcttg agagtcctgg    4200
aactcatccc aggttttaga ccctgaatgg cctgtctggg gctggcgtct ggaggcagga    4260
tcaggagcca gctcagagca tagtttaact ttcacttttc ttttctccag aggagccagg    4320
aagagagctg tgaccagcag cgtcccttat tcgcttggcc ttggttcctg tttgcactgg    4380
ctacagcagg gcactggccc ctactgtcac cgccacctac acaaagaccc tatctctgag    4440
cgctgcagcc tactgttcag ccccaggttt gaggatggat gccctggacg cttcgaagct    4500
actggatgag gagctgtatt caagacagct gtgaggcccg aggtggggg tggagagtgg     4560 gatggtcttc agaccttgat ctacaactgc ttgccttctg cttcccatcc acaggtatgt    4620
gctgggctca cctgccatgc agaggattca gggagccagg gtcctggtgt caggcctgca    4680
gggcctgggg gccgaggtgg ccaagaactt ggttctgatg ggtgtgggca gcctcactct    4740
gcatgatccc cacccccacct gctggtccga cctggctgcc caggtaagtg tcctgggct    4800 atgggctgcc agaccaagtg gggcacggcc caagaggagt gtctttgctc aggctgcact    4860
ggctctctcc ctagtttctc ctctcagagc aggacttgga aaggagcaga gccgaggcct    4920
ctcaagagct cttggctcag ctcaacagag ctgtccaggt cgtcgtgcac acgggtgaca    4980
tcactgagga cctgctgttg gacttccagg tcagctcagg cctgcagccc tcaagagcag    5040
gaagggctgg gcaatggttt tggccctgct gatcactgtg tccacccagg tggtggtgct    5100
```

```
gactgctgca aagctggagg agcagctgaa ggtgggcacc ttgtgtcata agcatggagt    5160
ttgctttctg gcggctgaca cccgggggcct cgtggggtga gtaagactgc ctgcccagcc   5220
taccatatta cagccagcaa ctggcctcat gctgtcctca gctccaggct tgctccagtg    5280
cccctccaac cagcctcagg tctatcccag catgcctttc tgattctggt ccccagtcct    5340
gccctctggt tcctccaacc tagcctccag acctgctcca gtaaccctct caaattctag    5400
ttcccaagcc tctccttgca ttccttnccc aattctggcc ctctggccct gccctagtan    5460
nccctatcct taagtacaat ctgtaagcca cctcagtgac ccctaccacc ccatctcagg    5520
cagttgttct gtgactttgg tgaggacttc actgtgcagg accccacaga ggcagaaccc    5580
ctgacagctg ccatccagca catctcccag gtgggtgctg agctgtaggc attcacccgc    5640
tgaccaagga gaggctgcca gggcctgtgg aaggcaggtc caggcaaccc tgagccaagc    5700
ctcctcctac ccagggctcc cctggcattc tcactctgag gaaagggggcc aatacccact   5760
acttccgtga tggacttgtg tgactttct cgggaattga gggaatggtt gagctcaacg     5820
actgtgatcc ccggtctatc cacgtgcggg gtaagccaat cccattccaa ttccaggtgc    5880
agggcccaag cctccactgg aagtgagcac agcctggccc ttgggatggg ttttctccc    5940
tccaccttct acaaggtgca gcaaggtttg gacacagat gcaagatagg atggggtgtg     6000
ggaactactc aggctcaagg atcattactg actagactgg aactccctca gaggatgggt    6060
ccctggagat tggagacaca acaactttct ctcggtactt gcgtggtggg gctatcactg    6120
aagtcaagag acccaagact gtgagacatg tgagtgcaag tccatctgag gtaggggagc    6180
ttggtcgcct tgaggggccc atagcattct ggactagacc ctgagccagg tgcccttgca    6240
gaagtccctg gacacagccc tgctccagcc ccatgtggtg gcccagagct cccaggaagt    6300
tcaccatgcc cactgcctgc atcaggcctt ctgtgcactg cacaagttcc agcacctcca    6360
tggccggcca ccccagccct gggatcctgt gagtagtcct gttgctccca ccccagcct    6420
ctgtcattta ttggggtccc acctgccaga ggcaacaatg accattcaca aatccaagtc    6480
tgatctccca acactgcagc ctttagagta gagactggtt ccatggaagt gccaggcaca    6540
catcctgggg actcctgcta caccccgacc cctcagatct gtgctggaag ctgcactcag    6600
attagtgaag cctcctggac tgctgtctgg tactgggcat cctctggtgg tgctgtgcag    6660
gctggcagca gggccaggcc ttcccaccca ggcttctgct tcctcttctg tggaacaggg    6720
tggatggagg gtggctggaa ggatttgagt caggagtaga gctcaggctg gggctactat    6780
gcccacagag tcctaccaac aggttgatgc agagactgtg gtgggcctgg cccgggacct    6840
ggaaccactg aagcggacag aggaagagcc actggaagag ccactggatg aggccctagt    6900
gcggacagtc gccctaagca gtgcaaggtg tcttgagcct atggtggcat gctgggtcag    6960
tagctgccca ggaagtgctg aaggtgggca gaggcatagg tgtgggggt actgggaaga    7020
tgtggagatc agtgtgtgtg tcagagggca cccagcgcta gagagcagcc ctggagcctt    7080
caccaacctg ggtgaagcct ccagccagga tctgaggggg gtcaggaggt ggcaggagtg    7140
cccagcctga agtgctgccc ctaggcaatc tccagaagtt catgcctctg gaccagtggc    7200
tttactttga tgcctcgat tgtcttccgg aagatgggga gctccttccc agtcctgagg      7260
actgtgccct gagaggcagc cgctatgatg ggcaaattgc agtgtttggg gctggttttc    7320
aggagaaact gagacgccag cactacctcc tggtgagctg tggggtgaga ctgggggtgc    7380
ctttgggaga gccagcccag cccctctggc taaggctgtt cctgccaaca ggtgggcgct    7440
ggtgccattg gttgtgagct gctcaaagtc tttgccctag tgggactggg ggccgggaac    7500
```

```
agcgggggct tgactgttgt tgacatggac cacatagagc gctccaatct cagccgtcag    7560
ttcctcttca ggtcccagga cgttggtgtg agtgctgacc cctctccaca ctcctgcatc    7620
ccagaccgtc ctcccataca gcttcccacc caacatcttc ctgccttctt cccagagacc    7680
caaggcagag gtggctgcag cagctgcccg gggcctgaac ccagacttac aggtgatccc    7740
gctcacctac ccactggatc ccaccacaga gcacatctat ggggataact ttttctcccg    7800
tgtggatggt gtggctgctg ccctggacag tttccaggcc cgtgagtgct tgacttcgga    7860
ggtcagtccc ttgcccacag ctgtgccagt cccacttctg acccactgct cccctgccag    7920
ggcgctatgt ggctgctcgt tgcacccact atctgaagcc actgctggag gcaggcacat    7980
cgggcacctg ggcagtgct acagtattca tgccacatgt gactgaggcc tacagagccc    8040
ctgcctcagc tgcagcttct gaggatgccc cctaccctgt ctgtaccgtg cggtacttcc    8100
ctagcacagc cgagcacacc ctgcaggtag gaagcaccct ggagactccc accccaccca    8160
gctcagccct cagctgcaga cctgttctcc acctgatacc tcattcttcc tccctcctcc    8220
acagtgggcc cggcatgagt ttgaagaact cttccgactg tctgcagaga ccatcaacca    8280
ccaccaacag taaggccacc aacagaggca gatgggagtc cagggctcca agcatgagtc    8340
tgcaggactc agtctcacac ttcctcctct ctctgcaggg cacacacctc cctggcagac    8400
atggatgagc cacagacact caccttactg aagccagtgc ttggggtcct gagagtgcgt    8460
ccacagaact ggcaagactg tgtggcgtgg gctcttggcc actggaaact ctgctttcat    8520
tatggcatca aacagctgct gaggcacttc ccacctaata aagtgtgtgg ctaggggttg    8580
ggacgctggg ggctcagggg gaccagactg agcccagcag cttctactta cctacctagg    8640
tgcttgagga tggaactccc ttctggtcag gtcccaaaca gtgtcccag cccttggagt    8700 ttgacaccaa ccaagtgagt gggattctgt agggagctcc aagatagaga tgtggccct    8760 cagagcagag gtaggcattt ctgcattctg cagagatgca cagatgccca gagagagcca    8820
tgcttgtgca tatatgggtg tctacatgtg aggcaaaggc aggcactcaa acagatccac    8880
aaatggacag tgaccccacc catgcaccat gcctctctgt tctgctctct gctcttggtc    8940
tggctgcagg acacacacct cctctacgta ctggcagctg ccaacctgta tgcccagatg    9000
catgggctgc ctggctcaca ggactggact gcactcaggg agctgctgaa gctgctgcca    9060
cagcctgacc cccaacagat ggcccccatc tttgctagta atctagagct ggcttcggct    9120
tctgctgagt ttggtgaggc tcctggccct ggcccctcat gctgtctttc aaaggcctga    9180
acctgtcctg tcctcagcct gtgctgcaga aggaagatag ggcctagggg atctacagcc    9240
aatttgctac ctctcaggcc tcctaacctc actcctccat agtttcaggc ttatcctctg    9300
gtccctcagt aggtcttctc cctgctgcct accccacatc ccagttcttg tggcagattc    9360
ttggcaaaat aaataagtaa ataaataaag tccattggtt cctggggagt gtctagctat    9420
ggcctgcagg tgaggacagg gtcacagagg tcatgagcac acatgggtga agactggggc    9480
ttctagaggg gagattgtag cattaattaa gggggcttct tgatttgatc agggaatagt    9540
aagtgacagg cttggcaaag accaagaata ggcacagggc tccaagaaga gtgcaggaga    9600
caggggctaa ggactgcctc aacatcccct tccctgacag gccctgagca gcagaaggaa    9660
ctgaacaaag ccctggaagt ctggagtgtg ggccctcccc tgaagcctct gatgtttgag    9720
aaggtgggtg cccaagtggc agtgaggagt ggggctgggg agtttgtgga gaaaggtcag    9780
gagctaataa ggtagttttg gagcccccttg gcctgaattc cacagctgca gtgttaacac    9840
```

```
tactttgact tgggccttac aggatgatga cagcaacttc catgtggact ttgtggtagc   9900
ggcagctagc ctgagatgtc agaactacgg gattccaccg gtcaaccgtg cccaggtaac   9960
cccacccctt gaggcttggg cctggaggtg gagggcaaac cctggcccta cgccttgggc  10020
ccagaccaaa tctcttgtcc ttggcagagc aagcgaattg tgggccagat tatcccagcc  10080
attgccacca ctacagcagc tgtggcaggc ctgttgggcc tggagctgta taaggtggtg  10140
agtgggccac ggcctcgtag tgcctttcgc cacagctacc tacatctggc tgaaaactac  10200
ctcatccgct atatgccttt tgccccagcc atccagacgg ttgagcccat gatacccac   10260 ccttagccct actaggcctg ggtttcccct gcacctgccc atacaggccc caatctagct  10320
gccggctctc actgaaactc agactgtgca gaagtcctga agactccctc cagcccctct  10380
cctgctatga agccaggctg ggacctgtca gacacaggaa gcagccgtca gccatcccca  10440
cccccaatcc tccaaagccc aggatctggg ggagctgcag ctttaactca ttagtggagc  10500
cagacatccc ccacagtccc ctccttcctt ggagtacccc tgagggtagg tagtggggag  10560
gggaccaggg catcagccca gaaagagtct agcttccccc tgcatggtac gggggccctg  10620
gcctacctcc tacaagctga gttaaaaggt aataggcttg ccactagagg tgtgggtct   10680 gcagccctga gtgtatttgt gtcacagttg tgagtgcaac tggggtctgg gcatccccgg  10740
agtgtgggta tggaaggagc aagtttgcac atctgtgcat cagatgggag tgcagggctc  10800
ccatcttcct gtgtcctcaa tgtgggcatg catggagatg catgtgggca cacatgtgtg  10860
tgtttcctgg gcttgtgggc atttgtgttc ctgtgactgc agcgctgtga atgcctccag  10920
ccttgtgccc aggctctgca gttggcattt ccttggggca aggatgaggg tagaaggaat  10980
gccctcatga ggggagaggg cagaggtcat gggccagcac tgggtttctg ctgagcagcc  11040
tggggtccct ctggactagc acacagagcc cctttgtgag gcaccctgcc tctaaccagc  11100
atacaggctg cctttgtcca cagagtgaag caggtgaagg agaagccccc atctcacctc  11160
tagcctagtc tcagcttgac cccagtgtgt tttctcaggg gctgataagc accccctgtc  11220
ctggtctcta gatacctgcc agccatcctt ctgtccttag ctctaggtcc cagaacccca  11280
agactcttgg aaggaaggaa gggacaggag gaggaagcct ctatgcattg tatccctgct  11340
ggggtctctg gacagtgggg gccctggtgg tcactgtgcc cttttgcccct gtgtcccaat  11400 gagtagccca aggcactggc agtacataca agattggggg acaggatgtg ccccccagct  11460
cccagccttg tctttgagga acaagcagct ttatcagagg ctgcaggggc cctgctctgg  11520
gtttcctcag gaagcaccac cgccgcatcc cccactctca caactggccc atgtgatgga  11580
tcgtctgttt ccctgtgcgg gccccatagc cccatttcct gtgctggccc cggcctggac  11640 ggggagggg ctgagactct gggcccagat cccacctccc cccaccccc cacccctgg   11700 ctcctgttc ctgctagtcc agctcttccc ctaggaaagg ctgctggtaa ctgggatggg  11760
ggttgggggg aggtaagaag tctctgactc ctcctctacc tcatcccagt tccatcacct  11820
gaagtggacc tctgggacc gtctgaaggt accagctggg cagcctgaga ggaccctgga   11880
gtcgctgctg gctcatcttc aggagcagca cgggttgagg gtgaggatcc tgctgcacgg  11940
ctcagccctg ctctatgcgg ccggatggtc acctgaaaag caggcccagc acctgccct   12000 caggtgagcc cacttgggct ttagacaggc cccaccagtc cctggaggct ggggctaggg  12060
accacactgc ctttgtcctt ccagccccca ttctgggccc ctcacacctt cccaagcatt  12120
cttcccccaa atgagccag caaacaggct ggaggtgggg tgagggccga gagctgagga  12180
ggagtcttcn anggagctcg tatttggcca gcccatggct cccacatgct gcacagnnnn  12240
```

```
ttcacagcca ctcctaagga cccatagctt cctgcctcct gcttggcctc atcagctgct   12300
cctaaaatag tttcagatgt ttcctgtctt gagcagctcc tgctcctggc ttgggctcct   12360
gacggcctgc cagcaccctc tctagtccat gccaggctgc cttctgcttg ccatggctca   12420
cctctccaat ctccctaaa cccacccta ccagggtgac agaactggtt cagcagctga     12480
caggccaggc acctgctcct gggcagcggg tgttggtgct agagctgagc tgtgagggtg   12540
acgacgagga cactgccttc ccacctctgc actatgagct gtgacaaggc agccaccctg   12600
tcacctagct caatggagcc ccggatccca agccctgcat tgtaagccca cagtaggcac   12660
tcaataattg cttgttaaag gaaggcattg cagagaggac ggacgataga aacagtgca    12720 ctaatgcaca cgggtgtgac atgggcatga cagggaccttc acacagaga aaaaagctc    12780 ttcagaagat ttgtctccct gggcagtgct cacagggctg gggctgcctc ttagtgcctc   12840
aggggtatgg agccaggaca gtctagaaaa aaggcttta ttgtcccagg ctggagggca    12900
gggtcagagg tagctgacat cattgcagat gatgggctgg cggctacgac agctcatgag   12960
agctgcaaag ctgagacat                                                12979
```

<210> SEQ ID NO 80
<211> LENGTH: 1011
<212> TYPE: PRT
<213> ORGANISM: Homo sapiens

<400> SEQUENCE: 80

```
Met Asp Ala Leu Asp Ala Ser Lys Leu Leu Asp Glu Glu Leu Tyr Ser
1               5                   10                  15

Arg Gln Leu Tyr Val Leu Gly Ser Pro Ala Met Gln Arg Ile Gln Gly
            20                  25                  30

Ala Arg Val Leu Val Ser Gly Leu Gln Gly Leu Gly Ala Glu Val Ala
        35                  40                  45

Lys Asn Leu Val Leu Met Gly Val Gly Ser Leu Thr Leu His Asp Pro
    50                  55                  60

His Pro Thr Cys Trp Ser Asp Leu Ala Ala Gln Phe Leu Leu Ser Glu
65                  70                  75                  80

Gln Asp Leu Glu Arg Ser Arg Ala Glu Ala Ser Gln Glu Leu Leu Ala
                85                  90                  95

Gln Leu Asn Arg Ala Val Gln Val Val His Thr Gly Asp Ile Thr
            100                 105                 110

Glu Asp Leu Leu Leu Asp Phe Gln Val Val Leu Thr Ala Ala Lys
        115                 120                 125

Leu Glu Glu Gln Leu Lys Val Gly Thr Leu Cys His Lys His Gly Val
    130                 135                 140

Cys Phe Leu Ala Ala Asp Thr Arg Gly Leu Val Gly Gln Leu Phe Cys
145                 150                 155                 160

Asp Phe Gly Glu Asp Phe Thr Val Gln Asp Pro Thr Glu Ala Glu Pro
                165                 170                 175

Leu Thr Ala Ala Ile Gln His Ile Ser Gln Gly Ser Pro Gly Ile Leu
            180                 185                 190

Thr Leu Arg Lys Gly Ala Asn Thr His Tyr Phe Arg Asp Gly Asp Leu
        195                 200                 205

Val Thr Phe Ser Gly Ile Glu Gly Met Val Glu Leu Asn Asp Cys Asp
    210                 215                 220

Pro Arg Ser Ile His Val Arg Glu Asp Gly Ser Leu Glu Ile Gly Asp
225                 230                 235                 240
```

```
Thr Thr Thr Phe Ser Arg Tyr Leu Arg Gly Gly Ala Ile Thr Glu Val
            245                 250                 255

Lys Arg Pro Lys Thr Val Arg His Lys Ser Leu Asp Thr Ala Leu Leu
            260                 265                 270

Gln Pro His Val Val Ala Gln Ser Ser Gln Glu Val His His Ala His
            275                 280                 285

Cys Leu His Gln Ala Phe Cys Ala Leu His Lys Phe Gln His Leu His
            290                 295                 300

Gly Arg Pro Pro Gln Pro Trp Asp Pro Val Asp Ala Glu Thr Val Val
305                 310                 315                 320

Gly Leu Ala Arg Asp Leu Glu Pro Leu Lys Arg Thr Glu Glu Glu Pro
                325                 330                 335

Leu Glu Glu Pro Leu Asp Glu Ala Leu Val Arg Thr Val Ala Leu Ser
                340                 345                 350

Ser Ala Arg Cys Leu Glu Pro Met Val Ala Cys Trp Val Ser Ser Cys
            355                 360                 365

Pro Gly Ser Ala Glu Gly Asn Leu Gln Lys Phe Met Pro Leu Asp Gln
            370                 375                 380

Trp Leu Tyr Phe Asp Ala Leu Asp Cys Leu Pro Glu Asp Gly Glu Leu
385                 390                 395                 400

Leu Pro Ser Pro Glu Asp Cys Ala Leu Arg Gly Ser Arg Tyr Asp Gly
                405                 410                 415

Gln Ile Ala Val Phe Gly Ala Gly Phe Gln Glu Lys Leu Arg Arg Gln
            420                 425                 430

His Tyr Leu Leu Val Gly Ala Gly Ile Gly Cys Glu Leu Leu Lys
            435                 440                 445

Val Phe Ala Leu Val Gly Leu Gly Ala Gly Asn Ser Gly Gly Leu Thr
            450                 455                 460

Val Val Asp Met Asp His Ile Glu Arg Ser Asn Leu Ser Arg Gln Phe
465                 470                 475                 480

Leu Phe Arg Ser Gln Asp Val Gly Arg Pro Lys Ala Glu Val Ala Ala
                485                 490                 495

Ala Ala Ala Arg Gly Leu Asn Pro Asp Leu Gln Val Ile Pro Leu Thr
            500                 505                 510

Tyr Pro Leu Asp Pro Thr Thr Glu His Ile Tyr Gly Asp Asn Phe Phe
            515                 520                 525

Ser Arg Val Asp Gly Val Ala Ala Leu Asp Ser Phe Gln Ala Arg
            530                 535                 540

Arg Tyr Val Ala Ala Arg Cys Thr His Tyr Leu Lys Pro Leu Leu Glu
545                 550                 555                 560

Ala Gly Thr Ser Gly Thr Trp Gly Ser Ala Thr Val Phe Met Pro His
                565                 570                 575

Val Thr Glu Ala Tyr Arg Ala Pro Ala Ser Ala Ala Ser Glu Asp
            580                 585                 590

Ala Pro Tyr Pro Val Cys Thr Val Arg Tyr Phe Pro Ser Thr Ala Glu
            595                 600                 605

His Thr Leu Gln Trp Ala Arg His Glu Phe Glu Glu Leu Phe Arg Leu
            610                 615                 620

Ser Ala Glu Thr Ile Asn His His Gln Gln Ala His Thr Ser Leu Ala
625                 630                 635                 640

Asp Met Asp Glu Pro Gln Thr Leu Thr Leu Lys Pro Val Leu Gly
                645                 650                 655
```

```
Val Leu Arg Val Arg Pro Gln Asn Trp Gln Asp Cys Val Ala Trp Ala
            660                 665                 670

Leu Gly His Trp Lys Leu Cys Phe His Tyr Gly Ile Lys Gln Leu Leu
        675                 680                 685

Arg His Phe Pro Pro Asn Lys Val Leu Glu Asp Gly Thr Pro Phe Trp
    690                 695                 700

Ser Gly Pro Lys Gln Cys Pro Gln Pro Leu Glu Phe Asp Thr Asn Gln
705                 710                 715                 720

Asp Thr His Leu Leu Tyr Val Leu Ala Ala Asn Leu Tyr Ala Gln
                725                 730                 735

Met His Gly Leu Pro Gly Ser Gln Asp Trp Thr Ala Leu Arg Glu Leu
            740                 745                 750

Leu Lys Leu Leu Pro Gln Pro Asp Pro Gln Gln Met Ala Pro Ile Phe
        755                 760                 765

Ala Ser Asn Leu Glu Leu Ala Ser Ala Ser Ala Glu Phe Gly Pro Glu
    770                 775                 780

Gln Gln Lys Glu Leu Asn Lys Ala Leu Glu Val Trp Ser Val Gly Pro
785                 790                 795                 800

Pro Leu Lys Pro Leu Met Phe Glu Lys Asp Asp Ser Asn Phe His
            805                 810                 815

Val Asp Phe Val Val Ala Ala Ala Ser Leu Arg Cys Gln Asn Tyr Gly
        820                 825                 830

Ile Pro Pro Val Asn Arg Ala Gln Ser Lys Arg Ile Val Gly Gln Ile
    835                 840                 845

Ile Pro Ala Ile Ala Thr Thr Thr Ala Ala Val Ala Gly Leu Leu Gly
850                 855                 860

Leu Glu Leu Tyr Lys Val Val Ser Gly Pro Arg Pro Arg Ser Ala Phe
865                 870                 875                 880

Arg His Ser Tyr Leu His Leu Ala Glu Asn Tyr Leu Ile Arg Tyr Met
            885                 890                 895

Pro Phe Ala Pro Ala Ile Gln Thr Phe His His Leu Lys Trp Thr Ser
        900                 905                 910

Trp Asp Arg Leu Lys Val Pro Ala Gly Gln Pro Glu Arg Thr Leu Glu
    915                 920                 925

Ser Leu Leu Ala His Leu Gln Glu Gln His Gly Leu Arg Val Arg Ile
930                 935                 940

Leu Leu His Gly Ser Ala Leu Leu Tyr Ala Ala Gly Trp Ser Pro Glu
945                 950                 955                 960

Lys Gln Ala Gln His Leu Pro Leu Arg Val Thr Glu Leu Val Gln Gln
            965                 970                 975

Leu Thr Gly Gln Ala Pro Ala Pro Gly Gln Arg Val Leu Val Leu Glu
        980                 985                 990

Leu Ser Cys Glu Gly Asp Asp Glu Asp Thr Ala Phe Pro Pro Leu His
    995                 1000                1005

Tyr Glu Leu
    1010

<210> SEQ ID NO 81
<211> LENGTH: 1642
<212> TYPE: DNA
<213> ORGANISM: Homo sapiens

<400> SEQUENCE: 81
aagccacggg gagaaacgtt gcagcccgcg ccgaacgccg ggcagcacaa aggatccccg      60
```

```
actgccgggg agcggtgctc ggagggcaca ggtctacgcc atcccccacg cagtttcgga      120
gatggagcgc tgggcccatg gagggaaggc ggcaggctcg gcggctccgg cagcttgctg      180
gggcaggggc tcaaggcggc agtccgatag tggaggccgc tgagaactgt cacggagctg      240
cgtctgtaca gcgagcatcc cttatttatt cagggcgagt gtgtatttgg ggcggcgtgc      300
aggggggctga caaagaccgg agagctcccg gtgcggccgc cggcggagcg aagactggaa      360
cccgtatgag cgcccccag cgccctgag cgctcgccgc cggtgcacgg cgcaccccgc       420
gggaggcagg gatcagcaaa gccgtgcgcc ccgaggcccg ccccgtctc cgcacaaaga      480
ccgagctgga ggatcttcag aagaagcctc ccccatacct gcggaacctg tccagcgatg      540
atgccaatgt cctggtgtgg cacgctctcc tcctacccga ccaacctccc taccacctga      600
aagccttcaa cctgcgcatc agcttcccgc cggagtatcc gttcaagcct ccatgatca      660
aattcacaac caagatctac cacccaacg tggacgagaa cggacagatt tgcctgccca      720
tcatcagcag tgagaactgg aagccttgca ccaagacttg ccaagtcctg gaggccctca      780
atgtgctggt gaatagaccg aatatcaggg agccctgcg gatggacctc gctgacctgc      840
tgacacagaa tccggagctg ttcagaaaga atgccgaaga gttcacccctc gattcggag      900
tggaccggcc ctcctaactc atgttctgac cctctgtgca ctggatcctc ggcatagcgg      960
acggacacac ctcatggact gaggccagag cccctgtgg cccattcccc attcattttt      1020
cccttcttag gttgttagtc attagtttgt gtgtgtgtgt ggtggaggga agggagctat      1080
gagtgtgtgt gttgtgtatg gactcactcc caggttcacc tggccacagg tgcacccttc      1140
ccacaccctt tacattcccc agagccaagg gagtttaagt ttgcagttac aggccagttc      1200
tccagctctc catcttagag agacaggtca ccttgcaggc ctgcttgcag gaaatgaatc      1260
cagcagccaa ctcgaatccc ctagggctc aggcactgag ggcctgggga cagtggagca      1320
tatgggtggg agacagatgg agggtaccct atttacaact gagtcagcca agccactgat      1380
gggaatatac agatttaggt gctaaaccat ttatttccca cggatgagtc acaatctgaa      1440
gaatcaaact tccatcctga aaatctatat gttcaaaac cacttgccat cctgttagat      1500
tgccagttcc tgggaccagg cctcagactg tgaagtatat atcctccagc attcagtcca      1560
gggggagcca cggaaaccat gttcttgctt aagccattaa agtcagagat gaattctgga      1620
aaaaaaaaaa aaaaaaaaaa aa                                              1642
```

<210> SEQ ID NO 82
<211> LENGTH: 87
<212> TYPE: PRT
<213> ORGANISM: Homo sapiens

<400> SEQUENCE: 82

```
Met Ile Lys Phe Thr Thr Lys Ile Tyr His Pro Asn Val Asp Glu Asn
1               5                   10                  15

Gly Gln Ile Cys Leu Pro Ile Ile Ser Ser Glu Asn Trp Lys Pro Cys
            20                  25                  30

Thr Lys Thr Cys Gln Val Leu Glu Ala Leu Asn Val Leu Val Asn Arg
        35                  40                  45

Pro Asn Ile Arg Glu Pro Leu Arg Met Asp Leu Ala Asp Leu Leu Thr
    50                  55                  60

Gln Asn Pro Glu Leu Phe Arg Lys Asn Ala Glu Glu Phe Thr Leu Arg
65                  70                  75                  80

Phe Gly Val Asp Arg Pro Ser
                85
```

```
<210> SEQ ID NO 83
<211> LENGTH: 1283
<212> TYPE: DNA
<213> ORGANISM: Homo sapiens

<400> SEQUENCE: 83
gggggtgggg tccccggggc ggggcggggc gcgctgtgtc gcgggtcgga gctcggtcct     60
gctggaggcc acgggtgcca cacactcggt cccgacatga tggcgagcat gcgagtggtg    120
aaggagctgg aggatcttca agaagcct cccccatacc tgcggaacct gtccagcgat     180
gatgccaatg tcctggtgtg gcacgctctc ctcctacccg accaacctcc ctaccacctg    240
aaagccttca acctgcgcat cagcttcccg ccggagtatc cgttcaagcc tcccatgatc    300
aaattcacaa ccaagatcta ccaccccaac gtggacgaga acggacagat ttgcctgccc    360
atcatcagca gtgagaactg gaagccttgc accaagactt gccaagtcct ggaggccctc    420
aatgtgctgg tgaatagacc gaatatcagg gagcccctgc ggatggacct cgctgacctg    480
ctgacacaga atccggagct gttcagaaag aatgccgaag agttcaccct ccgattcgga    540
gtggaccggc cctcctaact catgttctga ccctctgtgc actggatcct cggcatagcg    600
gacggacaca cctcatggac tgaggccaga gcccctgtg gcccattccc cattcatttt    660
tcccttctta ggttgttagt cattagttg tgtgtgtg tggtggagg aagggagcta     720
tgagtgtgtg tgttgtgtat ggactcactc ccaggttcac ctggccacag gtgcacccttt   780
cccacaccct ttacattccc cagagccaag ggagtttaag tttgcagtta caggccagtt    840
ctccagctct ccatcttaga gagacaggtc accttgcagg cctgcttgca ggaaatgaat    900
ccagcagcca actcgaatcc ccctagggct caggcactga gggcctgggg acagtggagc    960
atatgggtgg gagacagatg gagggtaccc tatttacaac tgagtcagcc aagccactga   1020
tgggaatata cagatttagg tgctaaacca tttattttcc acggatgagt cacaatctga   1080
agaatcaaac ttccatcctg aaaatctata tgtttcaaaa ccacttgcca tcctgttaga   1140
ttgccagttc ctgggaccag gcctcagact gtgaagtata tatcctccag cattcagtcc   1200
aggggagcc acgaaaacca tgttcttgct taagccatta aagtcagaga tgaattctgg   1260
aaaaaaaaaa aaaaaaaaaa aaa                                          1283

<210> SEQ ID NO 84
<211> LENGTH: 153
<212> TYPE: PRT
<213> ORGANISM: Homo sapiens

<400> SEQUENCE: 84

Met Met Ala Ser Met Arg Val Val Lys Glu Leu Glu Asp Leu Gln Lys
1               5                   10                  15

Lys Pro Pro Pro Tyr Leu Arg Asn Leu Ser Ser Asp Asp Ala Asn Val
                20                  25                  30

Leu Val Trp His Ala Leu Leu Leu Pro Asp Gln Pro Pro Tyr His Leu
            35                  40                  45

Lys Ala Phe Asn Leu Arg Ile Ser Phe Pro Pro Glu Tyr Pro Phe Lys
        50                  55                  60

Pro Pro Met Ile Lys Phe Thr Thr Lys Ile Tyr His Pro Asn Val Asp
65                  70                  75                  80

Glu Asn Gly Gln Ile Cys Leu Pro Ile Ile Ser Ser Glu Asn Trp Lys
                85                  90                  95
```

Pro Cys Thr Lys Thr Cys Gln Val Leu Glu Ala Leu Asn Val Leu Val
            100                 105                 110

Asn Arg Pro Asn Ile Arg Glu Pro Leu Arg Met Asp Leu Ala Asp Leu
        115                 120                 125

Leu Thr Gln Asn Pro Glu Leu Phe Arg Lys Asn Ala Glu Glu Phe Thr
    130                 135                 140

Leu Arg Phe Gly Val Asp Arg Pro Ser
145                 150

<210> SEQ ID NO 85
<211> LENGTH: 665
<212> TYPE: DNA
<213> ORGANISM: Homo sapiens

<400> SEQUENCE: 85
gggaacacat ccaagcttaa gacggtgagg tcagcttcac attctcagga actctccttc      60
tttgggtctg gctgaagttg aggatctctt actctctagg ccacggaatt aacccgagca    120
ggcatggagg cctctgctct cacctcatca gcagtgacca gtgtggccaa gtggtcagg     180
gtggcctctg gctctgccgt agttttgccc ctggccagga ttgctacagt tgtgattgga    240
ggagttgtgg ccatggcggc tgtgcccatg gtgctcagtg ccatgggctt cactgcggcg    300
ggaatcgcct cgtcctccat agcagccaag atgatgtccg cggcggccat tgccaatggg    360
ggtggagttg cctcgggcag ccttgtggct actctgcagt cactgggagc aactggactc    420
tccggattga ccaagttcat cctgggctcc attgggtctg ccattgcggc tgtcattgcg    480
aggttctact agctccctgc ccctcgccct gcagagaaga gaaccatgcc aggggagaag    540
gcacccagcc atcctgaccc agcgaggagc caactatccc aaatatacct ggggtgaaat    600
ataccaaatt ctgcatctcc agaggaaaat aagaaataaa gatgaattgt tgcaactctt    660
caaaa                                                                 665

<210> SEQ ID NO 86
<211> LENGTH: 122
<212> TYPE: PRT
<213> ORGANISM: Homo sapiens

<400> SEQUENCE: 86

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30

Ile Ala Thr Val Val Ile Gly Val Val Ala Met Ala Ala Val Pro
        35                  40                  45

Met Val Leu Ser Ala Met Gly Phe Thr Ala Ala Gly Ile Ala Ser Ser
    50                  55                  60

Ser Ile Ala Ala Lys Met Met Ser Ala Ala Ile Ala Asn Gly Gly
65                  70                  75                  80

Gly Val Ala Ser Gly Ser Leu Val Ala Thr Leu Gln Ser Leu Gly Ala
            85                  90                  95

Thr Gly Leu Ser Gly Leu Thr Lys Phe Ile Leu Gly Ser Ile Gly Ser
            100                 105                 110

Ala Ile Ala Ala Val Ile Ala Arg Phe Tyr
        115                 120

<210> SEQ ID NO 87
<211> LENGTH: 656

<212> TYPE: DNA
<213> ORGANISM: Homo sapiens

<400> SEQUENCE: 87

```
gggaacacat ccaagcttaa gacggtgagg tcagcttcac attctcagga actctccttc      60
tttgggtctg gctgaagttg aggatctctt actctctagg ccacggaatt aacccgagca     120
ggcatggagg cctctgctct cacctcatca gcagtgacca gtgtggccaa agtggtcagg     180
gtggcctctg gctctgccgt agttttgccc ctggccagga ttgctacagt tgtgattgga     240
ggagttgtgg ctgtgcccat ggtgctcagt gccatgggct tcactgcggc gggaatcgcc     300
tcgtcctcca tagcagccaa gatgatgtcc gcggcggcca ttgccaatgg gggtggagtt     360
gcctcgggca gccttgtggc tactctgcag tcactgggag caactggact ctccggattg     420
accaagttca tcctgggctc cattgggtct gccattgcgg ctgtcattgc gaggttctac     480
tagctccctg cccctcgccc tgcagagaag agaaccatgc caggggagaa ggcacccagc     540
catcctgacc cagcgaggag ccaactatcc caaatatacc tggggtgaaa ataccaaat     600
tctgcatctc cagaggaaaa taagaaataa agatgaattg ttgcaactct tcaaaa        656
```

<210> SEQ ID NO 88
<211> LENGTH: 119
<212> TYPE: PRT
<213> ORGANISM: Homo sapiens

<400> SEQUENCE: 88

```
Met Glu Ala Ser Ala Leu Thr Ser Ser Ala Val Thr Ser Val Ala Lys
1               5                   10                  15
Val Val Arg Val Ala Ser Gly Ser Ala Val Val Leu Pro Leu Ala Arg
            20                  25                  30
Ile Ala Thr Val Val Ile Gly Gly Val Val Ala Val Pro Met Val Leu
        35                  40                  45
Ser Ala Met Gly Phe Thr Ala Ala Gly Ile Ala Ser Ser Ile Ala
    50                  55                  60
Ala Lys Met Met Ser Ala Ala Ala Ile Ala Asn Gly Gly Gly Val Ala
65                  70                  75                  80
Ser Gly Ser Leu Val Ala Thr Leu Gln Ser Leu Gly Ala Thr Gly Leu
                85                  90                  95
Ser Gly Leu Thr Lys Phe Ile Leu Gly Ser Ile Gly Ser Ala Ile Ala
            100                 105                 110
Ala Val Ile Ala Arg Phe Tyr
        115
```

<210> SEQ ID NO 89
<211> LENGTH: 3617
<212> TYPE: DNA
<213> ORGANISM: Homo sapiens

<400> SEQUENCE: 89

```
atcgaaacag aaaccaaagt caggcaaact ctgtaagaac tgcctgacag aaagctggac      60
tcaaagctcc tacccgagtg tgcagcagga tcgccccggt ccgggacccc aggcgcacac     120
cgcagagtcc aaagtgccgc gcctgccggc cgcacctgcc tgccgcggcc ccgcgcgccg     180
ccccgctgcc cacctgcccg cctgcccacc tgcccaggtg cgagtgcagc cccgcgcgcc     240
ggcctgagag ccctgtggac aacctcgtca ttgtcaggca cagagcggta gaccctgctt     300
ctctaagtgg gcagcggaca gcggcacgca catttcacct gtcccgcaga caacagcacc     360
```

```
atctgcttgg gagaaccctc tcccttctct gagaaagaaa gatgtcgaat gggtattcca    420
cagacgagaa tttccgctat ctcatctcgt gcttcagggc cagggtgaaa atgtacatcc    480
aggtggagcc tgtgctggac tacctgacct ttctgcctgc agaggtgaag gagcagattc    540
agaggacagt cgccacctcc gggaacatgc aggcagttga actgctgctg agcaccttgg    600
agaagggagt ctggcacctt ggttggactc gggaattcgt ggaggccctc cggagaaccg    660
gcagccctct ggccgcccgc tacatgaacc ctgagctcac ggacttgccc tctccatcgt    720
ttgagaacgc tcatgatgaa tatctccaac tgctgaacct ccttcagccc actctggtgg    780
acaagcttct agttagagac gtcttggata agtgcatgga ggaggaactg ttgacaattg    840
aagacagaaa ccggattgct gctgcagaaa acaatggaaa tgaatcaggt gtaagagagc    900
tactaaaaag gattgtgcag aaagaaaact ggttctctgc atttctgaat gttcttcgtc    960
aaacaggaaa caatgaactt gtccaagagt taacaggctc tgattgctca gaaagcaatg   1020
cagagattga gaatttatca caagttgatg gtcctcaagt ggaagagcaa cttctttcaa   1080
ccacagttca gccaaatctg gagaaggagg tctggggcat ggagaataac tcatcagaat   1140
catcttttgc agattcttct gtagtttcag aatcagacac aagtttggca gaaggaagtg   1200
tcagctgctt agatgaaagt cttggacata acagcaacat gggcagtgat tcaggcacca   1260
tgggaagtga ttcagatgaa gagaatgtgg cagcaagagc atccccggag ccagaactcc   1320
agctcaggcc ttaccaaatg gaagttgccc agccagcctt ggaagggaag aatatcatca   1380
tctgcctccc tacagggagt ggaaaaacca gagtggctgt ttacattgcc aaggatcact   1440
tagacaagaa gaaaaagca tctgagcctg aaaagttat agttcttgtc aataaggtac   1500
tgctagttga acagctcttc cgcaaggagt ccaaccatt tttgaagaaa tggtatcgtg   1560
ttattggatt aagtggtgat acccaactga aaatatcatt tccagaagtt gtcaagtcct   1620
gtgatattat tatcagtaca gctcaaatcc ttgaaaactc cctcttaaac ttggaaaatg   1680
gagaagatgc tggtgttcaa ttgtcagact tttcctcat tatcattgat gaatgtcatc   1740
acaccaacaa agaagcagtg tataataaca tcatgaggca ttatttgatg cagaagttga   1800
aaaacaatag actcaagaaa gaaaacaaac cagtgattcc ccttcctcag atactgggac   1860
taacagcttc acctggtgtt ggaggggcca cgaagcaagc caaagctgaa gaacacattt   1920
taaaactatg tgccaatctt gatgcattta ctattaaaac tgttaaagaa accttgatc   1980
aactgaaaaa ccaaatacag gagccatgca agaagtttgc cattgcagat gcaaccagag   2040
aagatccatt taagagaaa cttctagaaa taatgacaag gattcaaact tattgtcaaa   2100
tgagtccaat gtcagatttt ggaactcaac cctatgaaca atgggccatt caaatggaaa   2160
aaaagctgc aaaagaagga atcgcaaag aacgtgtttg tgcagaacat ttgaggaagt   2220
acaatgaggc cctacaaatt aatgacacaa ttcgaatgat agatgcgtat actcatcttg   2280
aaactttcta taatgaagag aaagataaga gtttgcagt catagaagat gatagtgatg   2340
agggtggtga tgatgagtat tgtgatggtg atgaagatga ggatgattta agaaaccttt   2400
tgaaactgga tgaaacagat agatttctca tgactttatt ttttgaaaac aataaaatgt   2460
tgaaaaggct ggctgaaaac ccagaatatg aaaatgaaaa gctgaccaaa ttaagaaata   2520
ccataatgga gcaatatact aggactgagg aatcagcacg aggaataatc tttacaaaaa   2580
cacgacagag tgcatatgcg ctttcccagt ggattactga aaatgaaaaa tttgctgaag   2640
taggagtcaa agcccaccat ctgattggag ctggacacag cagtgagttc aaacccatga   2700
cacagaatga acaaaagaa gtcattagta aatttcgcac tggaaaaata aatctgctta   2760
```

```
tcgctaccac agtggcagaa gaaggtctgg atattaaaga atgtaacatt gttatccgtt    2820
atggtctcgt caccaatgaa atagccatgg tccaggcccg tggtcgagcc agagctgatg    2880
agagcaccta cgtcctggtt gctcacagtg gttcaggagt tatcgaacat gagacagtta    2940
atgatttccg agagaagatg atgtataaag ctatacattg tgttcaaaat atgaaaccag    3000
aggagtatgc tcataagatt ttggaattac agatgcaaag tataatggaa agaaaatga     3060 aaaccaagag aaatattgcc aagcattaca agaataaccc atcactaata actttccttt    3120
gcaaaaactg cagtgtgcta gcctgttctg gggaagatat ccatgtaatt gagaaaatgc    3180
atcacgtcaa tatgacccca gaattcaagg aactttacat tgtaagagaa acaaagcac    3240 tgcaaaagaa gtgtgccgac tatcaaataa atggtgaaat catctgcaaa tgtggccagg    3300
cttggggaac aatgatggtg cacaaaggct tagatttgcc ttgtctcaaa ataaggaatt    3360
ttgtagtggt tttcaaaaat aattcaacaa agaaacaata caaaaagtgg gtagaattac    3420
ctatcacatt tcccaatctt gactattcag aatgctgttt atttagtgat gaggattagc    3480
acttgattga agattctttt aaaatactat cagttaaaca tttaatatga ttatgattaa    3540
tgtattcatt atgctacaga actgacataa gaatcaataa aatgattgtt ttactctgca    3600
aaaaaaaaaa aaaaaaa                                                   3617

<210> SEQ ID NO 90
<211> LENGTH: 1025
<212> TYPE: PRT
<213> ORGANISM: Homo sapiens

<400> SEQUENCE: 90

Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Arg Tyr Met Asn
            85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Leu Leu
    130                 135                 140

Thr Ile Glu Asp Arg Asn Arg Ile Ala Ala Glu Asn Asn Gly Asn
145                 150                 155                 160

Glu Ser Gly Val Arg Glu Leu Leu Lys Arg Ile Val Gln Lys Glu Asn
            165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
```

```
              210                 215                 220
Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
                245                 250                 255

Glu Ser Asp Thr Ser Leu Ala Glu Gly Ser Val Ser Cys Leu Asp Glu
                260                 265                 270

Ser Leu Gly His Asn Ser Asn Met Gly Ser Asp Ser Gly Thr Met Gly
            275                 280                 285

Ser Asp Ser Asp Glu Glu Asn Val Ala Ala Arg Ala Ser Pro Glu Pro
290                 295                 300

Glu Leu Gln Leu Arg Pro Tyr Gln Met Glu Val Ala Gln Pro Ala Leu
305                 310                 315                 320

Glu Gly Lys Asn Ile Ile Ile Cys Leu Pro Thr Gly Ser Gly Lys Thr
                325                 330                 335

Arg Val Ala Val Tyr Ile Ala Lys Asp His Leu Asp Lys Lys Lys Lys
                340                 345                 350

Ala Ser Glu Pro Gly Lys Val Ile Val Leu Val Asn Lys Val Leu Leu
            355                 360                 365

Val Glu Gln Leu Phe Arg Lys Glu Phe Gln Pro Phe Leu Lys Lys Trp
370                 375                 380

Tyr Arg Val Ile Gly Leu Ser Gly Asp Thr Gln Leu Lys Ile Ser Phe
385                 390                 395                 400

Pro Glu Val Val Lys Ser Cys Asp Ile Ile Ser Thr Ala Gln Ile
                405                 410                 415

Leu Glu Asn Ser Leu Leu Asn Leu Glu Asn Gly Glu Asp Ala Gly Val
                420                 425                 430

Gln Leu Ser Asp Phe Ser Leu Ile Ile Ile Asp Glu Cys His His Thr
            435                 440                 445

Asn Lys Glu Ala Val Tyr Asn Asn Ile Met Arg His Tyr Leu Met Gln
450                 455                 460

Lys Leu Lys Asn Asn Arg Leu Lys Lys Glu Asn Lys Pro Val Ile Pro
465                 470                 475                 480

Leu Pro Gln Ile Leu Gly Leu Thr Ala Ser Pro Gly Val Gly Gly Ala
                485                 490                 495

Thr Lys Gln Ala Lys Ala Glu Glu His Ile Leu Lys Leu Cys Ala Asn
            500                 505                 510

Leu Asp Ala Phe Thr Ile Lys Thr Val Lys Glu Asn Leu Asp Gln Leu
            515                 520                 525

Lys Asn Gln Ile Gln Glu Pro Cys Lys Lys Phe Ala Ile Ala Asp Ala
530                 535                 540

Thr Arg Glu Asp Pro Phe Lys Glu Lys Leu Leu Glu Ile Met Thr Arg
545                 550                 555                 560

Ile Gln Thr Tyr Cys Gln Met Ser Pro Met Ser Asp Phe Gly Thr Gln
                565                 570                 575

Pro Tyr Glu Gln Trp Ala Ile Gln Met Glu Lys Lys Ala Ala Lys Glu
            580                 585                 590

Gly Asn Arg Lys Glu Arg Val Cys Ala Glu His Leu Arg Lys Tyr Asn
            595                 600                 605

Glu Ala Leu Gln Ile Asn Asp Thr Ile Arg Met Ile Asp Ala Tyr Thr
610                 615                 620

His Leu Glu Thr Phe Tyr Asn Glu Glu Lys Asp Lys Lys Phe Ala Val
625                 630                 635                 640
```

```
Ile Glu Asp Asp Ser Asp Gly Gly Asp Glu Tyr Cys Asp Gly
                645             650             655

Asp Glu Asp Glu Asp Asp Leu Lys Lys Pro Leu Lys Leu Asp Glu Thr
            660             665             670

Asp Arg Phe Leu Met Thr Leu Phe Phe Glu Asn Asn Lys Met Leu Lys
        675             680             685

Arg Leu Ala Glu Asn Pro Glu Tyr Glu Asn Glu Lys Leu Thr Lys Leu
    690             695             700

Arg Asn Thr Ile Met Glu Gln Tyr Thr Arg Thr Glu Ser Ala Arg
705             710             715             720

Gly Ile Ile Phe Thr Lys Thr Arg Gln Ser Ala Tyr Ala Leu Ser Gln
                725             730             735

Trp Ile Thr Glu Asn Glu Lys Phe Ala Glu Val Gly Val Lys Ala His
            740             745             750

His Leu Ile Gly Ala Gly His Ser Ser Glu Phe Lys Pro Met Thr Gln
        755             760             765

Asn Glu Gln Lys Glu Val Ile Ser Lys Phe Arg Thr Gly Lys Ile Asn
    770             775             780

Leu Leu Ile Ala Thr Thr Val Ala Glu Glu Gly Leu Asp Ile Lys Glu
785             790             795             800

Cys Asn Ile Val Ile Arg Tyr Gly Leu Val Thr Asn Glu Ile Ala Met
                805             810             815

Val Gln Ala Arg Gly Arg Ala Arg Ala Asp Glu Ser Thr Tyr Val Leu
            820             825             830

Val Ala His Ser Gly Ser Gly Val Ile Glu His Glu Thr Val Asn Asp
        835             840             845

Phe Arg Glu Lys Met Met Tyr Lys Ala Ile His Cys Val Gln Asn Met
    850             855             860

Lys Pro Glu Glu Tyr Ala His Lys Ile Leu Glu Leu Gln Met Gln Ser
865             870             875             880

Ile Met Glu Lys Lys Met Lys Thr Lys Arg Asn Ile Ala Lys His Tyr
                885             890             895

Lys Asn Asn Pro Ser Leu Ile Thr Phe Leu Cys Lys Asn Cys Ser Val
            900             905             910

Leu Ala Cys Ser Gly Glu Asp Ile His Val Ile Glu Lys Met His His
        915             920             925

Val Asn Met Thr Pro Glu Phe Lys Glu Leu Tyr Ile Val Arg Glu Asn
    930             935             940

Lys Ala Leu Gln Lys Lys Cys Ala Asp Tyr Gln Ile Asn Gly Glu Ile
945             950             955             960

Ile Cys Lys Cys Gly Gln Ala Trp Gly Thr Met Met Val His Lys Gly
                965             970             975

Leu Asp Leu Pro Cys Leu Lys Ile Arg Asn Phe Val Val Phe Lys
            980             985             990

Asn Asn Ser Thr Lys Lys Gln Tyr Lys Lys Trp Val Glu Leu Pro Ile
        995             1000            1005

Thr Phe Pro Asn Leu Asp Tyr Ser Glu Cys Cys Leu Phe Ser Asp
    1010            1015            1020

Glu Asp
    1025

<210> SEQ ID NO 91
<211> LENGTH: 4992
```

<212> TYPE: DNA
<213> ORGANISM: Homo sapiens

<400> SEQUENCE: 91

```
gaagactcca gatataggat cactccatgc catcaagaaa gttgatgcta ttgggcccat      60
ctcaagctga tcttggcacc tctcatgctc tgctctcttc aaccagacct ctacattcca     120
ttttggaaga agactaaaaa tggtgtttcc aatgtggaca ctgaagagac aaattcttat     180
ccttttaac ataatcctaa tttccaaact ccttggggct agatggtttc ctaaaactct      240
gccctgtgat gtcactctgg atgttccaaa gaaccatgtg atcgtggact gcacagacaa     300
gcatttgaca gaaattcctg gaggtattcc cacgaacacc acgaacctca ccctcaccat     360
taaccacata ccagacatct ccccagcgtc ctttcacaga ctggaccatc tggtagagat     420
cgatttcaga tgcaactgtg tacctattcc actggggtca aaaaacaaca tgtgcatcaa     480
gaggctgcag attaaaccca aagctttag tggactcact tatttaaaat ccctttacct      540
ggatggaaac cagctactag ataccgca gggcctcccg cctagcttac agcttctcag       600
ccttgaggcc aacaacatct tttccatcag aaaagagaat ctaacagaac tggccaacat     660
agaaatactc tacctgggcc aaaactgtta ttatcgaaat ccttgttatg tttcatattc     720
aatagagaaa gatgccttcc taaacttgac aaagttaaaa gtgctctccc tgaaagataa     780
caatgtcaca gccgtcccta ctgttttgcc atctacttta acagaactat atctctacaa     840
caacatgatt gcaaaaatcc aagaagatga tttaataac ctcaaccaat tacaaattct      900
tgacctaagt ggaaattgcc ctcgttgtta taatgcccca tttccttgtg cgccgtgtaa     960
aaataattct ccctacaga tccctgtaaa tgcttttgat gcgctgacag aattaaaagt     1020
tttacgtcta cacagtaact ctcttcagca tgtgccccca agatggttta agaacatcaa    1080
caaactccag gaactggatc tgtcccaaaa cttcttggcc aaagaaattg gggatgctaa    1140
atttctgcat tttctcccca gcctcatcca attggatctg tctttcaatt ttgaacttca    1200
ggtctatcgt gcatctatga atctatcaca agcattttct tcactgaaaa gcctgaaaat    1260
tctgcggatc agaggatatg tcttaaaga gttgaaaagc tttaacctct cgccattaca     1320
taatcttcaa aatcttgaag ttcttgatct tggcactaac tttataaaaa ttgctaacct    1380
cagcatgttt aaacaattta aaagactgaa agtcatagat ctttcagtga ataaaatatc    1440
accttcagga gattcaagtg aagttggctt ctgctcaaat gccagaactt ctgtagaaag    1500
ttatgaaccc caggtcctgg aacaattaca ttatttcaga tatgataagt atgcaaggag    1560
ttgcagattc aaaaacaaag aggcttcttt catgtctgtt aatgaaagct gctacaagta    1620
tgggcagacc ttggatctaa gtaaaaatag tatatttttt gtcaagtcct ctgattttca    1680
gcatctttct ttcctcaaat gcctgaatct gtcaggaaat ctcattagcc aaactcttaa    1740
tggcagtgaa ttccaacctt tagcagagct gagatatttg gacttctcca caaccggct    1800
tgatttactc cattcaacag catttgaaga gcttcacaaa ctgaagttc tggatataag    1860
cagtaatagc cattattttc aatcagaagg aattactcat atgctaaact ttaccaagaa    1920
cctaaaggtt ctgcagaaac tgatgatgaa cgacaatgac atctcttcct ccaccagcag    1980
gaccatggag agtgagtctc ttagaactct ggaattcaga ggaaatcact tagatgtttt    2040
atggagagaa ggtgataaca gatacttaca attattcaag aatctgctaa aattagagga    2100
attagacatc tctaaaaatt ccctaagttt cttgccttct ggagttttg atggtatgcc     2160
tccaaatcta aagaatctct ctttggccaa aaatgggctc aaatctttca gttggaagaa    2220
```

```
actccagtgt ctaaagaacc tggaaacttt ggacctcagc cacaaccaac tgaccactgt   2280
ccctgagaga ttatccaact gttccagaag cctcaagaat ctgattctta agaataatca   2340
aatcaggagt ctgacgaagt attttctaca agatgccttc cagttgcgat atctggatct   2400
cagctcaaat aaaatccaga tgatccaaaa gaccagcttc ccagaaaatg tcctcaacaa   2460
tctgaagatg ttgcttttgc atcataatcg gtttctgtgc acctgtgatg ctgtgtggtt   2520
tgtctggtgg gttaaccata cggaggtgac tattccttac ctggccacag atgtgacttg   2580
tgtggggcca ggagcacaca agggccaaag tgtgatctcc ctggatctgt acacctgtga   2640
gttagatctg actaacctga ttctgttctc actttccata tctgtatctc tctttctcat   2700
ggtgatgatg acagcaagtc acctctattt ctgggatgtg tggtatattt accatttctg   2760
taaggccaag ataaagggt atcagcgtct aatatcacca gactgttgct atgatgcttt   2820
tattgtgtat gacactaaag acccagctgt gaccgagtgg gttttggctg agctggtggc   2880
caaactggaa gacccaagag agaaacattt taatttatgt ctcgaggaaa gggactggtt   2940
accagggcag ccagttctgg aaaacctttc ccagagcata cagcttagca aaaagacagt   3000
gtttgtgatg acagacaagt atgcaaagac tgaaaatttt aagatagcat tttacttgtc   3060
ccatcagagg ctcatggatg aaaaagttga tgtgattatc ttgatatttc ttgagaagcc   3120
ctttcagaag tccaagttcc tccagctccg gaaaaggctc tgtgggagtt ctgtccttga   3180
gtggccaaca aacccgcaag ctcacccata cttctggcag tgtctaaaga acgccctggc   3240
cacagacaat catgtggcct atagtcaggt gttcaaggaa acggtctagc ccttctttgc   3300
aaaacacaac tgcctagttt accaaggaga ggcctggctg tttaaattgt tttcatatat   3360
atcacaccaa aagcgtgttt tgaaattctt caagaaatga gattgcccat atttcagggg   3420
agccaccaac gtctgtcaca ggagttggaa agatgggtt tatataatgc atcaagtctt   3480
ctttcttatc tctctgtgtc tctatttgca cttgagtctc tcacctcagc tcctgtaaaa   3540
gagtggcaag taaaaaacat ggggctctga ttctcctgta attgtgataa ttaaatatac   3600
acacaatcat gacattgaga agaactgcat ttctacccct aaaaagtact ggtatataca   3660
gaaatagggt taaaaaaaac tcaagctctc tctatatgag accaaaatgt actagagtta   3720
gtttagtgaa ataaaaaacc agtcagctgg ccgggcatgg tggctcatgc ttgtaatccc   3780
agcactttgg gaggccgagg caggtggatc acgaggtcag gagtttgaga ccagtctggc   3840
caacatggtg aaaccccgtc tgtactaaaa atacaaaaat tagctgggcg tggtggtggg   3900
tgcctgtaat cccagctact ggggaggctg aggcaggaga tcgcttgaa cccgggaggt   3960 ggaggtggca gtgagccgag atcacgccac tgcaatgcag cccgggcaac agagctagac   4020
tgtctcaaaa gaacaaaaaa aaaaaaacac aaaaaaactc agtcagcttc ttaaccaatt   4080
gcttccgtgt catccagggc cccattctgt gcagattgag tgtgggcacc acacaggtgg   4140
ttgctgcttc agtgcttcct gctctttttc cttgggcctg cttctgggtt ccatagggaa   4200
acagtaagaa agaaagacac atccttacca taaatgcata tggtccacct acaaatagaa   4260
aaatatttaa atgatctgcc tttatacaaa gtgatattct ctacctttga taatttacct   4320
gcttaaatgt tttatctgc actgcaaagt actgtatcca agtaaaatt tcctcatcca   4380 atatctttca aactgttttg ttaactaatg ccatatattt gtaagtatct gcacacttga   4440
tacagcaacg ttagatggtt ttgatggtaa acccctaaagg aggactccaa gagtgtgtat   4500
ttatttatag ttttatcaga gatgacaatt atttgaatgc caattatatg gattccttc   4560 attttttgct ggaggatggg agaagaaacc aaagtttata gaccttcaca ttgagaaagc   4620
```

```
ttcagttttg aacttcagct atcagattca aaaacaacag aaagaaccaa gacattctta    4680
agatgcctgt actttcagct gggtataaat tcatgagttc aaagattgaa acctgaccaa    4740
tttgctttat ttcatggaag aagtgatcta caaggtgtt tgtgccattt ggaaaacagc     4800
gtgcatgtgt tcaagcctta gattggcgat gtcgtatttt cctcacgtgt ggcaatgcca    4860
aaggctttac tttacctgtg agtacacact atatgaatta tttccaacgt acatttaatc    4920
aataagggtc acaaattccc aaatcaatct ctggaataaa tagagaggta attaaattgc    4980
tggagccaac ta                                                        4992
```

<210> SEQ ID NO 92
<211> LENGTH: 1049
<212> TYPE: PRT
<213> ORGANISM: Homo sapiens

<400> SEQUENCE: 92

```
Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300
```

```
Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
            325                 330                 335

His Phe Leu Pro Ser Leu Ile Gln Leu Asp Leu Ser Phe Asn Phe Glu
                340                 345                 350

Leu Gln Val Tyr Arg Ala Ser Met Asn Leu Ser Gln Ala Phe Ser Ser
            355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
    435                 440                 445

Arg Thr Ser Val Glu Ser Tyr Glu Pro Gln Val Leu Glu Gln Leu His
450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
            515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
    595                 600                 605

Ser Ser Ser Thr Ser Arg Thr Met Glu Ser Glu Ser Leu Arg Thr Leu
610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
            645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
            675                 680                 685

Ser Phe Ser Trp Lys Lys Leu Gln Cys Leu Lys Asn Leu Glu Thr Leu
            690                 695                 700

Asp Leu Ser His Asn Gln Leu Thr Thr Val Pro Glu Arg Leu Ser Asn
705                 710                 715                 720
```

Cys Ser Arg Ser Leu Lys Asn Leu Ile Leu Lys Asn Asn Gln Ile Arg
              725                 730                 735

Ser Leu Thr Lys Tyr Phe Leu Gln Asp Ala Phe Gln Leu Arg Tyr Leu
        740                 745                 750

Asp Leu Ser Ser Asn Lys Ile Gln Met Ile Gln Lys Thr Ser Phe Pro
    755                 760                 765

Glu Asn Val Leu Asn Asn Leu Lys Met Leu Leu Leu His His Asn Arg
770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe Leu Gln Leu Arg Lys Arg Leu Cys
        995                 1000                1005

Gly Ser Ser Val Leu Glu Trp Pro Thr Asn Pro Gln Ala His Pro
1010                1015                1020

Tyr Phe Trp Gln Cys Leu Lys Asn Ala Leu Ala Thr Asp Asn His
    1025                1030                1035

Val Ala Tyr Ser Gln Val Phe Lys Glu Thr Val
    1040                1045

<210> SEQ ID NO 93
<211> LENGTH: 1972
<212> TYPE: DNA
<213> ORGANISM: Homo sapiens

<400> SEQUENCE: 93
gaaactcccg cctggccacc ataaaagcgc cggccctccg cttccccgcg agacgaaact      60
tcccgtcccg gcggctctgg cacccagggt ccggcctgcg ccttcccgcc aggcctggac     120
actggttcaa cacctgtgac ttcatgtgtg cgcgccggcc acacctgcag tcacacctgt     180
agccccctct gccaagagat ccataccgag gcagcgtcgg tggctacaag ccctcagtcc     240

-continued

```
acacctgtgg acacctgtga cacctggcca cacgacctgt ggccgcggcc tggcgtctgc      300
tgcgacagga gcccttacct ccctgttat  aacacctgac cgccacctaa ctgcccctgc      360
agaaggagca atggccttgg ctcctgagag ggcagcccca cgcgtgctgt tcggagagtg      420
gctccttgga gagatcagca gcggctgcta tgaggggctg cagtggctgg acgaggcccg      480
cacctgtttc cgcgtgccct ggaagcactt cgcgcgcaag gacctgagcg aggccgacgc      540
gcgcatcttc aaggcctggg ctgtggcccg cggcaggtgg ccgcctagca gcaggggagg      600
tggcccgccc ccgaggctg  agactgcgga gcgcgccggc tggaaaacca acttccgctg      660
cgcactgcgc agcacgcgtc gcttcgtgat gctgcgggat aactcggggg acccggccga      720
cccgcacaag gtgtacgcgc tcagccggga gctgtgctgg cgagaaggcc caggcacgga      780
ccagactgag gcagaggccc ccgcagctgt cccaccacca cagggtgggc cccagggcc       840
attcctggca cacacacatg ctggactcca agccccaggc ccctccctg  cccagctgg       900
tgacaagggg gacctcctgc tccaggcagt gcaacagagc tgcctggcag accatctgct      960
gacagcgtca tgggggcag  atccagtccc aaccaaggct cctggagagg acaagaagg      1020
gcttcccctg actggggcct gtgctggagg cccagggctc cctgctgggg agctgtacgg     1080
gtgggcagta gagacgaccc ccagcccgg  gccccagccc gcggcactaa cgacaggcga     1140
ggccgcggcc ccagagtccc cgcaccaggc agagccgtac ctgtcaccct cccaagcgc      1200
ctgcaccgcg gtgcaagagc ccagcccagg ggcgctggac gtgaccatca tgtacaaggg     1260
ccgcacggtg ctgcagaagg tggtgggaca cccgagctgc acgttcctat acggcccccc     1320
agacccagct gtccgggcca cagacccca  gcaggtagca ttccccagcc ctgccgagct     1380
cccggaccag aagcagctgc gctacacgga ggaactgctg cggcacgtgg cccctgggtt     1440
gcacctggag cttcggggc  cacagctgtg ggccgcgc   atgggcaagt gcaaggtgta     1500
ctgggaggtg ggcggacccc caggctccgc cagcccctcc accccagcct gctgctgcc      1560
tcggaactgt gacaccccca tcttcgactt cagagtcttc ttccaagagc tggtggaatt     1620
ccgggcacgg cagcgccgtg gctccccacg ctataccatc tacctgggct cgggcagga     1680
cctgtcagct gggaggccca aggagaagag cctggtcctg gtgaagctgg aaccctggct     1740
gtgccgagtg cacctagagg gcacgcagcg tgagggtgtg tcttccctgg atagcagcag     1800
cctcagcctc tgcctgtcca gcgccaacag cctctatgac gacatcgagt gcttccttat     1860
ggagctggag cagcccgcct agaacccagt ctaatgagaa ctccagaaag ctggagcagc     1920
ccacctagag ctggccgcgg ccgcccagtc taataaaaag aactccagaa ca            1972
```

<210> SEQ ID NO 94
<211> LENGTH: 503
<212> TYPE: PRT
<213> ORGANISM: Homo sapiens

<400> SEQUENCE: 94

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro

-continued

```
                65                  70                  75                  80
Pro Glu Ala Glu Thr Ala Glu Arg Ala Gly Trp Lys Thr Asn Phe Arg
                    85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Gln Gly Gly Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
    275                 280                 285

Leu Asp Val Thr Ile Met Tyr Lys Gly Arg Thr Val Leu Gln Lys Val
290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Ser Ser Ser Leu Ser Leu
465                 470                 475                 480

Cys Leu Ser Ser Ala Asn Ser Leu Tyr Asp Asp Ile Glu Cys Phe Leu
                485                 490                 495
```

Met Glu Leu Glu Gln Pro Ala
            500

<210> SEQ ID NO 95
<211> LENGTH: 1885
<212> TYPE: DNA
<213> ORGANISM: Homo sapiens

<400> SEQUENCE: 95

| | | | | | |
|---|---|---|---|---|---|
| gaaactcccg | cctggccacc | ataaaagcgc | cggccctccg | cttccccgcg | agacgaaact | 60 |
| tcccgtcccg | gcggctctgg | cacccagggt | ccggcctgcg | ccttcccgcc | aggcctggac | 120 |
| actggttcaa | cacctgtgac | ttcatgtgtg | cgcgccggcc | acacctgcag | tcacacctgt | 180 |
| agcccctct | gccaagagat | ccataccgag | gcagcgtcgg | tggctacaag | ccctcagtcc | 240 |
| acacctgtgg | acacctgtga | cacctggcca | cacgacctgt | ggccgcggcc | tggcgtctgc | 300 |
| tgcgacagga | gcccttacct | cccctgttat | aacacctgac | cgccacctaa | ctgcccctgc | 360 |
| agaaggagca | atggccttgg | ctcctgagag | ggcagcccca | cgcgtgctgt | tcggagagtg | 420 |
| gctccttgga | gagatcagca | gcggctgcta | tgaggggctg | cagtggctgg | acgaggcccg | 480 |
| cacctgtttc | cgcgtgccct | ggaagcactt | cgcgcgcaag | acctgagcg | aggccgacgc | 540 |
| gcgcatcttc | aaggcctggg | ctgtggcccg | cggcaggtgg | ccgcctagca | gcaggggagg | 600 |
| tggcccgccc | cccgaggctg | agactgcgga | gcgcgccggc | tggaaaacca | acttccgctg | 660 |
| cgcactgcgc | agcacgcgtc | gcttcgtgat | gctgcgggat | aactcggggg | acccggccga | 720 |
| cccgcacaag | gtgtacgcgc | tcagccggga | gctgtgctgg | cgagaaggcc | caggcacgga | 780 |
| ccagactgag | gcagaggccc | ccgcagctgt | cccaccacca | cagggtgggc | cccagggcc | 840 |
| attcctggca | cacacacatg | ctggactcca | agccccaggc | cccctccctg | cccagctgg | 900 |
| tgacaagggg | gacctcctgc | tccaggcagt | gcaacagagc | tgcctggcag | accatctgct | 960 |
| gacagcgtca | tgggggggcag | atccagtccc | aaccaaggct | cctggagagg | acaagaagg | 1020 |
| gcttcccctg | actggggcct | gtgctggagg | cgaggccgcg | gccccagagt | ccccgcacca | 1080 |
| ggcagagccg | tacctgtcac | cctccccaag | cgcctgcacc | gcggtgcaag | agcccagccc | 1140 |
| aggggcgctg | gacgtgacca | tcatgtacaa | gggccgcacg | gtgctgcaga | aggtggtggg | 1200 |
| acacccgagc | tgcacgttcc | tatacggccc | cccagcccca | gctgtccggg | ccacagaccc | 1260 |
| ccagcaggta | gcattcccca | gccctgccga | gctcccggac | cagaagcagc | tgcgctacac | 1320 |
| ggaggaactg | ctgcggcacg | tggccctgg | gttgcacctg | gagcttcggg | ggccacagct | 1380 |
| gtgggcccgg | cgcatgggca | agtgcaaggt | gtactgggag | gtgggcggac | ccccaggctc | 1440 |
| cgccagcccc | tccaccccag | cctgcctgct | gcctcggaac | tgtgacaccc | ccatcttcga | 1500 |
| cttcagagtc | ttcttccaag | agctggtgga | attccgggca | cggcagcgcc | gtggctcccc | 1560 |
| acgctatacc | atctacctgg | gcttcgggca | ggacctgtca | gctgggaggc | caaggagaa | 1620 |
| gagcctggtc | ctggtgaagc | tggaaccctg | gctgtgccga | gtgcacctag | agggcacgca | 1680 |
| gcgtgagggt | gtgtcttccc | tggatagcag | cagcctcagc | ctctgcctgt | ccagcgccaa | 1740 |
| cagcctctat | gacgacatcg | agtgcttcct | tatggagctg | gagcagcccg | cctagaaccc | 1800 |
| agtctaatga | gaactccaga | aagctggagc | agcccaccta | gagctggccg | cggccgccca | 1860 |
| gtctaataaa | aagaactcca | gaaca | | | | 1885 |

<210> SEQ ID NO 96
<211> LENGTH: 474

<212> TYPE: PRT
<213> ORGANISM: Homo sapiens

<400> SEQUENCE: 96

```
Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Glu Ala Ala Pro Glu Ser Pro His Gln Ala Glu Pro
225                 230                 235                 240

Tyr Leu Ser Pro Ser Pro Ser Ala Cys Thr Ala Val Gln Glu Pro Ser
                245                 250                 255

Pro Gly Ala Leu Asp Val Thr Ile Met Tyr Lys Gly Arg Thr Val Leu
            260                 265                 270

Gln Lys Val Val Gly His Pro Ser Cys Thr Phe Leu Tyr Gly Pro Pro
        275                 280                 285

Asp Pro Ala Val Arg Ala Thr Asp Pro Gln Gln Val Ala Phe Pro Ser
    290                 295                 300

Pro Ala Glu Leu Pro Asp Gln Lys Gln Leu Arg Tyr Thr Glu Glu Leu
305                 310                 315                 320

Leu Arg His Val Ala Pro Gly Leu His Leu Glu Leu Arg Gly Pro Gln
                325                 330                 335

Leu Trp Ala Arg Arg Met Gly Lys Cys Lys Val Tyr Trp Glu Val Gly
            340                 345                 350

Gly Pro Pro Gly Ser Ala Ser Pro Ser Thr Pro Ala Cys Leu Leu Pro
        355                 360                 365

Arg Asn Cys Asp Thr Pro Ile Phe Asp Phe Val Phe Gln Glu
    370                 375                 380

Leu Val Glu Phe Arg Ala Arg Gln Arg Arg Gly Ser Pro Arg Tyr Thr
385                 390                 395                 400
```

```
Ile Tyr Leu Gly Phe Gly Gln Asp Leu Ser Ala Gly Arg Pro Lys Glu
                405                 410                 415
Lys Ser Leu Val Leu Val Lys Leu Glu Pro Trp Leu Cys Arg Val His
            420                 425                 430
Leu Glu Gly Thr Gln Arg Glu Gly Val Ser Ser Leu Asp Ser Ser Ser
        435                 440                 445
Leu Ser Leu Cys Leu Ser Ser Ala Asn Ser Leu Tyr Asp Asp Ile Glu
    450                 455                 460
Cys Phe Leu Met Glu Leu Gln Pro Ala
465                 470
```

<210> SEQ ID NO 97
<211> LENGTH: 860
<212> TYPE: DNA
<213> ORGANISM: Homo sapiens

<400> SEQUENCE: 97

```
ccagccttca gccggagaac cgtttactcg ctgctgtgcc catctatcag caggctccgg      60
gctgaagatt gcttctcttc tctcctccaa ggtctagtga cggagcccgc gcgcggcgcc    120
accatgcggc agaaggcggt atcgcttttc ttgtgctacc tgctgctctt cacttgcagt    180
ggggtggagg caggtgagaa tgcgggtaag gatgcaggta agaaaaagtg ctcggagagc    240
tcggacagcg gctccgggtt ctggaaggcc ctgaccttca tggccgtcgg aggaggactc    300
gcagtcgccg ggctgcccgc gctgggcttc accggcgccg gcatcgcggc caactcggtg    360
gctgcctcgc tgatgagctg gtctgcgatc ctgaatgggg gcggcgtgcc cgccgggggg    420
ctagtggcca cgctgcagag cctcggggct ggtggcagca gcgtcgtcat aggtaatatt    480
ggtgccctga tgggctacgc cacccacaag tatctcgata gtgaggagga tgaggagtag    540
ccagcagctc ccagaaccct cttcttcttc ttggcctaac tcttccagtt aggatctaga    600
actttgcctt tttttttttt ttttttttt tgagatgggt tctcactata ttgtccaggc    660
tagagtgcag tggctattca cagatgcgaa catagtacac tgcagcctcc aactcctagc    720
ctcaagtgat cctcctgtct caacctccca agtaggatta caagcatgcg ccgacgatgc    780
ccagaatcca gaactttgtc tatcactctc cccaacaacc tagatgtgaa aacagaataa    840
acttcacccca gaaaacactt                                               860
```

<210> SEQ ID NO 98
<211> LENGTH: 138
<212> TYPE: PRT
<213> ORGANISM: Homo sapiens

<400> SEQUENCE: 98

```
Met Arg Gln Lys Ala Val Ser Leu Phe Leu Cys Tyr Leu Leu Leu Phe
1               5                   10                  15
Thr Cys Ser Gly Val Glu Ala Gly Glu Asn Ala Gly Lys Asp Ala Gly
            20                  25                  30
Lys Lys Lys Cys Ser Glu Ser Ser Asp Ser Gly Ser Gly Phe Trp Lys
        35                  40                  45
Ala Leu Thr Phe Met Ala Val Gly Gly Gly Leu Ala Val Ala Gly Leu
    50                  55                  60
Pro Ala Leu Gly Phe Thr Gly Ala Gly Ile Ala Ala Asn Ser Val Ala
65                  70                  75                  80
Ala Ser Leu Met Ser Trp Ser Ala Ile Leu Asn Gly Gly Gly Val Pro
                85                  90                  95
```

Ala Gly Gly Leu Val Ala Thr Leu Gln Ser Leu Gly Ala Gly Gly Ser
            100                 105                 110

Ser Val Val Ile Gly Asn Ile Gly Ala Leu Met Gly Tyr Ala Thr His
        115                 120                 125

Lys Tyr Leu Asp Ser Glu Glu Asp Glu Glu
    130                 135

<210> SEQ ID NO 99
<211> LENGTH: 848
<212> TYPE: DNA
<213> ORGANISM: Homo sapiens

<400> SEQUENCE: 99
ccagccttca gccggagaac cgtttactcg ctgctgtgcc catctatcag caggctccgg      60
gctgaagatt gcttctcttc tctcctccaa ggtctagtga cggagcccgc gcgcggcgcc    120
accatgcggc agaaggcggt atcgcttttc ttgtgctacc tgctgctctt cacttgcagt    180
ggggtggagg caggtgagaa tgcgggtaag aaaaagtgct cggagagctc ggacagcggc    240
tccgggttct ggaaggccct gaccttcatg gccgtcggag gaggactcgc agtcgccggg    300
ctgcccgcgc tgggcttcac cggcgccggc atcgcggcca actcggtggc tgcctcgctg    360
atgagctggt ctgcgatcct gaatgggggc ggcgtgcccg ccgggggct agtggccacg     420
ctgcagagcc tcgggctgg tggcagcagc gtcgtcatag gtaatattgg tgccctgatg    480
ggctacgcca cccacaagta tctcgatagt gaggaggatg aggagtagcc agcagctccc    540
agaacctctt cttccttctt ggcctaactc ttccagttag gatctagaac tttgcctttt    600
tttttttttt tttttttttg agatgggttc tcactatatt gtccaggcta gagtgcagtg    660
gctattcaca gatgcgaaca tagtacactg cagcctccaa ctcctagcct caagtgatcc    720
tcctgtctca acctcccaag taggattaca agcatgcgcc gacgatgccc agaatccaga    780
actttgtcta tcactctccc caacaaccta gatgtgaaaa cagaataaac ttcacccaga    840
aaacactt                                                            848

<210> SEQ ID NO 100
<211> LENGTH: 134
<212> TYPE: PRT
<213> ORGANISM: Homo sapiens

<400> SEQUENCE: 100

Met Arg Gln Lys Ala Val Ser Leu Phe Leu Cys Tyr Leu Leu Leu Phe
1               5                   10                  15

Thr Cys Ser Gly Val Glu Ala Gly Glu Asn Ala Gly Lys Lys Lys Cys
            20                  25                  30

Ser Glu Ser Ser Asp Ser Gly Ser Gly Phe Trp Lys Ala Leu Thr Phe
        35                  40                  45

Met Ala Val Gly Gly Gly Leu Ala Val Ala Gly Leu Pro Ala Leu Gly
    50                  55                  60

Phe Thr Gly Ala Gly Ile Ala Ala Asn Ser Val Ala Ala Ser Leu Met
65                  70                  75                  80

Ser Trp Ser Ala Ile Leu Asn Gly Gly Gly Val Pro Ala Gly Gly Leu
                85                  90                  95

Val Ala Thr Leu Gln Ser Leu Gly Ala Gly Gly Ser Ser Val Val Ile
            100                 105                 110

Gly Asn Ile Gly Ala Leu Met Gly Tyr Ala Thr His Lys Tyr Leu Asp
        115                 120                 125

Ser Glu Glu Asp Glu Glu
    130

<210> SEQ ID NO 101
<211> LENGTH: 836
<212> TYPE: DNA
<213> ORGANISM: Homo sapiens

<400> SEQUENCE: 101
ccagccttca gccggagaac cgtttactcg ctgctgtgcc catctatcag caggctccgg      60
gctgaagatt gcttctcttc tctcctccaa ggtctagtga cggagcccgc gcgcggcgcc     120
accatgcggc agaaggcggt atcgcttttc ttgtgctacc tgctgctctt cacttgcagt     180
ggggtggagg caggtaagaa aaagtgctcg gagagctcgg acagcggctc cgggttctgg     240
aaggccctga ccttcatggc cgtcggagga ggactcgcag tcgccgggct gcccgcgctg     300
ggcttcaccg gcgccggcat cgcggccaac tcggtggctg cctcgctgat gagctggtct     360
gcgatcctga atggggcgg cgtgcccgcc ggggggctag tggccacgct gcagagcctc     420
ggggctggtg gcagcagcgt cgtcataggt aatattggtg ccctgatggg ctacgccacc     480
cacaagtatc tcgatagtga ggaggatgag gagtagccag cagctcccag aacctcttct     540
tccttcttgg cctaactctt ccagttagga tctagaactt tgccttttt tttttttttt     600
tttttttgag atgggttctc actatattgt ccaggctaga gtgcagtggc tattcacaga     660
tgcgaacata gtacactgca gcctccaact cctagcctca agtgatcctc ctgtctcaac     720
ctcccaagta ggattacaag catgcgccga cgatgcccag aatccagaac tttgtctatc     780
actctcccca caacctaga tgtgaaaaca gaataaactt cacccagaaa acactt        836

<210> SEQ ID NO 102
<211> LENGTH: 130
<212> TYPE: PRT
<213> ORGANISM: Homo sapiens

<400> SEQUENCE: 102

Met Arg Gln Lys Ala Val Ser Leu Phe Leu Cys Tyr Leu Leu Leu Phe
1               5                   10                  15

Thr Cys Ser Gly Val Glu Ala Gly Lys Lys Lys Cys Ser Glu Ser Ser
            20                  25                  30

Asp Ser Gly Ser Gly Phe Trp Lys Ala Leu Thr Phe Met Ala Val Gly
        35                  40                  45

Gly Gly Leu Ala Val Ala Gly Leu Pro Ala Leu Gly Phe Thr Gly Ala
    50                  55                  60

Gly Ile Ala Ala Asn Ser Val Ala Ala Ser Leu Met Ser Trp Ser Ala
65                  70                  75                  80

Ile Leu Asn Gly Gly Val Pro Ala Gly Gly Leu Val Ala Thr Leu
                85                  90                  95

Gln Ser Leu Gly Ala Gly Gly Ser Val Val Ile Gly Asn Ile Gly
            100                 105                 110

Ala Leu Met Gly Tyr Ala Thr His Lys Tyr Leu Asp Ser Glu Glu Asp
        115                 120                 125

Glu Glu
    130

<210> SEQ ID NO 103
<211> LENGTH: 4326
<212> TYPE: DNA

<213> ORGANISM: Homo sapiens

<400> SEQUENCE: 103

| | | | | | |
|---|---|---|---|---|---|
| gctgagcgcg | gagccgcccg | gtgattggtg | ggggcggaag | ggggccgggc | gccagcgctg | 60
| ccttttctcc | tgccgggtag | tttcgctttc | ctgcgcagag | tctgcggagg | ggctcggctg | 120
| caccgggggg | atcgcgcctg | gcagacccca | gaccgagcag | aggcgaccca | gcgcgctcgg | 180
| gagaggctgc | accgccgcgc | ccccgcctag | cccttccgga | tcctgcgcgc | agaaaagttt | 240
| catttgctgt | atgccatcct | cgagagctgt | ctaggttaac | gttcgcactc | tgtgtatata | 300
| acctcgacag | tcttggcacc | taacgtgctg | tgcgtagctg | ctcctttggt | tgaatcccca | 360
| ggcccttgtt | ggggcacaag | gtggcaggat | gtctcagtgg | tacgaacttc | agcagcttga | 420
| ctcaaaattc | ctggagcagg | ttcaccagct | ttatgatgac | agttttccca | tggaaatcag | 480
| acagtacctg | gcacagtggt | tagaaaagca | agactgggag | cacgctgcca | atgatgtttc | 540
| atttgccacc | atccgttttc | atgacctcct | gtcacagctg | gatgatcaat | atagtcgctt | 600
| ttctttggag | aataacttct | tgctacagca | taacataagg | aaaagcaagc | gtaatcttca | 660
| ggataatttt | caggaagacc | caatccagat | gtctatgatc | atttacagct | gtctgaagga | 720
| agaaaggaaa | attctggaaa | acgcccgag | atttaatcag | gctcagtcgg | ggaatattca | 780
| gagcacagtg | atgttagaca | aacagaaaga | gcttgacagt | aaagtcagaa | atgtgaagga | 840
| caaggttatg | tgtatagagc | atgaaatcaa | gagcctggaa | gatttacaag | atgaatatga | 900
| cttcaaatgc | aaaaccttgc | agaacagaga | acacgagacc | aatggtgtgg | caaagagtga | 960
| tcagaaacaa | gaacagctgt | tactcaagaa | gatgtatttta | atgcttgaca | taagagaaa | 1020
| ggaagtagtt | cacaaaataa | tagagttgct | gaatgtcact | gaacttaccc | agaatgccct | 1080
| gattaatgat | gaactagtgg | agtggaagcg | gagacagcag | agcgcctgta | ttggggggcc | 1140
| gcccaatgct | tgcttggatc | agctgcagaa | ctggttcact | atagttgcgg | agagtctgca | 1200
| gcaagttcgg | cagcagctta | aaagttgga | ggaattggaa | cagaaataca | cctacgaaca | 1260
| tgaccctatc | acaaaaaaca | aacaagtgtt | atgggaccgc | accttcagtc | ttttccagca | 1320
| gctcattcag | agctcgtttg | tggtggaaag | acagccctgc | atgccaacgc | accctcagag | 1380
| gccgctggtc | ttgaagacag | gggtccagtt | cactgtgaag | ttgagactgt | tggtgaaatt | 1440
| gcaagagctg | aattataatt | tgaaagtcaa | agtcttattt | gataaagatg | tgaatgagag | 1500
| aaatacagta | aaaggattta | ggaagttcaa | cattttgggc | acgcacacaa | aagtgatgaa | 1560
| catggaggag | tccaccaatg | gcagtctggc | ggctgaattt | cggcacctgc | aattgaaaga | 1620
| acagaaaaat | gctggcacca | gaacgaatga | gggtcctctc | atcgttactg | aagagcttca | 1680
| ctcccttagt | tttgaaaccc | aattgtgcca | gcctggtttg | gtaattgacc | tcgagacgac | 1740
| ctctctgccc | gttgtggtga | tctccaacgt | cagccagctc | ccgagcggtt | gggcctccat | 1800
| cctttggtac | aacatgctgg | tggcggaacc | caggaatctg | tccttcttcc | tgactccacc | 1860
| atgtgcacga | tgggctcagc | tttcagaagt | gctgagttgg | cagttttctt | ctgtcaccaa | 1920
| aagaggtctc | aatgtggacc | agctgaacat | gttgggagag | aagcttcttg | gtcctaacgc | 1980
| cagccccgat | ggtctcattc | cgtggacgag | gttttgtaag | gaaaatataa | atgataaaaa | 2040
| ttttccttc | tggctttgga | ttgaaagcat | cctagaactc | attaaaaaac | acctgctccc | 2100
| tctctggaat | gatgggtgca | tcatgggctt | catcagcaag | gagcgagagc | gtgccctgtt | 2160
| gaaggaccag | cagccgggga | ccttcctgct | gcggttcagt | gagagctccc | gggaagggggc | 2220
| catcacattc | acatgggtgg | agcggtccca | gaacggaggc | gaacctgact | tccatgcggt | 2280

```
tgaaccctac acgaagaaag aactttctgc tgttactttc cctgacatca ttcgcaatta    2340
caaagtcatg gctgctgaga atattcctga gaatcccctg aagtatctgt atccaaatat    2400
tgacaaagac catgcctttg gaaagtatta ctccaggcca aaggaagcac cagagccaat    2460
ggaacttgat ggccctaaag gaactggata tatcaagact gagttgattt ctgtgtctga    2520
agttcaccct tctagacttc agaccacaga caacctgctc cccatgtctc ctgaggagtt    2580
tgacgaggtg tctcggatag tgggctctgt agaattcgac agtatgatga acacagtata    2640
gagcatgaat tttttcatc ttctctggcg acagttttcc ttctcatctg tgattccctc    2700
ctgctactct gttccttcac atcctgtgtt tctagggaaa tgaaagaaag gccagcaaat    2760
tcgctgcaac ctgttgatag caagtgaatt tttctctaac tcagaaacat cagttactct    2820
gaagggcatc atgcatctta ctgaaggtaa aattgaaagg cattctctga agagtgggtt    2880
tcacaagtga aaacatcca gatacaccca agtatcagg acgagaatga gggtcctttg    2940
ggaaaggaga agttaagcaa catctagcaa atgttatgca taaagtcagt gcccaactgt    3000
tataggttgt tggataaatc agtggttatt tagggaactg cttgacgtag gaacggtaaa    3060
tttctgtggg agaattctta catgttttct ttgctttaag tgtaactggc agttttccat    3120
tggtttacct gtgaaatagt tcaaagccaa gtttatatac aattatatca gtcctctttc    3180
aaaggtagcc atcatggatc tggtagggg aaaatgtgta ttttattaca tctttcacat    3240
tggctattta aagacaaaga caaattctgt ttcttgagaa gagaatatta gctttactgt    3300
ttgttatggc ttaatgacac tagctaatat caatagaagg atgtacattt ccaaattcac    3360
aagttgtgtt tgatatccaa agctgaatac attctgcttt catcttggtc acatacaatt    3420
atttttacag ttctcccaag ggagttaggc tattcacaac cactcattca aaagttgaaa    3480
ttaaccatag atgtagataa actcagaaat ttaattcatg tttcttaaat gggctacttt    3540
gtcctttttg ttattagggt ggtatttagt ctattagcca caaaattggg aaaggagtag    3600
aaaaagcagt aactgacaac ttgaataata caccagagat aatatgagaa tcagatcatt    3660
tcaaaactca tttcctatgt aactgcattg agaactgcat atgtttcgct gatatatgtg    3720
tttttcacat ttgcgaatgg ttccattctc tctcctgtac ttttccaga cacttttttg    3780 agtggatgat gtttcgtgaa gtatactgta tttttacctt tttccttcct tatcactgac    3840
acaaaaagta gattaagaga tgggtttgac aaggttcttc cctttacat actgctgtct    3900 atgtggctgt atcttgtttt tccactactg ctaccacaac tatattatca tgcaaatgct    3960
gtattcttct ttggtggaga taagatttc ttgagttttc tttttaaaatt aaagctaaag    4020 tatctgtatt gcattaaata taatatgcac acagtgcttt ccgtggcact gcatacaatc    4080
tgaggcctcc tctctcagtt tttatataga tggcgagaac ctaagtttca gttgatttta    4140
caattgaaat gactaaaaaa caaagaagac aacattaaaa caatattgtt tctaattgct    4200
gaggtttagc tgtcagttct ttttgccctt tgggaattcg gcatggtttc attttactgc    4260
actagccaag agactttact tttaagaagt attaaaattc taaaattcaa aaaaaaaaaa    4320
aaaaaa                                                                4326
```

<210> SEQ ID NO 104
<211> LENGTH: 2798
<212> TYPE: DNA
<213> ORGANISM: Homo sapiens

<400> SEQUENCE: 104

```
gctgagcgcg gagccgcccg gtgattggtg ggggcggaag ggggccgggc gccagcgctg      60
ccttttctcc tgccgggtag tttcgctttc ctgcgcagag tctgcggagg ggctcggctg     120
caccgggggg atcgcgcctg gcagacccca gaccgagcag aggcgaccca gcgcgctcgg     180
gagaggctgc accgccgcgc ccccgcctag cccttccgga tcctgcgcgc agaaaagttt     240
catttgctgt atgccatcct cgagagctgt ctaggttaac gttcgcactc tgtgtatata     300
acctcgacag tcttggcacc taacgtgctg tgcgtagctg ctcctttggt tgaatcccca     360
ggcccttgtt ggggcacaag gtggcaggat gtctcagtgg tacgaacttc agcagcttga     420
ctcaaaattc ctggagcagg ttcaccagct ttatgatgac agttttccca tggaaatcag     480
acagtacctg gcacagtggt tagaaaagca agactgggag cacgctgcca atgatgtttc     540
atttgccacc atccgttttc atgacctcct gtcacagctg gatgatcaat atagtcgctt     600
ttctttggag aataacttct tgctacagca taacataagg aaaagcaagc gtaatcttca     660
ggataatttt caggaagacc caatccagat gtctatgatc atttacagct gtctgaagga     720
agaaaggaaa attctggaaa acgcccagag atttaatcag gctcagtcgg ggaatattca     780
gagcacagtg atgttagaca aacagaaaga gcttgacagt aaagtcagaa atgtgaagga     840
caaggttatg tgtatagagc atgaaatcaa gagcctggaa gatttacaag atgaaatga     900
cttcaaatgc aaaaccttgc agaacagaga cacgagacc aatggtgtgg caaagagtga     960
tcagaaacaa gaacagctgt tactcaagaa gatgtattta atgcttgaca ataagagaaa    1020
ggaagtagtt cacaaaataa tagagttgct gaatgtcact gaacttaccc agaatgccct    1080
gattaatgat gaactagtgg agtggaagcg gagacagcag agcgcctgta ttgggggggcc    1140
gcccaatgct tgcttggatc agctgcagaa ctggttcact atagttgcgg agagtctgca    1200
gcaagttcgg cagcagctta aaaagttgga ggaattggaa cagaaataca cctacgaaca    1260
tgaccctatc acaaaaaaca aacaagtgtt atgggaccgc accttcagtc ttttccagca    1320
gctcattcag agctcgtttg tggtggaaag acagccctgc atgccaacgc accctcagag    1380
gccgctggtc ttgaagacag gggtccagtt cactgtgaag ttgagactgt tggtgaaatt    1440
gcaagagctg aattataatt tgaaagtcaa agtcttattt gataaagatg tgaatgagag    1500
aaatacagta aaaggattta ggaagttcaa cattttgggc acgcacacaa aagtgatgaa    1560
catggaggag tccaccaatg gcagtctggc ggctgaattt cggcacctgc aattgaaaga    1620
acagaaaaat gctggcacca gaacgaatga gggtcctctc atcgttactg aagagcttca    1680
ctcccttagt tttgaaaccc aattgtgcca gcctggtttg gtaattgacc tcgagacgac    1740
ctctctgccc gttgtggtga tctccaacgt cagccagctc ccgagcggtt gggcctccat    1800
cctttggtac aacatgctgg tggcggaacc caggaatctg tccttcttcc tgactccacc    1860
atgtgcacga tgggctcagc tttcagaagt gctgagttgg cagttttctt ctgtcaccaa    1920
aagaggtctc aatgtggacc agctgaacat gttgggagag aagcttcttg gtcctaacgc    1980
cagccccgat ggtctcattc cgtggacgag gtttttgtaag gaaaatataa atgataaaaa    2040
ttttcccttc tggctttgga ttgaaagcat cctagaactc attaaaaaac acctgctccc    2100
tctctggaat gatgggtgca tcatgggctt catcagcaag gagcgagagc gtgccctgtt    2160
gaaggaccag cagccgggga ccttcctgct gcggttcagt gagagctccc gggaagggggc    2220
catcacattc acatgggtgg agcggtccca gaacggaggc gaacctgact tccatgcggt    2280
tgaaccctac acgaagaaag aactttctgc tgttactttc cctgacatca ttcgcaatta    2340
caaagtcatg gctgctgaga atattcctga gaatcccctg aagtatctgt atccaaatat    2400
```

```
tgacaaagac catgcctttg gaaagtatta ctccaggcca aaggaagcac cagagccaat    2460
ggaacttgat ggccctaaag gaactggata tatcaagact gagttgattt ctgtgtctga    2520
agtgtaagtg aacacagaag agtgacatgt ttacaaacct caagccagcc ttgctcctgg    2580
ctggggcctg ttgaagatgc ttgtatttta ctttccatt gtaattgcta tcgccatcac     2640
agctgaactt gttgagatcc ccgtgttact gcctatcagc attttactac tttaaaaaaa    2700
aaaaaaaagc caaaaaccaa atttgtattt aaggtatata aattttccca aaactgatac    2760
cctttgaaaa agtataaata aaatgagcaa aagttgat                            2798
```

<210> SEQ ID NO 105
<211> LENGTH: 750
<212> TYPE: PRT
<213> ORGANISM: Homo sapiens

<400> SEQUENCE: 105

```
Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300
```

-continued

```
Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Val Lys Leu Gln
            340                 345                 350

Glu Leu Asn Tyr Asn Leu Lys Val Lys Val Leu Phe Asp Lys Asp Val
                355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
            435                 440                 445

Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720
```

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750

<210> SEQ ID NO 106
<211> LENGTH: 712
<212> TYPE: PRT
<213> ORGANISM: Homo sapiens

<400> SEQUENCE: 106

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

```
Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
                435                 440                 445

Glu Thr Thr Ser Leu Pro Val Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
    530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
    690                 695                 700

Glu Leu Ile Ser Val Ser Glu Val
705                 710

<210> SEQ ID NO 107
<211> LENGTH: 1742
<212> TYPE: DNA
<213> ORGANISM: Homo sapiens

<400> SEQUENCE: 107
tctttgaagc ttcaaggctg ctgaataatt tccttctccc attttgtgcc tgcctagcta      60
```

```
tccagacaga gcagctaccc tcagctctag ctgatactac agacagtaca acagatcaag    120
aagtatggca gtgacaactc gtttgacatg gttgcacgaa aagatcctgc aaaatcattt    180
tggagggaag cggcttagcc ttctctataa gggtagtgtc catggattcc gtaatggagt    240
tttgcttgac agatgttgta atcaagggcc tactctaaca gtgatttata gtgaagatca    300
tattattgga gcatatgcag aagagagtta ccaggaagga agtatgctt ccatcatcct    360 ttttgcactt caagatacta aaatttcaga atggaaacta ggactatgta caccagaaac    420
actgttttgt tgtgatgtta caaaatataa ctccccaact aatttccaga tagatggaag    480
aaatagaaaa gtgattatgg acttaaagac aatggaaaat cttggacttg ctcaaaattg    540
tactatctct attcaggatt atgaagtttt tcgatgcgaa gattcactgg atgaaagaaa    600
gataaaaggg gtcattgagc tcaggaagag cttactgtct gccttgagaa cttatgaacc    660
atatggatcc ctggttcaac aaatacgaat tctgctgctg gtccaattg agctgggaa     720 gtccagcttt tcaactcag tgaggtctgt tttccaaggg catgtaacgc atcaggcttt    780
ggtgggcact aatacaactg ggatatctga aagtatagg acatactcta ttagagacgg    840
gaaagatggc aaatacctgc cgtttattct gtgtgactca ctggggctga gtgagaaaga    900
aggcggcctg tgcagggatg acatattcta tatcttgaac ggtaacattc gtgatagata    960
ccagtttaat cccatggaat caatcaaatt aaatcatcat gactacattg attccccatc   1020
gctgaaggac agaattcatt gtgtggcatt tgtatttgat gccagctcta ttcaatactt   1080
ctcctctcag atgatagtaa agatcaaaag aattcgaagg gagttggtaa acgctggtgt   1140
ggtacatgtg gctttgctca ctcatgtgga tagcatggat ttgattacaa aggtgacct    1200 tatagaaata gagagatgtg agcctgtgag gtccaagcta gaggaagtcc aaagaaaact   1260
tggatttgct ctttctgaca tctcggtggt tagcaattat tcctctgagt gggagctgga   1320
ccctgtaaag gatgttctaa ttctttctgc tctgagacga atgctatggg ctgcagatga   1380
cttcttagag gatttgcctt tgagcaaat agggaatcta agggaggaaa ttatcaactg   1440
tgcacaagga aaaaatagat atgtgaaag gttcacgtaa atttcctcac atcacagaag   1500
attaaaattc agaaggaga aaacacagac caaagagaag tatctaagac caagggatg   1560 tgttttatta atgtctagga tgaagaaatg catagaacat tgtagtactt gtaaataact   1620
agaaataaca tgatttagtc ataattgtga aaaataataa taattttct tggatttatg   1680 ttctgtatct gtgaaaaaat aaatttctta taaaactcgg gtctaaaaa aaaaaaaaa    1740 aa                                                                  1742
```

<210> SEQ ID NO 108
<211> LENGTH: 444
<212> TYPE: PRT
<213> ORGANISM: Homo sapiens

<400> SEQUENCE: 108

Met Ala Val Thr Thr Arg Leu Thr Trp Leu His Glu Lys Ile Leu Gln
1               5                   10                  15

Asn His Phe Gly Gly Lys Arg Leu Ser Leu Leu Tyr Lys Gly Ser Val
            20                  25                  30

His Gly Phe Arg Asn Gly Val Leu Leu Asp Arg Cys Cys Asn Gln Gly
        35                  40                  45

Pro Thr Leu Thr Val Ile Tyr Ser Glu Asp His Ile Ile Gly Ala Tyr
    50                  55                  60

Ala Glu Glu Ser Tyr Gln Glu Gly Lys Tyr Ala Ser Ile Ile Leu Phe
 65                  70                  75                  80

Ala Leu Gln Asp Thr Lys Ile Ser Glu Trp Lys Leu Gly Leu Cys Thr
             85                  90                  95

Pro Glu Thr Leu Phe Cys Cys Asp Val Thr Lys Tyr Asn Ser Pro Thr
            100                 105                 110

Asn Phe Gln Ile Asp Gly Arg Asn Arg Lys Val Ile Met Asp Leu Lys
        115                 120                 125

Thr Met Glu Asn Leu Gly Leu Ala Gln Asn Cys Thr Ile Ser Ile Gln
    130                 135                 140

Asp Tyr Glu Val Phe Arg Cys Glu Asp Ser Leu Asp Glu Arg Lys Ile
145                 150                 155                 160

Lys Gly Val Ile Glu Leu Arg Lys Ser Leu Leu Ser Ala Leu Arg Thr
                165                 170                 175

Tyr Glu Pro Tyr Gly Ser Leu Val Gln Gln Ile Arg Ile Leu Leu Leu
            180                 185                 190

Gly Pro Ile Gly Ala Gly Lys Ser Ser Phe Phe Asn Ser Val Arg Ser
        195                 200                 205

Val Phe Gln Gly His Val Thr His Gln Ala Leu Val Gly Thr Asn Thr
    210                 215                 220

Thr Gly Ile Ser Glu Lys Tyr Arg Thr Tyr Ser Ile Arg Asp Gly Lys
225                 230                 235                 240

Asp Gly Lys Tyr Leu Pro Phe Ile Leu Cys Asp Ser Leu Gly Leu Ser
                245                 250                 255

Glu Lys Glu Gly Gly Leu Cys Arg Asp Asp Ile Phe Tyr Ile Leu Asn
            260                 265                 270

Gly Asn Ile Arg Asp Arg Tyr Gln Phe Asn Pro Met Glu Ser Ile Lys
        275                 280                 285

Leu Asn His His Asp Tyr Ile Asp Ser Pro Ser Leu Lys Asp Arg Ile
    290                 295                 300

His Cys Val Ala Phe Val Phe Asp Ala Ser Ser Ile Gln Tyr Phe Ser
305                 310                 315                 320

Ser Gln Met Ile Val Lys Ile Lys Arg Ile Arg Arg Glu Leu Val Asn
                325                 330                 335

Ala Gly Val Val His Val Ala Leu Leu Thr His Val Asp Ser Met Asp
            340                 345                 350

Leu Ile Thr Lys Gly Asp Leu Ile Glu Ile Glu Arg Cys Glu Pro Val
        355                 360                 365

Arg Ser Lys Leu Glu Val Gln Arg Lys Leu Gly Phe Ala Leu Ser
    370                 375                 380

Asp Ile Ser Val Val Ser Asn Tyr Ser Ser Glu Trp Glu Leu Asp Pro
385                 390                 395                 400

Val Lys Asp Val Leu Ile Leu Ser Ala Leu Arg Arg Met Leu Trp Ala
                405                 410                 415

Ala Asp Asp Phe Leu Glu Asp Leu Pro Phe Glu Gln Ile Gly Asn Leu
            420                 425                 430

Arg Glu Glu Ile Ile Asn Cys Ala Gln Gly Lys Lys
        435                 440

<210> SEQ ID NO 109
<211> LENGTH: 2808
<212> TYPE: DNA
<213> ORGANISM: Homo sapiens

<400> SEQUENCE: 109

```
gcggcggcgg cggcgcagtt tgctcatact ttgtgacttg cggtcacagt ggcattcagc    60
tccacacttg gtagaaccac aggcacgaca agcatagaaa catcctaaac aatcttcatc   120
gaggcatcga ggtccatccc aataaaaatc aggagaccct ggctatcata gaccttagtc   180
ttcgctggta tactcgctgt ctgtcaacca gcggttgact tttttttaagc cttcttttttt   240 ctcttttacc agtttctgga gcaaattcag tttgccttcc tggatttgta aattgtaatg   300
acctcaaaac tttagcagtt cttccatctg actcaggttt gcttctctgg cggtcttcag   360
aatcaacatc cacacttccg tgattatctg cgtgcatttt ggacaaagct tccaaccagg   420
atacgggaag aagaaatggc tggtgatctt tcagcaggtt tcttcatgga ggaacttaat   480
acataccgtc agaagcaggg agtagtactt aaatatcaag aactgcctaa ttcaggacct   540
ccacatgata ggaggtttac atttcaagtt ataatagatg gaagagaatt tccagaaggt   600
gaaggtagat caaagaagga agcaaaaaat gccgcagcca aattagctgt tgagatactt   660
aataaggaaa agaaggcagt tagtcccttta ttattgacaa caacgaattc ttcagaagga   720
ttatccatgg ggaattacat aggccttatc aatagaattg cccagaagaa aagactaact   780
gtaaattatg aacagtgtgc atcgggggtg catgggccag aaggatttca ttataaatgc   840
aaaatgggac agaaagaata tagtattggt acaggttcta ctaaacagga agcaaaacaa   900
ttggccgcta aacttgcata tcttcagata ttatcagaag aaacctcagt gaaatctgac   960
tacctgtcct ctggttcttt tgctactacg tgtgagtccc aaagcaactc tttagtgacc  1020
agcacactcg cttctgaatc atcatctgaa ggtgacttct cagcagatac atcagagata  1080
aattctaaca gtgacagttt aaacagttct tcgttgctta tgaatggtct cagaaataat  1140
caaaggaagg caaaaagatc tttggcaccc agatttgacc ttcctgacat gaaagaaaca  1200
aagtatactg tggacaagag gtttggcatg gattttaaag aaatagaatt aattggctca  1260
ggtggatttg gccaagtttt caaagcaaaa cacagaattg acggaaagac ttacgttatt  1320
aaacgtgtta aatataataa cgagaaggcg gagcgtgaag taaaagcatt ggcaaaactt  1380
gatcatgtaa atattgttca ctacaatggc tgttgggatg gatttgatta tgatcctgag  1440
accagtgatg attctcttga gagcagtgat tatgatcctg agaacagcaa aaatagttca  1500
aggtcaaaga ctaagtgcct tttcatccaa atggaattct gtgataaagg gaccttggaa  1560
caatggattg aaaaaagaag aggcgagaaa ctagacaaag ttttggcttt ggaactcttt  1620
gaacaaataa caaaaggggt ggattatata cattcaaaaa aattaattca tagagatctt  1680
aagccaagta atatattctt agtagataca aaacaagtaa agattggaga ctttggactt  1740
gtaacatctc tgaaaaatga tggaaagcga acaaggagta agggaacttt gcgatacatg  1800
agcccagaac agatttcttc gcaagactat ggaaggaag tggacctcta cgctttgggg  1860
ctaattcttg ctgaacttct tcatgtatgt gacactgctt ttgaaacatc aaagttttc  1920 acagacctac gggatggcat catctcagat atatttgata aaaagaaaaa actcttcta  1980 cagaaattac tctcaaagaa acctgaggat cgacctaaca catctgaaat actaaggacc  2040
ttgactgtgt ggaagaaaag cccagagaaa atgaacgac acacatgtta gagcccttct  2100
gaaaaagtat cctgcttctg atatgcagtt ttccttaaat tatctaaaat ctgctaggga  2160
atatcaatag atatttacct tttatttttaa tgtttccttt aatttttac tatttttact  2220 aatcttctg cagaaacaga aaggtttct tcttttttgct tcaaaaacat tcttacattt  2280
tactttttcc tggctcatct ctttattctt ttttttttt ttaaagacag agtctcgctc  2340
```

-continued

```
tgttgcccag gctggagtgc aatgacacag tcttggctca ctgcaacttc tgcctcttgg    2400
gttcaagtga ttctcctgcc tcagcctcct gagtagctgg attacaggca tgtgccaccc    2460
acccaactaa tttttgtgtt tttaataaag acagggtttc accatgttgg ccaggctggt    2520
ctcaaactcc tgacctcaag taatccacct gcctcggcct cccaaagtgc tgggattaca    2580
gggatgagcc accgcgccca gcctcatctc tttgttctaa agatggaaaa accaccccca    2640
aatttctttt ttatactatt aatgaatcaa tcaattcata tctatttatt aaatttctac    2700
cgcttttagg ccaaaaaaat gtaagatcgt tctctgcctc acatagctta caagccagct    2760
ggagaaatat ggtactcatt aaaaaaaaaa aaaagtgat gtacaacc                  2808
```

<210> SEQ ID NO 110
<211> LENGTH: 551
<212> TYPE: PRT
<213> ORGANISM: Homo sapiens

<400> SEQUENCE: 110

```
Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
                20                  25                  30

Ser Gly Pro Pro His Asp Arg Arg Phe Thr Phe Gln Val Ile Ile Asp
            35                  40                  45

Gly Arg Glu Phe Pro Glu Glu Gly Arg Ser Lys Lys Glu Ala Lys
        50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
                100                 105                 110

Arg Leu Thr Val Asn Tyr Glu Gln Cys Ala Ser Gly Val His Gly Pro
            115                 120                 125

Glu Gly Phe His Tyr Lys Cys Lys Met Gly Gln Lys Glu Tyr Ser Ile
        130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
                180                 185                 190

Leu Val Thr Ser Thr Leu Ala Ser Glu Ser Ser Glu Gly Asp Phe
            195                 200                 205

Ser Ala Asp Thr Ser Glu Ile Asn Ser Asn Ser Asp Ser Leu Asn Ser
        210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
                260                 265                 270

Ile Gly Ser Gly Gly Phe Gly Gln Val Phe Lys Ala Lys His Arg Ile
            275                 280                 285

Asp Gly Lys Thr Tyr Val Ile Lys Arg Val Lys Tyr Asn Asn Glu Lys
```

```
                290                 295                 300
Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
                340                 345                 350

Asn Ser Ser Arg Ser Lys Thr Lys Cys Leu Phe Ile Gln Met Glu Phe
                355                 360                 365

Cys Asp Lys Gly Thr Leu Glu Gln Trp Ile Glu Lys Arg Arg Gly Glu
                370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
                420                 425                 430

Phe Gly Leu Val Thr Ser Leu Lys Asn Asp Gly Lys Arg Thr Arg Ser
                435                 440                 445

Lys Gly Thr Leu Arg Tyr Met Ser Pro Glu Gln Ile Ser Ser Gln Asp
                450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
                500                 505                 510

Thr Leu Leu Gln Lys Leu Leu Ser Lys Lys Pro Glu Asp Arg Pro Asn
                515                 520                 525

Thr Ser Glu Ile Leu Arg Thr Leu Thr Val Trp Lys Lys Ser Pro Glu
                530                 535                 540

Lys Asn Glu Arg His Thr Cys
545                 550

<210> SEQ ID NO 111
<211> LENGTH: 2613
<212> TYPE: DNA
<213> ORGANISM: Homo sapiens

<400> SEQUENCE: 111
agtttcagtt tccatttctg atttctgctc tctgcgctga gcacagcggc accaggctga    60
gctaagcagg gccgccttgg gcaggcctac gtggtggtgc aggcgagacc caggctgggc   120
aaggcgcagt ttcagtttcc atcttgggtc tctgagctga gcagagtggc accaggctga   180
gttaagtggg actgccctgg gcagacctac ctactagagc agaatggagc ttcggtccta   240
ccaatgggag gtgatcatgc ctgccctgga gggcaagaat atcatcatct ggctgcccac   300
gggtgccggg aagacccggg cggctgctta tgtggccaag cggcacctag agactgtgga   360
tggagccaag gtggttgtat tggtcaacag ggtgcacctg gtgacccagc atggtgaaga   420
gttcaggcgc atgctggatg acgctggacc cgtgacaacc ctgagtgggg acatgggacc   480
acgtgctggc tttggccacc tggcccggtg ccatgacctg ctcatctgca cagcagagct   540
tctgcagatg gcactgacca gccccgagga ggaggagcac gtggagctca ctgtcttctc   600
cctgatcgtg gtggatgagt gccaccacac gcacaaggac accgtctaca cgtcatcat    660
```

```
gagccagtac ctagaactta aactccagag ggcacagccg ctaccccagg tgctgggtct    720
cacagcctcc ccaggcactg gcggggcctc caaactcgat ggggccatca accacgtcct    780
gcagctctgt gccaacttgg acacgtggtg catcatgtca ccccagaact gctgccccca    840
gctgcaggag cacagccaac agccttgcaa acagtacaac ctctgccaca ggcgcagcca    900
ggatccgttt ggggacttgc tgaagaagct catggaccaa atccatgacc acctggagat    960
gcctgagttg agccggaaat ttgggacgca aatgtatgag cagcaggtgg tgaagctgag   1020
tgaggctgcg gctttggctg gcttcagga gcaacgggtg tatgcgcttc acctgaggcg   1080
ctacaatgac gcgctgctca tccatgacac cgtccgcgcc gtggatgcct ggctgcgct   1140
gcaggatttc tatcacaggg agcacgtcac taaaacccag atcctgtgtg ccgagcgccg   1200
gctgctggcc ctgttcgatg accgcaagaa tgagctggcc cacttggcaa ctcatggccc   1260
agagaatcca aaactggaga tgctggaaaa gatcctgcaa aggcagttca gtagctctaa   1320
cagccctcgg ggtatcatct tcacccgcac ccgccaaagc gcacactccc tcctgctctg   1380
gctccagcag caacagggcc tgcagactgt ggacatccgg gcccagctac tgattggggc   1440
tgggaacagc agccagagca cccacatgac ccagagggac cagcaagaag tgatccagaa   1500
gttccaagat ggaacccctga accttctggt ggccacgagt gtggcggagg aggggctgga   1560
catcccacat tgcaatgtgg tggtgcgtta tgggctcttg accatgaaa tctccatggt   1620
ccaggccagg ggccgtgcct gggccgatca gagtgtatac gcgtttgtag caactgaagg   1680
tagccgggag ctgaagcggg agctgatcaa cgaggcgctg gagacgctaa tggagcaggc   1740
agtggctgct gtgcagaaaa tggaccaggc cgagtaccag gccaagatcc gggatctgca   1800
gcaggcagcc ttgaccaagc gggcggccca ggcagcccag cgggagaacc agcggcagca   1860
gttcccagtg gagcacgtgc agctactctg catcaactgc atggtggctg tgggccatgg   1920
cagcgacctg cggaaggtgg agggcaccca ccatgtcaat gtgaacccca acttctcgaa   1980
ctactataat gtctccaggg atcctgtggt catcaacaaa gtcttcaagg actggaagcc   2040
tgggggtgtc atcagctgca ggaactgtgg ggaggtctgg ggtctgcaga tgatctacaa   2100
gtcagtgaag ctgccagtgc tcaaagtccg cagcatgctg ctggagaccc ctcaggggcg   2160
gatccaggcc aaaaagtggt cccgcgtgcc cttctccgtg cctgactttg acttcctgca   2220
gcattgtgcc gagaacttgt cggacctctc cctggactga ccacctcatt gctgcagtgc   2280
ccggttttggg ctgtagggggg cgggagagtc tgcagcagac tccaggcccc tccttcctga   2340
atcatcagct gtgggcatca ggcccaccag ccacacagga gtcctgggca ccctggctta   2400
ggctcccgca atgggaaaac aaccggaggg ccagagctta gtccagacct accttgtacg   2460
cacatagaca tttcatatg cactggatgg agttagggaa actgaggcaa agaatttgc   2520
catactgtac tcagaatcac gacattcctt ccctaccaag gccacttcta ttttttgagg   2580
ctcctcataa aaataaatga aaaaatggga tag                                2613
```

<210> SEQ ID NO 112
<211> LENGTH: 678
<212> TYPE: PRT
<213> ORGANISM: Homo sapiens

<400> SEQUENCE: 112

Met Glu Leu Arg Ser Tyr Gln Trp Glu Val Ile Met Pro Ala Leu Glu
1               5                   10                  15

Gly Lys Asn Ile Ile Ile Trp Leu Pro Thr Gly Ala Gly Lys Thr Arg

```
                20                  25                  30
Ala Ala Ala Tyr Val Ala Lys Arg His Leu Glu Thr Val Asp Gly Ala
            35                  40                  45

Lys Val Val Val Leu Val Asn Arg Val His Leu Val Thr Gln His Gly
        50                  55                  60

Glu Glu Phe Arg Arg Met Leu Asp Gly Arg Trp Thr Val Thr Thr Leu
65                  70                  75                  80

Ser Gly Asp Met Gly Pro Arg Ala Gly Phe Gly His Leu Ala Arg Cys
                85                  90                  95

His Asp Leu Leu Ile Cys Thr Ala Glu Leu Leu Gln Met Ala Leu Thr
            100                 105                 110

Ser Pro Glu Glu Glu His Val Glu Leu Thr Val Phe Ser Leu Ile
        115                 120                 125

Val Val Asp Glu Cys His His Thr His Lys Asp Thr Val Tyr Asn Val
    130                 135                 140

Ile Met Ser Gln Tyr Leu Glu Leu Lys Leu Gln Arg Ala Gln Pro Leu
145                 150                 155                 160

Pro Gln Val Leu Gly Leu Thr Ala Ser Pro Gly Thr Gly Gly Ala Ser
                165                 170                 175

Lys Leu Asp Gly Ala Ile Asn His Val Leu Gln Leu Cys Ala Asn Leu
            180                 185                 190

Asp Thr Trp Cys Ile Met Ser Pro Gln Asn Cys Cys Pro Gln Leu Gln
        195                 200                 205

Glu His Ser Gln Gln Pro Cys Lys Gln Tyr Asn Leu Cys His Arg Arg
    210                 215                 220

Ser Gln Asp Pro Phe Gly Asp Leu Leu Lys Lys Leu Met Asp Gln Ile
225                 230                 235                 240

His Asp His Leu Glu Met Pro Glu Leu Ser Arg Lys Phe Gly Thr Gln
                245                 250                 255

Met Tyr Glu Gln Gln Val Val Lys Leu Ser Glu Ala Ala Ala Leu Ala
            260                 265                 270

Gly Leu Gln Glu Gln Arg Val Tyr Ala Leu His Leu Arg Arg Tyr Asn
        275                 280                 285

Asp Ala Leu Leu Ile His Asp Thr Val Arg Ala Val Asp Ala Leu Ala
    290                 295                 300

Ala Leu Gln Asp Phe Tyr His Arg Glu His Val Thr Lys Thr Gln Ile
305                 310                 315                 320

Leu Cys Ala Glu Arg Arg Leu Leu Ala Leu Phe Asp Asp Arg Lys Asn
                325                 330                 335

Glu Leu Ala His Leu Ala Thr His Gly Pro Glu Asn Pro Lys Leu Glu
            340                 345                 350

Met Leu Glu Lys Ile Leu Gln Arg Gln Phe Ser Ser Ser Asn Ser Pro
        355                 360                 365

Arg Gly Ile Ile Phe Thr Arg Thr Arg Gln Ser Ala His Ser Leu Leu
    370                 375                 380

Leu Trp Leu Gln Gln Gln Gly Leu Gln Thr Val Asp Ile Arg Ala
385                 390                 395                 400

Gln Leu Leu Ile Gly Ala Gly Asn Ser Ser Gln Ser Thr His Met Thr
                405                 410                 415

Gln Arg Asp Gln Gln Glu Val Ile Gln Lys Phe Gln Asp Gly Thr Leu
            420                 425                 430

Asn Leu Leu Val Ala Thr Ser Val Ala Glu Glu Gly Leu Asp Ile Pro
        435                 440                 445
```

-continued

```
His Cys Asn Val Val Val Arg Tyr Gly Leu Leu Thr Asn Glu Ile Ser
        450                 455             460

Met Val Gln Ala Arg Gly Arg Ala Arg Ala Asp Gln Ser Val Tyr Ala
465                 470             475                 480

Phe Val Ala Thr Glu Gly Ser Arg Glu Leu Lys Arg Glu Leu Ile Asn
                485             490                 495

Glu Ala Leu Glu Thr Leu Met Glu Gln Ala Val Ala Ala Val Gln Lys
                500             505             510

Met Asp Gln Ala Glu Tyr Gln Ala Lys Ile Arg Asp Leu Gln Gln Ala
            515             520             525

Ala Leu Thr Lys Arg Ala Ala Gln Ala Ala Gln Arg Glu Asn Gln Arg
        530             535             540

Gln Gln Phe Pro Val Glu His Val Gln Leu Leu Cys Ile Asn Cys Met
545             550             555             560

Val Ala Val Gly His Gly Ser Asp Leu Arg Lys Val Glu Gly Thr His
                565             570             575

His Val Asn Val Asn Pro Asn Phe Ser Asn Tyr Tyr Asn Val Ser Arg
            580             585             590

Asp Pro Val Val Ile Asn Lys Val Phe Lys Asp Trp Lys Pro Gly Gly
        595             600             605

Val Ile Ser Cys Arg Asn Cys Gly Glu Val Trp Gly Leu Gln Met Ile
        610             615             620

Tyr Lys Ser Val Lys Leu Pro Val Leu Lys Val Arg Ser Met Leu Leu
625             630             635             640

Glu Thr Pro Gln Gly Arg Ile Gln Ala Lys Lys Trp Ser Arg Val Pro
            645             650             655

Phe Ser Val Pro Asp Phe Asp Phe Leu Gln His Cys Ala Glu Asn Leu
            660             665             670

Ser Asp Leu Ser Leu Asp
            675
```